US008008299B2

(12) United States Patent
Kinney et al.

(10) Patent No.: US 8,008,299 B2
(45) Date of Patent: Aug. 30, 2011

(54) UROTENSIN II RECEPTOR ANTAGONISTS

(75) Inventors: William A. Kinney, Newtown, PA (US); Edward C. Lawson, Pipersville, PA (US); Shyamali Ghosh, Norristown, PA (US); Diane K. Luci, Horsham, PA (US); David F. McComsey, Warminster, PA (US)

(73) Assignee: Janssen Pharmaceutica, N.V., Belgium (FR)

( * ) Notice: Subject to any disclaimer, the term of this patent is extended or adjusted under 35 U.S.C. 154(b) by 347 days.

(21) Appl. No.: 12/156,884

(22) Filed: Jun. 5, 2008

(65) Prior Publication Data
US 2008/0318973 A1    Dec. 25, 2008

Related U.S. Application Data

(60) Provisional application No. 60/933,577, filed on Jun. 7, 2007.

(51) Int. Cl.
| A61K 316/496 | (2006.01) |
| A61K 31/501 | (2006.01) |
| A61K 31/506 | (2006.01) |
| C07D 209/46 | (2006.01) |
| C07D 401/06 | (2006.01) |
| C07D 403/06 | (2006.01) |
| C07D 403/12 | (2006.01) |
| C07D 409/12 | (2006.01) |
| A61P 25/00 | (2006.01) |
| A61P 25/28 | (2006.01) |
| A61P 9/00 | (2006.01) |

(52) U.S. Cl. ......... 514/252.02; 514/253.04; 514/253.06; 514/253.09; 514/254.02; 514/254.04; 514/254.05; 514/254.08; 514/323; 514/417; 544/238; 544/295; 544/363; 544/364; 544/366; 544/367; 544/370; 544/373; 546/200; 546/277.1; 548/455; 548/466; 548/472

(58) Field of Classification Search .................. None
See application file for complete search history.

(56) References Cited

U.S. PATENT DOCUMENTS

| 6,583,144 B2 * | 6/2003 | Ohkura et al. ........... 514/252.12 |
| 6,884,887 B1 | 4/2005 | Riermeier et al. |
| 6,911,464 B2 | 6/2005 | Man et al. |
| 7,043,052 B2 | 5/2006 | Rhoads |
| 2004/0259873 A1 | 12/2004 | Man et al. |
| 2004/0267051 A1 | 12/2004 | Boerner et al. |
| 2005/0203090 A1 | 9/2005 | Man et al. |
| 2007/0027163 A1 | 2/2007 | Bissantz et al. |

FOREIGN PATENT DOCUMENTS

| WO | WO 98/52919 | 11/1998 |
| WO | WO 01/05741 | 1/2001 |
| WO | WO 01/05741 A1 | 1/2001 |
| WO | WO 03/014061 | 2/2003 |
| WO | WO 2004/078114 | 9/2004 |
| WO | WO 2004/080422 A2 | 9/2004 |
| WO | WO 2004/080422 A3 | 9/2004 |
| WO | WO 2004/080423 A2 | 9/2004 |
| WO | WO 2004/080423 A3 | 9/2004 |
| WO | WO 2005/034873 A2 | 4/2005 |
| WO | WO 2005/034873 A3 | 4/2005 |
| WO | WO2007/081995 A2 | 7/2007 |
| WO | WO 2008/153902 | 12/2008 |

OTHER PUBLICATIONS

Vippagunta et al. Advanced Drug Delivery Reviews, vol. 48, pp. 3-26 (2001).*
European Search Report, Application No. 08768153.2-1219/2161994; PCT/US2008007076.
International Search Report, PCT/US08/07076, Jun. 5, 2008.
Pearson et al, "Urotensin II: A somatostatin-like peptide in the caudal neurosecretory system of fishes," Proc. Natl. Acad. Sci. USA, 1980, pp. 5021-5024, vol. 77, No. 8.
Ames, et al, "Human-urotensin-II is a potent vasoconstrictor and agonist for the orphan receptor GPR14," Nature, 1999, pp. 282-286, vol. 401, London.
Tal, et al, "A Novel Putative Neuropeptide Receptor Expressed in Neural Tissue, Including Sensory Epithelia," Biochem. Biophys. Res. Commun., 1995, pp. 752-759, vol. 209.
Marchese, et al, "Cloning and Chromosomal Mapping of Three Novel Genes, GPR9, GPR10, and GPR14, Encoding Receptors Related to Interleukin 8, Neuropeptide Y, and Somatostatin Receptors," Genomics, 1995, pp. 335-344; vol. 29.
Conlon, et al, "Distribution and Molecular Forms of Urotensin II and its role in Cardiovascular Regulation in Vertebrates," J. Exp. Zool., 1996, pp. 226-238, vol. 275.
Bohn, et al, "Urotensin II evokes potent vasoconstriction in humans in vivo," Br. J. Pharmacol., 2002, pp. 25-27, vol. 135.
Douglas, et al, "Human Urotensin-II, the Most Potent Mammalian Vasoconstrictor Identified to Date, as a Therapeutic Target for the Management of Cardiovascular Disease," Trends Cardiovasc. Med., 2000, pp. 229-237, vol. 10.
Zou, et al, "Urotensin II induces hypertrophic responses in cultured cardiomyocytes from neonatal rats," FEBS Letters, 2001, pp. 57-60, vol. 508.
Watanabe, et al, "Synergistic Effect of Urotensin II With Mildly Oxidized LDL on DNA Synthesis in Vascular Smooth Muscle Cells," Circulation, 2001, pp. 16-18, vol. 104.

(Continued)

*Primary Examiner* — Emily Bernhardt
(74) *Attorney, Agent, or Firm* — Yuriy P. Stercho

(57) ABSTRACT

This invention is directed to a compound of Formula (I):

Formula (I)

and forms thereof, wherein A, B, E, G, X and $L_2$ are as defined herein and their use as urotensin II receptor antagonists.

19 Claims, No Drawings

OTHER PUBLICATIONS

Lim, et al, "Differential Effect of Urotensin II on Vascular Tone in Normal Subjects and Patients With Chronic Heart Failure," Circulation, 2004, pp. 1212-1214, vol. 109.

Bousette, et al, "Increased expression of urotensin II and its cognate receptor GPR 14 in atherosclerotic lesions of the human aorta," Antherosclerosis, 2004, pp. 117-123, vol. 176.

Totsune, et al, "Role of urotensin II in patients on dialysis," Lancet, 2001, pp. 810-811, vol. 358.

Totsune, et al, "Increased plasma urotensin II levels in patients with diabetes mellitus," Clin. Sci., 2003, pp. 1-5, vol. 104.

Gartlon, et al, "Central effects of urotensin-II following ICV administration in rats," Psychopharmacology, 2001, pp. 426-433, vol. 155.

Gartlon, et al, "Urotensin-II, a neuropeptide ligand for GPR 14, induces c-*fos* in the rat brain," Eur. J. of Pharmacol., 2004, pp. 95-98, vol. 493.

Matsumoto, et al, "Intracerebroventricular administration of urotensin II promotes anxiogenic-like behaviors in rodents," Neuroscience Letters, 2004, pp. 99-102, vol. 358.

Kinney, et al, "Structure-Function Analysis of Urotensin II and its Use in the Construction of a Ligand-Receptor Working Model", Angew. Chem. Int. Ed., 2002, pp. 2940-2944, vol. 41, No. 16.

Silvestre, et al, "Inhibition of Insulin Release by Urotensin II—A Study on the Perfused Rat Pancreas," Horm. Metab. Res., 2001, pp. 379-381, vol. 33.

Gillaspy, et al, "A Simple Method for the Formation of Cycolpropylamines: The First Synthesis of Tricyclopropylamine," Tetrahedron Letters, 1995, pp. 7399-7402, vol. 36.

Qi et al, "Characterization of functional urotensin II receptors in human skeletal muscle myoblasts: comparison with angiotensin II receptors," Peptides, 2005, pp. 683-690, No. 26, Elsevier.

* cited by examiner

UROTENSIN II RECEPTOR ANTAGONISTS

CROSS REFERENCE TO RELATED APPLICATIONS

This application claims priority from U.S. provisional application No. 60/933,577, filed on Jun. 7, 2007, which is incorporated herein by reference.

FIELD OF THE INVENTION

The present invention relates to certain novel compounds, methods for preparing compounds, compositions, intermediates and derivatives thereof and methods for treating urotensin-II mediated disorders. More particularly, the compounds of the present invention are urotensin-II receptor antagonists useful for treating urotensin-II mediated disorders.

BACKGROUND OF THE INVENTION

Urotensin-II (U-II) is a cysteine-linked cyclic peptide, which exerts potent effects on the cardiovascular, renal, pancreatic, and central nervous systems. Originally, this substance was isolated from the urophysis (a caudal neurosecretory organ) of the goby fish (*Gillichthys mirabilis*) as a 12-mer, AGTAD-cyclo(CFWKYC)-V (D. Pearson. J. E. Shively, B. R. Clark, I. I. Geschwind, M. Barkley, R. S. Nishioka, H. A. Bern, *Proc. Natl. Acad. Sci. USA* 1980, 77, 5021-5024), but it has now been identified in all classes of vertebrates. The composition of U-II ranges from 11 amino acids in humans to 14 amino acids in mice, always with a conserved cysteine-linked macrocycle, CFWKYC. Recently, the U-II receptor was identified (R. S. Ames, H. M. Sarau, J. K. Chambers, R. N. Willette, N. V. Aiyar, A. M. Romanic, C. S. Louden, J. J. Foley, C. F. Sauermelch, R. W. Coatney, Z. Ao, J. Disa, S. D. Holmes, J. M. Stadel, J. D. Martin, W.-S. Liu, G. I. Glover, S. Wilson, D. E. McNulty, C. E. Ellis, N. A. Elshourbagy, U. Shabon, J. J. Trill, D. W. P. Hay, E. H. Ohlstein, D. J. Bergsma, S. A. Douglas, *Nature* (London) 1999, 401, 282-286) as a G-protein-coupled receptor (GPCR) previously known as the GPR14 orphan receptor, (M. Tal, D. A. Ammar, M. Karpuj, V. Krizhanovsky, M. Naim, D. A. Thompson, *Biochem. Biophys. Res. Commun.* 1995, 209, 752-759; and A. Marchese, M. Heiber, T. Nguyen, H. H. Q. Heng, V. R. Saldivia, R. Cheng, P. M. Murphy, L.-C. Tsui, X. Shi, P. Gregor, S. R. George, B. F. O'Dowd, J. M. Docherty, *Genomics* 1995, 29, 335-344) which is expressed predominantly in cardiovascular tissues.

Goby U-II possesses powerful vasoconstrictor activity in fish, mammals, and humans (J. M. Conlon, K. Yano, D. Waugh, N. Hazon, *J. Exp. Zool.* 1996, 275, 226-238; F. Böhm, J. Pernow, *Br. J. Pharmacol.* 2002, 135, 25-27). Moreover, it appears to be the most potent vasoconstrictor known, (S. A. Douglas, E. H. Ohlstein, *Trends Cardiovasc. Med.* 2000, 10, 229-237), causing concentration-dependent contraction of isolated arterial rings of rats and humans with an $EC_{50}$ value of less than 1 nM, which is ca. ten times more potent than endothelin-1. Recently, Kikkawa, H. and Kushida, H. in International Publication WO 2005/072226 disclosed the use of Urotensin-II antagonists for the prevention and/or treatment of inflammatory bowel diseases including, but not limited to, Crohn's disease, ulcerative colitis, and inflammatory colitis caused by bacteria, ischemia, radiation, drugs, or chemical substances.

Relative to the role of U-II in chronic vascular disease, this peptide was reported to induce hypertrophy in cardiomyocytes (Y. Zou, R. Nagai, T. Yamazaki, *FEBS Letters* 2001, 508, 57-60) and the proliferation of smooth muscle cells (T. Watanabe, R. Pakala, T. Katagiri, C. R. Benedict, *Circulation* 2001, 104, 16-18), which suggests an involvement in heart failure and atherosclerosis. In addition, U-II has been shown to increase peripheral vascular tone, a characteristic of chronic heart failure (M. Lim, S. Honisett, C. D. Sparkes, P. Komesaroff, A. Kompa, H. Krum, *Circulation* 2004, 109, 1212-1214). Recent results have shown increased U-II receptor levels observed in the atherosclerotic lesions of the human aorta (N. Bousette, L. Patel, S. A. Douglas, E. H. Ohistein, A. Giaid, *Atherosclerosis* 2004, 176, 117-123).

Relative to healthy individuals, the expression of U-II-like immunoreactivity was 2-fold higher in the plasma of patients with renal dysfunction who were not on dialysis, and 3-fold higher in those on haemodialysis (K. Totsune, K. Takahashi, Z. Arihara, M. Sone, F. Satoh, S. Ito, Y. Kimura, H. Sasano, O. Murakami, *Lancet* 2001, 358, 810-811). Recently, Kinoshita, M. and Kushida, H. in International Publication WO 2005/034873 disclosed the use of Urotensin-II antagonists for reducing nephrotoxicity and diarrhea caused by anti-neoplastic agents.

U-II has been described as a potential mediator in diabetes. For instance, U-II was shown to inhibit the release of insulin in the perfused rat pancreas in response to increasing glucose levels (R. A. Silvestre, J. Rodríguez-Gallardo, E. M. Egido, J. Marco, *Horm. Metab. Res.* 2001, 33, 379-381). Elevated U-II levels were seen in patients with diabetis mellitus (K. Totsune, K. Takahashi, Z. Arihara, M. Sone, S. Ito, O. Murakami, *Clin. Sci.* 2003, 104, 1-5) even without renal failure.

A U-II antagonist may be useful for the treatment of pain, neurological and psychiatric conditions, migraine, neuromuscular deficit, and cardiovascular disorders. ICV (intracerebroventricular) administration of U-II increases rearing, grooming, and motor activity suggesting a CNS stimulatory activity (J. Gartlon, F. Parker, D. C. Harrison, S. A. Douglas, T. E. Ashmeade, G. J. Riley, Z. A. Hughes, S. G. Taylor, R. P. Munton, J. J. Hagan, J. A. Hunter, D. N. C. Jones, *Psychopharmacology* 2001, 155, 426-433). U-II increases Fos expression in the cingulate cortex and periaqueductal grey brain regions important in cognitive, emotional, and motor responses; the perceptions of pain; and panic responses (J. E. Gartlon, T. Ashmeade, M. Duxon, J. J. Hagan, D. N. C. Jones, *Eur. J. of Pharmacol.* 2004, 493, 95-98). U-II induces anxiogenic-like responses in rodents in the elevated plus maze and hole-board tests (Y. Matsumoto, M. Abe, T. Watanabe, Y. Adachi, T. Yano, H. Takahashi, T. Sugo, M. Mori, C. Kitada, T. Kurokawa, M. Fujino, *Neuroscience Letters* 2004, 358, 99-102).

U.S. Pat. No. 6,911,464 and Application Publications US2004/0259873 and US2005/0203090 (corresponding to Man, H-W. and Muller, G. W. International Publication WO/2004080422) disclose N-alkyl-hydroxamic acid-isoindolyl compounds for treatment or prevention of various diseases and disorders mediated by PDE4 inhibition, associated with abnormal TNA-alpha levels, and/or mediated by MMP inhibition.

U.S. Pat. No. 7,043,052 and Application Publications US2004/0259873 and US2005/0203090 (corresponding to Man, H-W., Muller, G. W., and Zhang, W. International Publication WO2004/080423) disclose 7-amido-isoindolyl compounds for the treatment, prevention or management of various diseases and disorders, including but not limited to cancer, inflammatory bowel disease and myelodysplastic syndrome.

Kawasaki, H., Shinagawa, Y., and Mimura, T. in International Publication WO98/52919 disclose phthalamide derivatives and an antiallergic agent containing the same, having selective IgE and IL-5 production inhibitory activities.

United States Patent Application Publication US2004/0267051 (corresponding to International Publication WO2003/014061) describes a method for the production of amines by reductive amination of carbonyl compounds under transfer-hydrogenation conditions.

U.S. Pat. No. 6,884,887 (corresponding to PCT Publication WO2001/005741) describes a method for producing amines by homogeneously catalyzed reductive amination of carbonyl compounds.

Accordingly, it is an object of the present invention to provide compounds that are urotensin-II antagonists useful for treating urotensin-II mediated disorders. It is another object of the invention to provide a process for preparing compounds, compositions, intermediates and derivatives thereof. It is a further object of the invention to provide methods for treating urotensin-II mediated disorders including, but not limited to, vascular hypertension, heart failure, atherosclerosis, renal failure, nephrotoxicity and diarrhea caused by anti-neoplastic agents, post-myocardial infarction, pulmonary hypertension/fibrosis, diabetes, and CNS indications including pain, Alzheimer's, convulsions, depression, migraine, psychosis, anxiety, neuromuscular deficit, and stroke.

SUMMARY OF THE INVENTION

The present invention is directed to a compound of Formula (I):

Formula (I)

and forms thereof, wherein A, B, E, G, X and $L_2$ are as defined herein.

Illustrative of the invention is a pharmaceutical composition comprising a pharmaceutically acceptable carrier and a compound of Formula (I). Illustrative of the invention is a process for making a pharmaceutical composition comprising mixing a compound of Formula (I) and a pharmaceutically acceptable carrier.

The present invention is further directed to methods for treating or ameliorating a urotensin II-mediated disorder. In particular, the method of the present invention is directed to treating or ameliorating a urotensin II-mediated disorder including, but not limited to, vascular hypertension, heart failure, atherosclerosis, renal failure, nephrotoxicity and diarrhea caused by anti-neoplastic agents, post-myocardial infarction, pulmonary hypertension/fibrosis, diabetes, and CNS indications including pain, Alzheimer's, convulsions, depression, migraine, psychosis, anxiety, neuromuscular deficit, and stroke.

The present invention is also directed to methods for producing the instant compounds and pharmaceutical compositions and medicaments thereof.

DETAILED DESCRIPTION OF THE INVENTION

The present invention is directed to a compound of Formula (I):

Formula (I)

wherein:

A is a bond or is selected from the group consisting of a-1, optionally unsaturated a-2, a-3, a-4, optionally unsaturated a-5 and optionally unsaturated a-6, wherein, the lower portion of A is attached, relative to the nitrogen atom of Formula (I), to the 3 or 4 position on the benzene ring portion of Formula (I);

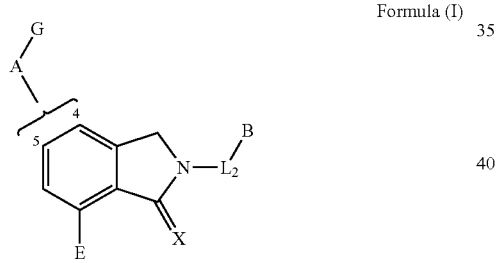

a-1 a-2 a-3 a-4 a-5 and

-continued

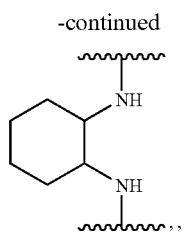
a-6 wherein, when A is present, then G is hydrogen, or one substituent selected from $C_{1-8}$alkyl, $C_{2-8}$alkenyl, $C_{3-14}$cycloalkyl or a —C[($R_1$)($R_{11}$)]-L-D moiety:

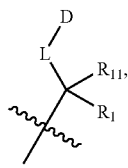

or two $C_{1-4}$alkyl substituents both attached to the common ring nitrogen atom of Formula (I), thus forming a quaternary ammonium salt;

$R_1$ is selected from the group consisting of hydrogen, $C_{1-8}$alkyl, $C_{2-8}$alkenyl, and $C_{2-8}$alkynyl;

$R_{11}$ is selected from the group consisting of hydrogen, $C_{1-8}$alkyl and cyclopropyl;

L is absent or $C_{1-4}$alkyl;

D is aryl, $C_{3-14}$cycloalkyl, $C_{5-14}$cycloalkenyl, heterocyclyl, or heteroaryl, wherein aryl and heteroaryl are optionally substituted with one, two, three or four substituents independently selected from the group consisting of $C_{1-3}$alkyl, $C_{1-3}$alkoxy, $C_{2-8}$alkenyl, $C_{2-3}$alkenyloxy, hydroxy, $C_{1-3}$alkylthio, fluoro, chloro, cyano, $C_{1-3}$alkylcarbonyl, ($C_{1-3}$alkylcarbonyl)amino, ($C_{1-3}$alkyl)amino, di($C_{1-3}$alkyl)amino and $C_{3-14}$cycloalkyl, wherein $C_{3-14}$cycloalkyl is optionally substituted with one, two, three or four $C_{1-3}$alkyl substituents;

$R_4$ is hydrogen or $C_{1-8}$alkyl;

$L_2$ is —C($R_2$)($R_5$)—(C$R_6R_7$)$_r$—, wherein r is 0, 1 or 2; and wherein $R_5$, $R_6$, and $R_7$ are independently hydrogen or $C_{1-3}$alkyl;

$R_2$ is selected from the group consisting of heteroaryl, phenyl, heterocyclyl and $C_{1-6}$alkyl, wherein phenyl is optionally substituted with [($R_{200}$—$C_{1-6}$alkyl)($R_a$)]amino, [($R_{200}$-sulfonyl)($R_a$)]amino or [(hydroxysulfonyl)($R_a$)]amino, wherein heterocyclyl is optionally substituted with $C_{1-4}$alkyl, aryl, heteroaryl, $R_{200}$—$C_{1-6}$alkyl or $R_{200}$-sulfonyl, and wherein $C_{1-6}$alkyl is optionally substituted with carboxy, hydroxy, $R_{200}$, $NR_aR_b$, $C_{1-6}$alkoxy, $R_{200}$—$C_{1-6}$alkoxy, $R_{200}$-oxy, $R_{200}$-thio, aminocarbonyl, carboxy-$C_{1-6}$alkoxy, aminocarbonyl-$C_{1-6}$alkoxy, ($C_{1-6}$alkyl)aminocarbonyl, di($C_{1-6}$alkyl)aminocarbonyl, [($R_{200}$—$C_{1-6}$alkyl)($R_a$)] amino, ($R_{200}$—$C_{1-6}$alkyl)$_2$-amino, ($C_{1-6}$alkylcarbonyl) amino, (trihalo-$C_{1-4}$alkylcarbonyl)amino, ($R_{200}$—$C_{1-6}$alkylcarbonyl)amino, ($C_{1-6}$alkoxycarbonyl)amino, ($R_{200}$—$C_{1-6}$alkoxycarbonyl)amino, ($C_{1-6}$alkoxy-$C_{1-6}$alkylcarbonyl)amino, ($R_{200}$-carbonyl)amino, (amino-$C_{1-6}$alkylcarbonyl)amino, [($C_{1-6}$alkyl)amino-$C_{1-6}$alkylcarbonyl]amino, [di($C_{1-6}$alkyl)amino-$C_{1-6}$alkylcarbonyl] amino, ($C_{1-6}$alkylcarbonyl-acetonitrile-carbonyl)amino, ureido, thioureido, acetamidino, guanidino, ({[($R_{200}$)($R_a$)] aminocarbonyl}($R_a$))amino, [($R_{200}$-oxycarbonyl)($R_a$)] amino, [($R_{200}$)($R_a$)]aminocarbonyloxy, aminosulfonyl, $C_{1-6}$alkylsulfonyl, hydroxysulfonyl, ($C_{1-6}$alkylsulfonyl) amino, ($R_{200}$—$C_{1-6}$alkylsulfonyl)amino, ($R_{200}$—$C_{2-6}$alkenylsulfonyl)amino, ($C_{1-6}$alkylsulfonyl-$C_{1-6}$alkylsulfonyl)amino, $R_{200}$-sulfonyloxy, aminosulfonyloxy, ($C_{1-6}$ alkyl)aminosulfonyloxy, di($C_{1-6}$alkyl)aminosulfonyloxy, [(aminosulfonyl)($R_a$)]amino, {[($C_{1-6}$alkyl)aminosulfonyl] ($R_a$)}amino, {[di($C_{1-6}$alkyl)aminosulfonyl]($R_a$)}amino, [(hydroxysulfonyl)($R_a$)]amino, [($R_{200}$-oxysulfonyl)($R_a$)] amino, [($R_{200}$-sulfonyl)($R_a$)]amino, [($R_{200}$)($R_a$)]aminosulfonyloxy, or ({[($R_{200}$)($R_a$)]aminosulfonyl}($R_c$))amino;

$R_a$ is selected from the group consisting of hydrogen, $C_{1-6}$alkyl, $C_{1-6}$alkylcarbonyl and $C_{3-8}$cycloalkyl;

$R_b$ is selected from the group consisting of hydrogen, $C_{1-6}$alkyl or $R_{201}$, $R_{200}$ is $C_{6-10}$aryl, heteroaryl, $C_{3-8}$cycloalkyl or heterocyclyl each optionally substituted with one, two or three substituents independently selected from the group consisting of $C_{1-4}$alkyl, trihalo-$C_{1-4}$alkyl, $C_{1-4}$alkoxy, trihalo-$C_{1-4}$ alkoxy, $C_{1-6}$alkylcarbonyl, $C_{1-6}$alkoxycarbonyl, amino, $C_{1-6}$alkyl-amino, di$C_{1-6}$alkyl-amino, ($C_{1-6}$alkylcarbonyl) amino, $C_{1-6}$alkylsulfonyl, hydroxysulfonyl, aminosulfonyl, chloro, fluoro, bromo and $R_{202}$, wherein $C_{3-8}$cycloalkyl or heterocyclyl is optionally substituted with one, two or three oxo substituents on available carbon atom ring members, and wherein heteroaryl having a nitrogen atom ring member is optionally substituted on the ring nitrogen atom with an oxy substituent and thus forms an oxide;

$R_{201}$ is $C_{6-10}$aryl, heteroaryl, $C_{3-8}$cycloalkyl or heterocyclyl, wherein aryl, heteroaryl, $C_{3-8}$cycloalkyl or heterocyclyl are each optionally substituted with one, two or three substituents independently selected from the group consisting of $C_{1-4}$alkyl, trihalo-$C_{1-4}$alkyl, $C_{1-4}$alkoxy, trihalo-$C_{1-4}$ alkoxy, amino, $C_{1-6}$alkyl-amino, di$C_{1-6}$alkyl-amino, $C_{1-6}$alkylcarbonyl, $C_{1-6}$alkoxycarbonyl, ($C_{1-6}$alkylcarbonyl)amino, $C_{1-6}$alkylsulfonyl, hydroxysulfonyl, aminosulfonyl, chloro, fluoro, bromo, aryl, heteroaryl, aryl-$C_{1-6}$ alkyl, aryl-sulfonyl and heteroaryl-sulfonyl, wherein $C_{3-8}$cycloalkyl or heterocyclyl is optionally substituted with one, two or three oxo substituents on available carbon atom ring members, and wherein heteroaryl having a nitrogen atom ring member is optionally substituted on the ring nitrogen atom with an oxy substituent and thus forms an oxide;

$R_{202}$ is aryl, heteroaryl, aryl-$C_{1-6}$alkyl, [(aryl-$C_{1-6}$alkyl)($R_a$)] amino, hydroxysulfonyl, aryl-sulfonyl, heteroaryl-sulfonyl or [(heteroaryl-sulfonyl)($R_a$)]amino, wherein each aryl and heteroaryl are optionally substituted with one, two or three $C_{1-4}$alkyl substituents;

B is $C_{6-10}$aryl, tetralinyl, indanyl, or a heteroaryl selected from the group consisting of pyridin-2-yl, pyridin-4-yl, pyrazol-4-yl, pyrimidin-4-yl, pyrimidin-5-yl, pyrazin-2-yl, imidazol-1-yl, thien-2-yl, isoquinolinyl, indolyl, quinolinyl, and thiazol-5-yl, wherein B is optionally substituted with one, two or three substituents independently selected from the group consisting of $C_{1-4}$alkyl, $C_{1-4}$alkoxy, fluorinated ($C_{1-4}$)alkoxy, halogen, cyano, hydroxy, aminocarbonyl, ($C_{1-4}$)alkylaminocarbonyl, di($C_{1-4}$)alkylaminocarbonyl, aminosulfonyl, ($C_{1-4}$)alkylaminosulfonyl, di($C_{1-4}$)alkylaminosulfonyl, hydroxysulfonyl, aminosulfonylamino, ($C_{1-4}$)alkylaminosulfonylamino, di($C_{1-4}$)alkylaminosulfonylamino, aminosulfonyloxy, ($C_{1-4}$)alkylaminosulfonyloxy, and di($C_{1-4}$) alkylaminosulfonyloxy, provided that when B is selected from the group consisting of C$_{6-10}$aryl, tetralinyl, indanyl, thien-2-yl, and indolyl, then B is independently substituted with two to three substitutents selected from the group consisting of C$_{1-3}$alkoxy and hydroxy, provided that, when B is phenyl substituted at the 3,4-, 3,5- or 4,5-positions with an unbranched C$_{1-3}$alkoxy substituent at each position, then phenyl may be further optionally substituted at a remaining open 3-, 4-, or 5-position with an additional C$_{1-3}$alkoxy or hydroxy substituent;

E is hydrogen, halogen, cyano, C$_{1-3}$alkyl, C$_{1-3}$alkoxy, C$_{2-5}$alkenyl, amino, (C$_{1-3}$alkyl)amino or di(C$_{1-3}$alkyl)amino;

X is O or S;

and enantiomers, diastereomers, tautomers, solvates, and pharmaceutically acceptable salts thereof.

Embodiment 1 of the present invention is directed to a compound of Formula (Ia):

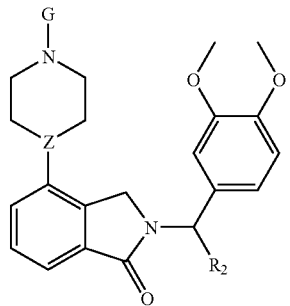

Formula (Ia)

wherein:

Z is CH or N;

G is hydrogen, or one substituent selected from C$_{1-8}$alkyl, C$_{2-8}$alkenyl, C$_{3-14}$cycloalkyl or a —C[(R$_1$)(R$_{11}$)]-L-D moiety:

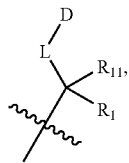

or two C$_{1-4}$alkyl substituents both attached to the common ring nitrogen atom of Formula (Ia), thus forming a quaternary ammonium salt;

R$_1$ is selected from the group consisting of hydrogen, C$_{1-8}$alkyl, C$_{2-8}$alkenyl, and C$_{2-8}$alkynyl;

R$_{11}$ is selected from the group consisting of hydrogen, C$_{1-8}$alkyl and cyclopropyl;

L is absent or C$_{1-4}$alkyl;

D is aryl, C$_{3-14}$cycloalkyl, C$_{5-14}$cycloalkenyl, heterocyclyl, or heteroaryl, wherein aryl and heteroaryl are optionally substituted with one, two, three or four substitutents independently selected from the group consisting of C$_{1-3}$alkyl, C$_{1-3}$alkoxy, C$_{2-8}$alkenyl, C$_{2-3}$alkenyloxy, hydroxy, C$_{1-3}$alkylthio, fluoro, chloro, cyano, C$_{1-3}$alkylcarbonyl, (C$_{1-3}$alkylcarbonyl)amino, (C$_{1-3}$alkyl)amino, di(C$_{1-3}$alkyl)amino and C$_{3-14}$cycloalkyl, wherein C$_{3-14}$cycloalkyl is optionally substituted with one, two, three or four C$_{1-3}$alkyl substituents;

R$_2$ is selected from the group consisting of heteroaryl, phenyl, heterocyclyl and C$_{1-6}$alkyl, wherein phenyl is optionally substituted with [(R$_{200}$—C$_{1-6}$alkyl)(R$_a$)]amino, [(R$_{200}$-sulfonyl)(R$_a$)]amino or [(hydroxysulfonyl)(R$_a$)]amino, wherein heterocyclyl is optionally substituted with C$_{1-4}$alkyl, aryl, heteroaryl, R$_{200}$—C$_{1-6}$alkyl or R$_{200}$-sulfonyl, and wherein C$_{1-6}$alkyl is optionally substituted with carboxy, hydroxy, R$_{200}$, NR$_a$R$_b$, C$_{1-6}$alkoxy, R$_{200}$—C$_{1-6}$alkoxy, R$_{200}$-oxy, R$_{200}$-thio, aminocarbonyl, carboxy-C$_{1-6}$alkoxy, aminocarbonyl-C$_{1-6}$alkoxy, (C$_{1-6}$alkyl)aminocarbonyl, di(C$_{1-6}$alkyl)aminocarbonyl, [(R$_{200}$—C$_{1-6}$alkyl)(R$_a$)]amino, (R$_{200}$—C$_{1-6}$alkyl)$_2$-amino, (C$_{1-6}$alkylcarbonyl)amino, (trihalo-C$_{1-4}$alkylcarbonyl)amino, (R$_{200}$—C$_{1-6}$alkylcarbonyl)amino, (C$_{1-6}$alkoxycarbonyl)amino, (R$_{200}$—C$_{1-6}$alkoxycarbonyl)amino, (C$_{1-6}$alkoxy-C$_{1-6}$alkylcarbonyl)amino, (R$_{200}$-carbonyl)amino, (amino-C$_{1-6}$alkylcarbonyl)amino, [(C$_{1-6}$alkyl)amino-C$_{1-6}$alkylcarbonyl]amino, [di(C$_{1-6}$alkyl)amino-C$_{1-6}$alkylcarbonyl]amino, (C$_{1-6}$alkylcarbonyl-acetonitrile-carbonyl)amino, ureido, thioureido, acetamidino, guanidino, ({[(R$_{200}$)(R$_a$)]aminocarbonyl}(R$_a$))amino, [(R$_{200}$-oxycarbonyl)(R$_a$)]amino, [(R$_{200}$)(R$_a$)]aminocarbonyloxy, aminosulfonyl, C$_{1-6}$alkylsulfonyl, hydroxysulfonyl, (C$_{1-6}$alkylsulfonyl)amino, (R$_{200}$—C$_{1-6}$alkylsulfonyl)amino, (R$_{200}$—C$_{2-6}$alkenylsulfonyl)amino, (C$_{1-6}$alkylsulfonyl-C$_{1-6}$alkylsulfonyl)amino, R$_{200}$-sulfonyloxy, aminosulfonyloxy, (C$_{1-6}$alkyl)aminosulfonyloxy, di(C$_{1-6}$alkyl)aminosulfonyloxy, [(aminosulfonyl)(R$_a$)]amino, {[(C$_{1-6}$alkyl)aminosulfonyl](R$_a$)}amino, {[di(C$_{1-6}$alkyl)aminosulfonyl](R$_a$)}amino, [(hydroxysulfonyl)(R$_a$)]amino, [(R$_{200}$-oxysulfonyl)(R$_a$)]amino, [(R$_{200}$-sulfonyl)(R$_a$)]amino, [(R$_{200}$)(R$_a$)]aminosulfonyloxy, or ({[(R$_{200}$)(R$_a$)]aminosulfonyl}(R$_c$))amino;

R$_a$ is selected from the group consisting of hydrogen, C$_{1-6}$alkyl, C$_{1-6}$alkylcarbonyl and C$_{3-8}$cycloalkyl;

R$_b$ is selected from the group consisting of hydrogen, C$_{1-6}$alkyl or R$_{201}$, R$_{200}$ is C$_{6-10}$ aryl, heteroaryl, C$_{3-8}$cycloalkyl or heterocyclyl each optionally substituted with one, two or three substituents independently selected from the group consisting of C$_{1-4}$alkyl, trihalo-C$_{1-4}$alkyl, C$_{1-4}$alkoxy, trihalo-C$_{1-4}$alkoxy, C$_{1-6}$alkylcarbonyl, C$_{1-6}$alkoxycarbonyl, amino, C$_{1-6}$alkyl-amino, diC$_{1-6}$alkyl-amino, (C$_{1-6}$alkylcarbonyl)amino, C$_{1-6}$alkylsulfonyl, hydroxysulfonyl, aminosulfonyl, chloro, fluoro, bromo and R$_{202}$, wherein C$_{3-8}$cycloalkyl or heterocyclyl is optionally substituted with one, two or three oxo substituents on available carbon atom ring members, and wherein heteroaryl having a nitrogen atom ring member is optionally substituted on the ring nitrogen atom with an oxy substituent and thus forms an oxide;

R$_{201}$ is C$_{6-10}$aryl, heteroaryl, C$_{3-8}$cycloalkyl or heterocyclyl, wherein aryl, heteroaryl, C$_{3-8}$cycloalkyl or heterocyclyl are each optionally substituted with one, two or three substituents independently selected from the group consisting of C$_{1-4}$alkyl, trihalo-C$_{1-4}$alkyl, C$_{1-4}$alkoxy, trihalo-C$_{1-4}$alkoxy, amino, C$_{1-6}$alkyl-amino, diC$_{1-6}$alkyl-amino, C$_{1-6}$alkylcarbonyl, C$_{1-6}$alkoxycarbonyl, (C$_{1-6}$alkylcarbonyl)amino, C$_{1-6}$alkylsulfonyl, hydroxysulfonyl, aminosulfonyl, chloro, fluoro, bromo, aryl, heteroaryl, aryl-C$_{1-6}$alkyl, aryl-sulfonyl and heteroaryl-sulfonyl, wherein $C_{3-8}$cycloalkyl or heterocyclyl is optionally substituted with one, two or three oxo substituents on available carbon atom ring members, and wherein heteroaryl having a nitrogen atom ring member is optionally substituted on the ring nitrogen atom with an oxy substituent and thus forms an oxide; and, $R_{202}$ is aryl, heteroaryl, aryl-$C_{1-6}$alkyl, [(aryl-$C_{1-6}$alkyl)($R_a$)]amino, hydroxysulfonyl, aryl-sulfonyl, heteroaryl-sulfonyl or [(heteroaryl-sulfonyl)($R_a$)]amino, wherein each aryl and heteroaryl are optionally substituted with one, two or three $C_{1-4}$alkyl substituents;

and enantiomers, diastereomers, tautomers, solvates, and pharmaceutically acceptable salts thereof.

Embodiment 2 of the present invention includes a compound of Formula (Ia), wherein Z is CH.

Embodiment 3 of the present invention includes a compound of Formula (Ia), wherein Z is N.

Embodiment 4 of the present invention includes a compound of Formula (Ia), wherein G is hydrogen, or one substituent selected from $C_{1-8}$alkyl, $C_{3-14}$cycloalkyl, —$CH_2$-aryl or —$CH(C_{1-8}$alkyl)-aryl.

Embodiment 5 of the present invention includes a compound of Formula (Ia), wherein G is hydrogen, or one substituent selected from $C_{1-6}$alkyl, $C_{3-8}$cycloalkyl, —$CH_2$-aryl or —$CH(C_{1-4}$alkyl)-aryl.

Embodiment 6 of the present invention includes a compound of Formula (Ia), wherein G is hydrogen, or one substituent selected from methyl, ethyl, isopropyl, cyclopropyl, cyclobutyl, —$CH_2$-phenyl or —CH (methyl)-phenyl.

Embodiment 7 of the present invention includes a compound of Formula (Ia), wherein G is $C_{1-6}$alkyl, wherein $C_{1-6}$alkyl is selected from methyl, ethyl or isopropyl.

Embodiment 8 of the present invention includes a compound of Formula (Ia), wherein G is ethyl.

Embodiment 9 of the present invention includes a compound of Formula (Ia), wherein $R_2$ is selected from the group consisting of heteroaryl, phenyl, heterocyclyl and $C_{1-6}$alkyl, wherein phenyl is optionally substituted with [($R_{200}$—$C_{1-6}$alkyl)($R_a$)]amino or [($R_{200}$-sulfonyl)($R_a$)]amino, wherein heterocyclyl is optionally substituted with $C_{1-4}$alkyl, $R_{200}$—$C_{1-6}$alkyl or $R_{200}$-sulfonyl, and wherein $C_{1-6}$alkyl is substituted with $R_{200}$, $NR_aR_b$, $R_{200}$—$C_{1-6}$alkoxy, $R_{200}$-oxy, $R_{200}$-thio, [($R_{200}$—$C_{1-6}$alkyl)($R_a$)]amino, ($R_{200}$—$C_{1-6}$alkyl)$_2$-amino, ($C_{1-6}$alkylcarbonyl)amino, (trihalo-$C_{1-4}$alkylcarbonyl)amino, ($R_{200}$-carbonyl)amino, ureido, ({[($R_{200}$)($R_a$)]aminocarbonyl}($R_a$))amino, hydroxysulfonyl, [(aminosulfonyl)($R_a$)]amino, {[di($C_{1-6}$alkyl)aminosulfonyl]($R_a$)}amino, [(hydroxysulfonyl)($R_a$)]amino or [($R_{200}$-sulfonyl)($R_a$)]amino;

$R_a$ is selected from the group consisting of hydrogen, $C_{1-6}$alkyl, $C_{1-6}$alkylcarbonyl and $C_{3-8}$cycloalkyl;

$R_b$ is selected from the group consisting of hydrogen, $C_{1-6}$alkyl or $R_{201}$, $R_{200}$ is $C_{6-10}$aryl, heteroaryl, $C_{3-8}$cycloalkyl or heterocyclyl each optionally substituted with one or two substituents independently selected from the group consisting of $C_{1-4}$alkyl, hydroxysulfonyl, chloro, fluoro or $R_{202}$, wherein heteroaryl, having a nitrogen atom, is optionally substituted on the nitrogen atom with an oxy substituent and thus forms an oxide;

$R_{201}$ is $C_{6-10}$aryl, heteroaryl or $C_{3-8}$cycloalkyl, wherein heteroaryl and $C_{3-8}$cycloalkyl are each optionally substituted with one or two substituents independently selected from the group consisting of $C_{1-4}$alkyl, trihalo-$C_{1-4}$ alkyl, $C_{1-4}$alkoxy, amino and chloro, wherein $C_{3-8}$cycloalkyl is optionally substituted with two oxo substituents on available carbon atom ring members, and wherein heteroaryl having a nitrogen atom ring member is optionally substituted on the ring nitrogen atom with an oxy substituent and thus forms an oxide; and, $R_{202}$ is aryl-$C_{1-6}$alkyl, [(aryl-$C_{1-6}$alkyl)($R_a$)]amino, hydroxysulfonyl, heteroaryl-sulfonyl or [(heteroaryl-sulfonyl)($R_a$)]amino, wherein each heteroaryl is optionally substituted with two $C_{1-4}$alkyl substituents.

Embodiment 10 of the present invention includes a compound of Formula (Ia), wherein $R_2$ is selected from the group consisting of heteroaryl, phenyl, piperidinyl and $C_{1-6}$alkyl, wherein phenyl is optionally substituted with [($R_{200}$—$C_{1-6}$alkyl)($R_a$)]amino or [($R_{200}$-sulfonyl)($R_a$)]amino, wherein piperidinyl is optionally substituted with $C_{1-4}$alkyl, $R_{200}$—$C_{1-6}$alkyl or $R_{200}$-sulfonyl, and wherein $C_{1-6}$alkyl is substituted with $R_{200}$, $NR_aR_b$, $R_{200}$—$C_{1-6}$alkoxy, $R_{200}$-oxy, $R_{200}$-thio, [($R_{200}$—$C_{1-6}$alkyl)($R_a$)]amino, ($R_{200}$—$C_{1-6}$alkyl)$_2$-amino, ($C_{1-6}$alkylcarbonyl)amino, (trihalo-$C_{1-4}$alkylcarbonyl)amino, ($R_{200}$-carbonyl)amino, ureido, ({[($R_{200}$)($R_a$)]aminocarbonyl}($R_a$))amino, hydroxysulfonyl, [(aminosulfonyl)($R_a$)]amino, {[di($C_{1-6}$alkyl)aminosulfonyl]($R_a$)}amino, [(hydroxysulfonyl)($R_a$)]amino or [($R_{200}$-sulfonyl)($R_a$)]amino;

$R_a$ is selected from the group consisting of hydrogen, $C_{1-6}$alkyl, $C_{1-6}$alkylcarbonyl and cyclopropyl;

$R_b$ is selected from the group consisting of hydrogen, $C_{1-6}$alkyl or $R_{201}$, $R_{200}$ is phenyl, thienyl, furanyl, isoxazolyl, pyrazolyl, pyridinyl, pyrimidinyl, pyridazinyl, benzoimidazolyl, [1,2,4]triazolyl, cyclobutyl, piperidinyl, 1H-imidazolyl, 1H-tetrazolyl, 2H-tetrazolyl, 1,3-dihydro-isoindolyl, 3,4-dihydro-1H-isoquinolinyl or 5,6,7,8-tetrahydro-[1,8]naphthyridinyl, each optionally substituted with one or two substituents independently selected from the group consisting of $C_{1-4}$alkyl, hydroxysulfonyl, chloro, fluoro or $R_{202}$, wherein pyridinyl, having a nitrogen atom, is optionally substituted on the nitrogen atom with an oxy substituent and thus forms an oxide;

$R_{201}$ is phenyl, pyrimidinyl, pyridinyl, quinolinyl or cyclobut-3-enyl, wherein pyrimidinyl and cyclobut-3-enyl are each optionally substituted with one or two substituents independently selected from the group consisting of $C_{1-4}$alkyl, trihalo-$C_{1-4}$ alkyl, $C_{1-4}$alkoxy, amino and chloro, wherein cyclobut-3-enyl is optionally substituted with two oxo substituents on available carbon atom ring members, and wherein pyridinyl having a nitrogen atom ring member is optionally substituted on the ring nitrogen atom with an oxy substituent and thus forms an oxide; and, $R_{202}$ is phenyl-$C_{1-6}$alkyl, hydroxysulfonyl or thienyl-sulfonyl.

Embodiment 11 of the present invention includes a compound of Formula (Ia), wherein $R_2$ is $C_{1-6}$alkyl substituted with $R_{200}$, $R_{200}$—$C_{1-6}$alkoxy or ($R_{200}$-sulfonyl)amino; and, $R_{200}$ is phenyl or thienyl, Embodiment 12 of the present invention includes a compound of Formula (Ia), wherein $R_2$ is n-propyl substituted with phenyl, benzyloxy or (thienyl-sulfonyl)amino.

Embodiment 13 of the present invention includes a compound of Formula (Ia), wherein:

Z is CH or N;

G is hydrogen, or one substituent selected from methyl, ethyl, isopropyl, cyclopropyl, cyclobutyl, —CH$_2$-phenyl or —CH(methyl)-phenyl, or two methyl or ethyl substituents both attached to the common ring nitrogen atom of Formula (Ia), thus forming a quaternary ammonium salt;

$R_2$ is selected from the group consisting of heteroaryl, phenyl, piperidinyl and $C_{1-6}$alkyl, wherein phenyl is optionally substituted with [($R_{200}$—$C_{1-6}$alkyl)($R_a$)]amino or [($R_{200}$-sulfonyl)($R_a$)]amino, wherein piperidinyl is optionally substituted with $C_{1-4}$alkyl, $R_{200}$—$C_{1-6}$alkyl or $R_{200}$-sulfonyl, and wherein $C_{1-6}$alkyl is substituted with $R_{200}$, $NR_aR_b$, $R_{200}$—$C_{1-6}$alkoxy, $R_{200}$-oxy, $R_{200}$-thio, [($R_{200}$—$C_{1-6}$alkyl)($R_a$)]amino, ($R_{200}$—$C_{1-6}$alkyl)$_2$-amino, ($C_{1-6}$alkylcarbonyl)amino, (trihalo-$C_{1-4}$alkylcarbonyl)amino, ($R_{200}$-carbonyl)amino, ureido, ({[($R_{200}$)($R_a$)]aminocarbonyl}($R_a$))amino, hydroxysulfonyl, [(aminosulfonyl)($R_a$)]amino, {[di($C_{1-6}$alkyl)aminosulfonyl]($R_a$)}amino, [(hydroxysulfonyl)($R_a$)]amino or [($R_{200}$-sulfonyl)($R_a$)]amino;

$R_a$ is selected from the group consisting of hydrogen, $C_{1-6}$alkyl, $C_{1-6}$alkylcarbonyl and cyclopropyl;

$R_b$ is selected from the group consisting of hydrogen, $C_{1-6}$alkyl or $R_{201}$, $R_{200}$ is phenyl, thienyl, furanyl, isoxazolyl, pyrazolyl, pyridinyl, pyrimidinyl, pyridazinyl, benzoimidazolyl, [1,2,4]triazolyl, cyclobutyl, piperidinyl, 1H-imidazolyl, 1H-tetrazolyl, 2H-tetrazolyl, 1,3-dihydro-isoindolyl, 3,4-dihydro-1H-isoquinolinyl or 5,6,7,8-tetrahydro-[1,8]naphthyridinyl, each optionally substituted with one or two substituents independently selected from the group consisting of $C_{1-4}$alkyl, hydroxysulfonyl, chloro, fluoro or $R_{202}$, wherein pyridinyl, having a nitrogen atom, is optionally substituted on the nitrogen atom with an oxy substituent and thus forms an oxide;

$R_{201}$ is phenyl, pyrimidinyl, pyridinyl, quinolinyl or cyclobut-3-enyl, wherein pyrimidinyl and cyclobut-3-enyl are each optionally substituted with one or two substituents independently selected from the group consisting of $C_{1-4}$alkyl, trihalo-$C_{1-4}$ alkyl, $C_{1-4}$alkoxy, amino and chloro, wherein cyclobut-3-enyl is optionally substituted with two oxo substituents on available carbon atom ring members, and wherein pyridinyl having a nitrogen atom ring member is optionally substituted on the ring nitrogen atom with an oxy substituent and thus forms an oxide; and, $R_{202}$ is phenyl-$C_{1-6}$alkyl, hydroxysulfonyl or thienyl-sulfonyl.

Embodiment 14 of the present invention includes a compound selected from the group consisting of:

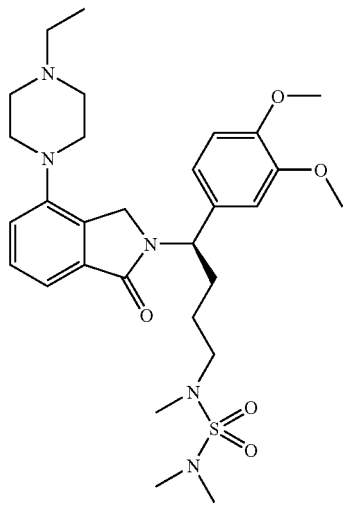

Cpd 1 (Ex 1)

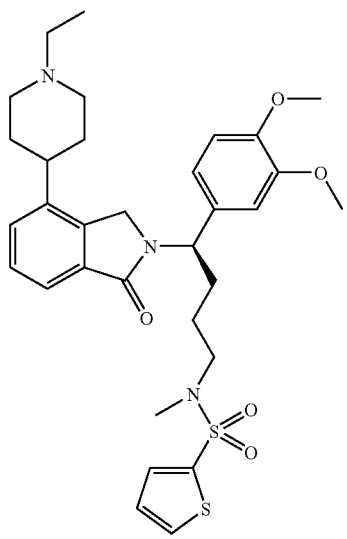

Cpd 2 (Ex 7)

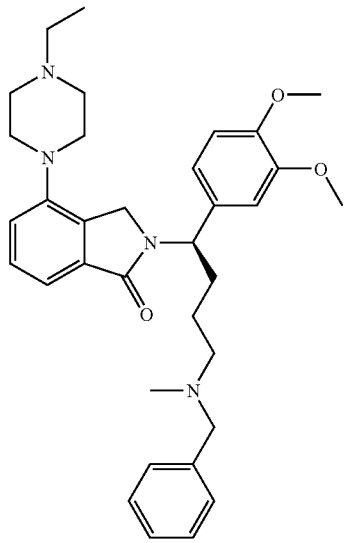

Cpd 3 (Ex 3)

Cpd 4 (Ex 5)
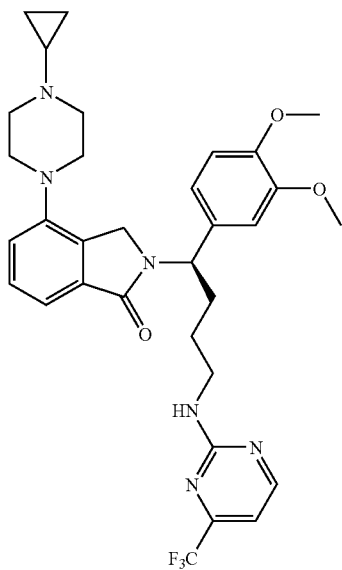
Cpd 5 (Ex 5)
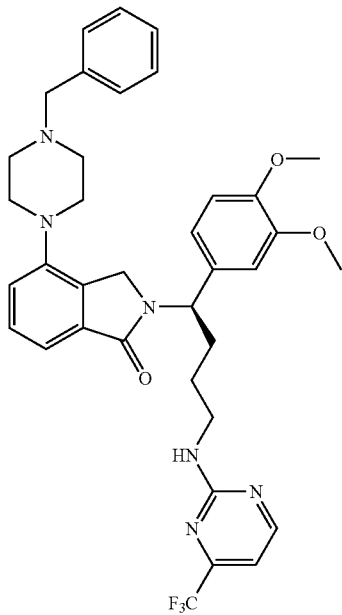
Cpd 6 (Ex 5)
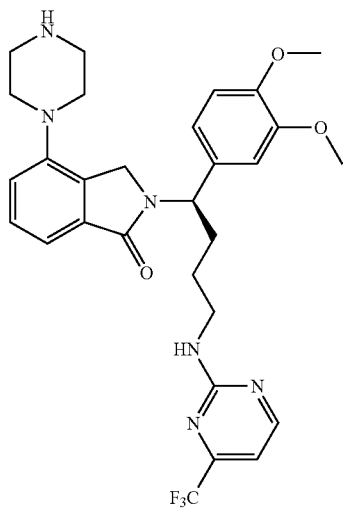
Cpd 7 (Ex 5)
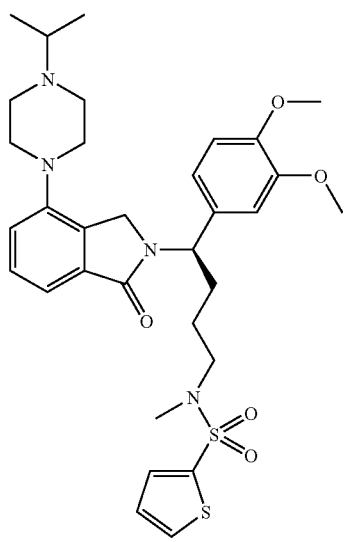
Cpd 8 (Ex 5)

-continued
Cpd 9 (Ex 5)
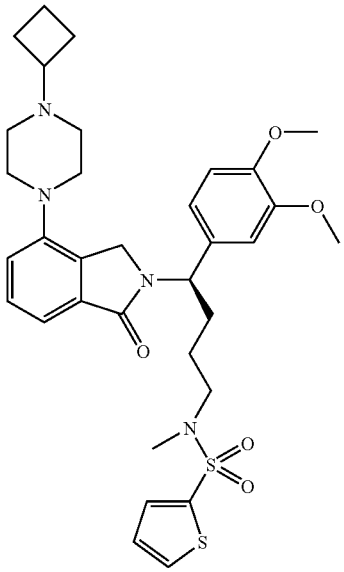
Cpd 10 (Ex 4)
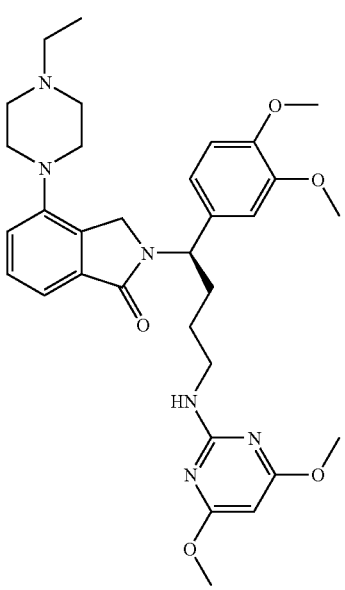
-continued
Cpd 11 (Ex 4)
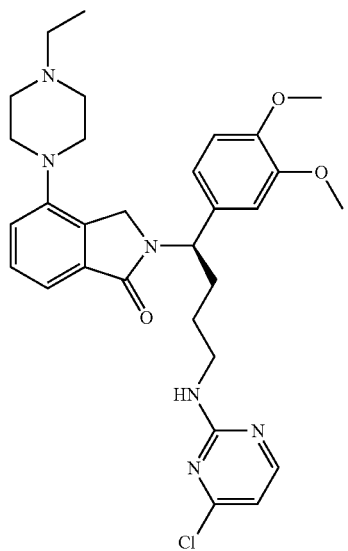
Cpd 12 (Ex 4)
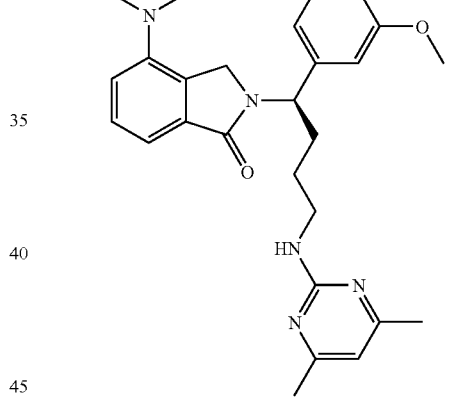
Cpd 13 (Ex 3)
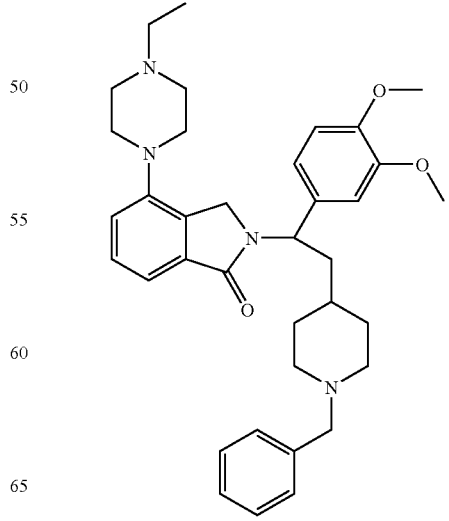

Cpd 14 (Ex 10)
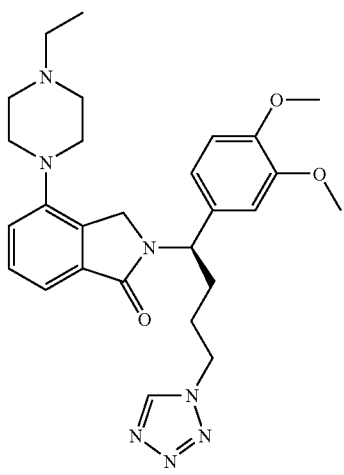
Cpd 17 (Ex 1)
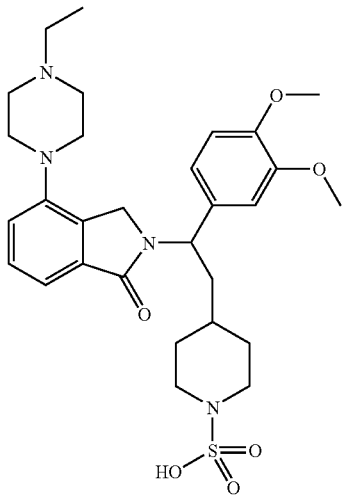
Cpd 15 (Ex 10)
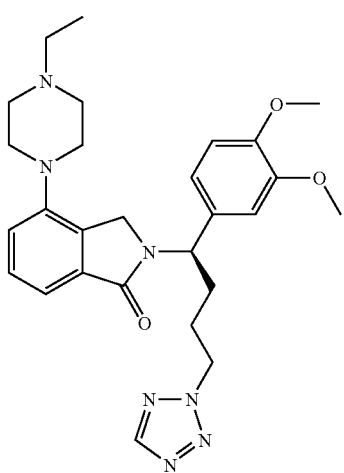
Cpd 18 (Ex 2)
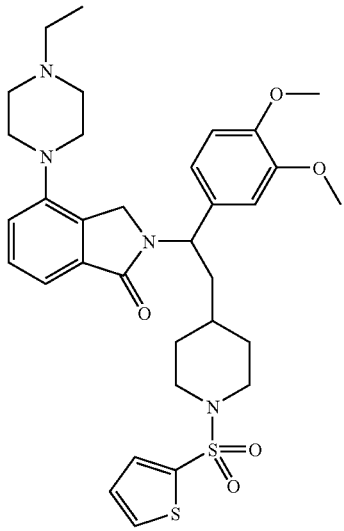
Cpd 16 (Ex 2)
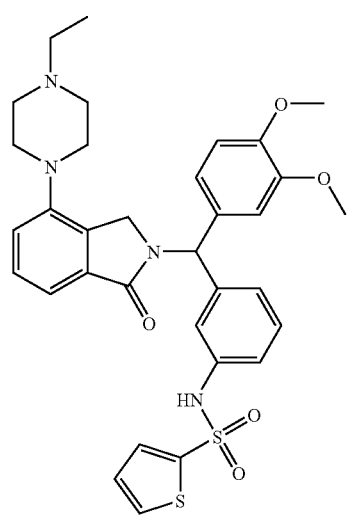
Cpd 19 (Ex 3)
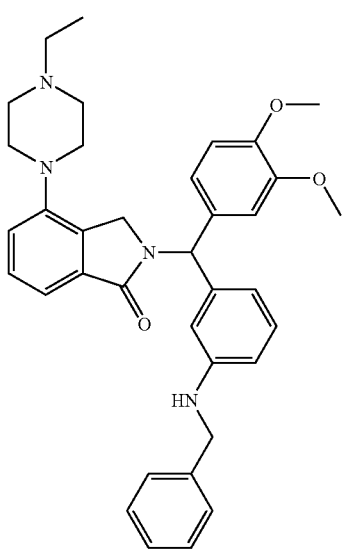

Cpd 20 (Ex 4)
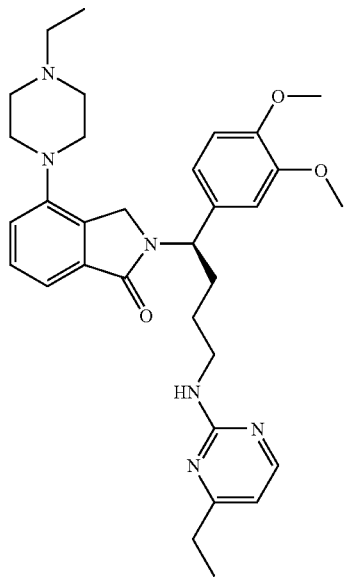
Cpd 21 (Ex 4)
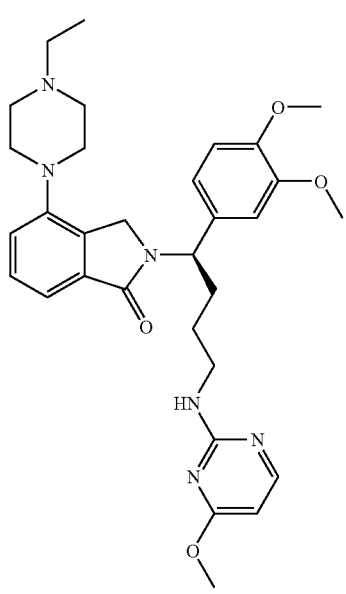
Cpd 22 (Ex 4)
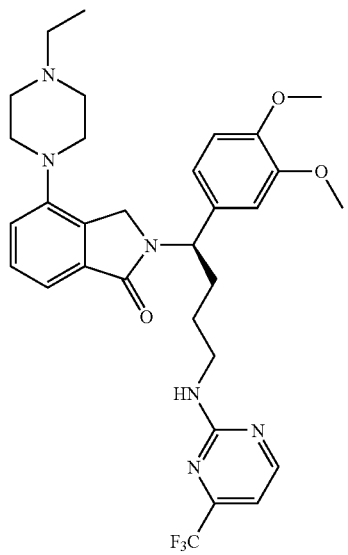
Cpd 23 (Ex 4)
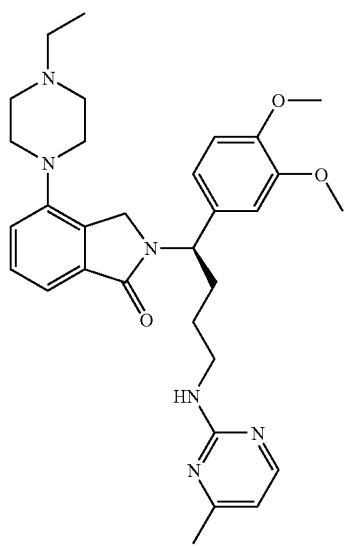
Cpd 24 (Ex 12)
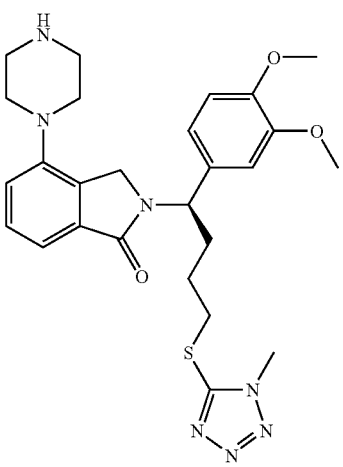

-continued
Cpd 25 (Ex 10)
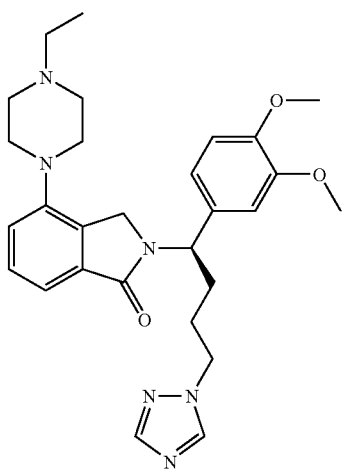
Cpd 26 (Ex 5)
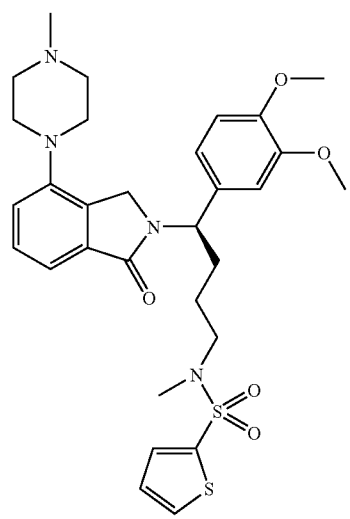
Cpd 27 (Ex 10)
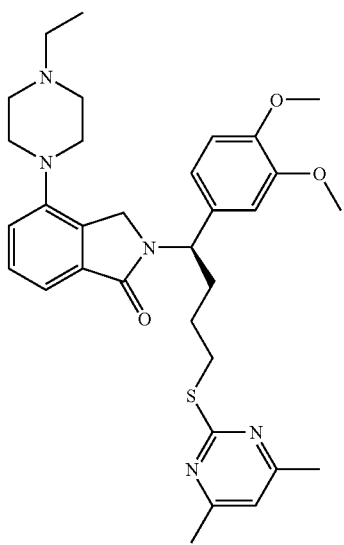
-continued
Cpd 28 (Ex 12)
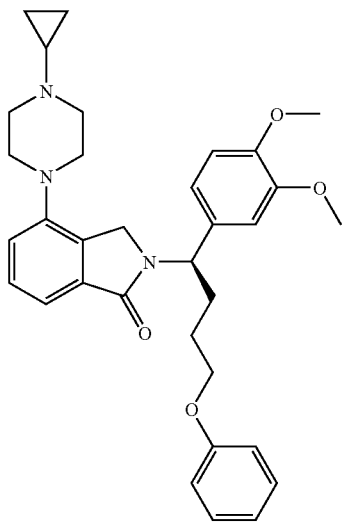
Cpd 29 (Ex 10)
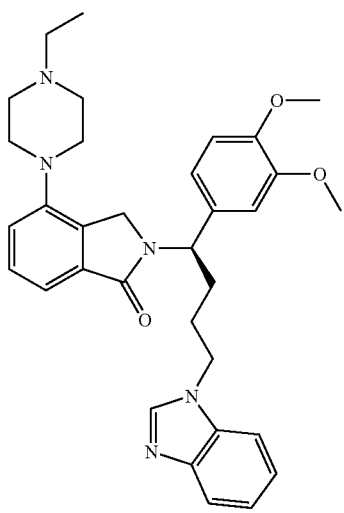
Cpd 30 (Ex 5)
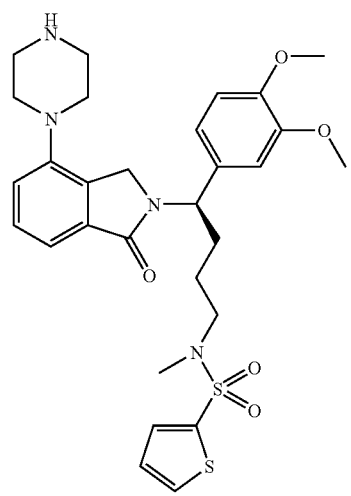

Cpd 31 (Ex 10)
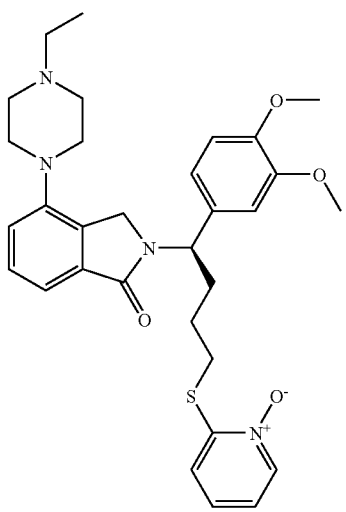
Cpd 34 (Ex 12)
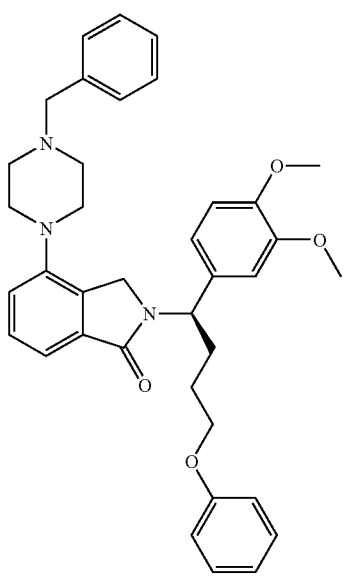
Cpd 32 (Ex 10)
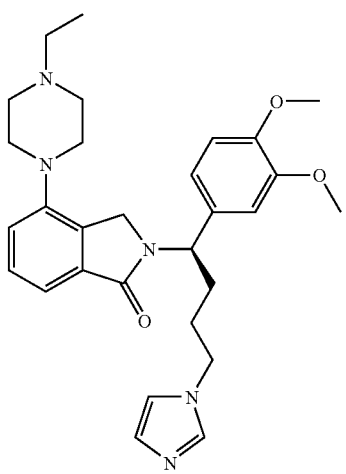
Cpd 35 (Ex 12)
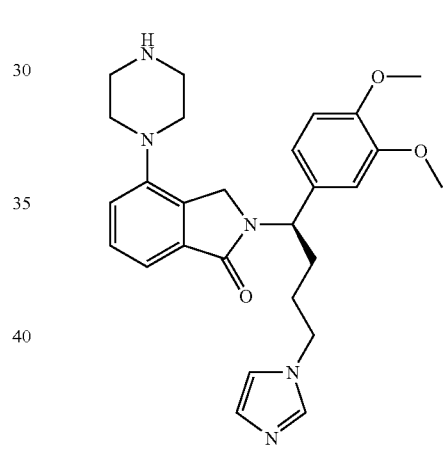
Cpd 33 (Ex 12)
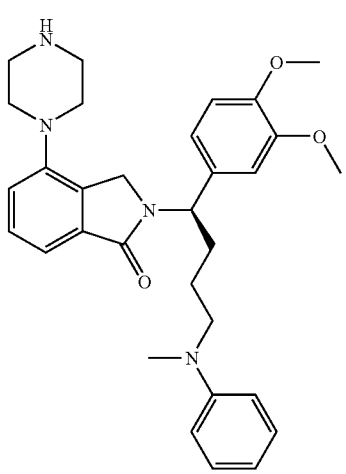
Cpd 36 (Ex 12)
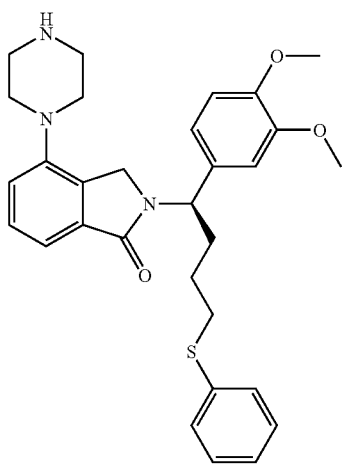

Cpd 37 (Ex 12)
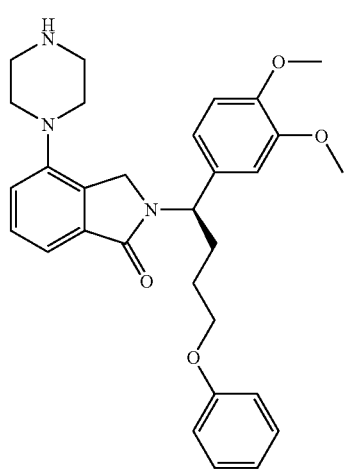
Cpd 38 (Ex 8)
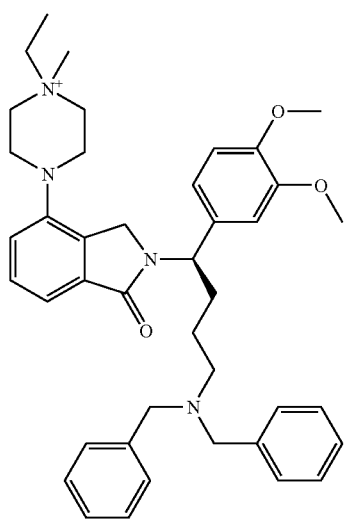
Cpd 39 (Ex 1)
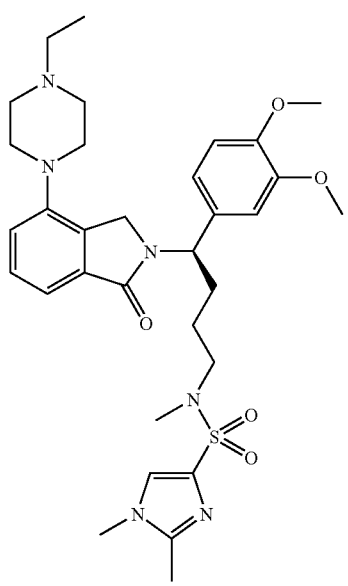
Cpd 40 (Ex 9)
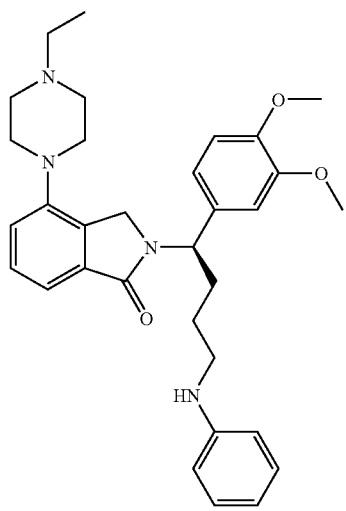
Cpd 41 (Ex 12)
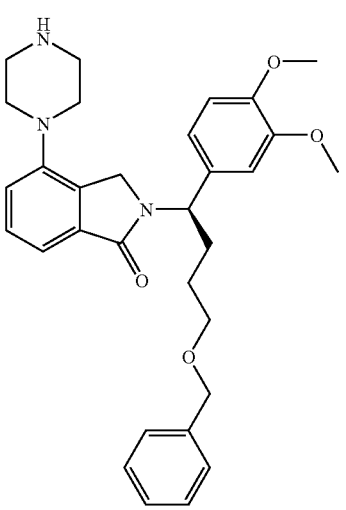
Cpd 42 (Ex 3)
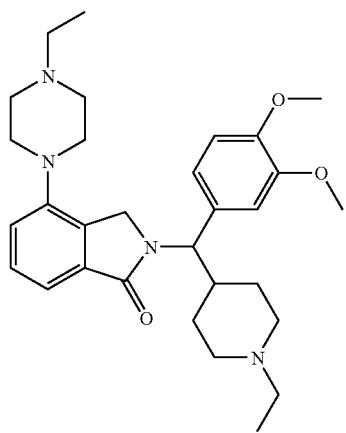

Cpd 43 (Ex 3)
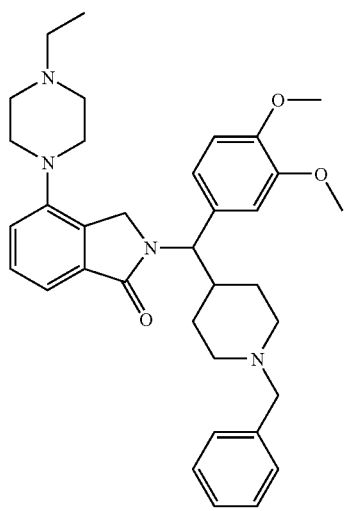
Cpd 46 (Ex 11)
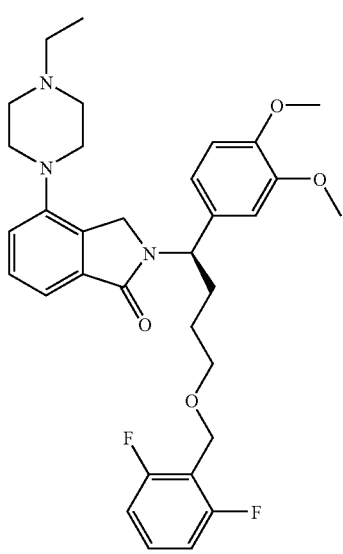
Cpd 44 (Ex 2)
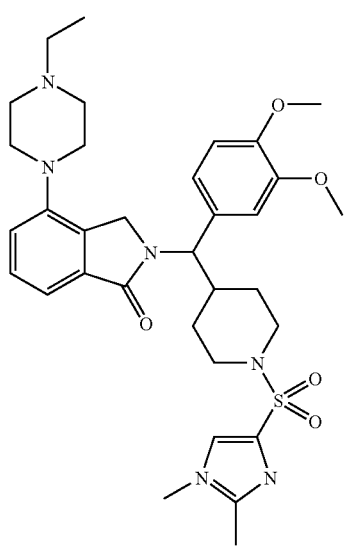
Cpd 47 (Ex 11)
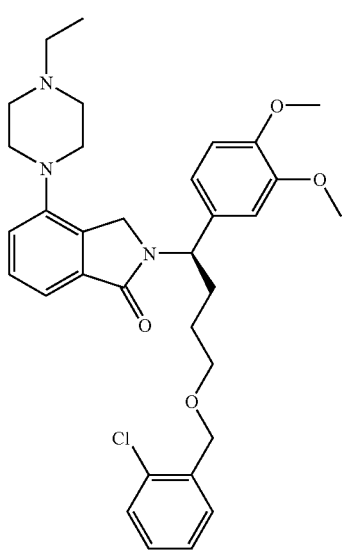
Cpd 45 (Ex 2)
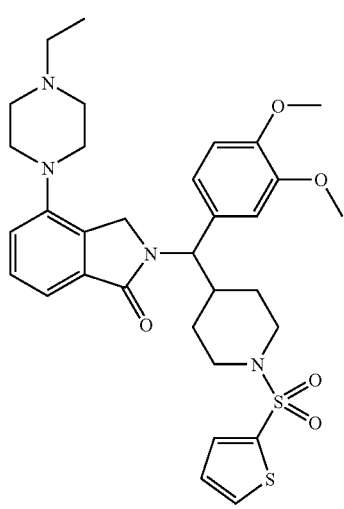
Cpd 48 (Ex 4)
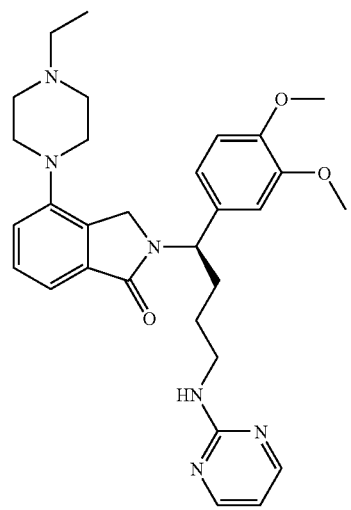

-continued
Cpd 49 (Ex 1)
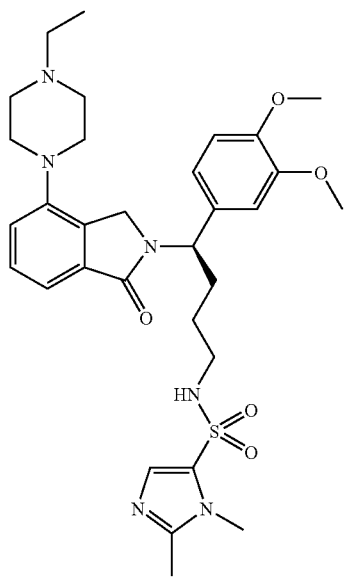
Cpd 50 (Ex 10)
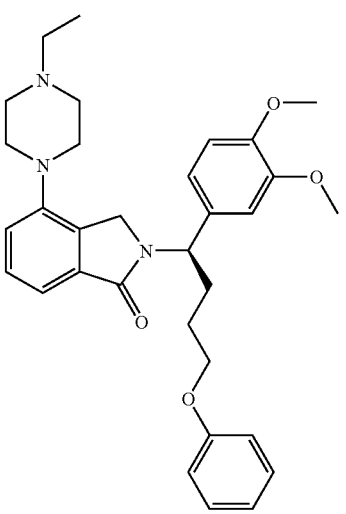
Cpd 51 (Ex 11)
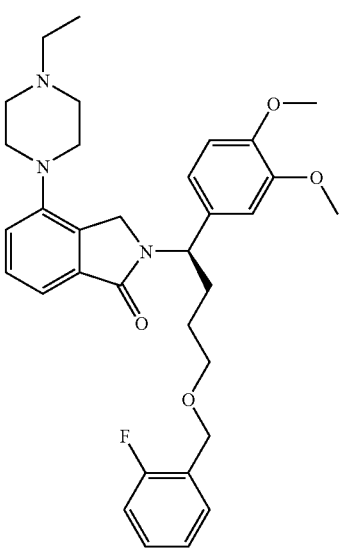
-continued
Cpd 52 (Ex 11)
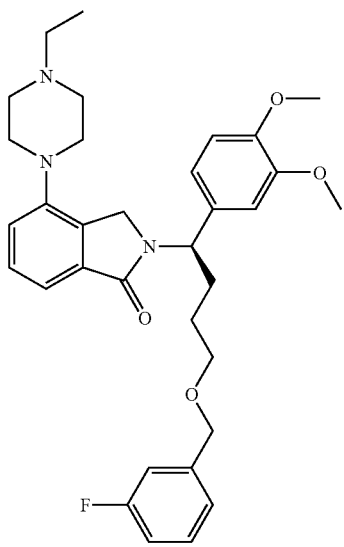
Cpd 53 (Ex 1)
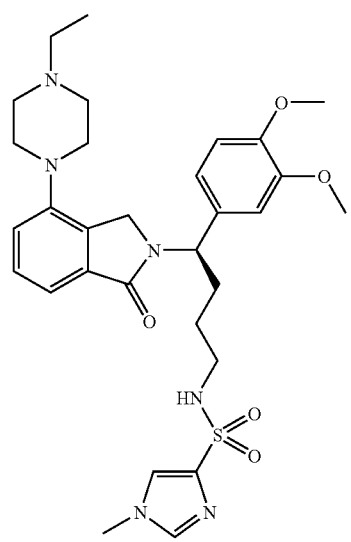
Cpd 54 (Ex 1)
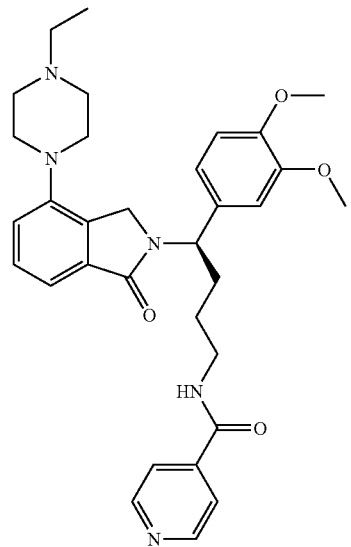

Cpd 55 (Ex 11)
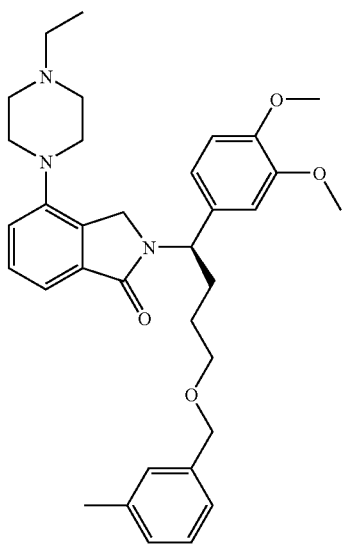
Cpd 56 (Ex 1)
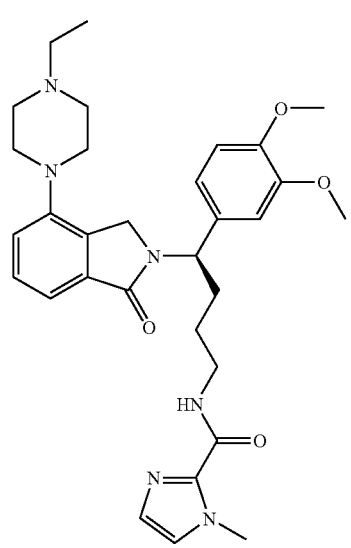
Cpd 57 (Ex 1)
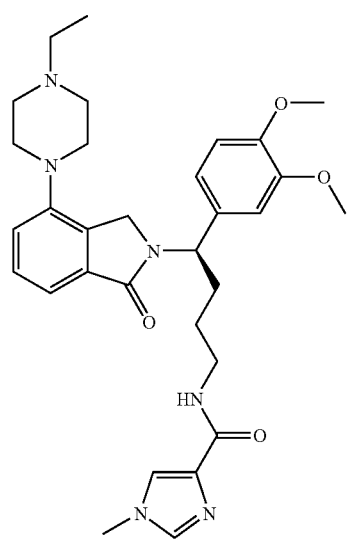
Cpd 58 (Ex 1)
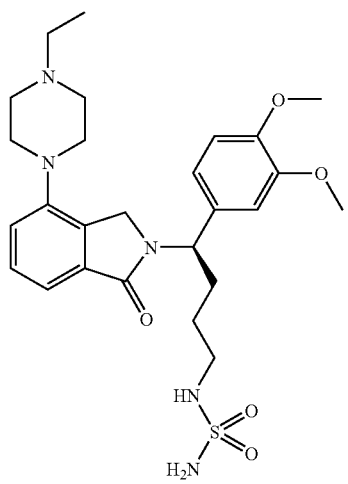
Cpd 59 (Ex 1)
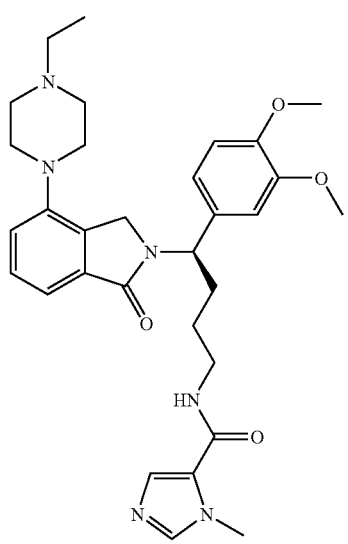
Cpd 60 (Ex 1)
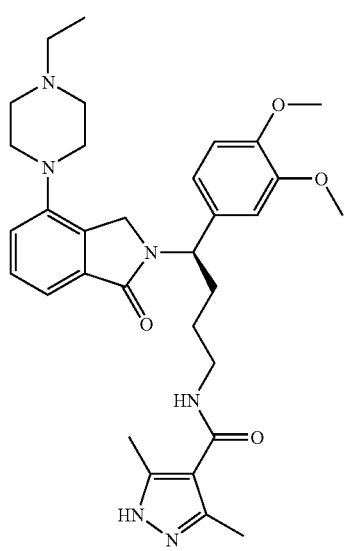

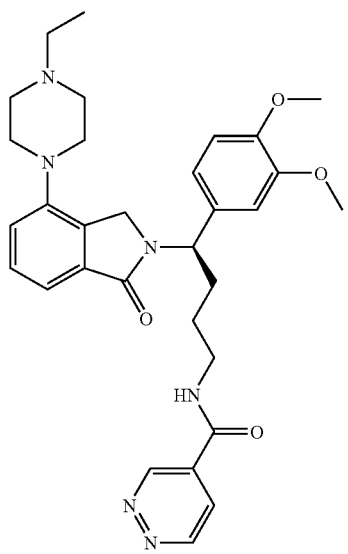
Cpd 61 (Ex 1)
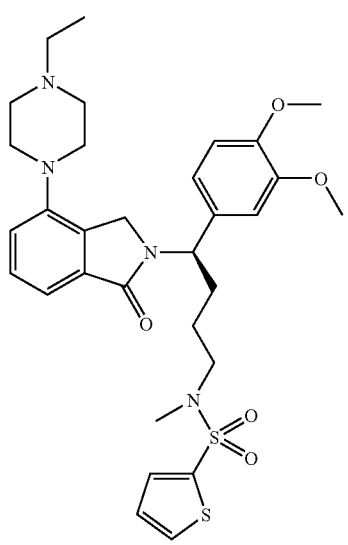
Cpd 62 (Ex 5)
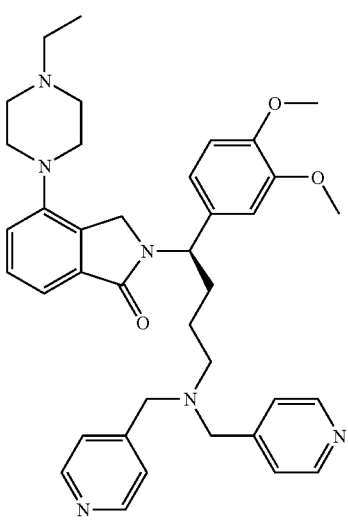
Cpd 63 (Ex 3)
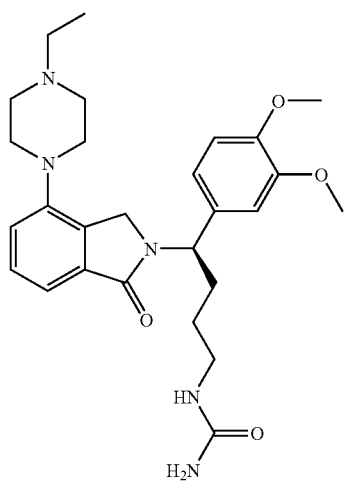
Cpd 64 (Ex 1)
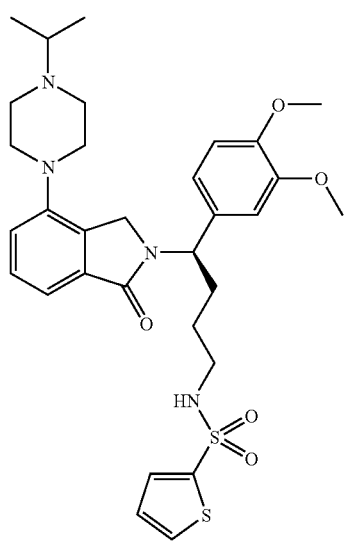
Cpd 65 (Ex 1)
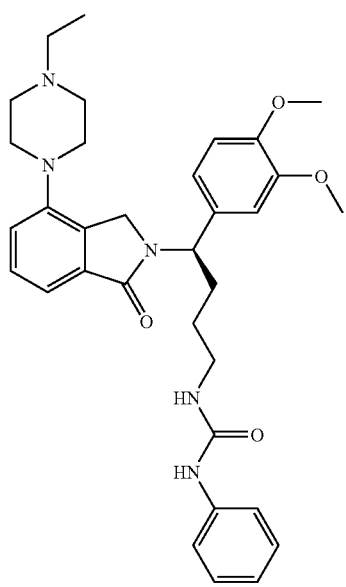
Cpd 66 (Ex 1)

-continued
Cpd 67 (Ex 1)
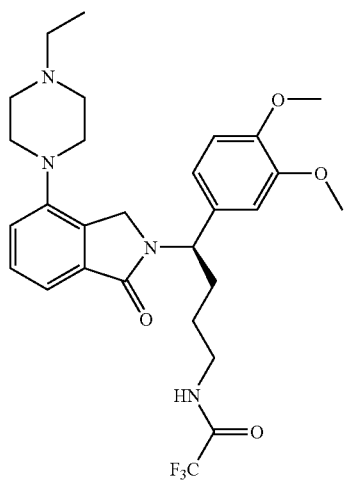
Cpd 70 (Ex 1)
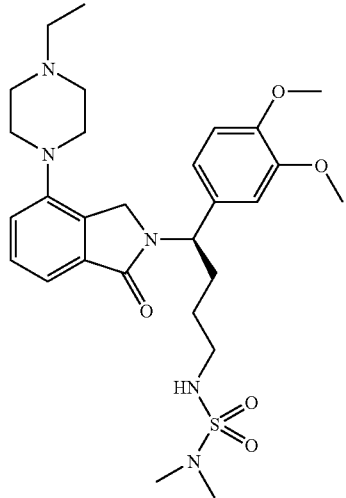
Cpd 68 (Ex 3)
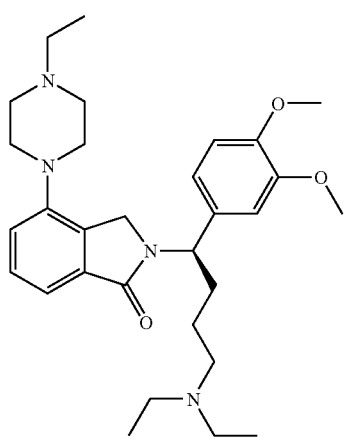
Cpd 71 (Ex 1)
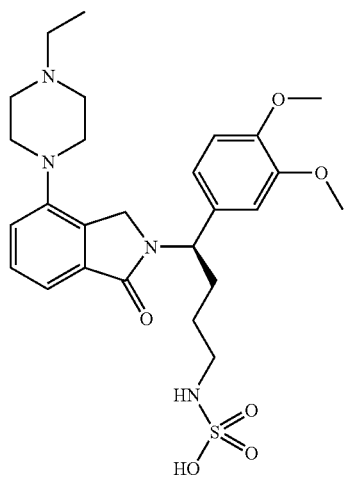
Cpd 69 (Ex 3)
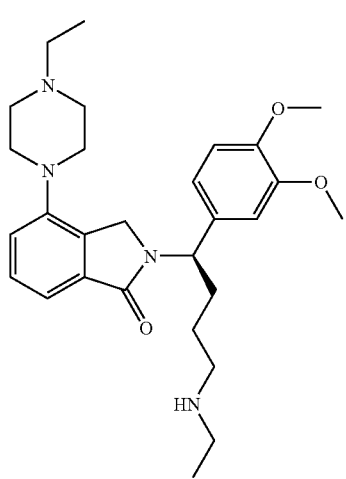
Cpd 72 (Ex 3)
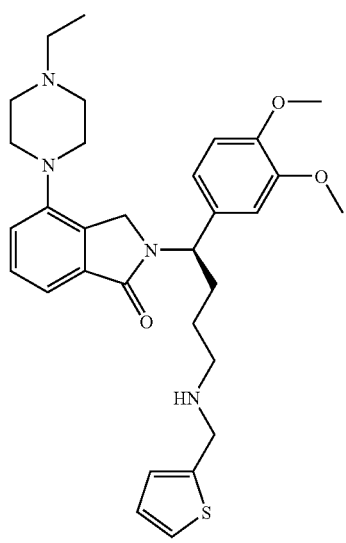

Cpd 73 (Ex 3)
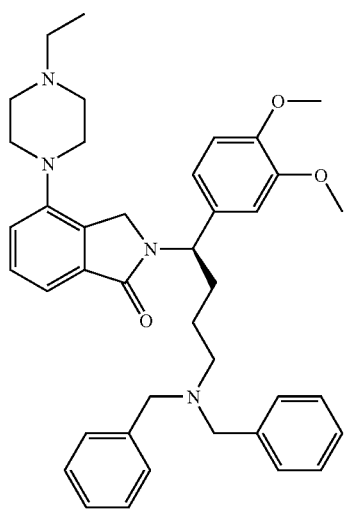
Cpd 76 (Ex 1)
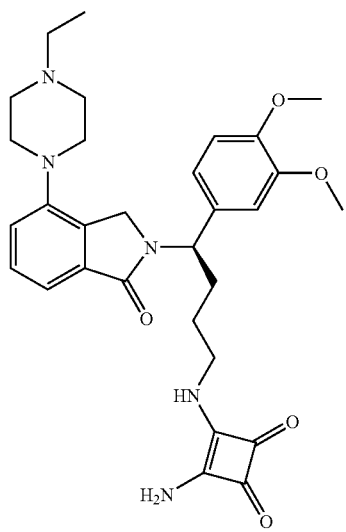
Cpd 74 (Ex 10)
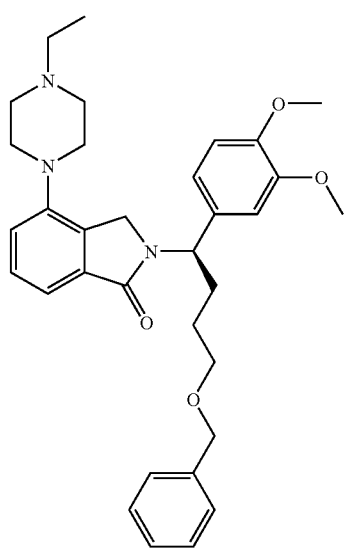
Cpd 77 (Ex 3)
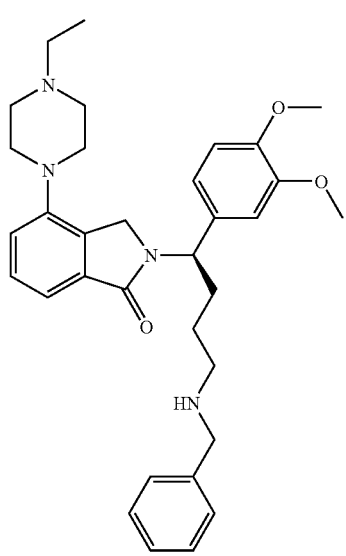
Cpd 75 (Ex 3)
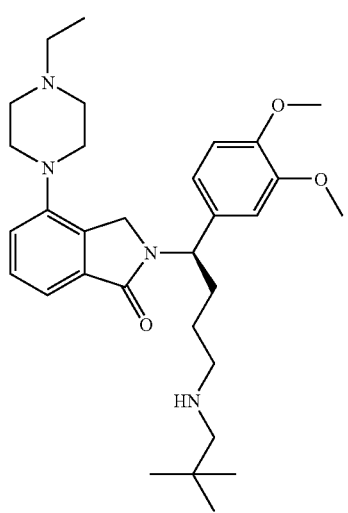
Cpd 78 (Ex 1)
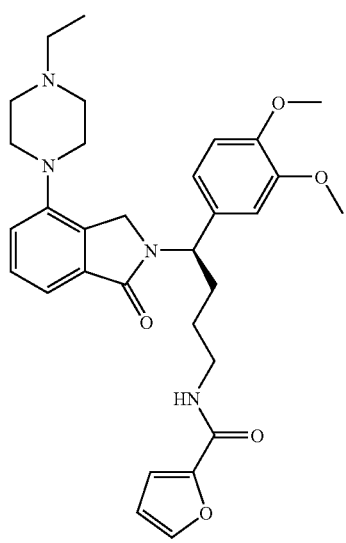

Cpd 79 (Ex 1)
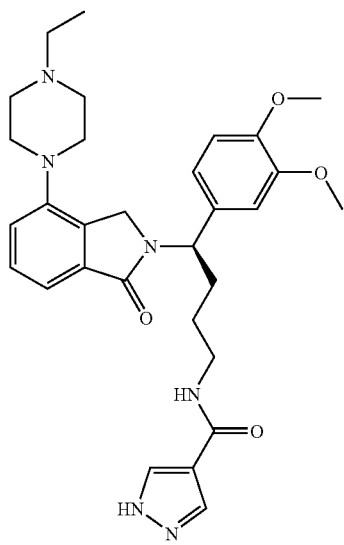
Cpd 80 (Ex 1)
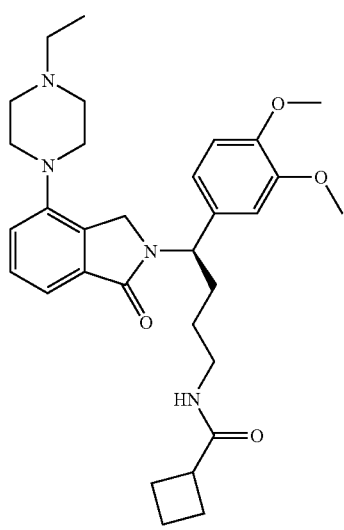
Cpd 81 (Ex 1)
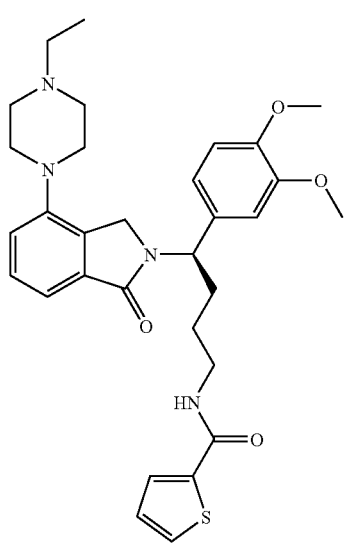
Cpd 82 (Ex 1)
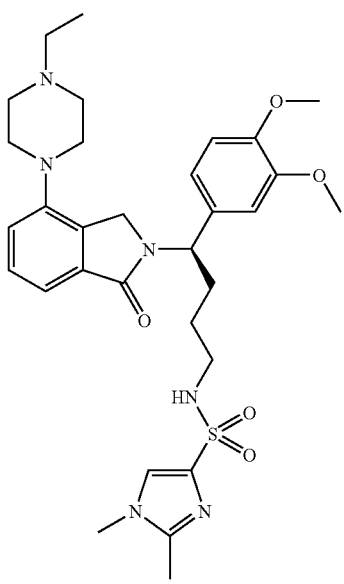
Cpd 83 (Ex 1)
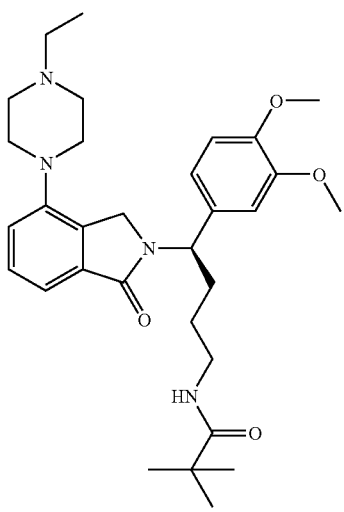
Cpd 84 (Ex 1)
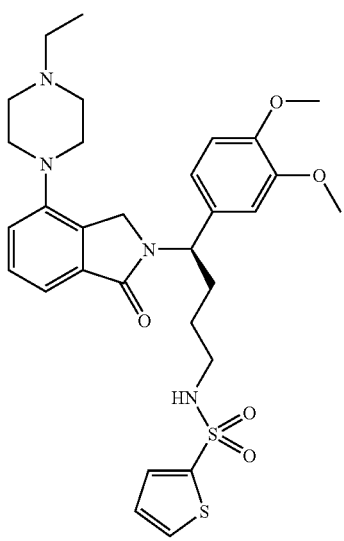

Cpd 85 (Ex 6)
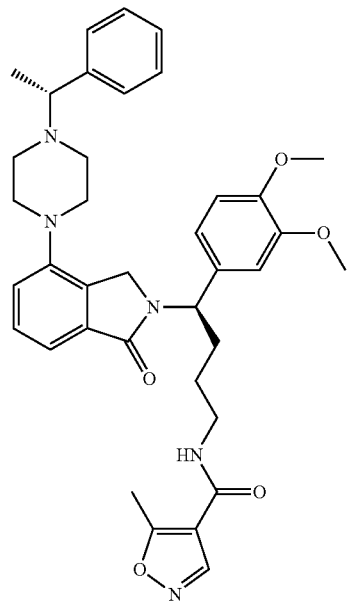
Cpd 86 (Ex 1)
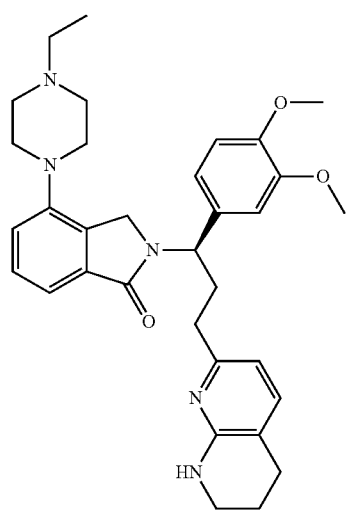
Cpd 87 (Ex 1)
Cpd 88 (Ex 13)
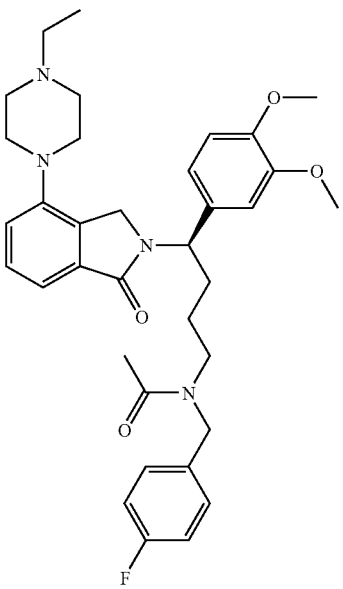
Cpd 89 (Ex 4)
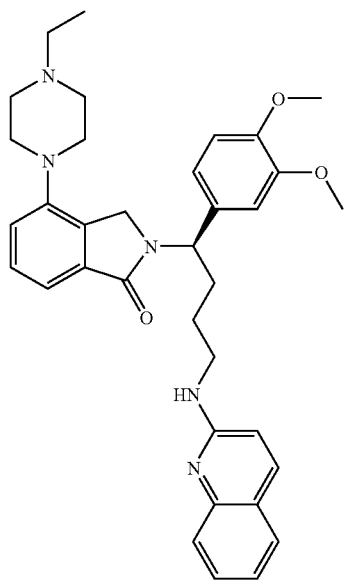

-continued
Cpd 90 (Ex 10)
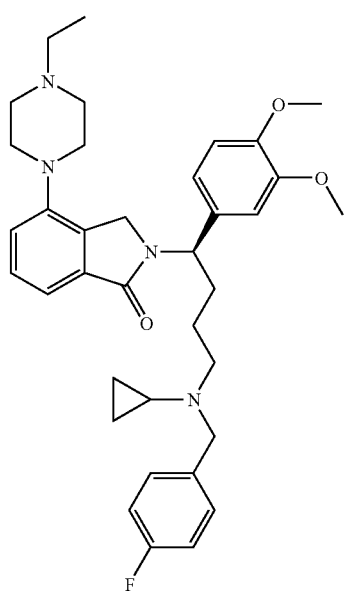
Cpd 91 (Ex 10)
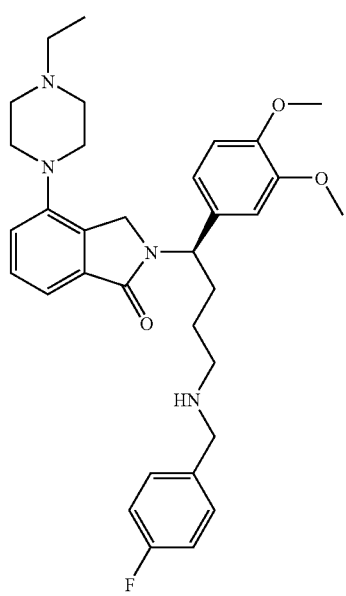
Cpd 92 (Ex 14)
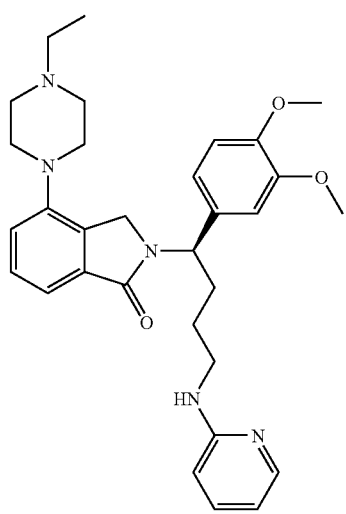
-continued
Cpd 93 (Ex 4)
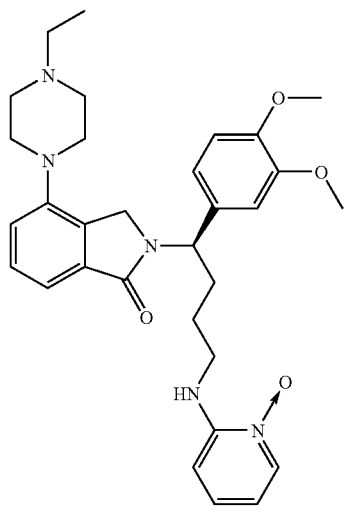
Cpd 94 (Ex 3)
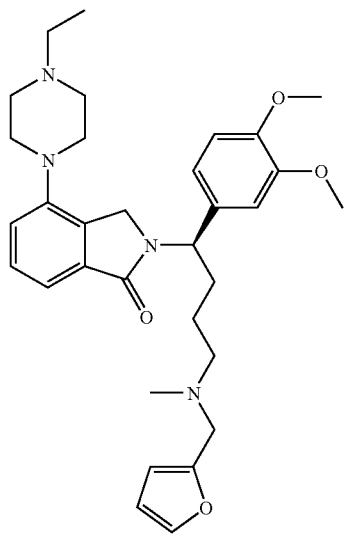
Cpd 95 (Ex 3)
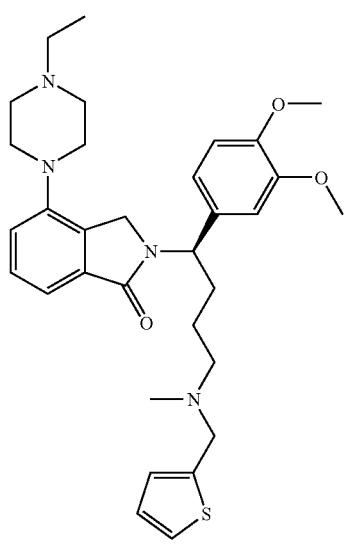

Cpd 96 (Ex 10)
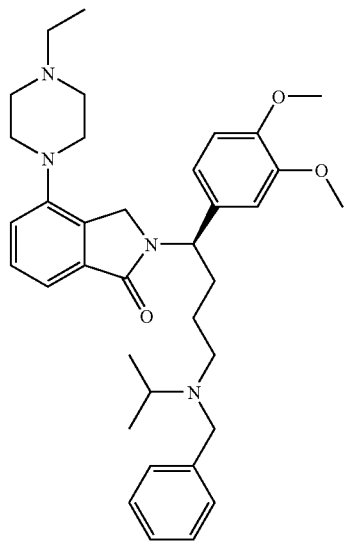
Cpd 97 (Ex 10)
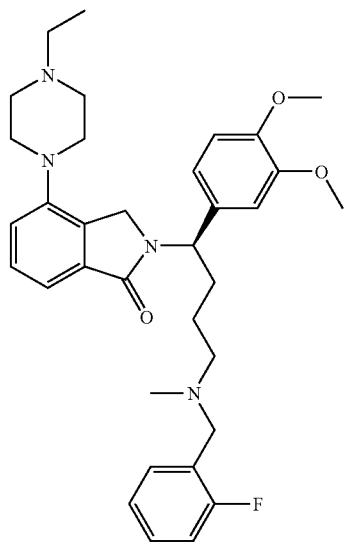
Cpd 98 (Ex 10)
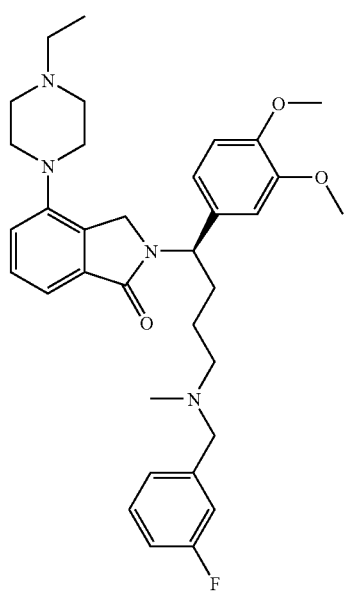
Cpd 99 (Ex 10)
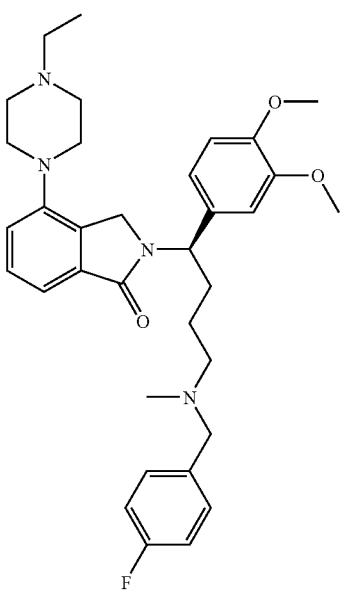
Cpd 100 (Ex 10)
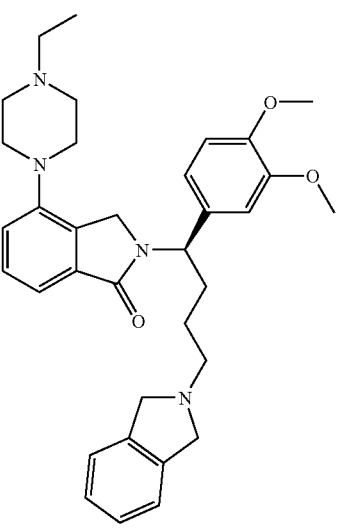
Cpd 101 (Ex 10)
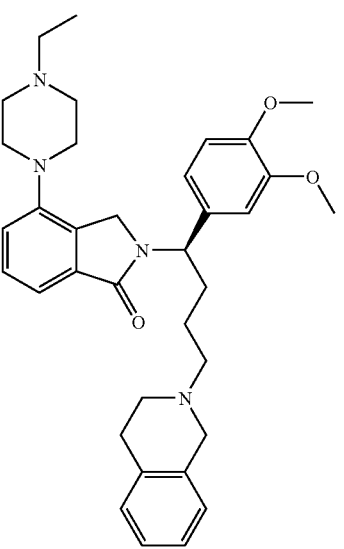

Cpd 102 (Ex 10)

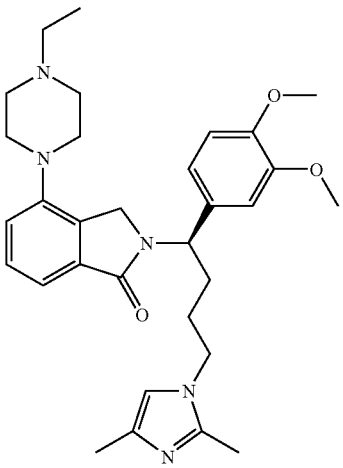

Cpd 103 (Ex 10)

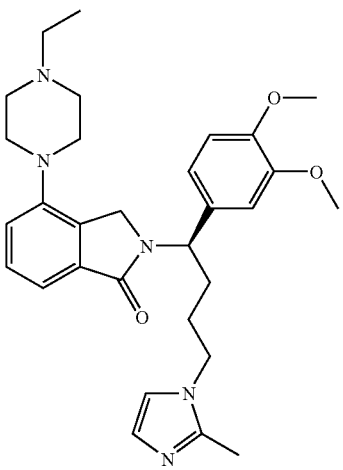

Cpd 104 (Ex 10)

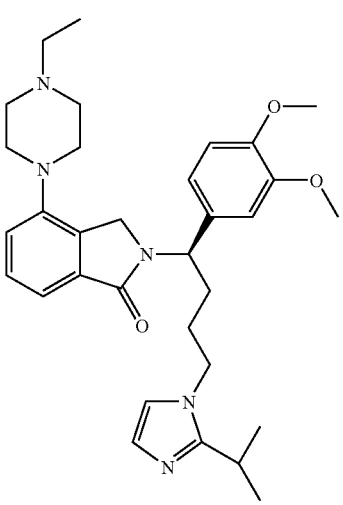

Embodiment 15 of the present invention is directed to compounds of Formula (I) or a form thereof as described herein selected from the group consisting of:

| Cpd | Name |
|---|---|
| 1 | dimethylaminosulfonic acid {(4R)-4-(3,4-dimethoxy-phenyl)-4-[4-(4-ethyl-piperazin-1-yl)-1-oxo-1,3-dihydro-isoindol-2-yl]-butyl}-methyl-amide, |
| 2 | thiophene-2-sulfonic acid {(4R)-4-(3,4-dimethoxy-phenyl)-4-[4-(1-ethyl-piperidin-4-yl)-1-oxo-1,3-dihydro-isoindol-2-yl]-butyl}-methyl-amide, |
| 3 | 2-[(1R)-4-(benzyl-methyl-amino)-1-(3,4-dimethoxy-phenyl)-butyl]-4-(4-ethyl-piperazin-1-yl)-2,3-dihydro-isoindol-1-one, |
| 4 | 4-(4-cyclopropyl-piperazin-1-yl)-2-[(1R)-1-(3,4-dimethoxy-phenyl)-4-(4-trifluoromethyl-pyrimidin-2-ylamino)-butyl]-2,3-dihydro-isoindol-1-one, |
| 5 | 4-(4-benzyl-piperazin-1-yl)-2-[(1R)-1-(3,4-dimethoxy-phenyl)-4-(4-trifluoromethyl-pyrimidin-2-ylamino)-butyl]-2,3-dihydro-isoindol-1-one, |
| 6 | 2-[(1R)-1-(3,4-dimethoxy-phenyl)-4-(4-trifluoromethyl-pyrimidin-2-ylamino)-butyl]-4-piperazin-1-yl-2,3-dihydro-isoindol-1-one, |
| 7 | thiophene-2-sulfonic acid [(4R)-4-[4-(4-cyclopropyl-piperazin-1-yl)-1-oxo-1,3-dihydro-isoindol-2-yl]-4-(3,4-dimethoxy-phenyl)-butyl]-methyl-amide, |
| 8 | thiophene-2-sulfonic acid {(4R)-4-(3,4-dimethoxy-phenyl)-4-[4-(4-isopropyl-piperazin-1-yl)-1-oxo-1,3-dihydro-isoindol-2-yl]-butyl}-methyl-amide, |
| 9 | thiophene-2-sulfonic acid [(4R)-4-[4-(4-cyclobutyl-piperazin-1-yl)-1-oxo-1,3-dihydro-isoindol-2-yl]-4-(3,4-dimethoxy-phenyl)-butyl]-methyl-amide, |
| 10 | 2-[(1R)-1-(3,4-dimethoxy-phenyl)-4-(4,6-dimethoxy-pyrimidin-2-ylamino)-butyl]-4-(4-ethyl-piperazin-1-yl)-2,3-dihydro-isoindol-1-one, |
| 11 | 2-[(1R)-4-(4-chloro-pyrimidin-2-ylamino)-1-(3,4-dimethoxy-phenyl)-butyl]-4-(4-ethyl-piperazin-1-yl)-2,3-dihydro-isoindol-1-one, |
| 12 | 2-[(1R)-1-(3,4-dimethoxy-phenyl)-4-(4,6-dimethyl-pyrimidin-2-ylamino)-butyl]-4-(4-ethyl-piperazin-1-yl)-2,3-dihydro-isoindol-1-one, |
| 13 | 2-[2-(1-benzyl-piperidin-4-yl)-1-(3,4-dimethoxy-phenyl)-ethyl]-4-(4-ethyl-piperazin-1-yl)-2,3-dihydro-isoindol-1-one, |
| 14 | 2-[(1R)-1-(3,4-dimethoxy-phenyl)-4-tetrazol-1-yl-butyl]-4-(4-ethyl-piperazin-1-yl)-2,3-dihydro-isoindol-1-one, |
| 15 | 2-[(1R)-1-(3,4-dimethoxy-phenyl)-4-tetrazol-2-yl-butyl]-4-(4-ethyl-piperazin-1-yl)-2,3-dihydro-isoindol-1-one, |
| 16 | thiophene-2-sulfonic acid (3-{(3,4-dimethoxy-phenyl)-[4-(4-ethyl-piperazin-1-yl)-1-oxo-1,3-dihydro-isoindol-2-yl]-methyl}-phenyl)-amide, |
| 17 | 4-{2-(3,4-dimethoxy-phenyl)-2-[4-(4-ethyl-piperazin-1-yl)-1-oxo-1,3-dihydro-isoindol-2-yl]-ethyl}-piperidine-1-sulfonic acid, |
| 18 | 2-{1-(3,4-dimethoxy-phenyl)-2-[1-(thiophene-2-sulfonyl)-piperidin-4-yl]-ethyl}-4-(4-ethyl-piperazin-1-yl)-2,3-dihydro-isoindol-1-one, |
| 19 | 2-[(3-benzylamino-phenyl)-(3,4-dimethoxy-phenyl)-methyl]-4-(4-ethyl-piperazin-1-yl)-2,3-dihydro-isoindol-1-one, |
| 20 | 2-[(1R)-1-(3,4-dimethoxy-phenyl)-4-(4-ethyl-pyrimidin-2-ylamino)-butyl]-4-(4-ethyl-piperazin-1-yl)-2,3-dihydro-isoindol-1-one, |
| 21 | 2-[(1R)-1-(3,4-dimethoxy-phenyl)-4-(4-methoxy-pyrimidin-2-ylamino)-butyl]-4-(4-ethyl-piperazin-1-yl)-2,3-dihydro-isoindol-1-one, |
| 22 | 2-[(1R)-1-(3,4-dimethoxy-phenyl)-4-(4-trifluoromethyl-pyrimidin-2-ylamino)-butyl]-4-(4-ethyl-piperazin-1-yl)-2,3-dihydro-isoindol-1-one, |
| 23 | 2-[(1R)-1-(3,4-dimethoxy-phenyl)-4-(4-methyl-pyrimidin-2-ylamino)-butyl]-4-(4-ethyl-piperazin-1-yl)-2,3-dihydro-isoindol-1-one, |
| 24 | 2-[(1R)-1-(3,4-dimethoxy-phenyl)-4-(1-methyl-1H-tetrazol-5-ylsulfanyl)-butyl]-4-piperazin-1-yl-2,3-dihydro-isoindol-1-one, |
| 25 | 2-[(1R)-1-(3,4-dimethoxy-phenyl)-4-[1,2,4]triazol-1-yl-butyl]-4-(4-ethyl-piperazin-1-yl)-2,3-dihydro-isoindol-1-one, |
| 26 | thiophene-2-sulfonic acid {(4R)-4-(3,4-dimethoxy-phenyl)-4-[4-(4-methyl-piperazin-1-yl)-1-oxo-1,3-dihydro-isoindol-2-yl]-butyl}-methyl-amide, |
| 27 | 2-[(1R)-1-(3,4-dimethoxy-phenyl)-4-(4,6-dimethyl-pyrimidin-2-ylsulfanyl)-butyl]-4-(4-ethyl-piperazin-1-yl)-2,3-dihydro-isoindol-1-one, |
| 28 | 4-(4-cyclopropyl-piperazin-1-yl)-2-[(1R)-1-(3,4-dimethoxy-phenyl)-4-phenoxy-butyl]-2,3-dihydro-isoindol-1-one, |
| 29 | 2-[(1R)-4-benzoimidazol-1-yl-1-(3,4-dimethoxy-phenyl)-butyl]-4-(4-ethyl-piperazin-1-yl)-2,3-dihydro-isoindol-1-one, |
| 30 | thiophene-2-sulfonic acid [(4R)-4-(3,4-dimethoxy-phenyl)-4-(1-oxo-4-piperazin-1-yl-1,3-dihydro-isoindol-2-yl)-butyl]-methyl-amide, |
| 31 | {(4R)-4-(3,4-dimethoxy-phenyl)-4-[4-(4-ethyl-piperazin-1-yl)-1-oxo-1,3-dihydro-isoindol-2-yl]-butylsulfanyl}-pyridine 1-oxide, |

| Cpd | Name |
|---|---|
| 32 | 2-[(1R)-1-(3,4-dimethoxy-phenyl)-4-imidazol-1-yl-butyl]-4-(4-ethyl-piperazin-1-yl)-2,3-dihydro-isoindol-1-one, |
| 33 | 2-[(1R)-1-(3,4-dimethoxy-phenyl)-4-(methyl-phenyl-amino)-butyl]-4-piperazin-1-yl-2,3-dihydro-isoindol-1-one, |
| 34 | 4-(4-benzyl-piperazin-1-yl)-2-[(1R)-1-(3,4-dimethoxy-phenyl)-4-phenoxy-butyl]-2,3-dihydro-isoindol-1-one, |
| 35 | 2-[(1R)-1-(3,4-dimethoxy-phenyl)-4-imidazol-1-yl-butyl]-4-piperazin-1-yl-2,3-dihydro-isoindol-1-one, |
| 36 | 2-[(1R)-1-(3,4-dimethoxy-phenyl)-4-phenylsulfanyl-butyl]-4-piperazin-1-yl-2,3-dihydro-isoindol-1-one, |
| 37 | 2-[(1R)-1-(3,4-dimethoxy-phenyl)-4-phenoxy-butyl]-4-piperazin-1-yl-2,3-dihydro-isoindol-1-one, |
| 38 | 4-{2-[(1R)-4-dibenzylamino-1-(3,4-dimethoxy-phenyl)-butyl]-1-oxo-2,3-dihydro-1H-isoindol-4-yl}-1-ethyl-1-methyl-piperazin-1-ium, |
| 39 | 1,2-dimethyl-1H-imidazole-4-sulfonic acid {(4R)-4-(3,4-dimethoxy-phenyl)-4-[4-(4-ethyl-piperazin-1-yl)-1-oxo-1,3-dihydro-isoindol-2-yl]-butyl}-methyl-amide, |
| 40 | 2-[(1R)-1-(3,4-dimethoxy-phenyl)-4-phenylamino-butyl]-4-(4-ethyl-piperazin-1-yl)-2,3-dihydro-isoindol-1-one, |
| 41 | 2-[(1R)-4-benzyloxy-1-(3,4-dimethoxy-phenyl)-butyl]-4-piperazin-1-yl-2,3-dihydro-isoindol-1-one, |
| 42 | 2-[(3,4-dimethoxy-phenyl)-(1-ethyl-piperidin-4-yl)-methyl]-4-(4-ethyl-piperazin-1-yl)-2,3-dihydro-isoindol-1-one, |
| 43 | 2-[(1-benzyl-piperidin-4-yl)-(3,4-dimethoxy-phenyl)-methyl]-4-(4-ethyl-piperazin-1-yl)-2,3-dihydro-isoindol-1-one, |
| 44 | 2-{(3,4-dimethoxy-phenyl)-[1-(1,2-dimethyl-1H-imidazole-4-sulfonyl)-piperidin-4-yl]-methyl}-4-(4-ethyl-piperazin-1-yl)-2,3-dihydro-isoindol-1-one, |
| 45 | 2-{(3,4-dimethoxy-phenyl)-[1-(thiophene-2-sulfonyl)-piperidin-4-yl]-methyl}-4-(4-ethyl-piperazin-1-yl)-2,3-dihydro-isoindol-1-one, |
| 46 | 2-[(1R)-4-(2,6-difluoro-benzyloxy)-1-(3,4-dimethoxy-phenyl)-butyl]-4-(4-ethyl-piperazin-1-yl)-2,3-dihydro-isoindol-1-one, |
| 47 | 2-[(1R)-4-(2-chloro-benzyloxy)-1-(3,4-dimethoxy-phenyl)-butyl]-4-(4-ethyl-piperazin-1-yl)-2,3-dihydro-isoindol-1-one, |
| 48 | 2-[(1R)-1-(3,4-dimethoxy-phenyl)-4-(pyrimidin-2-ylamino)-butyl]-4-(4-ethyl-piperazin-1-yl)-2,3-dihydro-isoindol-1-one, |
| 49 | 2,3-dimethyl-3H-imidazole-4-sulfonic acid {(4R)-4-(3,4-dimethoxy-phenyl)-4-[4-(4-ethyl-piperazin-1-yl)-1-oxo-1,3-dihydro-isoindol-2-yl]-butyl}-amide, |
| 50 | 2-[(1R)-1-(3,4-dimethoxy-phenyl)-4-phenoxy-butyl]-4-(4-ethyl-piperazin-1-yl)-2,3-dihydro-isoindol-1-one, |
| 51 | 2-[(1R)-1-(3,4-dimethoxy-phenyl)-4-(2-fluoro-benzyloxy)-butyl]-4-(4-ethyl-piperazin-1-yl)-2,3-dihydro-isoindol-1-one, |
| 52 | 2-[(1R)-1-(3,4-dimethoxy-phenyl)-4-(3-fluoro-benzyloxy)-butyl]-4-(4-ethyl-piperazin-1-yl)-2,3-dihydro-isoindol-1-one, |
| 53 | 1-methyl-1H-imidazole-4-sulfonic acid {(4R)-4-(3,4-dimethoxy-phenyl)-4-[4-(4-ethyl-piperazin-1-yl)-1-oxo-1,3-dihydro-isoindol-2-yl]-butyl}-amide, |
| 54 | N-{(4R)-4-(3,4-dimethoxy-phenyl)-4-[4-(4-ethyl-piperazin-1-yl)-1-oxo-1,3-dihydro-isoindol-2-yl]-butyl}-isonicotinamide, |
| 55 | 2-[(1R)-1-(3,4-dimethoxy-phenyl)-4-(3-methyl-benzyloxy)-butyl]-4-(4-ethyl-piperazin-1-yl)-2,3-dihydro-isoindol-1-one, |
| 56 | 1-methyl-1H-imidazole-2-carboxylic acid {(4R)-4-(3,4-dimethoxy-phenyl)-4-[4-(4-ethyl-piperazin-1-yl)-1-oxo-1,3-dihydro-isoindol-2-yl]-butyl}-amide, |
| 57 | 1-methyl-1H-imidazole-4-carboxylic acid {(4R)-4-(3,4-dimethoxy-phenyl)-4-[4-(4-ethyl-piperazin-1-yl)-1-oxo-1,3-dihydro-isoindol-2-yl]-butyl}-amide, |
| 58 | aminosulfonic acid {(4R)-4-(3,4-dimethoxy-phenyl)-4-[4-(4-ethyl-piperazin-1-yl)-1-oxo-1,3-dihydro-isoindol-2-yl]-butyl}-amide, |
| 59 | 3-methyl-3H-imidazole-4-carboxylic acid {(4R)-4-(3,4-dimethoxy-phenyl)-4-[4-(4-ethyl-piperazin-1-yl)-1-oxo-1,3-dihydro-isoindol-2-yl]-butyl}-amide, |
| 60 | 3,5-dimethyl-1H-pyrazole-4-carboxylic acid {(4R)-4-(3,4-dimethoxy-phenyl)-4-[4-(4-ethyl-piperazin-1-yl)-1-oxo-1,3-dihydro-isoindol-2-yl]-butyl}-amide, |
| 61 | pyridazine-4-carboxylic acid {(4R)-4-(3,4-dimethoxy-phenyl)-4-[4-(4-ethyl-piperazin-1-yl)-1-oxo-1,3-dihydro-isoindol-2-yl]-butyl}-amide, |
| 62 | thiophene-2-sulfonic acid {(4R)-4-(3,4-dimethoxy-phenyl)-4-[4-(4-ethyl-piperazin-1-yl)-1-oxo-1,3-dihydro-isoindol-2-yl]-butyl}-methyl-amide, |
| 63 | 2-[(1R)-4-(bis-pyridin-4-ylmethyl-amino)-1-(3,4-dimethoxy-phenyl)-butyl]-4-(4-ethyl-piperazin-1-yl)-2,3-dihydro-isoindol-1-one, |
| 64 | {(4R)-4-(3,4-dimethoxy-phenyl)-4-[4-(4-ethyl-piperazin-1-yl)-1-oxo-1,3-dihydro-isoindol-2-yl]-butyl}-urea, |
| 65 | thiophene-2-sulfonic acid {(4R)-4-(3,4-dimethoxy-phenyl)-4-[4-(4-isopropyl-piperazin-1-yl)-1-oxo-1,3-dihydro-isoindol-2-yl]-butyl}-amide, |
| 66 | 1-{(4R)-4-(3,4-dimethoxy-phenyl)-4-[4-(4-ethyl-piperazin-1-yl)-1-oxo-1,3-dihydro-isoindol-2-yl]-butyl}-3-phenyl-urea, |
| 67 | N-{(4R)-4-(3,4-dimethoxy-phenyl)-4-[4-(4-ethyl-piperazin-1-yl)-1-oxo-1,3-dihydro-isoindol-2-yl]-butyl}-2,2,2-trifluoro-acetamide, |
| 68 | 2-[(1R)-4-diethylamino-1-(3,4-dimethoxy-phenyl)-butyl]-4-(4-ethyl-piperazin-1-yl)-2,3-dihydro-isoindol-1-one, |
| 69 | 2-[(1R)-1-(3,4-dimethoxy-phenyl)-4-ethylamino-butyl]-4-(4-ethyl-piperazin-1-yl)-2,3-dihydro-isoindol-1-one, |
| 70 | dimethylaminosulfonic acid {(4R)-4-(3,4-dimethoxy-phenyl)-4-[4-(4-ethyl-piperazin-1-yl)-1-oxo-1,3-dihydro-isoindol-2-yl]-butyl}-amide, |
| 71 | {(4R)-4-(3,4-dimethoxy-phenyl)-4-[4-(4-ethyl-piperazin-1-yl)-1-oxo-1,3-dihydro-isoindol-2-yl]-butyl}-sulfamic acid, |
| 72 | 2-{(1R)-1-(3,4-dimethoxy-phenyl)-4-[(thiophen-2-ylmethyl)-amino]-butyl}-4-(4-ethyl-piperazin-1-yl)-2,3-dihydro-isoindol-1-one, |
| 73 | 2-[(1R)-4-dibenzylamino-1-(3,4-dimethoxy-phenyl)-butyl]-4-(4-ethyl-piperazin-1-yl)-2,3-dihydro-isoindol-1-one, |
| 74 | 2-[(1R)-4-benzyloxy-1-(3,4-dimethoxy-phenyl)-butyl]-4-(4-ethyl-piperazin-1-yl)-2,3-dihydro-isoindol-1-one, |
| 75 | 2-[(1R)-1-(3,4-dimethoxy-phenyl)-4-(2,2-dimethyl-propylamino)-butyl]-4-(4-ethyl-piperazin-1-yl)-2,3-dihydro-isoindol-1-one, |
| 76 | 3-amino-4-{(4R)-4-(3,4-dimethoxy-phenyl)-4-[4-(4-ethyl-piperazin-1-yl)-1-oxo-1,3-dihydro-isoindol-2-yl]-butylamino}-cyclobut-3-ene-1,2-dione, |
| 77 | 2-[(1R)-4-benzylamino-1-(3,4-dimethoxy-phenyl)-butyl]-4-(4-ethyl-piperazin-1-yl)-2,3-dihydro-isoindol-1-one, |
| 78 | furan-2-carboxylic acid {(4R)-4-(3,4-dimethoxy-phenyl)-4-[4-(4-ethyl-piperazin-1-yl)-1-oxo-1,3-dihydro-isoindol-2-yl]-butyl}-amide, |
| 79 | 1H-pyrazole-4-carboxylic acid {(4R)-4-(3,4-dimethoxy-phenyl)-4-[4-(4-ethyl-piperazin-1-yl)-1-oxo-1,3-dihydro-isoindol-2-yl]-butyl}-amide, |
| 80 | cyclobutanecarboxylic acid {(4R)-4-(3,4-dimethoxy-phenyl)-4-[4-(4-ethyl-piperazin-1-yl)-1-oxo-1,3-dihydro-isoindol-2-yl]-butyl}-amide, |
| 81 | thiophene-2-carboxylic acid {(4R)-4-(3,4-dimethoxy-phenyl)-4-[4-(4-ethyl-piperazin-1-yl)-1-oxo-1,3-dihydro-isoindol-2-yl]-butyl}-amide, |
| 82 | 1,2-dimethyl-1H-imidazole-4-sulfonic acid {(4R)-4-(3,4-dimethoxy-phenyl)-4-[4-(4-ethyl-piperazin-1-yl)-1-oxo-1,3-dihydro-isoindol-2-yl]-butyl}-amide, |
| 83 | N-{(4R)-4-(3,4-dimethoxy-phenyl)-4-[4-(4-ethyl-piperazin-1-yl)-1-oxo-1,3-dihydro-isoindol-2-yl]-butyl}-2,2-dimethyl-propionamide, |
| 84 | thiophene-2-sulfonic acid {(4R)-4-(3,4-dimethoxy-phenyl)-4-[4-(4-ethyl-piperazin-1-yl)-1-oxo-1,3-dihydro-isoindol-2-yl]-butyl}-amide, |
| 85 | 5-methyl-isoxazole-4-carboxylic acid ((4R)-4-(3,4-dimethoxy-phenyl)-4-{1-oxo-4-[4-(1-phenyl-ethyl)-piperazin-1-yl]-1,3-dihydro-isoindol-2-yl}-butyl)-amide, |
| 86 | 2-[(1R)-1-(3,4-dimethoxy-phenyl)-3-(5,6,7,8-tetrahydro-[1,8]naphthyridin-2-yl)-propyl]-4-(4-ethyl-piperazin-1-yl)-2,3-dihydro-isoindol-1-one, |
| 87 | 2-[(1R)-1-(3,4-dimethoxy-phenyl)-4-phenyl-butyl]-4-(4-ethyl-piperazin-1-yl)-2,3-dihydro-isoindol-1-one, |
| 88 | N-{(4R)-4-(3,4-dimethoxy-phenyl)-4-[4-(4-ethyl-piperazin-1-yl)-1-oxo-1,3-dihydro-isoindol-2-yl]-butyl}-N-(4-fluoro-benzyl)-acetamide, |
| 89 | 2-[(1R)-1-(3,4-dimethoxy-phenyl)-4-(quinolin-2-ylamino)-butyl]-4-(4-ethyl-piperazin-1-yl)-2,3-dihydro-isoindol-1-one, |
| 90 | 2-[(1R)-4-[cyclopropyl-(4-fluoro-benzyl)-amino]-1-(3,4-dimethoxy-phenyl)-butyl]-4-(4-ethyl-piperazin-1-yl)-2,3-dihydro-isoindol-1-one, |
| 91 | 2-[(1R)-1-(3,4-dimethoxy-phenyl)-4-(4-fluoro-benzylamino)-butyl]-4-(4-ethyl-piperazin-1-yl)-2,3-dihydro-isoindol-1-one, |
| 92 | 2-[(1R)-1-(3,4-dimethoxy-phenyl)-4-(pyridin-2-ylamino)-butyl]-4-(4-ethyl-piperazin-1-yl)-2,3-dihydro-isoindol-1-one, |
| 93 | 2-[(1R)-1-(3,4-dimethoxy-phenyl)-4-(1-oxy-pyridin-2-ylamino)-butyl]-4-(4-ethyl-piperazin-1-yl)-2,3-dihydro-isoindol-1-one, |
| 94 | 2-[(1R)-1-(3,4-dimethoxy-phenyl)-4-(furan-2-ylmethyl-methyl-amino)-butyl]-4-(4-ethyl-piperazin-1-yl)-2,3-dihydro-isoindol-1-one, |
| 95 | 2-[(1R)-1-(3,4-dimethoxy-phenyl)-4-(methyl-thiophen-2-ylmethyl-amino)-butyl]-4-(4-ethyl-piperazin-1-yl)-2,3-dihydro-isoindol-1-one, |
| 96 | 2-[(1R)-4-(benzyl-isopropyl-amino)-1-(3,4-dimethoxy-phenyl)-butyl]-4-(4-ethyl-piperazin-1-yl)-2,3-dihydro-isoindol-1-one, |
| 97 | 2-{(1R)-1-(3,4-dimethoxy-phenyl)-4-[(2-fluoro-benzyl)-methyl-amino]-butyl}-4-(4-ethyl-piperazin-1-yl)-2,3-dihydro-isoindol-1-one, |
| 98 | 2-{(1R)-1-(3,4-dimethoxy-phenyl)-4-[(3-fluoro-benzyl)-methyl-amino]-butyl}-4-(4-ethyl-piperazin-1-yl)-2,3-dihydro-isoindol-1-one, |
| 99 | 2-{(1R)-1-(3,4-dimethoxy-phenyl)-4-[(4-fluoro-benzyl)-methyl-amino]-butyl}-4-(4-ethyl-piperazin-1-yl)-2,3-dihydro-isoindol-1-one, |

| Cpd | Name |
|---|---|
| 100 | 2-[(1R)-4-(1,3-dihydro-isoindol-2-yl)-1-(3,4-dimethoxy-phenyl)-butyl]-4-(4-ethyl-piperazin-1-yl)-2,3-dihydro-isoindol-1-one, |
| 101 | 2-[(1R)-4-(3,4-dihydro-1H-isoquinolin-2-yl)-1-(3,4-dimethoxy-phenyl)-butyl]-4-(4-ethyl-piperazin-1-yl)-2,3-dihydro-isoindol-1-one, |
| 102 | 2-[(1R)-1-(3,4-dimethoxy-phenyl)-4-(2,4-dimethyl-imidazol-1-yl)-butyl]-4-(4-ethyl-piperazin-1-yl)-2,3-dihydro-isoindol-1-one, |
| 103 | 2-[(1R)-1-(3,4-dimethoxy-phenyl)-4-(2-methyl-imidazol-1-yl)-butyl]-4-(4-ethyl-piperazin-1-yl)-2,3-dihydro-isoindol-1-one, and |
| 104 | 2-[(1R)-1-(3,4-dimethoxy-phenyl)-4-(2-isopropyl-imidazol-1-yl)-butyl]-4-(4-ethyl-piperazin-1-yl)-2,3-dihydro-isoindol-1-one. |

Embodiment 16 of the present invention is directed to compounds of Formula (I) or a form thereof as described herein selected from the group consisting of:

| Cpd | Name |
|---|---|
| 1 | dimethylaminosulfonic acid {(4R)-4-(3,4-dimethoxy-phenyl)-4-[4-(4-ethyl-piperazin-1-yl)-1-oxo-1,3-dihydro-isoindol-2-yl]-butyl}-methyl-amide, |
| 2 | thiophene-2-sulfonic acid {(4R)-4-(3,4-dimethoxy-phenyl)-4-[4-(1-ethyl-piperidin-4-yl)-1-oxo-1,3-dihydro-isoindol-2-yl]-butyl}-methyl-amide, |
| 3 | 2-[(1R)-4-(benzyl-methyl-amino)-1-(3,4-dimethoxy-phenyl)-butyl]-4-(4-ethyl-piperazin-1-yl)-2,3-dihydro-isoindol-1-one, |
| 5 | 4-(4-benzyl-piperazin-1-yl)-2-[(1R)-1-(3,4-dimethoxy-phenyl)-4-(4-trifluoromethyl-pyrimidin-2-ylamino)-butyl]-2,3-dihydro-isoindol-1-one, |
| 6 | 2-[(1R)-1-(3,4-dimethoxy-phenyl)-4-(4-trifluoromethyl-pyrimidin-2-ylamino)-butyl]-4-piperazin-1-yl-2,3-dihydro-isoindol-1-one, |
| 7 | thiophene-2-sulfonic acid [(4R)-4-[4-(4-cyclopropyl-piperazin-1-yl)-1-oxo-1,3-dihydro-isoindol-2-yl]-4-(3,4-dimethoxy-phenyl)-butyl]-methyl-amide, |
| 8 | thiophene-2-sulfonic acid {(4R)-4-(3,4-dimethoxy-phenyl)-4-[4-(4-isopropyl-piperazin-1-yl)-1-oxo-1,3-dihydro-isoindol-2-yl]-butyl}-methyl-amide, |
| 9 | thiophene-2-sulfonic acid [(4R)-4-[4-(4-cyclobutyl-piperazin-1-yl)-1-oxo-1,3-dihydro-isoindol-2-yl]-4-(3,4-dimethoxy-phenyl)-butyl]-methyl-amide, |
| 10 | 2-[(1R)-1-(3,4-dimethoxy-phenyl)-4-(4,6-dimethoxy-pyrimidin-2-ylamino)-butyl]-4-(4-ethyl-piperazin-1-yl)-2,3-dihydro-isoindol-1-one, |
| 11 | 2-[(1R)-4-(4-chloro-pyrimidin-2-ylamino)-1-(3,4-dimethoxy-phenyl)-butyl]-4-(4-ethyl-piperazin-1-yl)-2,3-dihydro-isoindol-1-one, |
| 12 | 2-[(1R)-1-(3,4-dimethoxy-phenyl)-4-(4,6-dimethyl-pyrimidin-2-ylamino)-butyl]-4-(4-ethyl-piperazin-1-yl)-2,3-dihydro-isoindol-1-one, |
| 13 | 2-[2-(1-benzyl-piperidin-4-yl)-1-(3,4-dimethoxy-phenyl)-ethyl]-4-(4-ethyl-piperazin-1-yl)-2,3-dihydro-isoindol-1-one, |
| 14 | 2-[(1R)-1-(3,4-dimethoxy-phenyl)-4-tetrazol-1-yl-butyl]-4-(4-ethyl-piperazin-1-yl)-2,3-dihydro-isoindol-1-one, |
| 15 | 2-[(1R)-1-(3,4-dimethoxy-phenyl)-4-tetrazol-2-yl-butyl]-4-(4-ethyl-piperazin-1-yl)-2,3-dihydro-isoindol-1-one, |
| 16 | thiophene-2-sulfonic acid (3-{(3,4-dimethoxy-phenyl)-[4-(4-ethyl-piperazin-1-yl)-1-oxo-1,3-dihydro-isoindol-2-yl]-methyl}-phenyl)-amide, |
| 17 | 4-{2-(3,4-dimethoxy-phenyl)-2-[4-(4-ethyl-piperazin-1-yl)-1-oxo-1,3-dihydro-isoindol-2-yl]-ethyl}-piperidine-1-sulfonic acid, |
| 18 | 2-{1-(3,4-dimethoxy-phenyl)-2-[1-(thiophene-2-sulfonyl)-piperidin-4-yl]-ethyl}-4-(4-ethyl-piperazin-1-yl)-2,3-dihydro-isoindol-1-one, |
| 19 | 2-[(3-benzylamino-phenyl)-(3,4-dimethoxy-phenyl)-methyl]-4-(4-ethyl-piperazin-1-yl)-2,3-dihydro-isoindol-1-one, |
| 20 | 2-[(1R)-1-(3,4-dimethoxy-phenyl)-4-(4-ethyl-pyrimidin-2-ylamino)-butyl]-4-(4-ethyl-piperazin-1-yl)-2,3-dihydro-isoindol-1-one, |
| 21 | 2-[(1R)-1-(3,4-dimethoxy-phenyl)-4-(4-methoxy-pyrimidin-2-ylamino)-butyl]-4-(4-ethyl-piperazin-1-yl)-2,3-dihydro-isoindol-1-one, |
| 22 | 2-[(1R)-1-(3,4-dimethoxy-phenyl)-4-(4-trifluoromethyl-pyrimidin-2-ylamino)-butyl]-4-(4-ethyl-piperazin-1-yl)-2,3-dihydro-isoindol-1-one, |
| 23 | 2-[(1R)-1-(3,4-dimethoxy-phenyl)-4-(4-methyl-pyrimidin-2-ylamino)-butyl]-4-(4-ethyl-piperazin-1-yl)-2,3-dihydro-isoindol-1-one, |
| 24 | 2-[(1R)-1-(3,4-dimethoxy-phenyl)-4-(1-methyl-1H-tetrazol-5-ylsulfanyl)-butyl]-4-piperazin-1-yl-2,3-dihydro-isoindol-1-one, |
| 25 | 2-[(1R)-1-(3,4-dimethoxy-phenyl)-4-[1,2,4]triazol-1-yl-butyl]-4-(4-ethyl-piperazin-1-yl)-2,3-dihydro-isoindol-1-one, |
| 26 | thiophene-2-sulfonic acid {(4R)-4-(3,4-dimethoxy-phenyl)-4-[4-(4-methyl-piperazin-1-yl)-1-oxo-1,3-dihydro-isoindol-2-yl]-butyl}-methyl-amide, |
| 27 | 2-[(1R)-1-(3,4-dimethoxy-phenyl)-4-(4,6-dimethyl-pyrimidin-2-ylsulfanyl)-butyl]-4-(4-ethyl-piperazin-1-yl)-2,3-dihydro-isoindol-1-one, |
| 28 | 4-(4-cyclopropyl-piperazin-1-yl)-2-[(1R)-1-(3,4-dimethoxy-phenyl)-4-phenoxy-butyl]-2,3-dihydro-isoindol-1-one, |
| 29 | 2-[(1R)-4-benzoimidazol-1-yl-1-(3,4-dimethoxy-phenyl)-butyl]-4-(4-ethyl-piperazin-1-yl)-2,3-dihydro-isoindol-1-one, |
| 30 | thiophene-2-sulfonic acid [(4R)-4-(3,4-dimethoxy-phenyl)-4-(1-oxo-4-piperazin-1-yl-1,3-dihydro-isoindol-2-yl)-butyl]-methyl-amide, |
| 31 | {(4R)-4-(3,4-dimethoxy-phenyl)-4-[4-(4-ethyl-piperazin-1-yl)-1-oxo-1,3-dihydro-isoindol-2-yl]-butylsulfanyl}-pyridine 1-oxide, |
| 32 | 2-[(1R)-1-(3,4-dimethoxy-phenyl)-4-imidazol-1-yl-butyl]-4-(4-ethyl-piperazin-1-yl)-2,3-dihydro-isoindol-1-one, |
| 34 | 4-(4-benzyl-piperazin-1-yl)-2-[(1R)-1-(3,4-dimethoxy-phenyl)-4-phenoxy-butyl]-2,3-dihydro-isoindol-1-one, |
| 36 | 2-[(1R)-1-(3,4-dimethoxy-phenyl)-4-phenylsulfanyl-butyl]-4-piperazin-1-yl-2,3-dihydro-isoindol-1-one, |
| 37 | 2-[(1R)-1-(3,4-dimethoxy-phenyl)-4-phenoxy-butyl]-4-piperazin-1-yl-2,3-dihydro-isoindol-1-one, |
| 38 | 4-{2-[(1R)-4-dibenzylamino-1-(3,4-dimethoxy-phenyl)-butyl]-1-oxo-2,3-dihydro-1H-isoindol-4-yl}-1-ethyl-1-methyl-piperazin-1-ium, |
| 39 | 1,2-dimethyl-1H-imidazole-4-sulfonic acid {(4R)-4-(3,4-dimethoxy-phenyl)-4-[4-(4-ethyl-piperazin-1-yl)-1-oxo-1,3-dihydro-isoindol-2-yl]-butyl}-methyl-amide, |
| 40 | 2-[(1R)-1-(3,4-dimethoxy-phenyl)-4-phenylamino-butyl]-4-(4-ethyl-piperazin-1-yl)-2,3-dihydro-isoindol-1-one, |
| 41 | 2-[(1R)-4-benzyloxy-1-(3,4-dimethoxy-phenyl)-butyl]-4-piperazin-1-yl-2,3-dihydro-isoindol-1-one, |
| 43 | 2-[(1R)-(1-benzyl-piperidin-4-yl)-(3,4-dimethoxy-phenyl)-methyl]-4-(4-ethyl-piperazin-1-yl)-2,3-dihydro-isoindol-1-one, |
| 48 | 2-[(1R)-1-(3,4-dimethoxy-phenyl)-4-(pyrimidin-2-ylamino)-butyl]-4-(4-ethyl-piperazin-1-yl)-2,3-dihydro-isoindol-1-one, |
| 49 | 2,3-dimethyl-3H-imidazole-4-sulfonic acid {(4R)-4-(3,4-dimethoxy-phenyl)-4-[4-(4-ethyl-piperazin-1-yl)-1-oxo-1,3-dihydro-isoindol-2-yl]-butyl}-amide, |
| 50 | 2-[(1R)-1-(3,4-dimethoxy-phenyl)-4-phenoxy-butyl]-4-(4-ethyl-piperazin-1-yl)-2,3-dihydro-isoindol-1-one, |
| 53 | 1-methyl-1H-imidazole-4-sulfonic acid {(4R)-4-(3,4-dimethoxy-phenyl)-4-[4-(4-ethyl-piperazin-1-yl)-1-oxo-1,3-dihydro-isoindol-2-yl]-butyl}-amide, |
| 54 | N-{(4R)-4-(3,4-dimethoxy-phenyl)-4-[4-(4-ethyl-piperazin-1-yl)-1-oxo-1,3-dihydro-isoindol-2-yl]-butyl}-isonicotinamide, |
| 56 | 1-methyl-1H-imidazole-2-carboxylic acid {(4R)-4-(3,4-dimethoxy-phenyl)-4-[4-(4-ethyl-piperazin-1-yl)-1-oxo-1,3-dihydro-isoindol-2-yl]-butyl}-amide, |
| 57 | 1-methyl-1H-imidazole-4-carboxylic acid {(4R)-4-(3,4-dimethoxy-phenyl)-4-[4-(4-ethyl-piperazin-1-yl)-1-oxo-1,3-dihydro-isoindol-2-yl]-butyl}-amide, |
| 58 | aminosulfonic acid {(4R)-4-(3,4-dimethoxy-phenyl)-4-[4-(4-ethyl-piperazin-1-yl)-1-oxo-1,3-dihydro-isoindol-2-yl]-butyl}-amide, |
| 59 | 3-methyl-3H-imidazole-4-carboxylic acid {(4R)-4-(3,4-dimethoxy-phenyl)-4-[4-(4-ethyl-piperazin-1-yl)-1-oxo-1,3-dihydro-isoindol-2-yl]-butyl}-amide, |
| 60 | 3,5-dimethyl-1H-pyrazole-4-carboxylic acid {(4R)-4-(3,4-dimethoxy-phenyl)-4-[4-(4-ethyl-piperazin-1-yl)-1-oxo-1,3-dihydro-isoindol-2-yl]-butyl}-amide, |
| 61 | pyridazine-4-carboxylic acid {(4R)-4-(3,4-dimethoxy-phenyl)-4-[4-(4-ethyl-piperazin-1-yl)-1-oxo-1,3-dihydro-isoindol-2-yl]-butyl}-amide, |

| Cpd | Name |
|---|---|
| 62 | thiophene-2-sulfonic acid {(4R)-4-(3,4-dimethoxy-phenyl)-4-[4-(4-ethyl-piperazin-1-yl)-1-oxo-1,3-dihydro-isoindol-2-yl]-butyl}-methyl-amide, |
| 63 | 2-[(1R)-4-(bis-pyridin-4-ylmethyl-amino)-1-(3,4-dimethoxy-phenyl)-butyl]-4-(4-ethyl-piperazin-1-yl)-2,3-dihydro-isoindol-1-one, |
| 64 | {(4R)-4-(3,4-dimethoxy-phenyl)-4-[4-(4-ethyl-piperazin-1-yl)-1-oxo-1,3-dihydro-isoindol-2-yl]-butyl}-urea, |
| 65 | thiophene-2-sulfonic acid {(4R)-4-(3,4-dimethoxy-phenyl)-4-[4-(4-isopropyl-piperazin-1-yl)-1-oxo-1,3-dihydro-isoindol-2-yl]-butyl}-amide, |
| 66 | 1-{(4R)-4-(3,4-dimethoxy-phenyl)-4-[4-(4-ethyl-piperazin-1-yl)-1-oxo-1,3-dihydro-isoindol-2-yl]-butyl}-3-phenyl-urea, |
| 67 | N-{(4R)-4-(3,4-dimethoxy-phenyl)-4-[4-(4-ethyl-piperazin-1-yl)-1-oxo-1,3-dihydro-isoindol-2-yl]-butyl}-2,2,2-trifluoro-acetamide, |
| 68 | 2-[(1R)-4-diethylamino-1-(3,4-dimethoxy-phenyl)-butyl]-4-(4-ethyl-piperazin-1-yl)-2,3-dihydro-isoindol-1-one, |
| 69 | 2-[(1R)-1-(3,4-dimethoxy-phenyl)-4-ethylamino-butyl]-4-(4-ethyl-piperazin-1-yl)-2,3-dihydro-isoindol-1-one, |
| 70 | dimethylaminosulfonic acid {(4R)-4-(3,4-dimethoxy-phenyl)-4-[4-(4-ethyl-piperazin-1-yl)-1-oxo-1,3-dihydro-isoindol-2-yl]-butyl}-amide, |
| 72 | 2-{(1R)-1-(3,4-dimethoxy-phenyl)-4-[(thiophen-2-ylmethyl)-amino]-butyl}-4-(4-ethyl-piperazin-1-yl)-2,3-dihydro-isoindol-1-one, |
| 73 | 2-[(1R)-4-dibenzylamino-1-(3,4-dimethoxy-phenyl)-butyl]-4-(4-ethyl-piperazin-1-yl)-2,3-dihydro-isoindol-1-one, |
| 74 | 2-[(1R)-4-benzyloxy-1-(3,4-dimethoxy-phenyl)-butyl]-4-(4-ethyl-piperazin-1-yl)-2,3-dihydro-isoindol-1-one, |
| 75 | 2-[(1R)-1-(3,4-dimethoxy-phenyl)-4-(2,2-dimethyl-propylamino)-butyl]-4-(4-ethyl-piperazin-1-yl)-2,3-dihydro-isoindol-1-one, |
| 76 | 3-amino-4-{(4R)-4-(3,4-dimethoxy-phenyl)-4-[4-(4-ethyl-piperazin-1-yl)-1-oxo-1,3-dihydro-isoindol-2-yl]-butylamino}-cyclobut-3-ene-1,2-dione, |
| 77 | 2-[(1R)-4-benzylamino-1-(3,4-dimethoxy-phenyl)-butyl]-4-(4-ethyl-piperazin-1-yl)-2,3-dihydro-isoindol-1-one, |
| 78 | furan-2-carboxylic acid {(4R)-4-(3,4-dimethoxy-phenyl)-4-[4-(4-ethyl-piperazin-1-yl)-1-oxo-1,3-dihydro-isoindol-2-yl]-butyl}-amide, |
| 79 | 1H-pyrazole-4-carboxylic acid {(4R)-4-(3,4-dimethoxy-phenyl)-4-[4-(4-ethyl-piperazin-1-yl)-1-oxo-1,3-dihydro-isoindol-2-yl]-butyl}-amide, |
| 80 | cyclobutanecarboxylic acid {(4R)-4-(3,4-dimethoxy-phenyl)-4-[4-(4-ethyl-piperazin-1-yl)-1-oxo-1,3-dihydro-isoindol-2-yl]-butyl}-amide, |
| 81 | thiophene-2-carboxylic acid {(4R)-4-(3,4-dimethoxy-phenyl)-4-[4-(4-ethyl-piperazin-1-yl)-1-oxo-1,3-dihydro-isoindol-2-yl]-butyl}-amide, |
| 82 | 1,2-dimethyl-1H-imidazole-4-sulfonic acid {(4R)-4-(3,4-dimethoxy-phenyl)-4-[4-(4-ethyl-piperazin-1-yl)-1-oxo-1,3-dihydro-isoindol-2-yl]-butyl}-amide, |
| 83 | N-{(4R)-4-(3,4-dimethoxy-phenyl)-4-[4-(4-ethyl-piperazin-1-yl)-1-oxo-1,3-dihydro-isoindol-2-yl]-butyl}-2,2-dimethyl-propionamide, |
| 84 | thiophene-2-sulfonic acid {(4R)-4-(3,4-dimethoxy-phenyl)-4-[4-(4-ethyl-piperazin-1-yl)-1-oxo-1,3-dihydro-isoindol-2-yl]-butyl}-amide, |
| 85 | 5-methyl-isoxazole-4-carboxylic acid ((4R)-4-(3,4-dimethoxy-phenyl)-4-{1-oxo-4-[4-(1-phenyl-ethyl)-piperazin-1-yl]-1,3-dihydro-isoindol-2-yl}-butyl)-amide, |
| 87 | 2-[(1R)-1-(3,4-dimethoxy-phenyl)-4-phenyl-butyl]-4-(4-ethyl-piperazin-1-yl)-2,3-dihydro-isoindol-1-one, |
| 88 | N-{(4R)-4-(3,4-dimethoxy-phenyl)-4-[4-(4-ethyl-piperazin-1-yl)-1-oxo-1,3-dihydro-isoindol-2-yl]-butyl}-N-(4-fluoro-benzyl)-acetamide, |
| 89 | 2-[(1R)-1-(3,4-dimethoxy-phenyl)-4-(quinolin-2-ylamino)-butyl]-4-(4-ethyl-piperazin-1-yl)-2,3-dihydro-isoindol-1-one, |
| 90 | 2-[(1R)-4-[cyclopropyl-(4-fluoro-benzyl)-amino]-1-(3,4-dimethoxy-phenyl)-butyl]-4-(4-ethyl-piperazin-1-yl)-2,3-dihydro-isoindol-1-one, |
| 91 | 2-[(1R)-1-(3,4-dimethoxy-phenyl)-4-(4-fluoro-benzylamino)-butyl]-4-(4-ethyl-piperazin-1-yl)-2,3-dihydro-isoindol-1-one, |
| 92 | 2-[(1R)-1-(3,4-dimethoxy-phenyl)-4-(pyridin-2-ylamino)-butyl]-4-(4-ethyl-piperazin-1-yl)-2,3-dihydro-isoindol-1-one, |
| 93 | 2-[(1R)-1-(3,4-dimethoxy-phenyl)-4-(1-oxy-pyridin-2-ylamino)-butyl]-4-(4-ethyl-piperazin-1-yl)-2,3-dihydro-isoindol-1-one, |
| 94 | 2-[(1R)-1-(3,4-dimethoxy-phenyl)-4-(furan-2-ylmethyl-methyl-amino)-butyl]-4-(4-ethyl-piperazin-1-yl)-2,3-dihydro-isoindol-1-one, |
| 95 | 2-[(1R)-1-(3,4-dimethoxy-phenyl)-4-(methyl-thiophen-2-ylmethyl-amino)-butyl]-4-(4-ethyl-piperazin-1-yl)-2,3-dihydro-isoindol-1-one, |
| 96 | 2-[(1R)-4-(benzyl-isopropyl-amino)-1-(3,4-dimethoxy-phenyl)-butyl]-4-(4-ethyl-piperazin-1-yl)-2,3-dihydro-isoindol-1-one, |
| 97 | 2-{(1R)-1-(3,4-dimethoxy-phenyl)-4-[(2-fluoro-benzyl)-methyl-amino]-butyl}-4-(4-ethyl-piperazin-1-yl)-2,3-dihydro-isoindol-1-one, |
| 98 | 2-{(1R)-1-(3,4-dimethoxy-phenyl)-4-[(3-fluoro-benzyl)-methyl-amino]-butyl}-4-(4-ethyl-piperazin-1-yl)-2,3-dihydro-isoindol-1-one, |
| 99 | 2-{(1R)-1-(3,4-dimethoxy-phenyl)-4-[(4-fluoro-benzyl)-methyl-amino]-butyl}-4-(4-ethyl-piperazin-1-yl)-2,3-dihydro-isoindol-1-one, |
| 100 | 2-[(1R)-4-(1,3-dihydro-isoindol-2-yl)-1-(3,4-dimethoxy-phenyl)-butyl]-4-(4-ethyl-piperazin-1-yl)-2,3-dihydro-isoindol-1-one, |
| 101 | 2-[(1R)-4-(3,4-dihydro-1H-isoquinolin-2-yl)-1-(3,4-dimethoxy-phenyl)-butyl]-4-(4-ethyl-piperazin-1-yl)-2,3-dihydro-isoindol-1-one, |
| 102 | 2-[(1R)-1-(3,4-dimethoxy-phenyl)-4-(2,4-dimethyl-imidazol-1-yl)-butyl]-4-(4-ethyl-piperazin-1-yl)-2,3-dihydro-isoindol-1-one, |
| 103 | 2-[(1R)-1-(3,4-dimethoxy-phenyl)-4-(2-methyl-imidazol-1-yl)-butyl]-4-(4-ethyl-piperazin-1-yl)-2,3-dihydro-isoindol-1-one, and |
| 104 | 2-[(1R)-1-(3,4-dimethoxy-phenyl)-4-(2-isopropyl-imidazol-1-yl)-butyl]-4-(4-ethyl-piperazin-1-yl)-2,3-dihydro-isoindol-1-one. |

Embodiment 17 of the present invention is directed to compounds of Formula (I) or a form thereof as described herein selected from the group consisting of:

| Cpd | Name |
|---|---|
| 1 | dimethylaminosulfonic acid {(4R)-4-(3,4-dimethoxy-phenyl)-4-[4-(4-ethyl-piperazin-1-yl)-1-oxo-1,3-dihydro-isoindol-2-yl]-butyl}-methyl-amide, |
| 2 | thiophene-2-sulfonic acid {(4R)-4-(3,4-dimethoxy-phenyl)-4-[4-(1-ethyl-piperidin-4-yl)-1-oxo-1,3-dihydro-isoindol-2-yl]-butyl}-methyl-amide, |
| 3 | 2-[(1R)-4-(benzyl-methyl-amino)-1-(3,4-dimethoxy-phenyl)-butyl]-4-(4-ethyl-piperazin-1-yl)-2,3-dihydro-isoindol-1-one, |
| 5 | 4-(4-benzyl-piperazin-1-yl)-2-[(1R)-1-(3,4-dimethoxy-phenyl)-4-(4-trifluoromethyl-pyrimidin-2-ylamino)-butyl]-2,3-dihydro-isoindol-1-one, |
| 6 | 2-[(1R)-1-(3,4-dimethoxy-phenyl)-4-(4-trifluoromethyl-pyrimidin-2-ylamino)-butyl]-4-piperazin-1-yl-2,3-dihydro-isoindol-1-one, |
| 7 | thiophene-2-sulfonic acid [(4R)-4-[4-(4-cyclopropyl-piperazin-1-yl)-1-oxo-1,3-dihydro-isoindol-2-yl]-4-(3,4-dimethoxy-phenyl)-butyl]-methyl-amide, |
| 8 | thiophene-2-sulfonic acid {(4R)-4-(3,4-dimethoxy-phenyl)-4-[4-(4-isopropyl-piperazin-1-yl)-1-oxo-1,3-dihydro-isoindol-2-yl]-butyl}-methyl-amide, |
| 9 | thiophene-2-sulfonic acid [(4R)-4-[4-(4-cyclobutyl-piperazin-1-yl)-1-oxo-1,3-dihydro-isoindol-2-yl]-4-(3,4-dimethoxy-phenyl)-butyl]-methyl-amide, |
| 10 | 2-[(1R)-1-(3,4-dimethoxy-phenyl)-4-(4,6-dimethoxy-pyrimidin-2-ylamino)-butyl]-4-(4-ethyl-piperazin-1-yl)-2,3-dihydro-isoindol-1-one, |
| 11 | 2-[(1R)-4-(4-chloro-pyrimidin-2-ylamino)-1-(3,4-dimethoxy-phenyl)-butyl]-4-(4-ethyl-piperazin-1-yl)-2,3-dihydro-isoindol-1-one, |
| 12 | 2-[(1R)-1-(3,4-dimethoxy-phenyl)-4-(4,6-dimethyl-pyrimidin-2-ylamino)-butyl]-4-(4-ethyl-piperazin-1-yl)-2,3-dihydro-isoindol-1-one, |
| 14 | 2-[(1R)-1-(3,4-dimethoxy-phenyl)-4-tetrazol-1-yl-butyl]-4-(4-ethyl-piperazin-1-yl)-2,3-dihydro-isoindol-1-one, |

| Cpd | Name |
|---|---|
| 15 | 2-[(1R)-1-(3,4-dimethoxy-phenyl)-4-tetrazol-2-yl-butyl]-4-(4-ethyl-piperazin-1-yl)-2,3-dihydro-isoindol-1-one, |
| 16 | thiophene-2-sulfonic acid (3-{(3,4-dimethoxy-phenyl)-[4-(4-ethyl-piperazin-1-yl)-1-oxo-1,3-dihydro-isoindol-2-yl]-methyl}-phenyl)-amide, |
| 17 | 4-{2-(3,4-dimethoxy-phenyl)-2-[4-(4-ethyl-piperazin-1-yl)-1-oxo-1,3-dihydro-isoindol-2-yl]-ethyl}-piperidine-1-sulfonic acid, |
| 18 | 2-{1-(3,4-dimethoxy-phenyl)-2-[1-(thiophene-2-sulfonyl)-piperidin-4-yl]-ethyl}-4-(4-ethyl-piperazin-1-yl)-2,3-dihydro-isoindol-1-one, |
| 20 | 2-[(1R)-1-(3,4-dimethoxy-phenyl)-4-(4-ethyl-pyrimidin-2-ylamino)-butyl]-4-(4-ethyl-piperazin-1-yl)-2,3-dihydro-isoindol-1-one, |
| 21 | 2-[(1R)-1-(3,4-dimethoxy-phenyl)-4-(4-methoxy-pyrimidin-2-ylamino)-butyl]-4-(4-ethyl-piperazin-1-yl)-2,3-dihydro-isoindol-1-one, |
| 22 | 2-[(1R)-1-(3,4-dimethoxy-phenyl)-4-(4-trifluoromethyl-pyrimidin-2-ylamino)-butyl]-4-(4-ethyl-piperazin-1-yl)-2,3-dihydro-isoindol-1-one, |
| 23 | 2-[(1R)-1-(3,4-dimethoxy-phenyl)-4-(4-methyl-pyrimidin-2-ylamino)-butyl]-4-(4-ethyl-piperazin-1-yl)-2,3-dihydro-isoindol-1-one, |
| 26 | thiophene-2-sulfonic acid {(4R)-4-(3,4-dimethoxy-phenyl)-4-[4-(4-methyl-piperazin-1-yl)-1-oxo-1,3-dihydro-isoindol-2-yl]-butyl}-methyl-amide, |
| 27 | 2-[(1R)-1-(3,4-dimethoxy-phenyl)-4-(4,6-dimethyl-pyrimidin-2-ylsulfanyl)-butyl]-4-(4-ethyl-piperazin-1-yl)-2,3-dihydro-isoindol-1-one, |
| 28 | 4-(4-cyclopropyl-piperazin-1-yl)-2-[(1R)-1-(3,4-dimethoxy-phenyl)-4-phenoxy-butyl]-2,3-dihydro-isoindol-1-one, |
| 29 | 2-[(1R)-4-benzoimidazol-1-yl-1-(3,4-dimethoxy-phenyl)-butyl]-4-(4-ethyl-piperazin-1-yl)-2,3-dihydro-isoindol-1-one, |
| 30 | thiophene-2-sulfonic acid [(4R)-4-(3,4-dimethoxy-phenyl)-4-(1-oxo-4-piperazin-1-yl-1,3-dihydro-isoindol-2-yl)-butyl]-methyl-amide, |
| 31 | {(4R)-4-(3,4-dimethoxy-phenyl)-4-[4-(4-ethyl-piperazin-1-yl)-1-oxo-1,3-dihydro-isoindol-2-yl]-butylsulfanyl}-pyridine 1-oxide, |
| 32 | 2-[(1R)-1-(3,4-dimethoxy-phenyl)-4-imidazol-1-yl-butyl]-4-(4-ethyl-piperazin-1-yl)-2,3-dihydro-isoindol-1-one, |
| 36 | 2-[(1R)-1-(3,4-dimethoxy-phenyl)-4-phenylsulfanyl-butyl]-4-piperazin-1-yl-2,3-dihydro-isoindol-1-one, |
| 37 | 2-[(1R)-1-(3,4-dimethoxy-phenyl)-4-phenoxy-butyl]-4-piperazin-1-yl-2,3-dihydro-isoindol-1-one, |
| 40 | 2-[(1R)-1-(3,4-dimethoxy-phenyl)-4-phenylamino-butyl]-4-(4-ethyl-piperazin-1-yl)-2,3-dihydro-isoindol-1-one, |
| 41 | 2-[(1R)-4-benzyloxy-1-(3,4-dimethoxy-phenyl)-butyl]-4-piperazin-1-yl-2,3-dihydro-isoindol-1-one, |
| 48 | 2-[(1R)-1-(3,4-dimethoxy-phenyl)-4-(pyrimidin-2-ylamino)-butyl]-4-(4-ethyl-piperazin-1-yl)-2,3-dihydro-isoindol-1-one, |
| 49 | 2,3-dimethyl-3H-imidazole-4-sulfonic acid {(4R)-4-(3,4-dimethoxy-phenyl)-4-[4-(4-ethyl-piperazin-1-yl)-1-oxo-1,3-dihydro-isoindol-2-yl]-butyl}-amide, |
| 50 | 2-[(1R)-1-(3,4-dimethoxy-phenyl)-4-phenoxy-butyl]-4-(4-ethyl-piperazin-1-yl)-2,3-dihydro-isoindol-1-one, |
| 53 | 1-methyl-1H-imidazole-4-sulfonic acid {(4R)-4-(3,4-dimethoxy-phenyl)-4-[4-(4-ethyl-piperazin-1-yl)-1-oxo-1,3-dihydro-isoindol-2-yl]-butyl}-amide, |
| 54 | N-{(4R)-4-(3,4-dimethoxy-phenyl)-4-[4-(4-ethyl-piperazin-1-yl)-1-oxo-1,3-dihydro-isoindol-2-yl]-butyl}-isonicotinamide, |
| 56 | 1-methyl-1H-imidazole-2-carboxylic acid {(4R)-4-(3,4-dimethoxy-phenyl)-4-[4-(4-ethyl-piperazin-1-yl)-1-oxo-1,3-dihydro-isoindol-2-yl]-butyl}-amide, |
| 57 | 1-methyl-1H-imidazole-4-carboxylic acid {(4R)-4-(3,4-dimethoxy-phenyl)-4-[4-(4-ethyl-piperazin-1-yl)-1-oxo-1,3-dihydro-isoindol-2-yl]-butyl}-amide, |
| 58 | aminosulfonic acid {(4R)-4-(3,4-dimethoxy-phenyl)-4-[4-(4-ethyl-piperazin-1-yl)-1-oxo-1,3-dihydro-isoindol-2-yl]-butyl}-amide, |
| 59 | 3-methyl-3H-imidazole-4-carboxylic acid {(4R)-4-(3,4-dimethoxy-phenyl)-4-[4-(4-ethyl-piperazin-1-yl)-1-oxo-1,3-dihydro-isoindol-2-yl]-butyl}-amide, |
| 60 | 3,5-dimethyl-1H-pyrazole-4-carboxylic acid {(4R)-4-(3,4-dimethoxy-phenyl)-4-[4-(4-ethyl-piperazin-1-yl)-1-oxo-1,3-dihydro-isoindol-2-yl]-butyl}-amide, |
| 61 | pyridazine-4-carboxylic acid {(4R)-4-(3,4-dimethoxy-phenyl)-4-[4-(4-ethyl-piperazin-1-yl)-1-oxo-1,3-dihydro-isoindol-2-yl]-butyl}-amide, |
| 62 | thiophene-2-sulfonic acid {(4R)-4-(3,4-dimethoxy-phenyl)-4-[4-(4-ethyl-piperazin-1-yl)-1-oxo-1,3-dihydro-isoindol-2-yl]-butyl}-methyl-amide, |
| 63 | 2-[(1R)-4-(bis-pyridin-4-ylmethyl-amino)-1-(3,4-dimethoxy-phenyl)-butyl]-4-(4-ethyl-piperazin-1-yl)-2,3-dihydro-isoindol-1-one, |
| 65 | thiophene-2-sulfonic acid {(4R)-4-(3,4-dimethoxy-phenyl)-4-[4-(4-isopropyl-piperazin-1-yl)-1-oxo-1,3-dihydro-isoindol-2-yl]-butyl}-amide, |
| 66 | 1-{(4R)-4-(3,4-dimethoxy-phenyl)-4-[4-(4-ethyl-piperazin-1-yl)-1-oxo-1,3-dihydro-isoindol-2-yl]-butyl}-3-phenyl-urea, |
| 67 | N-{(4R)-4-(3,4-dimethoxy-phenyl)-4-[4-(4-ethyl-piperazin-1-yl)-1-oxo-1,3-dihydro-isoindol-2-yl]-butyl}-2,2,2-trifluoro-acetamide, |
| 70 | dimethylaminosulfonic acid {(4R)-4-(3,4-dimethoxy-phenyl)-4-[4-(4-ethyl-piperazin-1-yl)-1-oxo-1,3-dihydro-isoindol-2-yl]-butyl}-amide, |
| 72 | 2-{(1R)-1-(3,4-dimethoxy-phenyl)-4-[(thiophen-2-ylmethyl)-amino]-butyl}-4-(4-ethyl-piperazin-1-yl)-2,3-dihydro-isoindol-1-one, |
| 73 | 2-[(1R)-4-dibenzylamino-1-(3,4-dimethoxy-phenyl)-butyl]-4-(4-ethyl-piperazin-1-yl)-2,3-dihydro-isoindol-1-one, |
| 74 | 2-[(1R)-4-benzyloxy-1-(3,4-dimethoxy-phenyl)-butyl]-4-(4-ethyl-piperazin-1-yl)-2,3-dihydro-isoindol-1-one, |
| 75 | 2-[(1R)-1-(3,4-dimethoxy-phenyl)-4-(2,2-dimethyl-propylamino)-butyl]-4-(4-ethyl-piperazin-1-yl)-2,3-dihydro-isoindol-1-one, |
| 76 | 3-amino-4-{(4R)-4-(3,4-dimethoxy-phenyl)-4-[4-(4-ethyl-piperazin-1-yl)-1-oxo-1,3-dihydro-isoindol-2-yl]-butylamino}-cyclobut-3-ene-1,2-dione, |
| 77 | 2-[(1R)-4-benzylamino-1-(3,4-dimethoxy-phenyl)-butyl]-4-(4-ethyl-piperazin-1-yl)-2,3-dihydro-isoindol-1-one, |
| 78 | furan-2-carboxylic acid {(4R)-4-(3,4-dimethoxy-phenyl)-4-[4-(4-ethyl-piperazin-1-yl)-1-oxo-1,3-dihydro-isoindol-2-yl]-butyl}-amide, |
| 79 | 1H-pyrazole-4-carboxylic acid {(4R)-4-(3,4-dimethoxy-phenyl)-4-[4-(4-ethyl-piperazin-1-yl)-1-oxo-1,3-dihydro-isoindol-2-yl]-butyl}-amide, |
| 80 | cyclobutanecarboxylic acid {(4R)-4-(3,4-dimethoxy-phenyl)-4-[4-(4-ethyl-piperazin-1-yl)-1-oxo-1,3-dihydro-isoindol-2-yl]-butyl}-amide, |
| 81 | thiophene-2-carboxylic acid {(4R)-4-(3,4-dimethoxy-phenyl)-4-[4-(4-ethyl-piperazin-1-yl)-1-oxo-1,3-dihydro-isoindol-2-yl]-butyl}-amide, |
| 82 | 1,2-dimethyl-1H-imidazole-4-sulfonic acid {(4R)-4-(3,4-dimethoxy-phenyl)-4-[4-(4-ethyl-piperazin-1-yl)-1-oxo-1,3-dihydro-isoindol-2-yl]-butyl}-amide, |
| 83 | N-{(4R)-4-(3,4-dimethoxy-phenyl)-4-[4-(4-ethyl-piperazin-1-yl)-1-oxo-1,3-dihydro-isoindol-2-yl]-butyl}-2,2-dimethyl-propionamide, |
| 84 | thiophene-2-sulfonic acid {(4R)-4-(3,4-dimethoxy-phenyl)-4-[4-(4-ethyl-piperazin-1-yl)-1-oxo-1,3-dihydro-isoindol-2-yl]-butyl}-amide, |
| 85 | 5-methyl-isoxazole-4-carboxylic acid ((4R)-4-(3,4-dimethoxy-phenyl)-4-{1-oxo-4-[4-(1-phenyl-ethyl)-piperazin-1-yl]-1,3-dihydro-isoindol-2-yl}-butyl)-amide, |
| 87 | 2-[(1R)-1-(3,4-dimethoxy-phenyl)-4-phenyl-butyl]-4-(4-ethyl-piperazin-1-yl)-2,3-dihydro-isoindol-1-one, |
| 88 | N-{(4R)-4-(3,4-dimethoxy-phenyl)-4-[4-(4-ethyl-piperazin-1-yl)-1-oxo-1,3-dihydro-isoindol-2-yl]-butyl}-N-(4-fluoro-benzyl)-acetamide, |
| 90 | 2-[(1R)-4-[cyclopropyl-(4-fluoro-benzyl)-amino]-1-(3,4-dimethoxy-phenyl)-butyl]-4-(4-ethyl-piperazin-1-yl)-2,3-dihydro-isoindol-1-one, |
| 91 | 2-[(1R)-1-(3,4-dimethoxy-phenyl)-4-(4-fluoro-benzylamino)-butyl]-4-(4-ethyl-piperazin-1-yl)-2,3-dihydro-isoindol-1-one, |
| 92 | 2-[(1R)-1-(3,4-dimethoxy-phenyl)-4-(pyridin-2-ylamino)-butyl]-4-(4-ethyl-piperazin-1-yl)-2,3-dihydro-isoindol-1-one, |
| 93 | 2-[(1R)-1-(3,4-dimethoxy-phenyl)-4-(1-oxy-pyridin-2-ylamino)-butyl]-4-(4-ethyl-piperazin-1-yl)-2,3-dihydro-isoindol-1-one, |

| Cpd | Name |
|---|---|
| 94 | 2-[(1R)-1-(3,4-dimethoxy-phenyl)-4-(furan-2-ylmethyl-methyl-amino)-butyl]-4-(4-ethyl-piperazin-1-yl)-2,3-dihydro-isoindol-1-one, |
| 95 | 2-[(1R)-1-(3,4-dimethoxy-phenyl)-4-(methyl-thiophen-2-ylmethyl-amino)-butyl]-4-(4-ethyl-piperazin-1-yl)-2,3-dihydro-isoindol-1-one, |
| 96 | 2-[(1R)-4-(benzyl-isopropyl-amino)-1-(3,4-dimethoxy-phenyl)-butyl]-4-(4-ethyl-piperazin-1-yl)-2,3-dihydro-isoindol-1-one, |
| 97 | 2-{(1R)-1-(3,4-dimethoxy-phenyl)-4-[(2-fluoro-benzyl)-methyl-amino]-butyl}-4-(4-ethyl-piperazin-1-yl)-2,3-dihydro-isoindol-1-one, |
| 98 | 2-{(1R)-1-(3,4-dimethoxy-phenyl)-4-[(3-fluoro-benzyl)-methyl-amino]-butyl}-4-(4-ethyl-piperazin-1-yl)-2,3-dihydro-isoindol-1-one, |
| 99 | 2-{(1R)-1-(3,4-dimethoxy-phenyl)-4-[(4-fluoro-benzyl)-methyl-amino]-butyl}-4-(4-ethyl-piperazin-1-yl)-2,3-dihydro-isoindol-1-one, |
| 100 | 2-[(1R)-4-(1,3-dihydro-isoindol-2-yl)-1-(3,4-dimethoxy-phenyl)-butyl]-4-(4-ethyl-piperazin-1-yl)-2,3-dihydro-isoindol-1-one, |
| 101 | 2-[(1R)-4-(3,4-dihydro-1H-isoquinolin-2-yl)-1-(3,4-dimethoxy-phenyl)-butyl]-4-(4-ethyl-piperazin-1-yl)-2,3-dihydro-isoindol-1-one, |
| 102 | 2-[(1R)-1-(3,4-dimethoxy-phenyl)-4-(2,4-dimethyl-imidazol-1-yl)-butyl]-4-(4-ethyl-piperazin-1-yl)-2,3-dihydro-isoindol-1-one, and |
| 104 | 2-[(1R)-1-(3,4-dimethoxy-phenyl)-4-(2-isopropyl-imidazol-1-yl)-butyl]-4-(4-ethyl-piperazin-1-yl)-2,3-dihydro-isoindol-1-one. |

Embodiment 18 of the present invention is directed to compounds of Formula (I) or a form thereof as described herein selected from the group consisting of:

| Cpd | Name |
|---|---|
| 1 | dimethylaminosulfonic acid {(4R)-4-(3,4-dimethoxy-phenyl)-4-[4-(4-ethyl-piperazin-1-yl)-1-oxo-1,3-dihydro-isoindol-2-yl]-butyl}-methyl-amide, |
| 2 | thiophene-2-sulfonic acid {(4R)-4-(3,4-dimethoxy-phenyl)-4-[4-(1-ethyl-piperidin-4-yl)-1-oxo-1,3-dihydro-isoindol-2-yl]-butyl}-methyl-amide, |
| 3 | 2-[(1R)-4-(benzyl-methyl-amino)-1-(3,4-dimethoxy-phenyl)-butyl]-4-(4-ethyl-piperazin-1-yl)-2,3-dihydro-isoindol-1-one, |
| 5 | 4-(4-benzyl-piperazin-1-yl)-2-[(1R)-1-(3,4-dimethoxy-phenyl)-4-(4-trifluoromethyl-pyrimidin-2-ylamino)-butyl]-2,3-dihydro-isoindol-1-one, |
| 6 | 2-[(1R)-1-(3,4-dimethoxy-phenyl)-4-(4-trifluoromethyl-pyrimidin-2-ylamino)-butyl]-4-piperazin-1-yl-2,3-dihydro-isoindol-1-one, |
| 7 | thiophene-2-sulfonic acid [(4R)-4-[4-(4-cyclopropyl-piperazin-1-yl)-1-oxo-1,3-dihydro-isoindol-2-yl]-4-(3,4-dimethoxy-phenyl)-butyl]-methyl-amide, |
| 8 | thiophene-2-sulfonic acid {(4R)-4-(3,4-dimethoxy-phenyl)-4-[4-(4-isopropyl-piperazin-1-yl)-1-oxo-1,3-dihydro-isoindol-2-yl]-butyl}-methyl-amide, |
| 9 | thiophene-2-sulfonic acid [(4R)-4-[4-(4-cyclobutyl-piperazin-1-yl)-1-oxo-1,3-dihydro-isoindol-2-yl]-4-(3,4-dimethoxy-phenyl)-butyl]-methyl-amide, |
| 10 | 2-[(1R)-1-(3,4-dimethoxy-phenyl)-4-(4,6-dimethoxy-pyrimidin-2-ylamino)-butyl]-4-(4-ethyl-piperazin-1-yl)-2,3-dihydro-isoindol-1-one, |
| 11 | 2-[(1R)-4-(4-chloro-pyrimidin-2-ylamino)-1-(3,4-dimethoxy-phenyl)-butyl]-4-(4-ethyl-piperazin-1-yl)-2,3-dihydro-isoindol-1-one, |
| 12 | 2-[(1R)-1-(3,4-dimethoxy-phenyl)-4-(4,6-dimethyl-pyrimidin-2-ylamino)-butyl]-4-(4-ethyl-piperazin-1-yl)-2,3-dihydro-isoindol-1-one, |
| 14 | 2-[(1R)-1-(3,4-dimethoxy-phenyl)-4-tetrazol-1-yl-butyl]-4-(4-ethyl-piperazin-1-yl)-2,3-dihydro-isoindol-1-one, |
| 16 | thiophene-2-sulfonic acid (3-{(3,4-dimethoxy-phenyl)-[4-(4-ethyl-piperazin-1-yl)-1-oxo-1,3-dihydro-isoindol-2-yl]-methyl}-phenyl)-amide, |
| 18 | 2-{1-(3,4-dimethoxy-phenyl)-2-[1-(thiophene-2-sulfonyl)-piperidin-4-yl]-ethyl}-4-(4-ethyl-piperazin-1-yl)-2,3-dihydro-isoindol-1-one, |
| 20 | 2-[(1R)-1-(3,4-dimethoxy-phenyl)-4-(4-ethyl-pyrimidin-2-ylamino)-butyl]-4-(4-ethyl-piperazin-1-yl)-2,3-dihydro-isoindol-1-one, |
| 21 | 2-[(1R)-1-(3,4-dimethoxy-phenyl)-4-(4-methoxy-pyrimidin-2-ylamino)-butyl]-4-(4-ethyl-piperazin-1-yl)-2,3-dihydro-isoindol-1-one, |
| 22 | 2-[(1R)-1-(3,4-dimethoxy-phenyl)-4-(4-trifluoromethyl-pyrimidin-2-ylamino)-butyl]-4-(4-ethyl-piperazin-1-yl)-2,3-dihydro-isoindol-1-one, |
| 23 | 2-[(1R)-1-(3,4-dimethoxy-phenyl)-4-(4-methyl-pyrimidin-2-ylamino)-butyl]-4-(4-ethyl-piperazin-1-yl)-2,3-dihydro-isoindol-1-one, |
| 26 | thiophene-2-sulfonic acid {(4R)-4-(3,4-dimethoxy-phenyl)-4-[4-(4-methyl-piperazin-1-yl)-1-oxo-1,3-dihydro-isoindol-2-yl]-butyl}-methyl-amide, |
| 27 | 2-[(1R)-1-(3,4-dimethoxy-phenyl)-4-(4,6-dimethyl-pyrimidin-2-ylsulfanyl)-butyl]-4-(4-ethyl-piperazin-1-yl)-2,3-dihydro-isoindol-1-one, |
| 29 | 2-[(1R)-4-benzoimidazol-1-yl-1-(3,4-dimethoxy-phenyl)-butyl]-4-(4-ethyl-piperazin-1-yl)-2,3-dihydro-isoindol-1-one, |
| 30 | thiophene-2-sulfonic acid [(4R)-4-(3,4-dimethoxy-phenyl)-4-(1-oxo-4-piperazin-1-yl-1,3-dihydro-isoindol-2-yl)-butyl]-methyl-amide, |
| 31 | {(4R)-4-(3,4-dimethoxy-phenyl)-4-[4-(4-ethyl-piperazin-1-yl)-1-oxo-1,3-dihydro-isoindol-2-yl]-butylsulfanyl}-pyridine 1-oxide, |
| 32 | 2-[(1R)-1-(3,4-dimethoxy-phenyl)-4-imidazol-1-yl-butyl]-4-(4-ethyl-piperazin-1-yl)-2,3-dihydro-isoindol-1-one, |
| 36 | 2-[(1R)-1-(3,4-dimethoxy-phenyl)-4-phenylsulfanyl-butyl]-4-piperazin-1-yl-2,3-dihydro-isoindol-1-one, |
| 37 | 2-[(1R)-1-(3,4-dimethoxy-phenyl)-4-phenoxy-butyl]-4-piperazin-1-yl-2,3-dihydro-isoindol-1-one, |
| 41 | 2-[(1R)-4-benzyloxy-1-(3,4-dimethoxy-phenyl)-butyl]-4-piperazin-1-yl-2,3-dihydro-isoindol-1-one, |
| 48 | 2-[(1R)-1-(3,4-dimethoxy-phenyl)-4-(pyrimidin-2-ylamino)-butyl]-4-(4-ethyl-piperazin-1-yl)-2,3-dihydro-isoindol-1-one, |
| 49 | 2,3-dimethyl-3H-imidazole-4-sulfonic acid {(4R)-4-(3,4-dimethoxy-phenyl)-4-[4-(4-ethyl-piperazin-1-yl)-1-oxo-1,3-dihydro-isoindol-2-yl]-butyl}-amide, |
| 50 | 2-[(1R)-1-(3,4-dimethoxy-phenyl)-4-phenoxy-butyl]-4-(4-ethyl-piperazin-1-yl)-2,3-dihydro-isoindol-1-one, |
| 57 | 1-methyl-1H-imidazole-4-carboxylic acid {(4R)-4-(3,4-dimethoxy-phenyl)-4-[4-(4-ethyl-piperazin-1-yl)-1-oxo-1,3-dihydro-isoindol-2-yl]-butyl}-amide, |
| 60 | 3,5-dimethyl-1H-pyrazole-4-carboxylic acid {(4R)-4-(3,4-dimethoxy-phenyl)-4-[4-(4-ethyl-piperazin-1-yl)-1-oxo-1,3-dihydro-isoindol-2-yl]-butyl}-amide, |
| 61 | pyridazine-4-carboxylic acid {(4R)-4-(3,4-dimethoxy-phenyl)-4-[4-(4-ethyl-piperazin-1-yl)-1-oxo-1,3-dihydro-isoindol-2-yl]-butyl}-amide, |
| 62 | thiophene-2-sulfonic acid {(4R)-4-(3,4-dimethoxy-phenyl)-4-[4-(4-ethyl-piperazin-1-yl)-1-oxo-1,3-dihydro-isoindol-2-yl]-butyl}-methyl-amide, |
| 63 | 2-[(1R)-4-(bis-pyridin-4-ylmethyl-amino)-1-(3,4-dimethoxy-phenyl)-butyl]-4-(4-ethyl-piperazin-1-yl)-2,3-dihydro-isoindol-1-one, |
| 65 | thiophene-2-sulfonic acid {(4R)-4-(3,4-dimethoxy-phenyl)-4-[4-(4-isopropyl-piperazin-1-yl)-1-oxo-1,3-dihydro-isoindol-2-yl]-butyl}-amide, |
| 66 | 1-{(4R)-4-(3,4-dimethoxy-phenyl)-4-[4-(4-ethyl-piperazin-1-yl)-1-oxo-1,3-dihydro-isoindol-2-yl]-butyl}-3-phenyl-urea, |
| 67 | N-{(4R)-4-(3,4-dimethoxy-phenyl)-4-[4-(4-ethyl-piperazin-1-yl)-1-oxo-1,3-dihydro-isoindol-2-yl]-butyl}-2,2,2-trifluoro-acetamide, |
| 70 | dimethylaminosulfonic acid {(4R)-4-(3,4-dimethoxy-phenyl)-4-[4-(4-ethyl-piperazin-1-yl)-1-oxo-1,3-dihydro-isoindol-2-yl]-butyl}-amide, |
| 72 | 2-{(1R)-1-(3,4-dimethoxy-phenyl)-4-[(thiophen-2-ylmethyl)-amino]-butyl}-4-(4-ethyl-piperazin-1-yl)-2,3-dihydro-isoindol-1-one, |
| 73 | 2-[(1R)-4-dibenzylamino-1-(3,4-dimethoxy-phenyl)-butyl]-4-(4-ethyl-piperazin-1-yl)-2,3-dihydro-isoindol-1-one, |

| Cpd | Name |
|---|---|
| 74 | 2-[(1R)-4-benzyloxy-1-(3,4-dimethoxy-phenyl)-butyl]-4-(4-ethyl-piperazin-1-yl)-2,3-dihydro-isoindol-1-one, |
| 75 | 2-[(1R)-1-(3,4-dimethoxy-phenyl)-4-(2,2-dimethyl-propylamino)-butyl]-4-(4-ethyl-piperazin-1-yl)-2,3-dihydro-isoindol-1-one, |
| 76 | 3-amino-4-{(4R)-4-(3,4-dimethoxy-phenyl)-4-[4-(4-ethyl-piperazin-1-yl)-1-oxo-1,3-dihydro-isoindol-2-yl]-butylamino}-cyclobut-3-ene-1,2-dione, |
| 77 | 2-[(1R)-4-benzylamino-1-(3,4-dimethoxy-phenyl)-butyl]-4-(4-ethyl-piperazin-1-yl)-2,3-dihydro-isoindol-1-one, |
| 78 | furan-2-carboxylic acid {(4R)-4-(3,4-dimethoxy-phenyl)-4-[4-(4-ethyl-piperazin-1-yl)-1-oxo-1,3-dihydro-isoindol-2-yl]-butyl}-amide, |
| 79 | 1H-pyrazole-4-carboxylic acid {(4R)-4-(3,4-dimethoxy-phenyl)-4-[4-(4-ethyl-piperazin-1-yl)-1-oxo-1,3-dihydro-isoindol-2-yl]-butyl}-amide, |
| 80 | cyclobutanecarboxylic acid {(4R)-4-(3,4-dimethoxy-phenyl)-4-[4-(4-ethyl-piperazin-1-yl)-1-oxo-1,3-dihydro-isoindol-2-yl]-butyl}-amide, |
| 81 | thiophene-2-carboxylic acid {(4R)-4-(3,4-dimethoxy-phenyl)-4-[4-(4-ethyl-piperazin-1-yl)-1-oxo-1,3-dihydro-isoindol-2-yl]-butyl}-amide, |
| 82 | 1,2-dimethyl-1H-imidazole-4-sulfonic acid {(4R)-4-(3,4-dimethoxy-phenyl)-4-[4-(4-ethyl-piperazin-1-yl)-1-oxo-1,3-dihydro-isoindol-2-yl]-butyl}-amide, |
| 83 | N-{(4R)-4-(3,4-dimethoxy-phenyl)-4-[4-(4-ethyl-piperazin-1-yl)-1-oxo-1,3-dihydro-isoindol-2-yl]-butyl}-2,2-dimethyl-propionamide, |
| 84 | thiophene-2-sulfonic acid {(4R)-4-(3,4-dimethoxy-phenyl)-4-[4-(4-ethyl-piperazin-1-yl)-1-oxo-1,3-dihydro-isoindol-2-yl]-butyl}-amide, |
| 85 | 5-methyl-isoxazole-4-carboxylic acid ((4R)-4-(3,4-dimethoxy-phenyl)-4-{1-oxo-4-[4-(1-phenyl-ethyl)-piperazin-1-yl]-1,3-dihydro-isoindol-2-yl}-butyl)-amide, |
| 87 | 2-[(1R)-1-(3,4-dimethoxy-phenyl)-4-phenyl-butyl]-4-(4-ethyl-piperazin-1-yl)-2,3-dihydro-isoindol-1-one, |
| 88 | N-{(4R)-4-(3,4-dimethoxy-phenyl)-4-[4-(4-ethyl-piperazin-1-yl)-1-oxo-1,3-dihydro-isoindol-2-yl]-butyl}-N-(4-fluoro-benzyl)-acetamide, |
| 90 | 2-[(1R)-4-[cyclopropyl-(4-fluoro-benzyl)-amino]-1-(3,4-dimethoxy-phenyl)-butyl]-4-(4-ethyl-piperazin-1-yl)-2,3-dihydro-isoindol-1-one, |
| 91 | 2-[(1R)-1-(3,4-dimethoxy-phenyl)-4-(4-fluoro-benzylamino)-butyl]-4-(4-ethyl-piperazin-1-yl)-2,3-dihydro-isoindol-1-one, |
| 94 | 2-[(1R)-1-(3,4-dimethoxy-phenyl)-4-(furan-2-ylmethyl-methyl-amino)-butyl]-4-(4-ethyl-piperazin-1-yl)-2,3-dihydro-isoindol-1-one, |
| 95 | 2-[(1R)-1-(3,4-dimethoxy-phenyl)-4-(methyl-thiophen-2-ylmethyl-amino)-butyl]-4-(4-ethyl-piperazin-1-yl)-2,3-dihydro-isoindol-1-one, |
| 96 | 2-[(1R)-4-(benzyl-isopropyl-amino)-1-(3,4-dimethoxy-phenyl)-butyl]-4-(4-ethyl-piperazin-1-yl)-2,3-dihydro-isoindol-1-one, |
| 97 | 2-{(1R)-1-(3,4-dimethoxy-phenyl)-4-[(2-fluoro-benzyl)-methyl-amino]-butyl}-4-(4-ethyl-piperazin-1-yl)-2,3-dihydro-isoindol-1-one, |
| 98 | 2-{(1R)-1-(3,4-dimethoxy-phenyl)-4-[(3-fluoro-benzyl)-methyl-amino]-butyl}-4-(4-ethyl-piperazin-1-yl)-2,3-dihydro-isoindol-1-one, |
| 99 | 2-{(1R)-1-(3,4-dimethoxy-phenyl)-4-[(4-fluoro-benzyl)-methyl-amino]-butyl}-4-(4-ethyl-piperazin-1-yl)-2,3-dihydro-isoindol-1-one, |
| 100 | 2-[(1R)-4-(1,3-dihydro-isoindol-2-yl)-1-(3,4-dimethoxy-phenyl)-butyl]-4-(4-ethyl-piperazin-1-yl)-2,3-dihydro-isoindol-1-one, |
| 101 | 2-[(1R)-4-(3,4-dihydro-1H-isoquinolin-2-yl)-1-(3,4-dimethoxy-phenyl)-butyl]-4-(4-ethyl-piperazin-1-yl)-2,3-dihydro-isoindol-1-one, and |
| 104 | 2-[(1R)-1-(3,4-dimethoxy-phenyl)-4-(2-isopropyl-imidazol-1-yl)-butyl]-4-(4-ethyl-piperazin-1-yl)-2,3-dihydro-isoindol-1-one. |

Embodiment 19 of the present invention is directed to compounds of Formula (I) or a form thereof as described herein selected from the group consisting of:

| Cpd | Name |
|---|---|
| 1 | dimethylaminosulfonic acid {(4R)-4-(3,4-dimethoxy-phenyl)-4-[4-(4-ethyl-piperazin-1-yl)-1-oxo-1,3-dihydro-isoindol-2-yl]-butyl}-methyl-amide, |
| 3 | 2-[(1R)-4-(benzyl-methyl-amino)-1-(3,4-dimethoxy-phenyl)-butyl]-4-(4-ethyl-piperazin-1-yl)-2,3-dihydro-isoindol-1-one, |
| 6 | 2-[(1R)-1-(3,4-dimethoxy-phenyl)-4-(4-trifluoromethyl-pyrimidin-2-ylamino)-butyl]-4-piperazin-1-yl-2,3-dihydro-isoindol-1-one, |
| 8 | thiophene-2-sulfonic acid {(4R)-4-(3,4-dimethoxy-phenyl)-4-[4-(4-isopropyl-piperazin-1-yl)-1-oxo-1,3-dihydro-isoindol-2-yl]-butyl}-methyl-amide, |
| 9 | thiophene-2-sulfonic acid [(4R)-4-[4-(4-cyclobutyl-piperazin-1-yl)-1-oxo-1,3-dihydro-isoindol-2-yl]-4-(3,4-dimethoxy-phenyl)-butyl]-methyl-amide, |
| 10 | 2-[(1R)-1-(3,4-dimethoxy-phenyl)-4-(4,6-dimethoxy-pyrimidin-2-ylamino)-butyl]-4-(4-ethyl-piperazin-1-yl)-2,3-dihydro-isoindol-1-one, |
| 11 | 2-[(1R)-4-(4-chloro-pyrimidin-2-ylamino)-1-(3,4-dimethoxy-phenyl)-butyl]-4-(4-ethyl-piperazin-1-yl)-2,3-dihydro-isoindol-1-one, |
| 18 | 2-{1-(3,4-dimethoxy-phenyl)-2-[1-(thiophene-2-sulfonyl)-piperidin-4-yl]-ethyl}-4-(4-ethyl-piperazin-1-yl)-2,3-dihydro-isoindol-1-one, |
| 21 | 2-[(1R)-1-(3,4-dimethoxy-phenyl)-4-(4-methoxy-pyrimidin-2-ylamino)-butyl]-4-(4-ethyl-piperazin-1-yl)-2,3-dihydro-isoindol-1-one, |
| 22 | 2-[(1R)-1-(3,4-dimethoxy-phenyl)-4-(4-trifluoromethyl-pyrimidin-2-ylamino)-butyl]-4-(4-ethyl-piperazin-1-yl)-2,3-dihydro-isoindol-1-one, |
| 26 | thiophene-2-sulfonic acid {(4R)-4-(3,4-dimethoxy-phenyl)-4-[4-(4-methyl-piperazin-1-yl)-1-oxo-1,3-dihydro-isoindol-2-yl]-butyl}-methyl-amide, |
| 27 | 2-[(1R)-1-(3,4-dimethoxy-phenyl)-4-(4,6-dimethyl-pyrimidin-2-ylsulfanyl)-butyl]-4-(4-ethyl-piperazin-1-yl)-2,3-dihydro-isoindol-1-one, |
| 49 | 2,3-dimethyl-3H-imidazole-4-sulfonic acid {(4R)-4-(3,4-dimethoxy-phenyl)-4-[4-(4-ethyl-piperazin-1-yl)-1-oxo-1,3-dihydro-isoindol-2-yl]-butyl}-amide, |
| 50 | 2-[(1R)-1-(3,4-dimethoxy-phenyl)-4-phenoxy-butyl]-4-(4-ethyl-piperazin-1-yl)-2,3-dihydro-isoindol-1-one, |
| 62 | thiophene-2-sulfonic acid {(4R)-4-(3,4-dimethoxy-phenyl)-4-[4-(4-ethyl-piperazin-1-yl)-1-oxo-1,3-dihydro-isoindol-2-yl]-butyl}-methyl-amide, |
| 63 | 2-[(1R)-4-(bis-pyridin-4-ylmethyl-amino)-1-(3,4-dimethoxy-phenyl)-butyl]-4-(4-ethyl-piperazin-1-yl)-2,3-dihydro-isoindol-1-one, |
| 65 | thiophene-2-sulfonic acid {(4R)-4-(3,4-dimethoxy-phenyl)-4-[4-(4-isopropyl-piperazin-1-yl)-1-oxo-1,3-dihydro-isoindol-2-yl]-butyl}-amide, |
| 70 | dimethylaminosulfonic acid {(4R)-4-(3,4-dimethoxy-phenyl)-4-[4-(4-ethyl-piperazin-1-yl)-1-oxo-1,3-dihydro-isoindol-2-yl]-butyl}-amide, |
| 72 | 2-{(1R)-1-(3,4-dimethoxy-phenyl)-4-[(thiophen-2-ylmethyl)-amino]-butyl}-4-(4-ethyl-piperazin-1-yl)-2,3-dihydro-isoindol-1-one, |
| 74 | 2-[(1R)-4-benzyloxy-1-(3,4-dimethoxy-phenyl)-butyl]-4-(4-ethyl-piperazin-1-yl)-2,3-dihydro-isoindol-1-one, |
| 77 | 2-[(1R)-4-benzylamino-1-(3,4-dimethoxy-phenyl)-butyl]-4-(4-ethyl-piperazin-1-yl)-2,3-dihydro-isoindol-1-one, |
| 79 | 1H-pyrazole-4-carboxylic acid {(4R)-4-(3,4-dimethoxy-phenyl)-4-[4-(4-ethyl-piperazin-1-yl)-1-oxo-1,3-dihydro-isoindol-2-yl]-butyl}-amide, |
| 81 | thiophene-2-carboxylic acid {(4R)-4-(3,4-dimethoxy-phenyl)-4-[4-(4-ethyl-piperazin-1-yl)-1-oxo-1,3-dihydro-isoindol-2-yl]-butyl}-amide, |
| 84 | thiophene-2-sulfonic acid {(4R)-4-(3,4-dimethoxy-phenyl)-4-[4-(4-ethyl-piperazin-1-yl)-1-oxo-1,3-dihydro-isoindol-2-yl]-butyl}-amide, |
| 85 | 5-methyl-isoxazole-4-carboxylic acid ((4R)-4-(3,4-dimethoxy-phenyl)-4-{1-oxo-4-[4-(1-phenyl-ethyl)-piperazin-1-yl]-1,3-dihydro-isoindol-2-yl}-butyl)-amide, |
| 87 | 2-[(1R)-1-(3,4-dimethoxy-phenyl)-4-phenyl-butyl]-4-(4-ethyl-piperazin-1-yl)-2,3-dihydro-isoindol-1-one, |

-continued

| Cpd | Name |
|---|---|
| 88 | N-{(4R)-4-(3,4-dimethoxy-phenyl)-4-[4-(4-ethyl-piperazin-1-yl)-1-oxo-1,3-dihydro-isoindol-2-yl]-butyl}-N-(4-fluoro-benzyl)-acetamide, |
| 90 | 2-[(1R)-4-[cyclopropyl-(4-fluoro-benzyl)-amino]-1-(3,4-dimethoxy-phenyl)-butyl]-4-(4-ethyl-piperazin-1-yl)-2,3-dihydro-isoindol-1-one, |
| 91 | 2-[(1R)-1-(3,4-dimethoxy-phenyl)-4-(4-fluoro-benzylamino)-butyl]-4-(4-ethyl-piperazin-1-yl)-2,3-dihydro-isoindol-1-one, |
| 94 | 2-[(1R)-1-(3,4-dimethoxy-phenyl)-4-(furan-2-ylmethyl-methyl-amino)-butyl]-4-(4-ethyl-piperazin-1-yl)-2,3-dihydro-isoindol-1-one, |
| 95 | 2-[(1R)-1-(3,4-dimethoxy-phenyl)-4-(methyl-thiophen-2-ylmethyl-amino)-butyl]-4-(4-ethyl-piperazin-1-yl)-2,3-dihydro-isoindol-1-one, |
| 97 | 2-{(1R)-1-(3,4-dimethoxy-phenyl)-4-[(2-fluoro-benzyl)-methyl-amino]-butyl}-4-(4-ethyl-piperazin-1-yl)-2,3-dihydro-isoindol-1-one, |
| 98 | 2-{(1R)-1-(3,4-dimethoxy-phenyl)-4-[(3-fluoro-benzyl)-methyl-amino]-butyl}-4-(4-ethyl-piperazin-1-yl)-2,3-dihydro-isoindol-1-one, |
| 99 | 2-{(1R)-1-(3,4-dimethoxy-phenyl)-4-[(4-fluoro-benzyl)-methyl-amino]-butyl}-4-(4-ethyl-piperazin-1-yl)-2,3-dihydro-isoindol-1-one, |
| 100 | 2-[(1R)-4-(1,3-dihydro-isoindol-2-yl)-1-(3,4-dimethoxy-phenyl)-butyl]-4-(4-ethyl-piperazin-1-yl)-2,3-dihydro-isoindol-1-one, and |
| 101 | 2-[(1R)-4-(3,4-dihydro-1H-isoquinolin-2-yl)-1-(3,4-dimethoxy-phenyl)-butyl]-4-(4-ethyl-piperazin-1-yl)-2,3-dihydro-isoindol-1-one. |

Embodiment 20 of the present invention is directed to compounds of Formula (I) or a form thereof as described herein selected from the group consisting of:

| Cpd | Name |
|---|---|
| 74 | 2-[(1R)-4-benzyloxy-1-(3,4-dimethoxy-phenyl)-butyl]-4-(4-ethyl-piperazin-1-yl)-2,3-dihydro-isoindol-1-one, |
| 84 | thiophene-2-sulfonic acid {(4R)-4-(3,4-dimethoxy-phenyl)-4-[4-(4-ethyl-piperazin-1-yl)-1-oxo-1,3-dihydro-isoindol-2-yl]-butyl}-amide, and |
| 87 | 2-[(1R)-1-(3,4-dimethoxy-phenyl)-4-phenyl-butyl]-4-(4-ethyl-piperazin-1-yl)-2,3-dihydro-isoindol-1-one. |

Compound Definitions

As used herein, with reference to substituents, the term "independently" means that when more than one of such substituent is possible, such substituents may be the same or different from each other.

The term "$C_{1-8}$alkyl" means a straight or branched chain hydrocarbon alkyl radical or alkyldiyl linking group, respectively, comprising from 1 to 8 carbon atoms, wherein the radical is derived by the removal of one hydrogen atom from a single carbon atom and the alkyldiyl linking group is derived by the removal of one hydrogen atom from each of two carbon atoms in the chain. Examples include methyl, ethyl, 1-propyl, 2-propyl, 1-butyl, 2-butyl, tertiary butyl (also referred to as t-butyl or tert-butyl), 1-pentyl, 2-pentyl, 3-pentyl, 1-hexyl, 2-hexyl, 3-hexyl and the like. Other examples include $C_{1-4}$alkyl groups. $C_{1-8}$alkyl is substituted on one or more available carbon chain atoms with one or more substituents where allowed by available valences.

The term "$C_{1-8}$alkylene" means a biradical substituent formed from an alkyl group, as defined herein, in which the biradical is formed by the removal of two hydrogen atoms.

The terms "$C_{2-8}$alkenyl" and "$C_{2-8}$alkynyl" mean straight or branched carbon chains having 2 to 8 carbon atoms or any number within this range, wherein a $C_{2-8}$alkenyl chain has at least one double bond in the chain and a $C_{2-8}$alkynyl chain has at least one triple bond in the chain.

The term "$C_{1-8}$alkoxy" means a straight or branched chain hydrocarbon alkyl radical or alkyldiyl linking group of the formula —O—$C_{1-8}$alkyl, comprising from 1 to 8 carbon atoms, wherein the alkyldiyl linking group is derived by the removal of one hydrogen atom from a carbon atom in the chain. Examples include methoxy, ethoxy, propoxy and the like. Other examples include $C_{1-4}$alkoxy and $C_{2-3}$alkenyloxy groups. $C_{1-8}$alkoxy is substituted on one or more available carbon chain atoms with one or more substituents where allowed by available valences.

The term "$C_{3-14}$cycloalkyl" means a saturated or partially unsaturated, monocyclic or polycyclic hydrocarbon ring system radical derived by the removal of one hydrogen atom from a single ring carbon atom. The term also includes $C_{3-8}$cycloalkyl, $C_{3-10}$cycloalkyl, $C_{5-6}$cycloalkyl, $C_{5-8}$cycloalkyl, $C_{5-12}$cycloalkyl, $C_{9-13}$ cycloalkyl, $C_{5-14}$cycloalkenyl or benzofused $C_{3-14}$cycloalkyl ring systems. Examples include cyclopropyl, cyclobutyl, cyclopentyl, cyclohexyl, cyclohexenyl, cycloheptyl, cyclooctyl, 1H-indenyl, indanyl, 9H-fluorenyl, tetrahydro-naphthalenyl, acenaphthenyl, adamantanyl, bicyclo[2.2.1]heptenyl and the like. $C_{3-14}$cycloalkyl radicals may be attached to a core molecule and further substituted on any atom where allowed by available valences.

The term "aryl" means monocyclic or bicyclic aromatic ring systems containing from 6 to 12 carbons in the ring. Examples include phenyl, biphenyl, naphthalene (also referred to as naphthalenyl and naphthyl), azulenyl, anthracenyl and the like. Aryl radicals may be attached to a core molecule and further substituted on any atom where allowed by available valences.

The term "hetero," when used as a prefix for a ring system, refers to the replacement of at least one carbon atom member in the ring system with a heteroatom selected from N, O, S, S(O), or $SO_2$. A hetero ring may have 1, 2, 3, or 4 carbon atom members replaced by a nitrogen atom. Alternatively, a ring may have 0, 1, 2, or 3 nitrogen atom members and 1 oxygen or sulfur atom member. Alternatively, up to two adjacent ring members may be heteroatoms, wherein one heteroatom is nitrogen and the other heteroatom is selected from N, S, or O.

The term "heterocyclyl" means a saturated or partially unsaturated monocyclic or polycyclic "hetero" ring system radical having a cycloalkyl ring as the core molecule. Heterocyclyl ring systems include 2H-pyrrole, 2-pyrrolinyl, 3-pyrrolinyl, pyrrolidinyl, 1,3-dioxolanyl, 2-imidazolinyl (also referred to as 4,5-dihydro-1H-imidazolyl), imidazolidinyl, 2-pyrazolinyl, pyrazolidinyl, tetrazolidinyl, piperidinyl, 1,4-dioxanyl, morpholinyl, 1,4-dithianyl, thiomorpholinyl, piperazinyl, azetidinyl, azepanyl, hexahydro-1,4-diazepinyl, hexahydro-1,4-oxazepanyl, tetrahydro-furanyl, tetrahydro-thienyl, tetrahydro-pyranyl, tetrahydro-pyridazinyl and the like.

The term "heterocyclyl" also includes a benzofused-heterocyclyl ring system radical and the like, such as indolinyl (also referred to as 2,3-dihydro-indolyl), benzo[1,3]dioxolyl (also referred to as 1,3-benzodioxolyl), 2,3-dihydro-1,4-benzodioxinyl, 2,3-dihydro-benzofuranyl, 1,2-dihydro-phthalazinyl and the like. Heterocyclyl radicals may be attached to a core molecule and further substituted on any atom where allowed by available valences.

The term "heteroaryl" means an aromatic monocyclic or polycyclic heterocyclyl radical. Heteroaryl ring systems include furanyl, thienyl, pyrrolyl, oxazolyl, thiazolyl, 1H-imidazolyl, pyrazolyl, isoxazolyl, isothiazolyl, oxadiazolyl, triazolyl, thiadiazolyl, 1H-tetrazolyl, 2H-tetrazolyl, 1H-

[1,2,3]triazolyl, 2H-[1,2,3]triazolyl, 4H-[1,2,4]triazolyl, pyridinyl, pyridazinyl, pyrimidinyl, pyrazinyl and the like. Heteroaryl radicals may be attached to a core molecule and further substituted on any atom where allowed by available valences.

The term "heteroaryl" also includes a benzofused-heteroaryl ring system radical and the like, such as indolizinyl, indolyl, indolinyl, azaindolyl, isoindolyl, benzo[b]furanyl, benzo[b]thienyl, indazolyl, azaindazolyl, benzoimidazolyl, benzothiazolyl, benzooxazolyl, benzoisoxazolyl, benzothiadiazolyl, benzotriazolyl, purinyl, 4H-quinolizinyl, quinolinyl, isoquinolinyl, cinnolinyl, phthalazinyl, quinazolinyl, quinoxalinyl, 1,8-naphthyridinyl, pteridinyl and the like. Benzofused-heteroaryl radicals may be attached to a core molecule and further substituted on any atom where allowed by available valences.

The term "benzofused," when used as a prefix for a ring system, refers to a radical formed by any monocyclic radical fused with a benzene ring; the benzofused radical may be attached to a core molecule via either ring of the bicyclic system.

The term "$C_{1-8}$alkoxycarbonyl" means a radical of the formula: —C(O)—O—$C_{1-8}$alkyl. Examples include $C_{1-6}$alkoxycarbonyl.

The term "($C_{1-8}$alkoxycarbonyl)amino" means a radical of the formula: —NH—C(O)—O—$C_{1-8}$alkyl. Examples include ($C_{1-6}$alkoxycarbonyl)amino. The term "($C_{1-6}$alkoxy-$C_{1-6}$alkylcarbonyl)amino" means a radical of the formula: —NH—C(O)—$C_{1-6}$alkyl-O—$C_{1-6}$alkyl.

The term "($C_{1-8}$alkyl)amino" means a radical of the formula: —NH—$C_{1-8}$alkyl. Examples include ($C_{1-3}$alkyl)amino.

The term "di($C_{1-8}$alkyl)amino" means a radical of the formula: —N($C_{1-8}$alkyl)$_2$. Examples include di($C_{1-3}$alkyl)amino.

The term "$C_{1-8}$alkylcarbonyl" means a radical of the formula: —C(O)—$C_{1-8}$alkyl. Examples include $C_{1-3}$alkylcarbonyl.

The term "$C_{1-8}$alkylthio" means a radical of the formula: —S—$C_{1-18}$alkyl.

The term "($C_{1-8}$alkylcarbonyl)amino" means a radical of the formula: —NH—C(O)—$C_{1-8}$alkyl. Examples include ($C_{1-6}$alkylcarbonyl)amino and ($C_{1-3}$alkylcarbonyl)amino.

The term "(amino-$C_{1-8}$alkylcarbonyl)amino" means a radical of the formula: —NH—C(O)—$C_{1-8}$alkyl-NH$_2$. Examples include ($C_{1-6}$alkylcarbonyl)amino and ($C_{1-3}$alkylcarbonyl)amino.

The term "[($C_{1-6}$alkyl)amino-$C_{1-6}$alkylcarbonyl]amino" means a radical of the formula: —NH—C(O)—$C_{1-6}$alkyl-NH—$C_{1-6}$alkyl.

The term "[di($C_{1-6}$alkyl)amino-$C_{1-6}$alkylcarbonyl]amino" means a radical of the formula: —NH—C(O)—$C_{1-6}$alkyl-N($C_{1-6}$alkyl)$_2$.

The term "$C_{1-6}$alkylcarbonyl-acetonitrile-carbonyl)amino" means a radical of the formula: —NH—C(O)—CH(CN)C(O)$C_{1-6}$alkyl.

The term "$C_{1-6}$alkylsulfonyl" means a radical of the formula: —SO$_2$—$C_{1-6}$alkyl.

The term "($C_{1-6}$alkylsulfonyl)amino" means a radical of the formula: —NH—SO$_2$—$C_{1-6}$alkyl.

The term "($C_{1-6}$alkylsulfonyl-$C_{1-6}$alkylsulfonyl)amino" means a radical of the formula: —NH—SO$_2$—$C_{1-6}$alkyl-SO$_2$—$C_{1-6}$alkyl.

The term "($C_{2-6}$alkenyl-sulfonyl)amino" means a radical of the formula: —NH—SO$_2$—$C_{2-6}$alkenyl.

The term "amino" means a radical of the formula: —NH$_2$.

The term "($C_{1-6}$alkyl)amino" means a radical of the formula: —NH—$C_{1-6}$alkyl. Examples include ($C_{1-4}$)alkylamino.

The term "di($C_{1-6}$alkyl)amino" means a radical of the formula: —N($C_{1-6}$alkyl)$_2$. Examples include di($C_{1-4}$)alkylamino.

The term "aminocarbonyl" means a radical of the formula: —C(O)—NH$_2$.

The term "aminocarbonyloxy" means a radical of the formula: —O—C(O)—NH$_2$.

The term "aminocarbonyl-$C_{1-6}$alkoxy" means a radical of the formula: —O—$C_{1-6}$alkyl-C(O)—NH$_2$.

The term "($C_{1-6}$alkyl)aminocarbonyl" means a radical of the formula: —C(O)—NH—$C_{1-6}$alkyl. Examples include ($C_{1-4}$)alkylaminocarbonyl.

The term "di($C_{1-6}$alkyl)aminocarbonyl" means a radical of the formula: —C(O)—N($C_{1-6}$alkyl)$_2$. Examples include di($C_{1-4}$)alkylaminocarbonyl.

The term "aminosulfonyl" means a radical of the formula: —SO$_2$—NH$_2$.

The term "($C_{1-6}$alkyl)aminosulfonyl" means a radical of the formula: —SO$_2$—NH—$C_{1-6}$alkyl. Examples include ($C_{1-4}$ alkyl)aminosulfonyl.

The term "di($C_{1-6}$alkyl)aminosulfonyl" means a radical of the formula: —SO$_2$—N($C_{1-6}$alkyl)$_2$. Examples include di($C_{1-4}$alkyl)aminosulfonyl.

The term "aminosulfonylamino" means a radical of the formula: —NH—SO$_2$—NH$_2$.

The term "($C_{1-6}$alkyl)aminosulfonylamino" means a radical of the formula: —NH—SO$_2$—NH—$C_{1-6}$alkyl. Examples include ($C_{1-4}$alkyl)aminosulfonylamino.

The term "di($C_{1-6}$alkyl)aminosulfonylamino" means a radical of the formula: —NH—SO$_2$—N($C_{1-6}$alkyl)$_2$. Examples include di($C_{1-4}$alkyl)aminosulfonylamino.

The term "aminosulfonyloxy" means a radical of the formula: —O—SO$_2$—NH$_2$.

The term "($C_{1-6}$alkyl)aminosulfonyloxy" means a radical of the formula: —O—SO$_2$—NH—$C_{1-6}$alkyl. Examples include ($C_{1-4}$alkyl)aminosulfonyloxy.

The term "di($C_{1-6}$alkyl)aminosulfonyloxy" means a radical of the formula: —O—SO$_2$—N($C_{1-6}$alkyl)$_2$. Examples include di($C_{1-4}$alkyl)aminosulfonyloxy.

The term "(benzyl)amino" means a radical of the formula: —NH—CH$_2$-phenyl.

The term "[(benzyl)($C_{1-4}$alkyl)]amino" means a radical of the formula: —N($C_{1-4}$alkyl)-CH$_2$-phenyl.

The term "carboxy" means a radical of the formula: —C(O)OH.

The term "carboxy-$C_{1-8}$alkoxy" means a radical of the formula: —O—$C_{1-8}$alkyl-C(O)OH. Examples include carboxy-$C_{1-6}$alkoxy.

The term "aryl-$C_{1-6}$alkyl" means a radical of the formula: —$C_{1-6}$alkyl-aryl.

The term "aryl-sulfonyl" means a radical of the formula: —SO$_2$-aryl.

The term "heterocyclyloxy" means a radical of the formula: —O-heterocyclyl.

The term "heteroaryl-sulfonyl" means a radical of the formula: —SO$_2$-heteroaryl.

The term "oxy" means a radical of the formula: —O—.

The term "ureido" mean a radical of the formula: —NH—C(O)—NH$_2$; also referred to as "aminocarbonylamino."

The term "thioureido" means a radical of the formula: —NH—C(S)—NH$_2$.

The term "acetamidino" means a radical of the formula: —C(NH)—NH$_2$.

The term "guanidino" means a radical of the formula: —NH—C(NH)—NH$_2$.

The term "halogen" or "halo" means the group chloro, bromo, fluoro or iodo. Substituents that are substituted with multiple halogens are substituted in a manner that provides compounds, which are stable.

The term "trihalo-C$_{1-4}$alkyl" means a radical of the formula: —C$_{1-4}$alkyl(halo)$_3$, wherein one or more halogen atoms may be substituted on C$_{1-4}$alkyl where allowed by available valences.

The term "trihalo-C$_{1-4}$alkoxy" means a radical of the formula: —O—C$_{1-4}$alkyl(halo)$_3$, wherein one or more halogen atoms may be substituted on C$_{1-4}$alkyl where allowed by available valences.

The term "fluorinated (C$_{1-4}$)alkoxy" means a radical of the formula: —O—C$_{1-4}$alkyl(fluoro)$_3$, where n represents one or more halogen atoms substituted on C$_{1-4}$alkyl where allowed by available valences.

The term "(trihalo-C$_{1-4}$alkylcarbonyl)amino" means a radical of the formula: —NH—C(O)—C$_{1-4}$alkyl(halo)$_3$, wherein one or more halogen atoms may be substituted on C$_{1-4}$alkyl where allowed by available valences.

The term "hydroxysulfonyl" means a radical of the formula: —SO$_2$—OH.

The term "(hydroxysulfonyl)amino" means a radical of the formula: —NH—SO$_2$—OH.

Whenever the term "alkyl" or "aryl" or either of their prefix roots appear in a name of a substituent (e.g., arylalkyl, alkylamino) it shall be interpreted as including those limitations given above for "alkyl" and "aryl." Designated numbers of carbon atoms (e.g., C$_1$-C$_6$) shall refer independently to the number of carbon atoms in an alkyl moiety or to the alkyl portion of a larger substituent in which alkyl appears as its prefix root. For alkyl, and alkoxy substituents, the designated number of carbon atoms includes all of the independent members included in the range specified individually and all the combination of ranges within the range specified. For example, C$_{1-6}$ alkyl would include methyl, ethyl, propyl, butyl, pentyl and hexyl individually as well as sub-combinations thereof (e.g. C$_{1-2}$, C$_{1-3}$, C$_{1-4}$, C$_{1-5}$, C$_{2-6}$, C$_{3-6}$, C$_{4-6}$, C$_{5-6}$, C$_{2-5}$, etc.).

In general, under standard nomenclature rules used throughout this disclosure, the terminal portion of the designated side chain is described first followed by the adjacent functionality toward the point of attachment.

Thus, for example, a "phenyl-C$_{1-6}$alkyl-amino-carbonyl-C$_{1-6}$alkyl" substituent refers to a group of the formula:

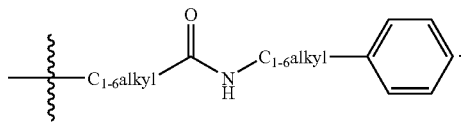

It is intended that the definition of any substituent or variable at a particular location in a molecule be independent of its definitions elsewhere in that molecule. It is understood that substituents and substitution patterns on the compounds of this invention can be selected by one of ordinary skill in the art to provide compounds that are chemically stable and that can be readily synthesized by techniques known in the art as well as those methods set forth herein.

Compound Forms

The term "form" means, in reference to compounds of the present invention, such may exist as, without limitation, a salt, stereoisomer, tautomer, crystalline, polymorph, amorphous, solvate, hydrate, ester, prodrug or metabolite form. The present invention encompasses all such compound forms and mixtures thereof.

The term "isolated form" means, in reference to compounds of the present invention, such may exist in an essentially pure state such as, without limitation, an enantiomer, a racemic mixture, a geometric isomer (such as a cis or trans stereoisomer), a mixture of geometric isomers, and the like. The present invention encompasses all such compound forms and mixtures thereof.

Certain compounds of Formula (I) or Formula (Ia) may exist in various stereoisomeric or tautomeric forms and mixtures thereof. The invention encompasses all such compounds, including active compounds in the form of essentially pure enantiomers, racemic mixtures and tautomers.

The compounds of the present invention may be present in the form of pharmaceutically acceptable salts. For use in medicines, the "pharmaceutically acceptable salts" of the compounds of this invention refer to non-toxic acidic/anionic or basic/cationic salt forms.

Suitable pharmaceutically acceptable salts of the compounds of this invention include acid addition salts which may, for example, be formed by mixing a solution of the compound according to the invention with a solution of a pharmaceutically acceptable acid such as hydrochloric acid, sulphuric acid, fumaric acid, maleic acid, succinic acid, acetic acid, benzoic acid, citric acid, tartaric acid, carbonic acid or phosphoric acid.

Furthermore, when the compounds of the present invention carry an acidic moiety, suitable pharmaceutically acceptable salts thereof may include alkali metal salts, e.g. sodium or potassium salts; alkaline earth metal salts, e.g. calcium or magnesium salts; and salts formed with suitable organic ligands, e.g. quaternary ammonium salts. Thus, representative pharmaceutically acceptable salts include the following: acetate, benzenesulfonate, benzoate, bicarbonate, bisulfate, bitartrate, borate, bromide, calcium, camsylate (or camphorsulphonate), carbonate, chloride, clavulanate, citrate, dihydrochloride, edetate, fumarate, gluconate, glutamate, hydrabamine, hydrobromine, hydrochloride, iodide, isothionate, lactate, malate, maleate, mandelate, mesylate, nitrate, oleate, pamoate, palmitate, phosphate/diphosphate, salicylate, stearate, sulfate, succinate, tartrate, tosylate.

The present invention includes within its scope prodrugs of the compounds of this invention. In general, such prodrugs will be functional derivatives of the compounds that are readily convertible in vivo into the required compound. Thus, in the methods of treatment of the present invention, the term "administering" shall encompass the treatment of the various disorders described with the compound specifically disclosed or with a compound which may not be specifically disclosed, but which converts to the specified compound in vivo after administration to the patient. Conventional procedures for the selection and preparation of suitable prodrug derivatives are described, for example, in "Design of Prodrugs", ed. H. Bundgaard, Elsevier, 1985.

The invention includes compounds of various isomers and mixtures thereof. The term "isomer" refers to compounds that have the same composition and molecular weight but differ in physical and/or chemical properties. Such substances have the same number and kind of atoms but differ in structure. The structural difference may be in constitution (geometric isomers) or in an ability to rotate the plane of polarized light (stereoisomers).

The term "optical isomer" means isomers of identical constitution that differ only in the spatial arrangement of their groups. Optical isomers rotate the plane of polarized light in different directions. The term "optical activity" means the degree to which an optical isomer rotates the plane of polarized light.

The term "racemate" or "racemic mixture" means an equimolar mixture of two enantiomeric species, wherein each of the isolated species rotates the plane of polarized light in the opposite direction such that the mixture is devoid of optical activity.

The term "enantiomer" means an isomer having a nonsuperimposable mirror image. The term "diastereomer" means stereoisomers that are not enantiomers.

The term "chiral" means a molecule which, in a given configuration, cannot be superimposed on its mirror image. This is in contrast to achiral molecules which can be superimposed on their mirror images.

The invention is considered to include the tautomeric forms of all compounds of Formula (I) or Formula (Ia). In addition, for chiral embodiments of the invention, the invention is considered to include pure enantiomers, racemic mixtures, as well as mixtures of enantiomers having 0.001% to 99.99% enantiomeric excess. In addition, some of the compounds represented by Formula (I) or Formula (Ia) may be prodrugs, i.e., derivatives of a drug that possess superior delivery capabilities and therapeutic value as compared to the active drug. Prodrugs are transformed into active drugs by in vivo enzymatic or chemical processes.

The two distinct mirror image versions of the chiral molecule are also known as levo (left-handed), abbreviated L, or dextro (right handed), abbreviated D, depending on which way they rotate polarized light. The symbols "R" and "S" represent the configuration of groups around a stereogenic carbon atom(s).

An example of an enantiomerically enriched form isolated from a racemic mixture includes a dextrorotatory enantiomer, wherein the mixture is substantially free of the levorotatory isomer. In this context, substantially free means the levorotatory isomer may, in a range, comprise less than 25% of the mixture, less than 10%, less than 5%, less than 2% or less than 1% of the mixture according to the formula:

$$\% \text{ levorotatory} = \frac{(\text{mass levorotatory})}{(\text{mass dextrorotatory}) + (\text{mass levorotatory})} \times 100$$

Similarly, an example of an enantiomerically enriched form isolated from a racemic mixture includes a levorotatory enantiomer, wherein the mixture is substantially free of the dextrorotatory isomer. In this context, substantially free means the dextrorotatory isomer may, in a range, comprise less than 25% of the mixture, less than 10%, less than 5%, less than 2% or less than 1% of the mixture according to the formula:

$$\% \text{ dextrorotatory} = \frac{(\text{mass dextrorotatory})}{(\text{mass dextrorotatory}) + (\text{mass dextrorotatory})} \times 100$$

"Geometric isomer" means isomers that differ in the orientation of substituent atoms in relationship to a carbon-carbon double bond, to a cycloalkyl ring, or to a bridged bicyclic system. Substituent atoms (other than hydrogen) on each side of a carbon-carbon double bond may be in an E or Z configuration. In the "E" configuration, the substituents are on opposite sides in relationship to the carbon-carbon double bond. In the "Z" configuration, the substituents are oriented on the same side in relationship to the carbon-carbon double bond.

Substituent atoms (other than hydrogen) attached to a ring system may be in a cis or trans configuration. In the "cis" configuration, the substituents are on the same side in relationship to the plane of the ring; in the "trans" configuration, the substituents are on opposite sides in relationship to the plane of the ring. Compounds having a mixture of "cis" and "trans" species are designated "cis/trans".

The isomeric descriptors ("R," "S," "E," and "Z") indicate atom configurations relative to a core molecule and are intended to be used as defined in the literature.

Where the processes for the preparation of the compounds according to the invention give rise to mixture of stereoisomers, these isomers may be separated by conventional techniques such as preparative chromatography. The compounds may be prepared in racemic form, or individual enantiomers may be prepared either by enantiospecific synthesis or by resolution. The compounds may, for example, be resolved into their component enantiomers by standard techniques, such as the formation of diastereomeric pairs by salt formation with an optically active acid, such as (−)-di-p-toluoyl-d-tartaric acid and/or (+)-di-p-toluoyl-l-tartaric acid followed by fractional crystallization and regeneration of the free base. The compounds may also be resolved by formation of diastereomeric esters or amides, followed by chromatographic separation and removal of the chiral auxiliary. Alternatively, the compounds may be resolved using a chiral HPLC column.

Furthermore, compounds of the present invention may have at least one crystalline, polymorph or amorphous form. The plurality of such forms is included in the scope of the invention. In addition, some of the compounds may form solvates with water (i.e., hydrates) or common organic solvents (e.g., organic esters such as ethanolate and the like). The plurality of such solvates is also intended to be encompassed within the scope of this invention.

During any of the processes for preparation of the compounds of the present invention, it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 1991. The protecting groups may be removed at a convenient subsequent stage using methods known from the art.

Therapeutic Uses

The present invention is directed to a method for treating a Urotensin-II mediated disorder in a patient in need thereof comprising administering to the patient an effective amount of a compound of Formula (I) or Formula (Ia).

An embodiment of the present invention is a method for treating a disorder including, but not limited to, vascular hypertension, heart failure, atherosclerosis, renal failure, nephrotoxicity and diarrhea caused by anti-neoplastic agents, post-myocardial infarction, pulmonary hypertension/fibrosis, diabetes, and CNS indications including pain, Alzheimer's, convulsions, depression, migraine, psychosis, anxiety, neuromuscular deficit, and stroke.

Another embodiment of the present invention is a method for treating a Urotensin II-mediated disorder selected from the group consisting of heart failure and renal failure.

The present invention also includes the use of an instant compound in the manufacture of a medicament for treating a Urotensin II-mediated disorder.

The present invention further includes the use of a compound of Formula (I) and Formula (Ia) as a medicine.

The present method of using urotensin II receptor antagonists to reduce anti-neoplastic agent induced diarrhea and nephrotoxicity is applicable in any situations when anti-neoplastic agents (such as cisplatin, cis-diaminedichloroplatinum) are being administered to treat cancers or tumors.

However, most often U-II antagonists are used when tumors or cancers being treated are those of solid malignancies, notably those of the bladder, cervix, lung, ovary, and testis such as testicular tumor; bladder cancer; ureterpyelonephritic tumor; prostatic cancer; ovarian cancer; head and neck cancer; non-small-cell lung cancer; esophageal cancer; cervical cancer; neuroblastoma; gastric cancer; small cell lung cancer; bone cancer; non-Hodgkin's lymphomas; tumors of brain, endometrium, upper gastrointestinal tract, head and neck, and thymus; neuroblastoma; and sarcoma of bone and soft tissue.

Recent data (American Heart Association Scientific Sessions 2005, "SB-611812 in the treatment of heart failure", by Nicolas Bousette at Montreal General Hospital, Canada) has demonstrated that urotensin II receptor antagonists may be useful for improving cardiac function and for cardiac remodeling associated with chronic heart failure (CHF).

An effective amount for use of the instant compounds or a pharmaceutical composition thereof comprises a dose range from about 0.1 mg to about 1000 mg, from about 10 mg to about 500 mg or from about 1 mg to about 100 mg of active ingredient in a regimen of about 1 to 4 times per day for an average (70 kg) human; although, it is apparent to one skilled in the art that the therapeutically effective amount for active compounds of the invention will vary as will the conditions being treated.

The term "patient" as used herein, refers to an animal, preferably a mammal, most preferably a human, who has been the object of treatment, observation or experiment.

The term "effective amount" as used herein, means that amount of active compound or pharmaceutical agent that elicits the biological or medicinal response in a tissue system, animal or human that is being sought by a researcher, veterinarian, medical doctor or other clinician, which includes alleviation of the symptoms of the disease or disorder being treated.

As used herein, the term "composition" is intended to encompass a product comprising the specified ingredients in the specified amounts, as well as any product which results, directly or indirectly, from combinations of the specified ingredients in the specified amounts.

As used herein, the term "neoplasm" refers to an abnormal growth of cells or tissue and is understood to include benign, i.e., non-cancerous growths, and malignant, i.e., cancerous growths. The term "neoplastic" means of or related to neoplasm.

As used herein, the term "agent" is understood to mean a substance that produces a desired effect in a tissue, system, animal, mammal (in particular human), or other subject. Accordingly, the term "anti-neoplastic agent" is understood to mean a substance producing an anti-neoplastic effect in a tissue, system, animal, mammal (in particular human), or other subject. It is understood that an "agent" may be a single compound or a combination or composition of two or more compounds.

Some of the typical anti-neoplastic agents include alkylating agents such as melphalan, chlorambucil, cyclophosphamide, mechlorethamine, hexamethylmelamine, busulfan, carmustine, lomustine, and dacarbazine; antimetabolites such as 5-fluorouracil, methotrexate, cytarabine, mercaptopurine, and thioguanine; antimitotic agents such as paclitaxel, docetaxel, vinblastine, vincristine; topoisomerase I inhibitors such as irinotecan, camptothecin and camptothecin derivatives, for example topotecan; topoisomerase II inhibitors such as doxorubicin; and platinum coordination complexes such as cisplatin and carboplatin.

Even though the compounds of the present invention (including their pharmaceutically, acceptable salts and pharmaceutically acceptable solvates) can be administered alone, they will generally be administered in admixture with a pharmaceutical carrier, excipient or diluent selected with regard to the intended route of administration and standard pharmaceutical or veterinary practice. Thus, the present invention is directed to pharmaceutical and veterinary compositions comprising compounds of Formula (I) and one or more pharmaceutically acceptable carriers, excipients or diluents.

By way of example, in the pharmaceutical and veterinary compositions of the present invention, the compounds of the present invention may be admixed with any suitable binder(s), lubricant(s), suspending agent(s), coating agent(s), and/or solubilizing agent(s).

Tablets or capsules of the compounds may be administered singly or two or more at a time, as appropriate. It is also possible to administer the compounds in sustained release formulations.

Alternatively, the compounds of the general Formula (I) can be administered by inhalation or in the form of a suppository or pessary, or they may be applied topically in the form of a lotion, solution, cream, ointment or dusting powder. An alternative means of transdermal administration is by use of a skin patch. For example, they can be incorporated into a cream consisting of an aqueous emulsion of polyethylene glycols or liquid paraffin. They can also be incorporated, at a concentration of between 1 and 10% by weight, into an ointment consisting of a white wax or white soft paraffin base together with such stabilizers and preservatives as may be required.

For some applications, preferably the compositions are administered orally in the form of tablets containing excipients such as starch or lactose, or in capsules either alone or in admixture with excipients, or in the form of elixirs, solutions or suspensions containing flavoring or coloring agents.

The compositions (as well as the compounds alone) can also be injected parenterally, for example intracavernosally, intravenously, intramuscularly or subcutaneously. In this case, the compositions will comprise a suitable carrier or diluent.

For parenteral administration, the compositions are best used in the form of a sterile aqueous solution that may contain other substances, for example enough salts or monosaccharides to make the solution isotonic with blood.

For buccal or sublingual administration the compositions may be administered in the form of tablets or lozenges which can be formulated in a conventional manner.

By way of further example, pharmaceutical and veterinary compositions containing one or more of the compounds of the invention described herein as the active ingredient can be prepared by intimately mixing the compound or compounds with a pharmaceutical carrier according to conventional pharmaceutical compounding techniques. The carrier may take a wide variety of forms depending upon the desired route of administration (e.g., oral, parenteral). Thus for liquid oral preparations such as suspensions, elixirs and solutions, suitable carriers and additives include water, glycols, oils, alcohols, flavoring agents, preservatives, stabilizers, coloring agents and the like; for solid oral preparations, such as powders, capsules and tablets, suitable carriers and additives include starches, sugars, diluents, granulating agents, lubricants, binders, disintegrating agents and the like. Solid oral preparations may also be coated with substances such as sugars or be enteric-coated so as to modulate the major site of absorption. For parenteral administration, the carrier will usually consist of sterile water and other ingredients may be added to increase solubility or preservation. Injectable suspensions or solutions may also be prepared utilizing aqueous carriers along with appropriate additives.

Advantageously, compounds of the present invention may be administered in a single daily dose, or the total daily dosage may be administered in divided doses of two, three or four times daily. Furthermore, compounds for the present invention can be administered in intranasal form via topical use of suitable intranasal vehicles, or via transdermal skin patches well known to those skilled in that art. To be administered in the form of a transdermal delivery system, the dosage administration will, of course, be continuous rather than intermittent throughout the dosage regimen.

It is also apparent to one skilled in the art that the effective dose for active compounds of the invention or a pharmaceutical composition thereof will vary according to the desired effect. Therefore, optimal dosages to be administered may be readily determined and will vary with the particular compound used, the mode of administration, the strength of the preparation, and the advancement of the disease condition. In addition, factors associated with the particular subject being treated, including subject age, weight, diet and time of administration, will result in the need to adjust the dose to an appropriate therapeutic level. The above dosages are thus exemplary of the average case. There can, of course, be individual instances where higher or lower dosage ranges are merited, and such are within the scope of this invention.

Optimal dosages of the compounds of Formula (I) to be administered for the treatment of or prevention of Urotensin II mediated disorders may be readily determined by those skilled in the art, and will vary with the particular compound used, the mode of administration, the strength of the preparation, and the advancement of the disease condition. In addition, factors associated with the particular patient being treated, including patient age, weight, diet and time of administration, will result in the need to adjust dosages.

For oral administration, a pharmaceutical composition is preferably provided in the form of tablets containing 0.01, 10.0, 50.0, 100, 150, 200, 250, and 500 milligrams of the active ingredient for the symptomatic adjustment of the dosage to the subject to be treated.

General Synthetic Methods

Representative compounds of the present invention can be synthesized in accordance with the general synthetic methods described below and are illustrated in the schemes that follow. Since the schemes are an illustration, the invention should not be construed as being limited by the chemical reactions and conditions expressed. The preparation of the various starting materials used in the schemes is well within the skill of persons versed in the art.

Abbreviations used in the instant specification, particularly the Schemes and Examples, are as follows:

| Abbreviation | Meaning |
| --- | --- |
| Boc | tert-butoxycarbonyl |
| BSA | bovine serum albumin |

-continued

| Abbreviation | Meaning |
| --- | --- |
| CBZ | benzyloxycarbonyl |
| DCM | dichloromethane |
| DMF | N,N-dimethylformamide |
| DMSO | dimethylsulfoxide |
| DIPEA | diisopropylethylamine |
| dppf | 1,1'-bis(iphenylphosphino)ferrocene |
| EtOAc | ethyl acetate |
| h | hour |
| HBTU | O-benzotriazol-1-yl-N,N,N',N'-tetramethyluronium hexafluorophosphate |
| HOBt | hydroxybenzotriazole hydrate |
| HPLC | high performance liquid chromatography |
| HEPES | 4-(2-hydroxyethyl)-1-piperazine-ethanesulfonic acid |
| MeOH | methanol |
| min | minutes |
| $Pd_2(dba)_3$ | tris(dibenzylideneacetone)dipalladium (0) chloroform adduct |
| psig | pounds per square inch (gauge) |
| rt | room temperature |
| SDS | sodium dodecasulfate |
| TEA | triethylamine |

Abbreviation Meaning

TFA trifluoroacetate or trifluoroacetic acid (R)-tol-BI NAP (R)-(+)-2,2'-bis(di-p-tolylphosphino)-1,1'-binaphthyl Scheme A describes the synthesis of compounds of the present invention in which A is a-1, a-3, a-4, or a-6.

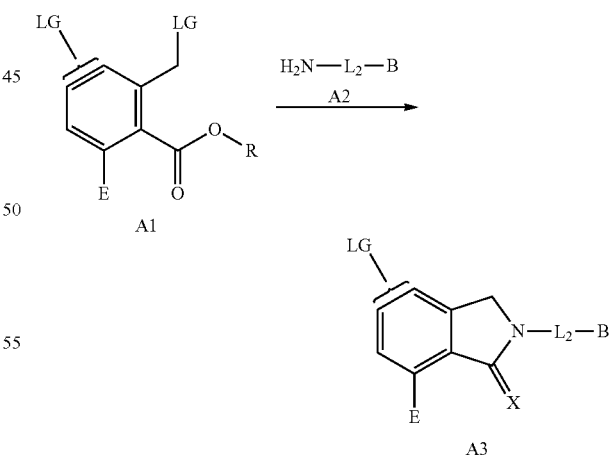

SCHEME A

A commercially available or readily prepared benzoic ester derivative of formula A1 (R=methyl or lower alkyl) may be reacted with an amine of formula A2 in the presence of a suitable base such as a tertiary amine to give a compound of formula A3, wherein the leaving groups (LG) would independently include bromide, chloride, iodide, triflate, and the like.

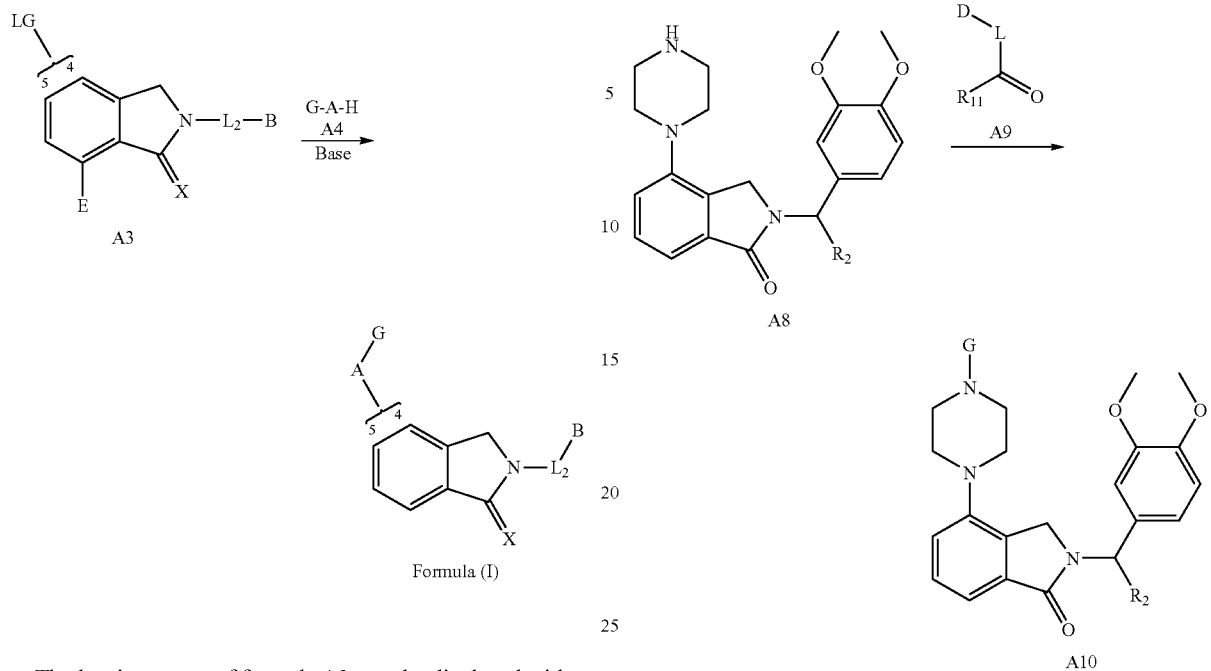

The leaving group of formula A3 may be displaced with a substituted Compound A4 using a palladium catalyst (e.g., bis-(tri-tert-butylphosphine)palladium(0)), a phase transfer agent (e.g., cetyl trimethylammonium bromide), and a base (e.g., potassium hydroxide) to give a compound of Formula (I).

The compound of formula A7 can be deprotected (e.g., using an acid such as HCl or TFA in the case when P=Boc) to afford the free amine compound of formula A8. A compound of formula A8 can be reductively aminated with an aldehyde or ketone of formula A9 in the presence of a reducing agent such as sodium triacetoxyborohydride and an acid such as acetic acid to afford compounds A10, representative of a compound of Formula (Ia).

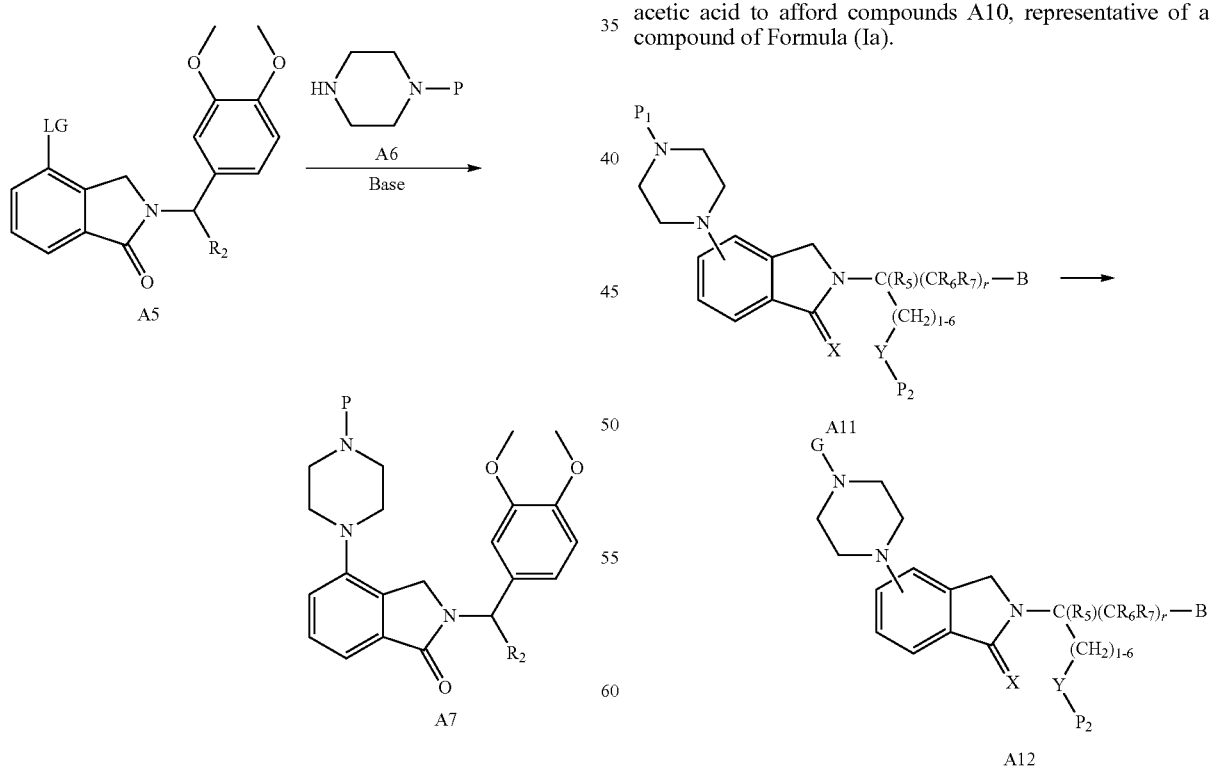

Alternatively, a protected piperazine compound of formula A6 (e.g., P is a Boc group) may be employed in the aryl amination of a compound of formula A5 to give a compound of formula A7.

Using the same general methodology described above, an orthoganally protected intermediate A11 can be prepared with two protecting groups $P_1$ and $P_2$. These protecting groups can be removed in any order. For example, the P₁ protecting group (e.g., Boc) can be removed and elaborated to substituent G (as previously defined above) to give A12.

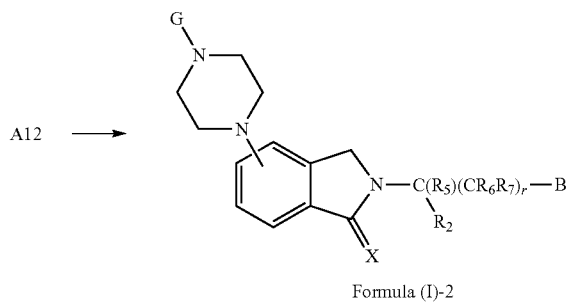

Formula (I)-2

The P₂ protecting group (e.g., CBZ or benzyl) can be removed and the A12-(CH₂)₁₋₆—Y— group (wherein Y represents O, N(R_a), or S) can be elaborated to substituent R₂ (as previously defined above) using the Y-group as a nucleophile in reaction with a reagent containing a leaving group (LG) (such as thionyl chloride, or another leaving group which can include bromide, iodide, triflate, mesylate, methoxy, ethoxy, ammonia, and the like, in the presence or absence of a base, such as TEA, sodium hydride, or the like to afford compounds of Formula (I)-2, representative of a compound of Formula (Ia).

Alternatively, the nucleophilic Y group (Y=NR_a) can be coupled to a carboxylic acid using standard amide coupling conditions such as HOBt, HBTU in the presence of a base such as N-methylmorpholine to yield compounds of Formula (I)-2.

Alternatively, the nucleophilic Y group (Y=NR_a) can be reacted with a reactive group such as an isocyanate to afford compounds of Formula (I)-2. Or the nucleophilic Y group (Y=NR_a) can be reacted with an aldehyde or ketone under reductive amination conditions such as tetramethylammonium triacetoxyborohydride to yield compounds of Formula (I)-2.

Alternatively, the nucleophilic Y group (Y=NR_a) can be reacted with an aryl-LG (LG=I, Br, Cl, OTf) under arylamination conditions, such as Pd₂(dba)₃, Xantphos®, and cesium carbonate to afford compounds of Formula (I)-2.

Alternatively, when Y=O, the oxygen can be converted to a leaving group such as bromide, chloride, iodide, triflate, mesylate, or the like, which can be displaced by a nucleophile R₂₀₀—YH (Y=O, NR_a, S) to yield compounds of Formula (I)-2.

These nucleophilic displacement reactions can be done in the presence or absence of a base, such as TEA, sodium hydride, or the like.

Scheme B describes the synthesis of compounds of the present invention wherein substituent A is an optionally unsaturated ring of formula a-2 or a-5.

SCHEME B

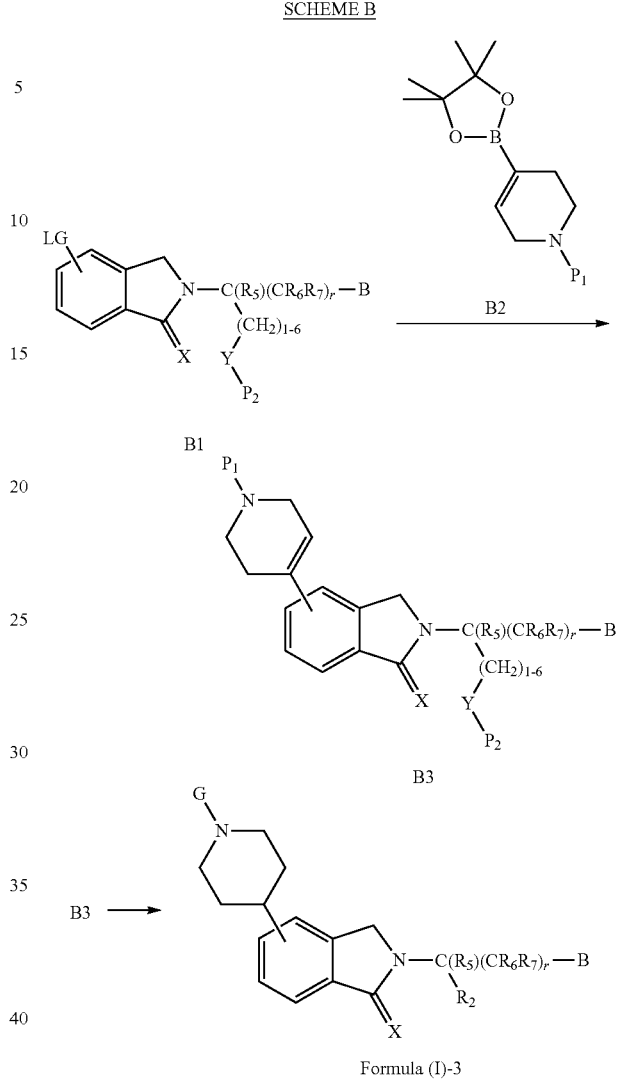

A compound of formula B1 (LG=Br, I, Cl, OTf) may be coupled with a boronate such as B2 in a Suzuki reaction using reagents such as potassium carbonate and [1,1'-bis(diphenylphosphino)-ferrocene]dichloropalladium(II) dichloromethane complex to afford intermediate B3. The double bond can be reduced by hydrogenation in the presence of a palladium catalyst and the protecting groups P₁ and P₂ protecting group can be removed and elaborated to compounds of Formula (I)-3 as described above and in detailed examples.

Alternatively, the substituent G (as previously defined above) can replace P₁ in reagent B2. Moreover, as described in Scheme A, the P₂ protecting group of intermediate B1 or B3 can be removed and, after Suzuki coupling and hydrogenation, the —(CH₂)₁₋₆—Y— group can be elaborated to substituent R₂ to yield compounds of Formula (I)-3, representative of a compound of Formula (I).

Scheme C describes the preparation of certain amino intermediate compounds of formula A2 wherein L₂ is —CH(R₂)—(CR₆R₇)_r—. A carboxylic acid C1 is converted to its Weinreb amide by usual amide coupling methodologies to afford compounds C2. The Weinreb amide C2 is reacted with an organometallic reagent such as Grignard reagent C3 to afford ketones C4. The ketone can be reductively aminated

SCHEME C

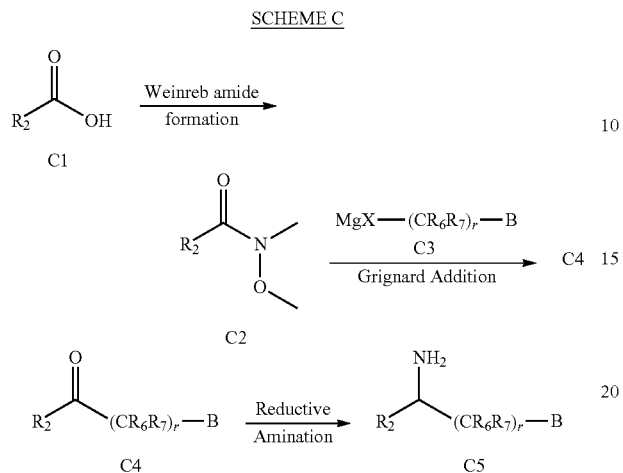

The following examples provide compounds representative of the present invention and should not be construed as limiting the scope of the invention by the chemical reactions and conditions expressed. The preparation of the various starting materials used in the examples is well within the skill of persons versed in the art.

EXAMPLE 1 thiophene-2-sulfonic acid {(4R)-4-(3,4-dimethoxy-phenyl)-4-[4-(4-ethyl-piperazin-1-yl)-1-oxo-1,3-dihydro-isoindol-2-yl]-butyl}-amide Cpd 84

1-methyl-1H-imidazole-2-carboxylic acid {(4R)-4-(3,4-dimethoxy-phenyl)-4-[4-(4-ethyl-piperazin-1-yl)-1-oxo-1,3-dihydro-isoindol-2-yl]-butyl}-amide Cpd 56 aminosulfonic acid {(4R)-4-(3,4-dimethoxy-phenyl)-4-[4-(4-ethyl-piperazin-1-yl)-1-oxo-1,3-dihydro-isoindol-2-yl]-butyl}-amide Cpd 58

1-{(4R)-4-(3,4-dimethoxy-phenyl)-4-[4-(4-ethyl-piperazin-1-yl)-1-oxo-1,3-dihydro-isoindol-2-yl]-butyl}-3-phenyl-urea Cpd 66

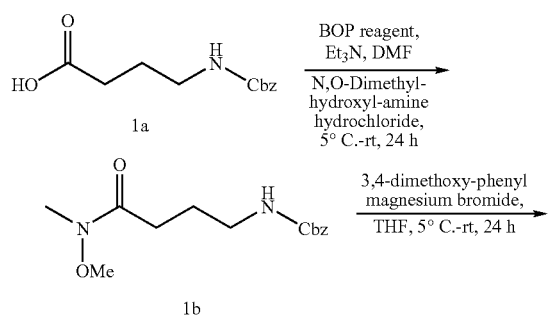

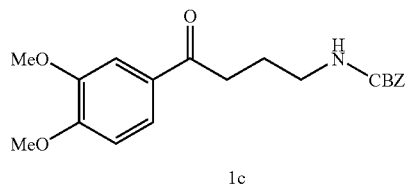

A. A 500-mL round bottom flask was charged with Compound 1a (4.2 g, 20.6 mmol) and DMF (207 mL). The mixture was cooled using an ice/water bath. TEA (8.8 mL, 63.1 mmol) was added to the mixture followed by the addition of benzotriazol-1-yloxy-tris(dimethylamino)phosphonium hexafluorophosphate (10.0 g, 22.6 mmol). N,O-dimethyl-hydroxyl-amine hydrochloride (3.1 g, 31.8 mmol) was also added and the mixture was stirred at room temperature for 24 h. The mixture was concentrated in vacuo. The crude oil was diluted with EtOAc (500 mL) and transferred to a separatory funnel. The organic layer was washed with 1N HCl (2×300 mL), 1N NaOH (2×300 mL), and water (2×300 mL). The organic layer was dried using $MgSO_4$, filtered through Celite®, and concentrated in vacuo to give 5.08 g of Compound 1b as a clear oil. $^1$H NMR (300 MHz, $CDCl_3$) δ 7.26-7.41 (m, 5H), 5.09 (s, 2H), 3.19-3.37 (m, 2H), 3.16 (s, 3H), 2.87-2.97 (m, 2H), 2.85 (s, 3H), and 1.83-1.90 (m, 2H).

B. A 1 L round bottom flask was charged with Compound 1b (5.08 g, 20.7 mmol) and THF (415 mL). The mixture was cooled using an ice/water bath. A solution of 3,4-dimethoxy-phenyl magnesium bromide in THF (207 mL, 104 mmol) was added dropwise via addition funnel over 30 minutes. The mixture was allowed to warm to room temperature and stirred for 20 h. Water (150 mL) was added to the mixture and concentrated in vacuo. The mixture was extracted with DCM (600 mL) and washed with water (2×300 mL). The organic layer was dried with $MgSO_4$, filtered through Celite®, concentrated in vacuo, and purified via flash chromatography (230-400 mesh silica gel 60, gradient 90:10-50:50 Hexanes:EtOAc) to give 4.0 g of Compound 1c as a white solid. $^1$H NMR (300 MHz, $CDCl_3$) δ 7.57 (d, J=8.4 Hz, 1H), 7.51 (s, 1H), 7.29-7.44 (m, 5H), 6.88 (d, J=8.4 Hz, 1H), 5.08 (s, 2H), 3.95 (s, 3H), 3.93 (s, 3H), 3.27-3.34 (m, 2H), 2.97-3.02 (m, 2H), and 1.92-2.01 (m, 2H); LC/MS (ES+) m/z 358 (M+1).

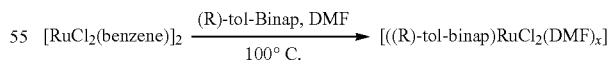

C. A 200-mL Schlenk tube was charged with [$RuCl_2$(benzene)]$_2$ (2.0 g, 4.0 mmol) and (R)-tol-BINAP (5.7 g, 8.4 mmol). The tube was put under vacuum for 15 minutes and then back flushed with argon. DMF (133 mL, degassed with argon) was added to the tube and the mixture was flushed with argon. The tube was closed and heated to 100° C. for 10 minutes (stirring). The DMF was then removed under high vacuum at 70° C. to give [((R)-tol-BINAP)$RuCl_2$(DMF)$_x$] as a reddish/brown solid (See, Org. Syn. 71, 1993, 1-13).

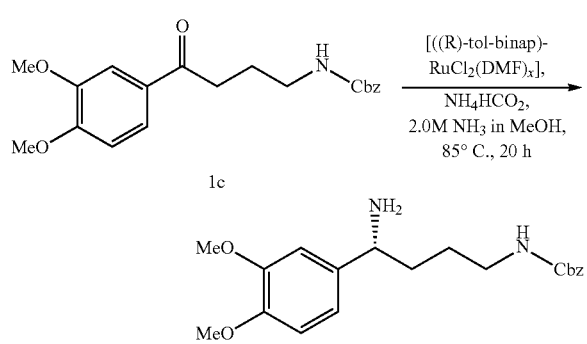

D. A 200-mL sealed tube was charged with Compound 1c (8.66 g, 24.2 mmol), [((R)-tol-BINAP)RuCl$_2$(DMF)$_x$] (2.1 g, 2.5 mmol), ammonium formate (15.3 g, 242.6 mmol), and a 2.0 M solution of ammonia in methanol (97 mL). The tube was flushed with argon and sealed. The mixture was heated to 85° C. for 22 h. The mixture was cooled to room temperature and the sealed tube was opened carefully due to the release of pressure from excess ammonia. The reaction mixture was concentrated in vacuo, diluted with 1N HCl (300 mL) and ethanol (150 mL), heated to reflux for 2 h, cooled to room temperature, and washed with diethyl ether (1×500 mL). The aqueous layer was basified with 3N NaOH to pH>10 and extracted using DCM (3×400 mL). The organic layers were combined and dried with MgSO$_4$, then filtered through Celite® and concentrated in vacuo to give 15.66 g of Compound 1d as a white solid. $^1$H NMR (300 MHz, CDCl$_3$) δ 7.30-7.34 (m, 5H), 6.81-6.87 (m, 3H), 5.08 (s, 2H), 3.83-3.90 (m, 7H), 3.16-3.22 (m, 2H), and 1.38-1.71 (m, 6H); LC/MS (ES+) m/z 359 (M+1); Daicel Chiralpak AD-H, 4.6 mm×15 cm, Hex:IPA:0.1% DEA (86:14), 1.0 mL/min, (S)-enantiomer: 13.57 min, (R)-enantiomer: 15.67 min (Compound 1d), 96% ee.

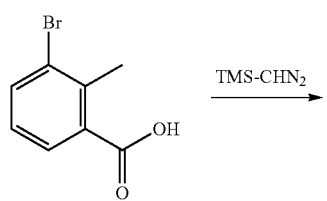

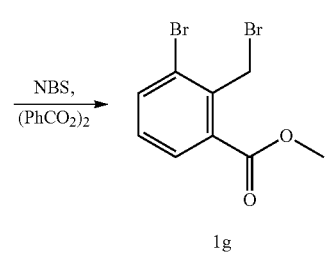

E. Compound 1e (15.3 g, 71 mmol) was dissolved in methanol (75 mL) and DCM (425 mL), cooled to −5° C., and treated with 2 M trimethylsilyidiazomethane in hexanes (100 mL, 200 mmol) dropwise from an addition funnel. One hour after the addition of reagent, the reaction was complete by LC/MS. Evaporation of volatiles afforded Compound 1f (16.6 g) as an oil. $^1$H NMR (300 MHz, CDCl$_3$) δ 7.71 (t, J=8 Hz, 2H), 7.10 (d, J=8 Hz, 1H), 3.90 (s, 3H), 2.63 (s, 3H).

F. A mixture of Compound 1f (16.6 g, 71 mmol), N-bromosuccinimide (13.09 g, 74 mmol), and benzoyl peroxide (0.56 g, 2.3 mmol) was dissolved in carbon tetrachloride (180 mL) and heated to 82° C. (bath) overnight. The reaction was cooled to rt, diluted with EtOAc (600 mL), washed with water (300 mL), dried (MgSO$_4$), filtered, and concentrated in vacuo to afford Compound 1g as a solid (20.7 g, 95%), which was stored under argon in a freezer. $^1$H NMR (300 MHz, CDCl$_3$) δ 7.89 (dd, J=7.8 and 1.3 Hz, 1H), 7.76 (dd, J=8.0 and 1.3 Hz, 1H), 7.23 (t, J=8.0 Hz, 1H), 5.13 (s, 2H), 3.96 (s, 3H).

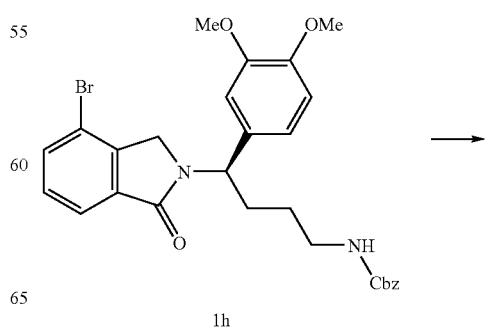

G. Compound 1d (3.04 g, 8.5 mmol) and TEA (1.2 mL, 8.6 mmol) were combined in toluene (50 mL) and treated with Compound 1g (2.4 g, 7.8 mmol) in toluene (100 mL) via addition funnel. The reaction mixture was stirred at rt (1 h), refluxed (5 h), and evaporated. Purification on silica gel by an Analogix system (SF40-150 g, gradient elution with 0 to 2% methanol in DCM) afforded Compound 1h (3.9 g, 90%) as a solid. $^1$H NMR (300 MHz, CDCl$_3$) δ 7.79 (d, J=8 Hz, 1H), 7.62 (d, J=8 Hz, 1H), 7.43-7.28 (m, 6H), 6.96-6.83 (m, 3H), 5.52 (t, J=8 Hz, 1H), 5.08 (s, 2H), 4.95 (br s, NH), 4.18 (d, J=18 Hz, 1H), 3.87 (s, 3H), 3.88 (buried d, J=18 Hz, 1H), 3.84 (s, 3H), 3.30 (br q, J=6.3 Hz, 2H), 2.16-2.04 (m, 2H), 1.7-1.5 (m, 2H); LC/MS (ES+) m/z 553, 555 (M+1).

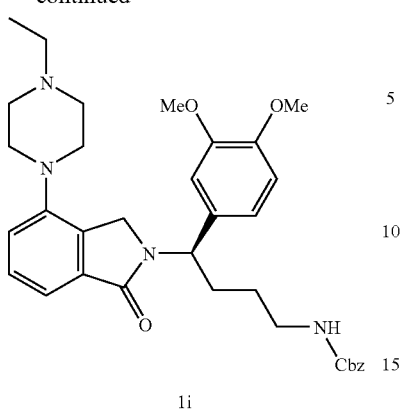

1i

H. Compound 1h (3.30 g, 6.0 mmol) was suspended in dry toluene (20 mL) under argon and treated with bis(tri-tert-butylphosphine)palladium(0) (307 mg, 0.60 mmol), cetyl trimethylammonium bromide (120 mg, 0.33 mmol), and N-ethyl-piperazine (2.75 g, 24 mmol). Finally, 45% potassium hydroxide solution (1.12 g, 9 mmol) was added, and the reaction mixture was purged well with argon, sealed with a teflon screw cap, and heated to 105° C. (bath) for 2 h. Analysis by LC/MS indicated 50% Compound 1i and 33% desbromo Compound 1h. The reaction mixture was cooled to rt, decanted from solids, washed with additional toluene (25 mL) and evaporated in vacuo to afford a brown oil, which was dissolved in DCM (200 mL), and washed with saturated sodium bicarbonate (50 mL), water (50 mL) and brine (50 mL), then dried (Na$_2$SO$_4$), and concentrated in vacuo to obtain a solid. The solid was dissolved in EtOAc, treated with silica gel (10 g), evaporated, and loaded onto a prepared column of silica gel (2 in diameter, 200 g, 40:4:0.5 EtOAc/methanol/ammonium hydroxide) and eluted with the same. The product containing fractions were evaporated, dissolved in EtOAc, dried (Na$_2$SO$_4$), and evaporated to give Compound 1l as a foamy solid (1.56 g, 44%). $^1$H NMR (300 MHz, CDCl$_3$) δ 7.51 (d, J=7 Hz, 1H), 7.43-7.28 (m, 6H), 7.08 (d, J=7 Hz, 1H), 6.94-6.82 (m, 3H), 5.54 (t, J=8 Hz, 1H), 5.08 (s, 2H), 4.86 (br s, NH), 4.20 (d, J=17 Hz, 1H), 3.92 (buried d, J=17 Hz, 1H), 3.88 (s, 3H), 3.83 (s, 3H), 3.29 (br q, J=6.5 Hz, 2H), 3.05 (m, 4H), 2.59 (m, 4H), 2.52-2.42 (m, 2H), 2.16-2.08 (m, 2H), 1.7-1.5 (m, 2H), 1.11 (m, 3H); LC/MS (ES+) m/z 587.3 (M+1).

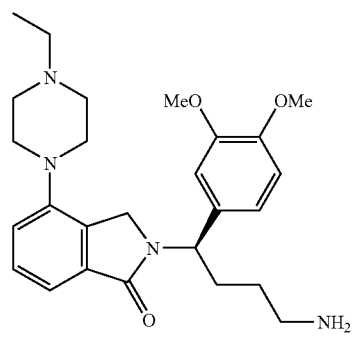

1j

I. Compound 1i (1.0 g, 1.7 mmol) was dissolved in EtOAc (20 mL) and anhydrous ethanol (20 mL), treated with 1N hydrochloric acid solution (10 drops), 10% palladium on carbon (140 mg), and shaken on a Parr apparatus under hydrogen (41 psig) overnight at rt. The reaction was not complete by LC, so additional 10% palladium on carbon (140 mg slurry in ethanol) and 1N hydrochloric acid solution (10 drops) were added and the bottle was shaken overnight again under hydrogen (42 psig). The reaction mixture was diluted with EtOAc/ethanol (1:1, 50 mL), filtered through Celatom FW-14, and evaporated to give an oil, which was dissolved in DCM (50 mL), washed with saturated sodium bicarbonate (20 mL) and brine (20 mL), dried (Na$_2$SO$_4$), and concentrated to yield Compound 1j as an oil (0.86 g, quantitative). $^1$H NMR (300 MHz, CDCl$_3$) δ 7.52 (d, J=7 Hz, 1H), 7.40 (t, J=7 Hz, 1H), 7.08 (d, J=7 Hz, 1H), 6.97 (dd, J=8.2 and 1.3 Hz, 1H), 6.92 (br s, 1H), 6.84 (d, J=8.2 Hz, 1H), 5.56 (t, J=8 Hz, 1H), 4.25 (d, J=17 Hz, 1H), 3.94 (d, J=17 Hz, 1H), 3.87 (s, 3H), 3.85 (s, 3H), 3.06 (m, 4H), 2.80 (m, 2H), 2.59 (m, 4H), 2.52-2.42 (m, 2H), 2.16-2.10 (m, 2H), 1.7-1.4 (m, 2H), 1.11 (m, 3H); LC/MS (ES+) m/z 453.3 (M+1).

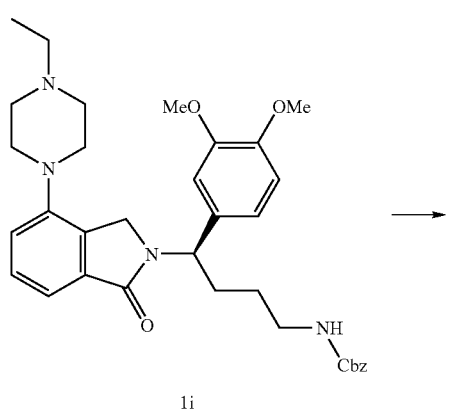

1i

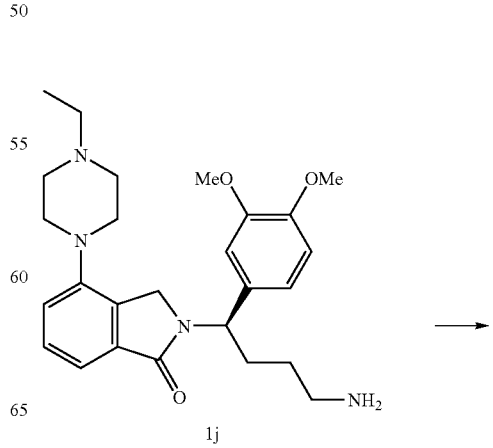

1j

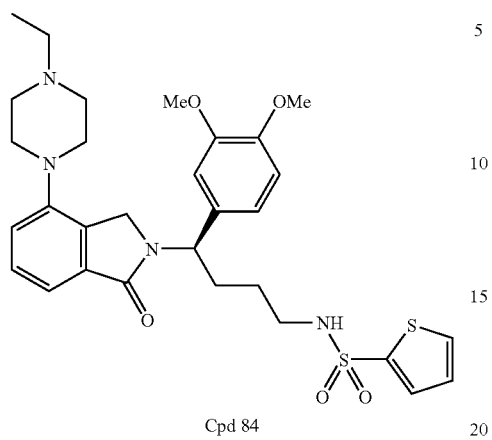

Cpd 84

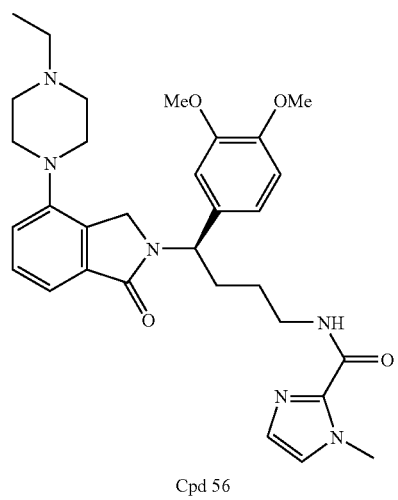

Cpd 56

J. Compound 1j-2HCl (870 mg, 1.7 mmol, prepared by dissolving in DCM, treating with excess 1N hydrogen chloride in diethyl ether, and evaporating) was dissolved in DCM (9 mL), cooled to 5° C., and treated with TEA (0.8 mL, 6 mmol) and 2-thiophenesulfonyl chloride (365 mg, 2.0 mmol) for 1 h. The reaction mixture was diluted with DCM (200 mL), washed with 1N hydrochloric acid (50 mL) and saturated sodium bicarbonate (50 mL), dried (MgSO$_4$), and concentrated in vacuo to give an oil that was dissolved in DCM (20 mL), treated with 1N hydrogen chloride in diethyl ether, and concentrated in vacuo overnight to afford Cpd 84 as a solid HCl salt (1.01 g, 88%). $^1$H NMR (300 MHz, CDCl$_3$) δ 7.57-7.40 (m, 3H), 7.37 (t, J=7 Hz, 1H), 7.06 (d, J=8 Hz, 1H), 7.00 (t, J=4 Hz, 1H), 6.92-6.80 (m, 3H), 5.68 (br s, NH), 5.49 (t, J=8 Hz, 1H), 4.22 (d, J=17 Hz, 1H), 3.90 (buried d, J=17 Hz, 1H), 3.86 (s, 3H), 3.82 (s, 3H), 3.2-3.0 (m, 6H), 2.61 (m, 4H), 2.50 (m, 2H), 2.16 (q, J=7 Hz, 2H), 1.59 (m, 2H), 1.12 (t, J=7 Hz, 3H); LC/MS (ES+) m/z 599.4 (M+1). Anal. Calcd for C$_{30}$H$_{38}$N$_4$O$_5$S$_2$·1.8HCl·0.5H$_2$O: C, 53.51; H, 6.11; N, 8.32; Cl, 9.48. Found: C, 53.27; H, 6.04; N, 7.95; Cl, 9.44. Karl Fisher Titration Calcd: 1.34%. Found: 1.46% (w/w).

K. Compound 1j-diTFA (30 mg, 0.044 mmol), prepared by purification of the free base on reversed phase HPLC, was dissolved in DMF (2 mL) under nitrogen and treated with N-methylmorpholine (0.022 mL, 0.20 mmol), 1-methylimidazole-2-carboxylic acid (10 mg, 0.079 mmol), HOBt (4 mg, 0.03 mmol), O-benzotriazol-1-yl-N,N,N',N'-tetramethyluronium hexafluorophosphate (HBTU, 30 mg, 0.079 mmol) at rt overnight. The reaction mixture was diluted with water (4 mL) and acetonitrile (3 mL), filtered, and purified by reversed phase HPLC [Phenomenex, Kromasil C18, 5μ, 100 Å, 100× 21 mm, gradient elution with 10-50% acetonitrile (0.16% TFA) in water (0.2% TFA)] to yield Cpd 56 (39 mg, quantitative) as the diTFA salt. $^1$H NMR (400 MHz, CDCl$_3$) δ 7.59 (d, J=7.2 Hz, 1H), 7.43 (t, J=7.7 Hz, 1H), 7.38 (d, J=1.6 Hz, 1H), 7.17 (d, J=1.6 Hz, 1H), 7.12 (d, J=7.4 Hz, 1H), 6.98 (dd, J=8.3 and 1.9 Hz, 1H), 6.92 (d, J=1.9 Hz, 1H), 6.83 (d, J=8.3 Hz, 1H), 5.55 (t, J=8 Hz, 1H), 4.40 (d, J=17 Hz, 1H), 4.16 (s, 3H), 3.92 (d, J=17 Hz, 1H), 3.86 (s, 3H), 3.84 (s, 3H), 3.7-3.2 (m, 10H), 2.99 (m, 2H), 2.24 (m, 2H), 1.8-1.6 (m, 2H), 1.42 (t, J=7.3 Hz, 3H); LC/MS (ES+) m/z 561.5 (M+1).

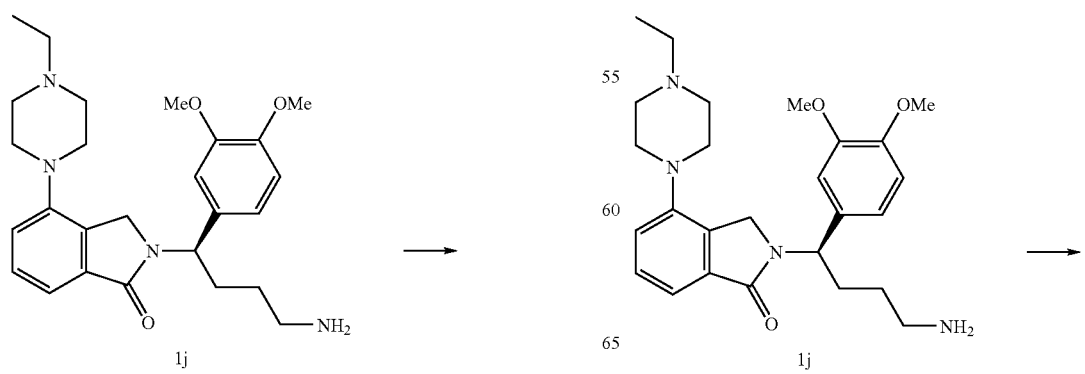

-continued

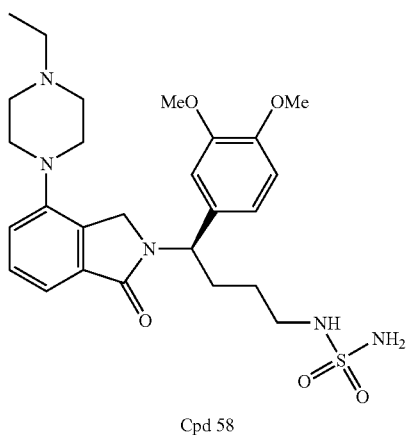

Cpd 58

L. Compound 1j (14 mg, 0.020 mmol) and sulfamide (15 mg, 0.16 mmol) were heated in refluxing dioxane (2 mL) for 2 h and then concentrated in vacuo. The crude reaction material was purified by reversed phase HPLC [Phenomenex, Kromasil C18, 10μ, 110 Å, 250×50 mm, gradient elution with 10-50% acetonitrile (0.16% TFA) in water (0.2% TFA)] to yield Cpd 58 (9 mg, 59%) as the diTFA salt. $^1$H NMR (400 MHz, CDCl$_3$) δ 7.62 (d, J=7.2 Hz, 1H), 7.44 (t, J=7.7 Hz, 1H), 7.17 (d, J=7.5 Hz, 1H), 6.96 (dd, J=8.3 and 1.9 Hz, 1H), 6.91 (d, J=1.9 Hz, 1H), 6.85 (d, J=8.3 Hz, 1H), 5.56 (m, 1H), 4.34 (d, J=17 Hz, 1H), 3.92 (d, J=17 Hz, 1H), 3.87 (s, 3H), 3.85 (s, 3H), 3.7-3.2 (m, 10H), 2.95 (m, 2H), 2.31 (m, 2H), 1.8-1.6 (m, 2H), 1.41 (t, J=7.3 Hz, 3H); LC/MS (ES+) m/z 532.3 (M+1).

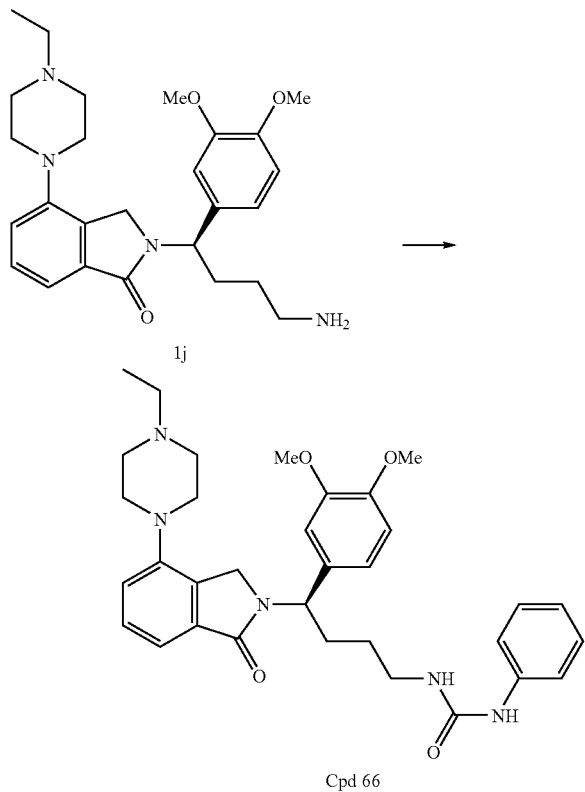

Cpd 66

M. Compound 1j-2TFA salt (29 mg, 0.042 mmol) was dissolved in anhydrous THF under nitrogen and treated with DIPEA (0.009 mL, 0.05 mmol) and phenylisocyanate (0.006 mL, 0.05 mmol) at rt for 4 h. The reaction mixture was concentrated and purified by reversed phase HPLC [Phenomenex, Kromasil C18, 10μ, 110 Å, 250×50 mm, gradient elution with 10-90% acetonitrile (0.16% TFA) in water (0.2% TFA)] to afford the urea Cpd 66 (21 mg, 62%) as the diTFA salt. $^1$H NMR (300 MHz, CDCl$_3$) δ 7.63 (d, J=7.5 Hz, 1H), 7.5-7.2 (m, 5H), 7.16 (d, J=7.7 Hz, 1H), 7.04 (t, J=7.2 Hz, 1H), 6.94 (t, J=8.2 Hz, 1H), 6.88 (d, J=1.7 Hz, 1H), 6.83 (d, J=8.2 Hz, 1H), 5.55 (m, 1H), 4.28 (d, J=17 Hz, 1H), 3.92 (d, J=17 Hz, 1H), 3.87 (s, 3H), 3.83 (s, 3H), 3.7-3.1 (m, 10H), 2.99 (m, 2H), 2.3-1.6 (m, 2H), 1.59 (m, 2H), 1.40 (t, J=7.3 Hz, 3H); LC/MS (ES+) m/z 572.4 (M+1).

Other compounds of the present invention may be prepared by those skilled in the art by varying the starting materials, reagent(s) and conditions used. Using the procedure of Example 1, the following compounds were prepared:

| Cpd | Name |
|---|---|
| 1 | dimethylaminosulfonic acid {(4R)-4-(3,4-dimethoxy-phenyl)-4-[4-(4-ethyl-piperazin-1-yl)-1-oxo-1,3-dihydro-isoindol-2-yl]-butyl}-methyl-amide<br>Observed Parent Peak 574.3; MS M + 1 calc'd: 574.3. |
| 17 | 4-{2-(3,4-dimethoxy-phenyl)-2-[4-(4-ethyl-piperazin-1-yl)-1-oxo-1,3-dihydro-isoindol-2-yl]-ethyl}-piperidine-1-sulfonic acid<br>Observed Parent Peak 573.3; MS M + 1 calc'd: 573.3. |
| 39 | 1,2-dimethyl-1H-imidazole-4-sulfonic acid {(4R)-4-(3,4-dimethoxy-phenyl)-4-[4-(4-ethyl-piperazin-1-yl)-1-oxo-1,3-dihydro-isoindol-2-yl]-butyl}-methyl-amide<br>Observed Parent Peak 625.3; MS M + 1 calc'd: 625.3. |
| 49 | 2,3-dimethyl-3H-imidazole-4-sulfonic acid {(4R)-4-(3,4-dimethoxy-phenyl)-4-[4-(4-ethyl-piperazin-1-yl)-1-oxo-1,3-dihydro-isoindol-2-yl]-butyl}-amide<br>Observed Parent Peak 611.4; MS M + 1 calc'd: 611.3. |
| 53 | 1-methyl-1H-imidazole-4-sulfonic acid {(4R)-4-(3,4-dimethoxy-phenyl)-4-[4-(4-ethyl-piperazin-1-yl)-1-oxo-1,3-dihydro-isoindol-2-yl]-butyl}-amide<br>Observed Parent Peak 597.3; MS M + 1 calc'd: 597.3. |
| 54 | N-{(4R)-4-(3,4-dimethoxy-phenyl)-4-[4-(4-ethyl-piperazin-1-yl)-1-oxo-1,3-dihydro-isoindol-2-yl]-butyl}-isonicotinamide<br>Observed Parent Peak 558.4; MS M + 1 calc'd: 558.3. |
| 57 | 1-methyl-1H-imidazole-4-carboxylic acid {(4R)-4-(3,4-dimethoxy-phenyl)-4-[4-(4-ethyl-piperazin-1-yl)-1-oxo-1,3-dihydro-isoindol-2-yl]-butyl}-amide<br>Observed Parent Peak 561.5; MS M + 1 calc'd: 561.3. |
| 59 | 3-methyl-3H-imidazole-4-carboxylic acid {(4R)-4-(3,4-dimethoxy-phenyl)-4-[4-(4-ethyl-piperazin-1-yl)-1-oxo-1,3-dihydro-isoindol-2-yl]-butyl}-amide<br>Observed Parent Peak 561.5; MS M + 1 calc'd: 561.3. |
| 60 | 3,5-dimethyl-1H-pyrazole-4-carboxylic acid {(4R)-4-(3,4-dimethoxy-phenyl)-4-[4-(4-ethyl-piperazin-1-yl)-1-oxo-1,3-dihydro-isoindol-2-yl]-butyl}-amide<br>Observed Parent Peak 575.4; MS M + 1 calc'd: 575.3. |
| 61 | pyridazine-4-carboxylic acid {(4R)-4-(3,4-dimethoxy-phenyl)-4-[4-(4-ethyl-piperazin-1-yl)-1-oxo-1,3-dihydro-isoindol-2-yl]-butyl}-amide<br>Observed Parent Peak 559.3; MS M + 1 calc'd: 559.3. |
| 64 | {(4R)-4-(3,4-dimethoxy-phenyl)-4-[4-(4-ethyl-piperazin-1-yl)-1-oxo-1,3-dihydro-isoindol-2-yl]-butyl}-urea<br>Observed Parent Peak 496.4; MS M + 1 calc'd: 496.3. |
| 65 | thiophene-2-sulfonic acid {(4R)-4-(3,4-dimethoxy-phenyl)-4-[4-(4-isopropyl-piperazin-1-yl)-1-oxo-1,3-dihydro-isoindol-2-yl]-butyl}-amide<br>Observed Parent Peak 613.3; MS M + 1 calc'd: 613.2. |

-continued

| Cpd | Name |
|---|---|
| 67 | N-{(4R)-4-(3,4-dimethoxy-phenyl)-4-[4-(4-ethyl-piperazin-1-yl)-1-oxo-1,3-dihydro-isoindol-2-yl]-butyl}-2,2,2-trifluoro-acetamide<br>Observed Parent Peak 549.3; MS M + 1 calc'd: 549.3. |
| 70 | dimethylaminosulfonic acid {(4R)-4-(3,4-dimethoxy-phenyl)-4-[4-(4-ethyl-piperazin-1-yl)-1-oxo-1,3-dihydro-isoindol-2-yl]-butyl}-amide<br>Observed Parent Peak 560.4; MS M + 1 calc'd: 560.3. |
| 71 | {(4R)-4-(3,4-dimethoxy-phenyl)-4-[4-(4-ethyl-piperazin-1-yl)-1-oxo-1,3-dihydro-isoindol-2-yl]-butyl}-sulfamic acid<br>Observed Parent Peak 533.3; MS M + 1 calc'd: 533.2. |
| 76 | 3-amino-4-{(4R)-4-(3,4-dimethoxy-phenyl)-4-[4-(4-ethyl-piperazin-1-yl)-1-oxo-1,3-dihydro-isoindol-2-yl]-butylamino}-cyclobut-3-ene-1,2-dione<br>Observed Parent Peak 548.4; MS M + 1 calc'd: 548.3. |
| 78 | furan-2-carboxylic acid {(4R)-4-(3,4-dimethoxy-phenyl)-4-[4-(4-ethyl-piperazin-1-yl)-1-oxo-1,3-dihydro-isoindol-2-yl]-butyl}-amide<br>Observed Parent Peak 547.3; MS M + 1 calc'd: 547.3. |
| 79 | 1H-pyrazole-4-carboxylic acid {(4R)-4-(3,4-dimethoxy-phenyl)-4-[4-(4-ethyl-piperazin-1-yl)-1-oxo-1,3-dihydro-isoindol-2-yl]-butyl}-amide<br>Observed Parent Peak 547.3; MS M + 1 calc'd: 547.3. |
| 80 | cyclobutanecarboxylic acid {(4R)-4-(3,4-dimethoxy-phenyl)-4-[4-(4-ethyl-piperazin-1-yl)-1-oxo-1,3-dihydro-isoindol-2-yl]-butyl}-amide<br>Observed Parent Peak 535.3; MS M + 1 calc'd: 535.3. |
| 81 | thiophene-2-carboxylic acid {(4R)-4-(3,4-dimethoxy-phenyl)-4-[4-(4-ethyl-piperazin-1-yl)-1-oxo-1,3-dihydro-isoindol-2-yl]-butyl}-amide<br>Observed Parent Peak 563.4; MS M + 1 calc'd: 563.3. |
| 82 | 1,2-dimethyl-1H-imidazole-4-sulfonic acid {(4R)-4-(3,4-dimethoxy-phenyl)-4-[4-(4-ethyl-piperazin-1-yl)-1-oxo-1,3-dihydro-isoindol-2-yl]-butyl}-amide<br>Observed Parent Peak 611.4; MS M + 1 calc'd: 611.3. |
| 83 | N-{(4R)-4-(3,4-dimethoxy-phenyl)-4-[4-(4-ethyl-piperazin-1-yl)-1-oxo-1,3-dihydro-isoindol-2-yl]-butyl}-2,2-dimethyl-propionamide<br>Observed Parent Peak 537.5; MS M + 1 calc'd: 537.3. |
| 86 | 2-[(1R)-1-(3,4-dimethoxy-phenyl)-3-(5,6,7,8-tetrahydro-[1,8]naphthyridin-2-yl)-propyl]-4-(4-ethyl-piperazin-1-yl)-2,3-dihydro-isoindol-1-one<br>Observed Parent Peak 556.3; MS M + 1 calc'd: 556.3. |
| 87 | 2-[(1R)-1-(3,4-dimethoxy-phenyl)-4-phenyl-butyl]-4-(4-ethyl-piperazin-1-yl)-2,3-dihydro-isoindol-1-one<br>Observed Parent Peak 514.3; MS M + 1 calc'd: 514.3. |

EXAMPLE 2 thiophene-2-sulfonic acid (3-{(3,4-dimethoxy-phenyl)-[4-(4-ethyl-piperazin-1-yl)-1-oxo-1,3-dihydro-isoindol-2-yl]-methyl}-phenyl)-amide Cpd 16

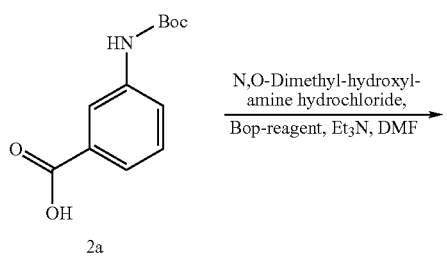

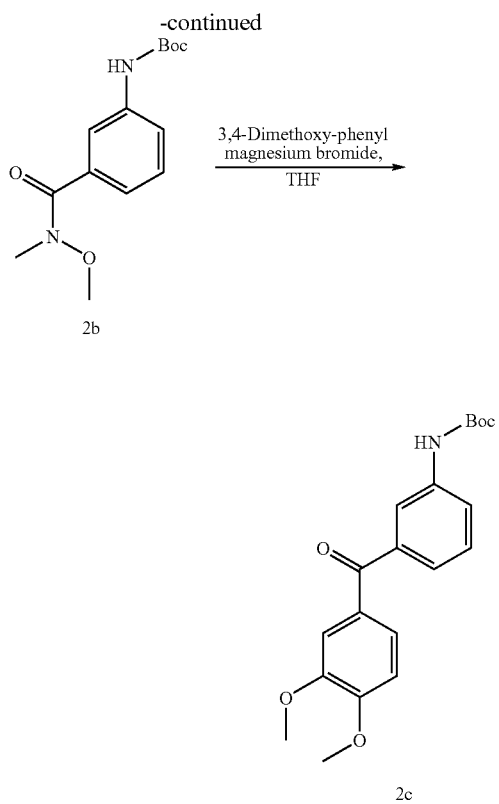

A 500-mL round bottom flask was charged with Compound 2a (5.0 g, 21.1 mmol) and DMF (70 mL) under nitrogen. The mixture was cooled using an ice/water bath. TEA (8.8 mL, 63.1 mmol) was added to the mixture followed by the benzotriazol-1-yloxy-tris(dimethylamino)phosphonium hexafluorophosphate (10.5 g, 23.7 mmol). N,O-dimethylhydroxylamine hydrochloride (3.19 g, 32.7 mmol) was added and the mixture was stirred at room temperature for 24 h and concentrated in vacuo. The crude oil was diluted with EtOAc (500 mL) and transferred to a separatory funnel. The organic layer was washed with 1N HCl (100 mL), 1N NaOH (100 mL), and water (100 mL), then dried using MgSO$_4$, filtered through Celite®, and concentrated in vacuo to give 5.80 g of Compound 2b. $^1$H NMR (300 MHz, CDCl$_3$) δ 7.63-7.69 (m, 1H), 7.53-7.59 (m, 1H), 7.31-7.35 (m, 2H), 6.71 (bs, 1H), 3.58 (s, 3H), 3.35 (s, 3H), and 1.52 (s, 9H); LC/MS (ES+) m/z 281 (M+1).

A 1-L round bottom flask was charged with Compound 2b (5.90 g, 21.1 mmol) and THF (400 mL) under nitrogen. The mixture was cooled using an ice/water bath. A solution of 3,4-dimethoxyphenyl magnesium bromide in THF (230 mL, 115 mmol) was added dropwise via addition funnel over 30 minutes. The mixture was allowed to warm to room temperature and stirred for 2 h. Water (150 mL) was added to the mixture and concentrated in vacuo. The mixture was extracted with DCM (500 mL) and washed with 1N NaOH (100 mL), 1N HCl (100 mL), and water (100 mL). The organic layer was dried with MgSO$_4$, filtered through Celite®, concentrated in vacuo to give 6.56 g of Compound 2c as a white solid. $^1$H NMR (300 MHz, CDCl$_3$) δ 7.66 (s, 1H), 7.40-7.50 (m, 3H), 6.88-6.92 (m, 2H), 6.73 (d, J=8.6 Hz, 1H), 3.95 (s, 3H), 3.82 (s, 3H), and 1.52 (s, 9H); LC/MS (ES+) m/z 358 (M+1).

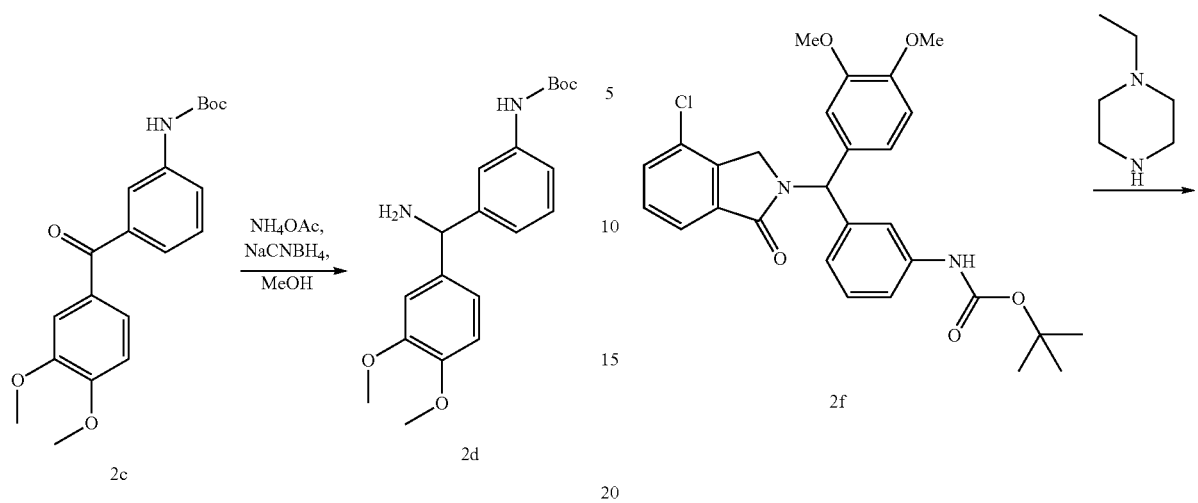

A 300-mL round bottom flask was charged with Compound 2c (2.08 g, 5.83 mmol), ammonium acetate (4.5 g, 58.4 mmol), and methanol (19.0 mL) under nitrogen. Sodium cyanoborohydride (0.27 g, 4.30 mmol) was added and the mixture was heated to 40° C. for 24 h. The mixture was cooled to room temperature and 1N NaOH (50 mL) was added. The mixture was transferred to a separatory funnel and extracted with DCM (2×200 mL). The organic layer was dried with MgSO₄, filtered through Celite®, and concentrated in vacuo. The mixture was purified on a Analogix IntelliFlash 280 with a normal phase Super Flash column (SF40-150 g, gradient 100:0-90:10 CH₂Cl₂:CH₃OH) to give 1.01 g of Compound 2d as a white solid. $^1$H NMR (300 MHz, CD₃OD) δ 7.68 (s, 1H), 7.32-7.42 (m, 2H), 6.98-7.10 (m, 4H), 5.55 (s, 1H), 4.95 (s, 6H), and 1.55 (s, 9H); LC/MS (ES+) m/z 359 (M+1).

Compound 2f was prepared by the methods described in Example 1, Step G for the synthesis of Compound 1h, by substituting Compound 2d for Compound 1d. Compound 2g was prepared by arylamination according to the methods in Example 1, Step H for the synthesis of Compound 1i, by substituting Compound 2f for Compound 1h.

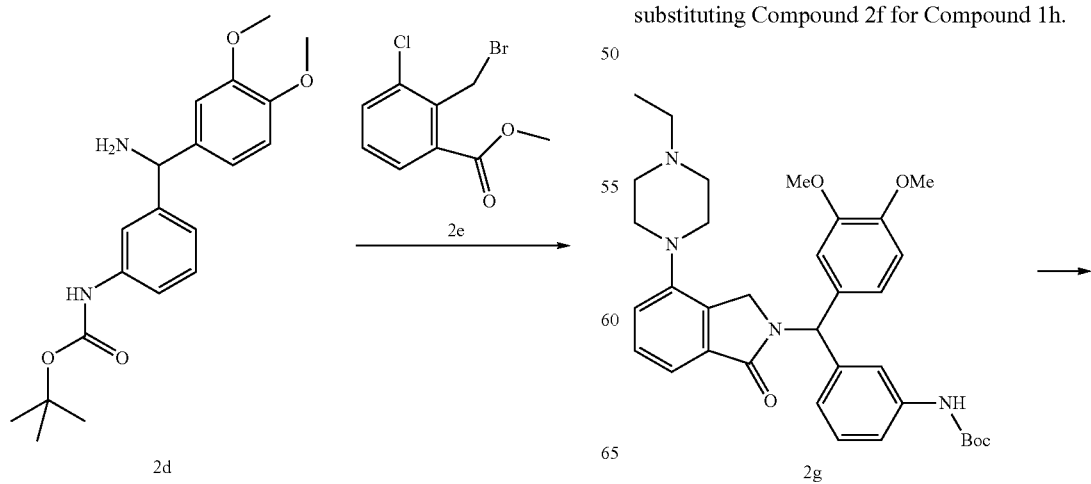

91

-continued

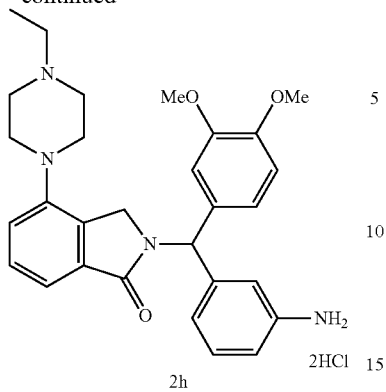

2h

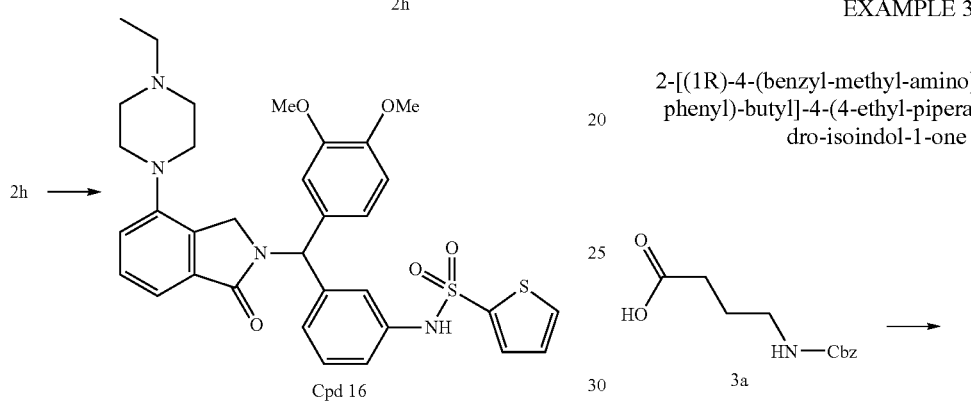

Cpd 16

Compound 2g (82 mg, 0.14 mmol) was dissolved in dioxane (0.3 mL) and combined with 4N hydrogen chloride in dioxane (0.3 mL, 1.2 mmol) for 4 h. Evaporation afforded Compound 2h as the HCl salt (61 mg, 0.11 mmol, 79%), which was used for the next step without purification. Compound 2h was dissolved in DCM (1.1 mL), cooled in an ice/water bath, and treated with TEA (50 µL, 0.36 mmol) and thiophenesulfonyl chloride (22 mg, 0.12 mmol). After 1 h the reaction mixture was diluted with DCM (100 mL), washed with 1N hydrochloric acid (10 mL) and saturated sodium bicarbonate (20 mL), dried (MgSO$_4$), and evaporated. The residue was taken up into DCM (5 mL), treated with 1N hydrogen chloride in diethyl ether (2 mL), and concentrated in vacuo overnight to afford Cpd 16 as a white solid (45 mg, 58%). $^1$H NMR (300 MHz, CD$_3$OD) δ 7.47 (dd, J=5 and 1 Hz, 1H), 7.39-7.36 (m, 2H), 7.23 (dd, J=4 and 1 Hz, 1H), 7.19-7.11 (m, 2H), 6.95-6.81 (m, 5H), 6.62 (d, J=1.9 Hz, 1H), 6.59-6.54 (m, 2H), 4.20 (d, J=18 Hz, 1H), 4.10 (d, J=18 Hz, 1H), 3.73 (s, 3H), 3.60 (s, 3H), 2.98 (m, 4H), 2.50 (m, 4H), 2.37 (q, J=7.2 Hz, 2H), 1.00 (t, J=7.2 Hz, 3H); LC/MS (ES+) m/z 633.3 (M+1).

Other compounds of the present invention may be prepared by those skilled in the art by varying the starting materials, reagent(s) and conditions used. Using the procedure of Example 2, the following compounds were prepared:

| Cpd | Name |
|---|---|
| 18 | 2-{1-(3,4-dimethoxy-phenyl)-2-[1-(thiophene-2-sulfonyl)-piperidin-4-yl]- ethyl}-4-(4-ethyl-piperazin-1-yl)-2,3-dihydro-isoindol-1-one<br>Observed Parent Peak 639.3; MS M + 1 calc'd: 639.3. |

92

-continued

| Cpd | Name |
|---|---|
| 44 | 2-{(3,4-dimethoxy-phenyl)-[1-(1,2-dimethyl-1H-imidazole-4-sulfonyl)-piperidin-4-yl]-methyl}-4-(4-ethyl-piperazin-1-yl)-2,3-dihydro-isoindol-1-one<br>Observed Parent Peak 637.3; MS M + 1 calc'd: 637.3. |
| 45 | 2-{(3,4-dimethoxy-phenyl)-[1-(thiophene-2-sulfonyl)-piperidin-4-yl]-methyl}-4-(4-ethyl-piperazin-1-yl)-2,3-dihydro-isoindol-1-one<br>Observed Parent Peak 625.3; MS M + 1 calc'd: 625.2. |

EXAMPLE 3

2-[(1R)-4-(benzyl-methyl-amino)-1-(3,4-dimethoxy-phenyl)-butyl]-4-(4-ethyl-piperazin-1-yl)-2,3-dihydro-isoindol-1-one Cpd 3

3a

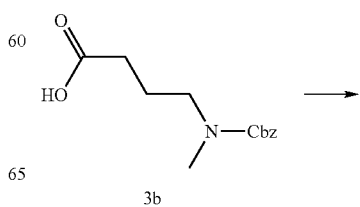

3b

Compound 3b was prepared by treating Compound 3a (10.00 g, 42 mmol) and iodomethane (6.55 g, 105 mmol) in anhydrous THF (50 mL) under nitrogen at 5° C. portionwise (10 min) with 60% sodium hydride (4.21 g, 105 mmol). The reaction mixture was allowed to warm to rt overnight and poured into ice-cold 1 N sodium hydroxide (200 mL). The aqueous layer was extracted with diethyl ether (2×100 mL), acidified with concentrated hydrochloric acid (0° C.), and extracted with EtOAc (2×100 mL). The EtOAc layer was washed with 1 M sodium thiosulfate solution (2×100 mL), dried (Na$_2$SO$_4$), and concentrated to afford Compound 3b as a colorless oil (11.15 g, quantitative), which was used without purification. $^1$H NMR (300 MHz, CD$_3$OD) δ 7.35 (m, 5H), 5.12 (s, 2H), 3.34 (m, 2H), 2.92 (s, 3H), 2.35 (m, 2H), 1.87 (m, 2H); LC/MS (ES+) m/z 252.1 (M+1).

3b

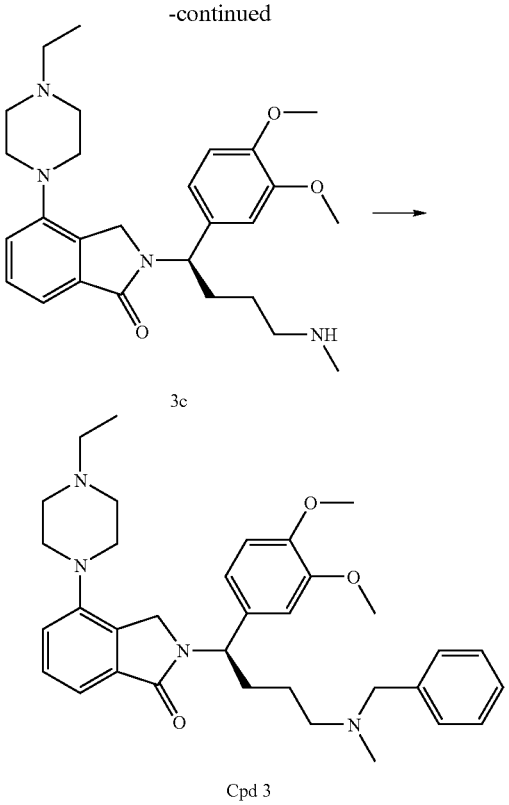

Cpd 3c

Cpd 3

Compound 3c was prepared by the methods described in Example 1, by substituting Compound 3b for Compound 1a. Compound 3c-2TFA (150 mg, 0.22 mmol) was dissolved in dichloroethane (10 mL) and combined with TEA (0.049 mL, 0.35 mmol) and benzaldehyde (0.033 mL, 0.32 mmol) under nitrogen. After stirring at rt for 2 h, tetramethylammonium triacetoxyborohydride (118 mg, 0.44 mmol) was added and the reaction was left overnight. The reaction mixture was diluted with dichloroethane (10 mL), washed with ammonium hydroxide in water (50% concentrated, 2×15 mL), dried ($Na_2SO_4$), filtered, and concentrated. The residue was purified by reversed phase HPLC [Phenomenex, Kromasil C18, 10μ, 110 Å, 250×50 mm, gradient elution with 10-75% acetonitrile (0.16% TFA) in water (0.2% TFA)] to yield pure Cpd 3(110 mg, 64%) as the TFA salt. $^1$H NMR (300 MHz, $CDCl_3$) δ 7.59 (t, J=7.3 Hz, 1H), 7.47-7.31 (m, 6H), 7.18 (m, 1H), 6.98-6.84 (m, 3H), 5.53 (m, 1H), 4.37 (d, J=17 Hz, 1H), 4.27 (d, J=14 Hz, 1H), 4.06 (t, J=14 Hz, 1H), 3.88 (buried d, J=17 Hz, 1H), 3.87 (s, 3H), 3.84 (s, 3H), 3.69 (m, 2H), 3.5-2.9 (m, 10H), 2.62 (s, 3H), 2.4-2.0 (m, 2H), 1.86 (m, 2H), 1.41 (t, J=7 Hz, 3H); LC/MS (ES+) m/z 557.4 (M+1).

Other compounds of the present invention may be prepared by those skilled in the art by varying the starting materials, reagent(s) and conditions used. In cases where the amine is primary, isolation of the mono- and di-alkylated materials occurred. Using the procedure of Example 3, the following compounds were prepared:

| Cpd | Name |
|---|---|
| 13 | 2-[2-(1-benzyl-piperidin-4-yl)-1-(3,4-dimethoxy-phenyl)-ethyl]-4-(4-ethyl-piperazin-1-yl)-2,3-dihydro-isoindol-1-one<br>Observed Parent Peak 583.5; MS M + 1 calc'd: 583.4. |
| 19 | 2-[(3-benzylamino-phenyl)-(3,4-dimethoxy-phenyl)-methyl]-4-(4-ethyl-piperazin-1-yl)-2,3-dihydro-isoindol-1-one<br>Observed Parent Peak 577.3; MS M + 1 calc'd: 577.3. |
| 42 | 2-[(3,4-dimethoxy-phenyl)-(1-ethyl-piperidin-4-yl)-methyl]-4-(4-ethyl-piperazin-1-yl)-2,3-dihydro-isoindol-1-one<br>Observed Parent Peak 507.5; MS M + 1 calc'd: 507.3. |
| 43 | 2-[(1-benzyl-piperidin-4-yl)-(3,4-dimethoxy-phenyl)-methyl]-4-(4-ethyl-piperazin-1-yl)-2,3-dihydro-isoindol-1-one<br>Observed Parent Peak 569.4; MS M + 1 calc'd: 569.4. |
| 63 | 2-[(1R)-4-(bis-pyridin-4-ylmethyl-amino)-1-(3,4-dimethoxy-phenyl)-butyl]-4-(4-ethyl-piperazin-1-yl)-2,3-dihydro-isoindol-1-one<br>Observed Parent Peak 635.4; MS M + 1 calc'd: 635.4. |
| 68 | 2-[(1R)-4-diethylamino-1-(3,4-dimethoxy-phenyl)-butyl]-4-(4-ethyl-piperazin-1-yl)-2,3-dihydro-isoindol-1-one<br>Observed Parent Peak 509.4; MS M + 1 calc'd: 509.4. |
| 69 | 2-[(1R)-1-(3,4-dimethoxy-phenyl)-4-ethylamino-butyl]-4-(4-ethyl-piperazin-1-yl)-2,3-dihydro-isoindol-1-one<br>Observed Parent Peak 481.4; MS M + 1 calc'd: 481.3. |
| 72 | 2-{(1R)-1-(3,4-dimethoxy-phenyl)-4-[(thiophen-2-ylmethyl)-amino]-butyl}-4-(4-ethyl-piperazin-1-yl)-2,3-dihydro-isoindol-1-one<br>Observed Parent Peak 549.4; MS M + 1 calc'd: 549.3. |
| 73 | 2-[(1R)-4-dibenzylamino-1-(3,4-dimethoxy-phenyl)-butyl]-4-(4-ethyl-piperazin-1-yl)-2,3-dihydro-isoindol-1-one<br>Observed Parent Peak 633.5; MS M + 1 calc'd: Exact Mass: 633.4. |
| 75 | 2-[(1R)-1-(3,4-dimethoxy-phenyl)-4-(2,2-dimethyl-propylamino)-butyl]-4-(4-ethyl-piperazin-1-yl)-2,3-dihydro-isoindol-1-one<br>Observed Parent Peak 523.5; MS M + 1 calc'd: 523.4. |
| 77 | 2-[(1R)-4-benzylamino-1-(3,4-dimethoxy-phenyl)-butyl]-4-(4-ethyl-piperazin-1-yl)-2,3-dihydro-isoindol-1-one<br>Observed Parent Peak 543.5; MS M + 1 calc'd: 543.3. |
| 94 | 2-[(1R)-1-(3,4-dimethoxy-phenyl)-4-(furan-2-ylmethyl-methyl-amino)-butyl]-4-(4-ethyl-piperazin-1-yl)-2,3-dihydro-isoindol-1-one<br>Observed Parent Peak 547.3; MS M + 1 calc'd: 547.3. |
| 95 | 2-[(1R)-1-(3,4-dimethoxy-phenyl)-4-(methyl-thiophen-2-ylmethyl-amino)-butyl]-4-(4-ethyl-piperazin-1-yl)-2,3-dihydro-isoindol-1-one<br>Observed Parent Peak 563.3; MS M + 1 calc'd: 563.3. |

EXAMPLE 4

2-[(1R)-1-(3,4-dimethoxy-phenyl)-4-(pyrimidin-2-ylamino)-butyl]-4-(4-ethyl-piperazin-1-yl)-2,3-dihydro-isoindol-1-one Cpd 48

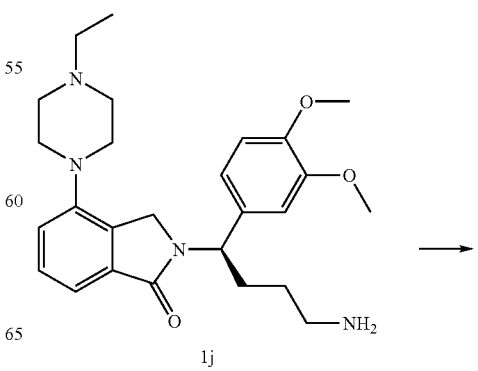

1j

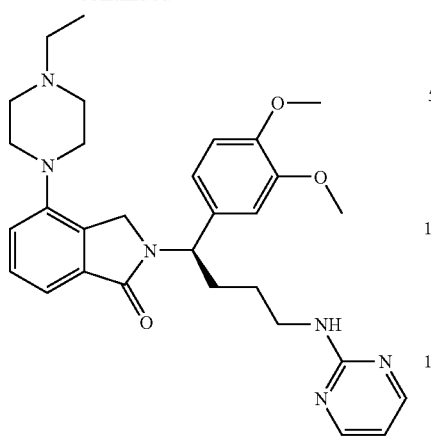

Cpd 48

Compound 1j·2HCl (53 mg, 0.10 mmol) was dissolved in ethanol (1.5 mL), treated with sodium bicarbonate (35 mg, 0.42 mmol) and 2-chloropyrimidine (12 mg, 0.10 mmol), and heated overnight at 65° C. The reaction mixture was diluted with water (4 mL) and acetonitrile (3 mL), filtered, and purified by reversed phase HPLC [Phenomenex, Kromasil C18, 5μ, 100 Å, 100×21 mm, gradient elution with 10-50% acetonitrile (0.16% TFA) in water (0.2% TFA)] to afford Cpd 48 as the TFA salt (50 mg, 77%). $^1$H NMR (300 MHz, DMSO-$d_6$) δ 8.24 (d, J=4.8 Hz, 2H), 7.46 (t, J=7.6 Hz, 1H), 7.37 (d, J=7.3 Hz, 1H), 7.30 (m, NH), 7.21 (d, J=7.8 Hz, 1H), 6.94-6.87 (m, 3H), 6.54 (t, J=4.8 Hz, 1H), 5.35 (t, J=8H, 1H), 4.51 (d, J=18 Hz, 1H), 4.01 (d, J=18 Hz, 1H), 3.73 (s, 3H), 3.72 (s, 3H), 3.6-2.9 (m, 12H), 2.13 (m, 2H), 1.50 (m, 2H), 1.25 (t, J=7.3 Hz, 3H); LC/MS (ES+) m/z 531.5 (M+1).

Other compounds of the present invention may be prepared by those skilled in the art by varying the starting materials, reagent(s) and conditions used. Using the procedure of Example 4, the following compounds were prepared:

| Cpd | Name |
|---|---|
| 10 | 2-[(1R)-1-(3,4-dimethoxy-phenyl)-4-(4,6-dimethoxy-pyrimidin-2-ylamino)-butyl]-4-(4-ethyl-piperazin-1-yl)-2,3-dihydro-isoindol-1-one<br>Observed Parent Peak 591.5; MS M + 1 calc'd: 591.3. |
| 11 | 2-[(1R)-4-(4-chloro-pyrimidin-2-ylamino)-1-(3,4-dimethoxy-phenyl)-butyl]-4-(4-ethyl-piperazin-1-yl)-2,3-dihydro-isoindol-1-one<br>Observed Parent Peak 565.3; MS M + 1 calc'd: 565.3. |
| 12 | 2-[(1R)-1-(3,4-dimethoxy-phenyl)-4-(4,6-dimethyl-pyrimidin-2-ylamino)-butyl]-4-(4-ethyl-piperazin-1-yl)-2,3-dihydro-isoindol-1-one<br>Observed Parent Peak 559.3; MS M + 1 calc'd: 559.3. |
| 20 | 2-[(1R)-1-(3,4-dimethoxy-phenyl)-4-(4-ethyl-pyrimidin-2-ylamino)-butyl]-4-(4-ethyl-piperazin-1-yl)-2,3-dihydro-isoindol-1-one<br>Observed Parent Peak 559.3; MS M + 1 calc'd: 559.3. |
| 21 | 2-[(1R)-1-(3,4-dimethoxy-phenyl)-4-(4-methoxy-pyrimidin-2-ylamino)-butyl]-4-(4-ethyl-piperazin-1-yl)-2,3-dihydro-isoindol-1-one<br>Observed Parent Peak 561.3; MS M + 1 calc'd: 561.3. |
| 22 | 2-[(1R)-1-(3,4-dimethoxy-phenyl)-4-(4-trifluoromethyl-pyrimidin-2-ylamino)-butyl]-4-(4-ethyl-piperazin-1-yl)-2,3-dihydro-isoindol-1-one<br>Observed Parent Peak 599.4; MS M + 1 calc'd: 599.3. |
| 23 | 2-[(1R)-1-(3,4-dimethoxy-phenyl)-4-(4-methyl-pyrimidin-2-ylamino)-butyl]-4-(4-ethyl-piperazin-1-yl)-2,3-dihydro-isoindol-1-one<br>Observed Parent Peak 545.4; MS M + 1 calc'd: 545.3. |
| 89 | 2-[(1R)-1-(3,4-dimethoxy-phenyl)-4-(quinolin-2-ylamino)-butyl]-4-(4-ethyl-piperazin-1-yl)-2,3-dihydro-isoindol-1-one<br>Observed Parent Peak 580.3; MS M + 1 calc'd: 580.3. |
| 93 | 2-[(1R)-1-(3,4-dimethoxy-phenyl)-4-(1-oxy-pyridin-2-ylamino)-butyl]-4-(4-ethyl-piperazin-1-yl)-2,3-dihydro-isoindol-1-one<br>Observed Parent Peak 546.3; MS M + 1 calc'd: 546.3. |

EXAMPLE 5 thiophene-2-sulfonic acid [(4R)-4-[4-(4-cyclopropyl-piperazin-1-yl)-1-oxo-1,3-dihydro-isoindol-2-yl]-4-(3,4-dimethoxy-phenyl)-butyl]-methyl-amide Cpd 7 thiophene-2-sulfonic acid {(4R)-4-(3,4-dimethoxy-phenyl)-4-[4-(4-isopropyl-piperazin-1-yl)-1-oxo-1,3-dihydro-isoindol-2-yl]-butyl}-methyl-amide Cpd 8 thiophene-2-sulfonic acid [(4R)-4-(3,4-dimethoxy-phenyl)-4-(1-oxo-4-piperazin-1-yl-1,3-dihydro-isoindol-2-yl)-butyl]-methyl-amide Cpd 30

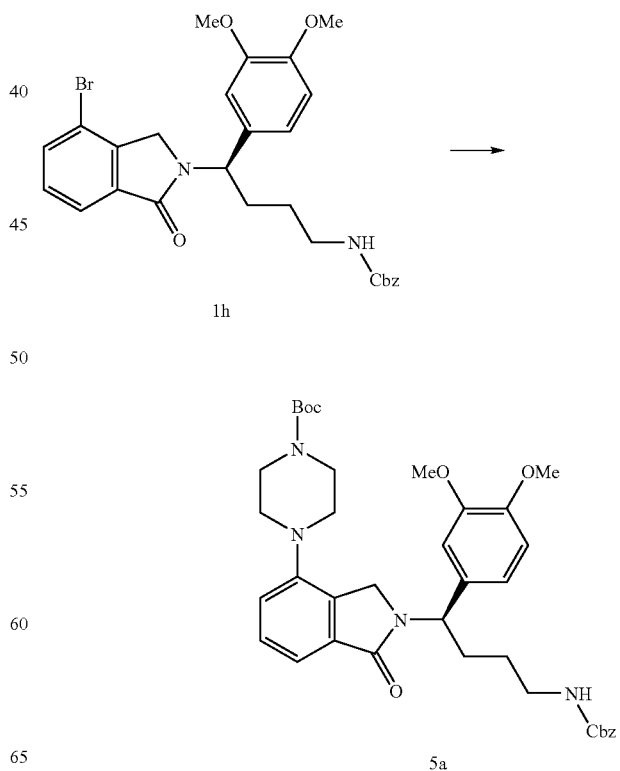

5a →

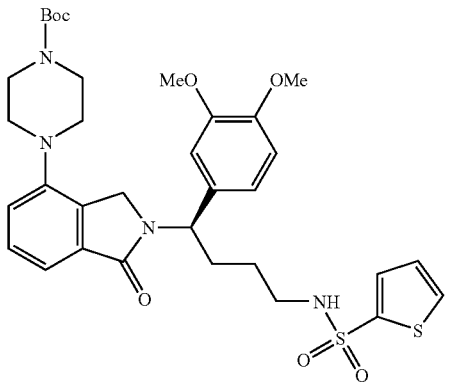

5b

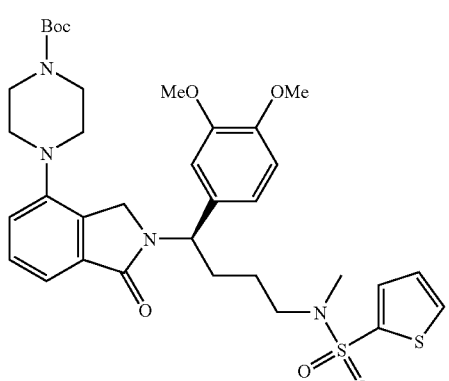

5c

5c →

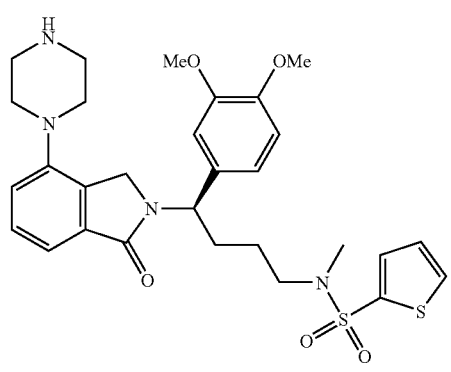

Cpd 30

-continued

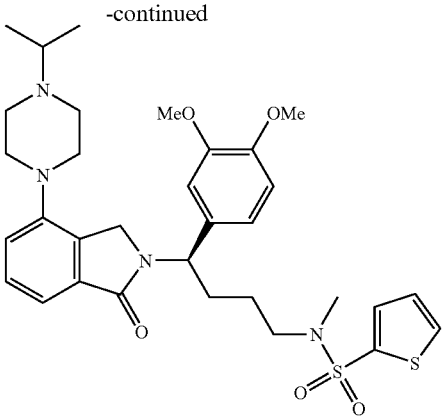

Cpd 8

Cpd 30 →

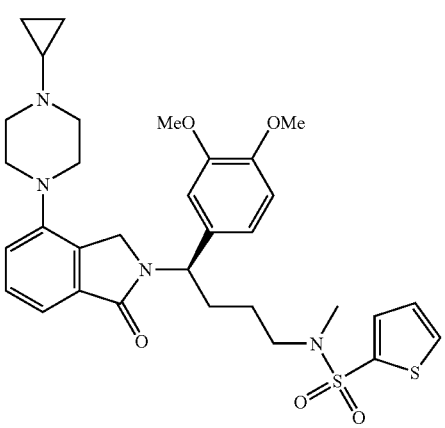

Cpd 7

Compound 1h was converted to Compound 5a by the same method as Compound 1h was converted to Compound 1i, using method H of Example 1. Compound 5a was converted to Compound 5b by the same methods that Compound 1i was converted to Cpd 84, using methods I and J of Example 1.

Compound 5b (167 mg, 0.25 mmol) was dissolved in THF (3 mL) under nitrogen and treated with 60% sodium hydride (15 mg, 0.38 mmol) at rt for 15 min, prior to the addition of iodomethane (0.023 mL, 0.38 mmol). After 2 h the reaction mixture was quenched with water (2 mL) and concentrated in vacuo. The residue was purified on silica gel by an ISCO system [40 g, gradient elution with 0 to 15% ethanol (0.1% TEA) in DCM] to afford Compound 5c (146 mg, 85%) as a glassy solid. $^1$H NMR (300 MHz, CDCl$_3$) δ 7.55-7.43 (m, 3H), 7.42 (t, J=7 Hz, 1H), 7.11-6.85 (m, 5H), 5.56 (m, 1H), 4.27 (d, J=17 Hz, 1H), 3.92 (buried d, J=17 Hz, 1H), 3.88 (s, 3H), 3.85 (s, 3H), 3.7-3.3 (m, 6H), 3.2-2.9 (m, 4H), 2.72 (s, 3H), 2.24 (m, 2H), 1.5 (m, 2H), 1.48 (s, 9H); LC/MS (ES+) m/z 685.3 (M+1).

Compound 5c (146 mg, 0.21 mmol) was dissolved in dioxane (5 mL) under nitrogen and treated with 4 N hydrogen chloride in dioxane (5 mL) and a drop of anisole. After 2 h at RT the reaction mixture was concentrated, dissolved with DCM (25 mL), washed with saturated sodium bicarbonate solution (2×10 mL), dried (Na$_2$SO$_4$), and concentrated to yield Cpd 30 (110 mg, 89%). LC/MS (ES+) m/z 585.3 (M+1).

According to the method of M. L. Gillaspy, B. A. Lefke, W. A. Hada, D. J. Hoover, *Tetrahedron Letters* 1995, 7399-7402, Cpd 30 (50 mg, 0.085 mmol), acetic acid (0.050 mL, 0.87 mmol), 3 Å molecular sieves (230 mg), [(1-ethoxycyclopropyl)oxy]trimethylsilane (0.102 mL, 0.51 mmol) were combined in methanol (4 mL) at rt. Sodium cyanoborohydride (24 mg, 0.38 mmol) was added and the reaction mixture was heated at reflux overnight, cooled to RT, filtered, and concentrated. The residue was dissolved in EtOAc (25 mL), washed with 2 N sodium hydroxide solution (2×10 mL) and brine (2×10 mL), dried (Na$_2$SO$_4$), concentrated, and purified by reversed phase HPLC [Phenomenex, Kromasil C18, 10μ, 110 Å, 250×50 mm, gradient elution with 20-90% acetonitrile (0.16% TFA) in water (0.2% TFA)] to yield Cpd 7 (12 mg, 19%) as a TFA salt. $^1$H NMR (300 MHz, CDCl$_3$) δ 7.63 (d, J=7.4 Hz, 1H), 7.59 (d, J=4 Hz, 1H), 7.52 (d, J=4 Hz, 1H), 7.47 (t, J=7.8 Hz, 1H), 7.18 (d, J=7.8 Hz, 1H), 7.13 (t, J=4 Hz, 1H), 6.99 (br d, J=8.2 Hz, 1H), 6.92 (br s, 1H), 6.86 (d, J=8.2 Hz, 1H), 5.56 (br t, J=7.5 Hz, 1H), 4.34 (d, J=17 Hz, 1H), 3.93 (buried d, J=17 Hz, 1H), 3.88 (s, 3H), 3.86 (s, 3H), 3.7-2.9 (m, 11H), 2.66 (s, 3H), 2.5-2.0 (m, 6H), 1.7 (m, 2H); LC/MS (ES+) m/z 625.3 (M+1).

Cpd 30 (27 mg, 0.046 mmol), acetone (0.02 mL, 0.2 mmol), and acetic acid (0.015 mL, 0.23 mmol) were combined in dichloroethane (4 mL) under nitrogen for 1 h, and then treated with sodium triacetoxyborohydride (14 mg, 0.066 mmol) over 2 h. Additional acetone (0.019 mL, 0.26 mmol), acetic acid (0.015 mL, 0.23 mmol), and sodium triacetoxyborohydride (44 mg, 0.21 mmol) were added and the reaction was left overnight. The reaction mixture was treated with saturated sodium bicarbonate, evaporated, dissolved in dichloroethane (15 mL), washed with saturated sodium bicarbonate, dried (Na$_2$SO$_4$), evaporated and purified by reversed phase HPLC [Phenomenex, Kromasil C18, 5μ, 100 Å, 100× 21 mm, gradient elution with 20-90% acetonitrile (0.16% TFA) in water (0.2% TFA)] to yield Cpd 8 (27 mg, 69%) as the di-TFA salt. $^1$H NMR (300 MHz, CDCl$_3$) δ 7.63 (d, J=7.4 Hz, 1H), 7.59 (dd, J=5 and 1 Hz, 1H), 7.52 (dd, J=4 and 1 Hz, 1H), 7.47 (t, J=7.7 Hz, 1H), 7.19 (d, J=7.7 Hz, 1H), 7.13 (dd, J=5 and 4 Hz, 1H), 6.98 (br d, J=8.2 Hz, 1H), 6.91 (br s, 1H), 6.85 (d, J=8.2 Hz, 1H), 5.57 (br t, J=8 Hz, 1H), 4.32 (d, J=17 Hz, 1H), 3.92 (buried d, J=17 Hz, 1H), 3.88 (s, 3H), 3.85 (s, 3H), 3.7-3.0 (m, 11H), 2.66 (s, 3H), 2.3 (m, 2H), 1.7 (m, 2H), 1.43 (d, J=Hz, 6H); LC/MS (ES+) m/z 627.3 (M+1).

Other compounds of the present invention may be prepared by those skilled in the art by varying the starting materials, reagent(s) and conditions used. Using the procedure of Example 5 and preceding examples, the following compounds were prepared:

| Cpd | Name |
|---|---|
| 4 | 4-(4-cyclopropyl-piperazin-1-yl)-2-[(1R)-1-(3,4-dimethoxy-phenyl)-4-(4-trifluoromethyl-pyrimidin-2-ylamino)-butyl]-2,3-dihydro-isoindol-1-one<br>Observed Parent Peak 610.3; MS M+ calc'd: 610.3. |
| 5 | 4-(4-benzyl-piperazin-1-yl)-2-[(1R)-1-(3,4-dimethoxy-phenyl)-4-(4-trifluoromethyl-pyrimidin-2-ylamino)-butyl]-2,3-dihydro-isoindol-1-one<br>Observed Parent Peak 661.3; MS M + 1 calc'd: 661.3. |
| 6 | 2-[(1R)-1-(3,4-dimethoxy-phenyl)-4-(4-trifluoromethyl-pyrimidin-2-ylamino)-butyl]-4-piperazin-1-yl-2,3-dihydro-isoindol-1-one<br>Observed Parent Peak 571.3; MS M + 1 calc'd: 571.3. |
| 9 | thiophene-2-sulfonic acid [(4R)-4-[4-(4-cyclobutyl-piperazin-1-yl)-1-oxo-1,3-dihydro-isoindol-2-yl]-4-(3,4-dimethoxy-phenyl)-butyl]-methyl-amide<br>Observed Parent Peak 639.3; MS M + 1 calc'd: 639.3. |
| 26 | thiophene-2-sulfonic acid {(4R)-4-(3,4-dimethoxy-phenyl)-4-[4-(4-methyl-piperazin-1-yl)-1-oxo-1,3-dihydro-isoindol-2-yl]-butyl}-methyl-amide<br>Observed Parent Peak 599.2; MS M + 1 calc'd: 599.2. |
| 62 | thiophene-2-sulfonic acid {(4R)-4-(3,4-dimethoxy-phenyl)-4-[4-(4-ethyl-piperazin-1-yl)-1-oxo-1,3-dihydro-isoindol-2-yl]-butyl}-methyl-amide<br>Observed Parent Peak 613.3; MS M + 1 calc'd: 613.2. |

EXAMPLE 6

5-methyl-isoxazole-4-carboxylic acid ((4R)-4-(3,4-dimethoxy-phenyl)-4-{1-oxo-4-[4-(1-phenyl-ethyl)-piperazin-1-yl]-1,3-dihydro-isoindol-2-yl}-butyl)-amide Cpd 85

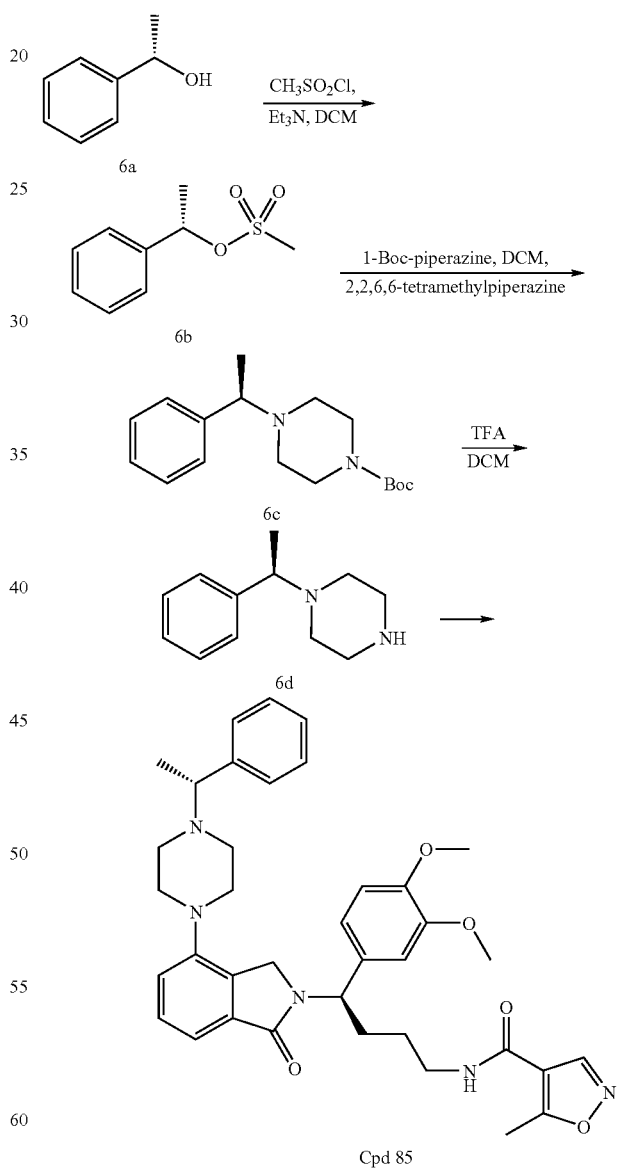

Cpd 85

A 100 mL round bottom flask was charged with S-phenethyl alcohol (Compound 6a, 5.0 mL, 41.3 mmol) and DCM (210 mL). The mixture was cooled using an ice/water bath. TEA (7.0 mL, 50.2 mmol) was added to the mixture followed by the dropwise addition methanesulfonyl chloride (3.6 mL, 46.5 mmol). The mixture was stirred for 4 h in the ice/water bath and then washed with 1N HCl (50 mL). The organic layer was dried with MgSO$_4$ and filtered through Celite® to give Compound 6b. 1-Boc-piperazine (7.70 g, 41.3 mmol) and 2,2,6,6-tetramethylpiperidine (15.4 mL, 90.7 mmol) were added to the crude solution of Compound 6b. The mixture was refluxed for 24 h, cooled to room temperature, and concentrated in vacuo. The crude oil was purified via flash chromatography (230-400 mesh silica gel 60, gradient 100:0-90:10 DCM:MeOH) to give 8.92 g (74%) of Compound 6c as a white solid. $^1$H NMR (300 MHz, CDCl$_3$) δ 7.29-7.32 (m, 5H), 3.34-3.41 (m, 5H), 2.29-2.44 (m, 4H), 1.43 (s, 9H), and 1.36 (d, J=6.7 Hz, 3H).

A 50 mL round bottom flask was charged with Compound 6c (8.92 g, 30.8 mmol) and DCM (120 mL). A portion of TFA (30 mL) was added and the mixture was stirred at room temperature for 1 h. The mixture was concentrated in vacuo. The crude oil was dissolved in DCM (400 mL) and washed with 1N NaOH (200 mL). The organic layer was dried using MgSO$_4$, filtered through Celite®, and concentrated in vacuo to give Compound 6d as a white solid. $^1$H NMR (300 MHz, CDCl$_3$) δ 7.36-7.40 (m, 5H), 4.98 (q, J=6.8 Hz, 1H), 3.45-3.48 (m, 4H), 3.24-3.33 (m, 2H), 3.09-3.13 (m, 2H), and 1.64 (d, J=6.7 Hz, 3H).

Compound 6d was converted to Cpd 85 by the same methods as N-ethyl piperazine was converted to Cpd 56 in Example 1. Cpd 85 analytical: $^1$H NMR (300 MHz, CDCl$_3$) δ 8.74 (s, 1H), 7.59 (d, J=7.4 Hz, 1H), 7.50-7.41 (m, 5H), 7.24 (m, 1H), 7.14 (d, J=7.9 Hz, 1H), 6.91-6.81 (m, 3H), 5.51 (m, 1H), 4.34 (q, J=6.5 Hz, 1H), 4.18 (d, J=17.5 Hz, 1H), 3.8 (buried d, J=17 Hz, 1H), 3.87 (s, 3H), 3.82 (s, 3H), 3.7-3.0 (m, 8H), 3.50 (s, 3H), 2.8 (m, 2H), 2.2 (m, 2H), 1.83 (d, J=6.8 Hz, 3H), 1.7 (m, 2H); LC/MS (ES+) m/z 638.4 (M+1).

EXAMPLE 7 thiophene-2-sulfonic acid {(4R)-4-(3,4-dimethoxy-phenyl)-4-[4-(1-ethyl-piperidin-4-yl)-1-oxo-1,3-dihydro-isoindol-2-yl]-butyl}-methyl-amide Cpd 2

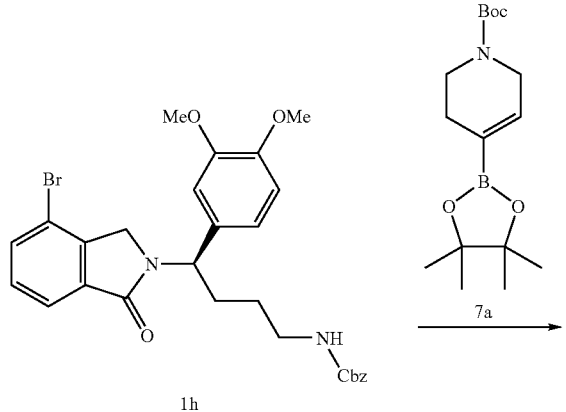

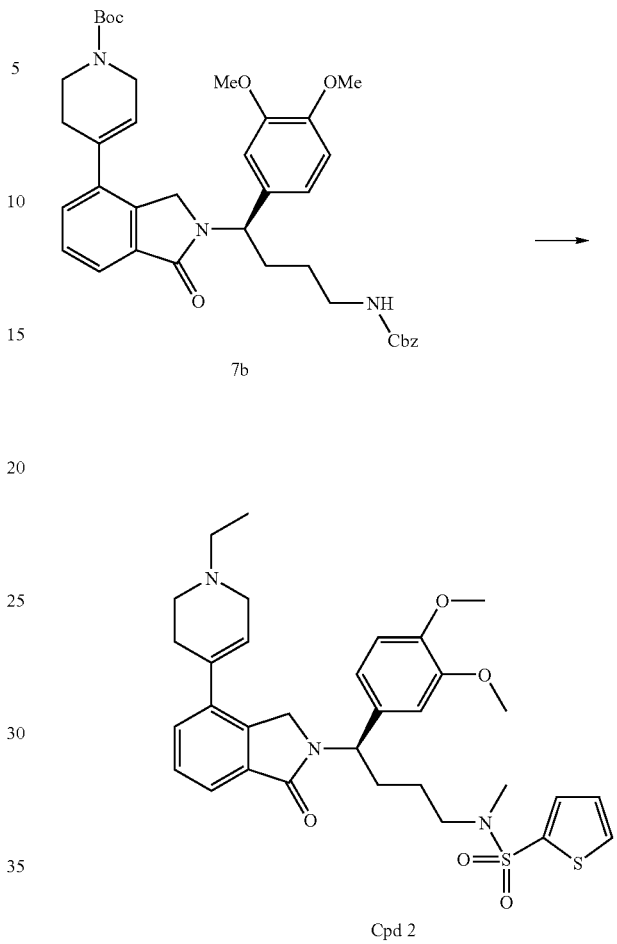

Compound 7a (100 mg, 0.32 mmol), potassium carbonate (134 mg, 0.97 mmol), [1,1'-bis(diphenylphosphino)-ferrocene]dichloropalladium(II) DCM complex (26 mg, 0.032 mmol) were combined in DMF (2 mL), and ethanol (0.5 mL). Compound 1h (184 mg, 0.33 mmol) was added and the reaction mixture was flushed with argon for 5 min, sealed in a tube, and heated at 100° C. overnight. The cooled reaction mixture was filtered through a Whatman 0.45 µm filter, concentrated, and purified twice on silica gel with an ISCO system [40 g, gradient elution with 0 to 1% ethanol (0.1% TEA) in DCM] to afford Compound 7b (214 mg, 100%) as a brown oil. $^1$H NMR (300 MHz, CDCl$_3$) δ 8.02 (br s, 1H), 7.77 (d, J=6.6 Hz, 1H), 7.45 (t, J=7.7 Hz, 1H), 7.39-7.30 (m, 6H), 6.96-6.84 (m, 3H), 5.78 (br s, 1H), 5.55 (t, J=7.8 Hz, 1H), 5.08 (s, 2H), 4.87 (br s, NH), 4.27 (d, J=17 Hz, 1H), 4.05 (m, 2H), 3.97 (d, J=17 Hz, 1H), 3.88 (s, 3H), 3.83 (s, 3H), 3.62 (br t, J=5 Hz, 2H), 3.49 (m, 2H), 3.30 (m, 2H), 2.42 (m, 2H), 2.12 (m, 2H), 1.50 (s, 9H); LC/MS (ES+) m/z 656.4 (M+1).

Compound 7b was converted to Cpd 2 by the same methods that Compound 5a was converted to Cpd 8 in Example 5, but acetaldehyde was used instead of acetone in the last step. Cpd 2-diTFA: $^1$H NMR (400 MHz, CDCl$_3$) δ 7.76 (d, J=7.3 Hz, 1H), 7.58-7.44 (m, 4H), 7.12 (m, 1H), 7.00 (m, 1H), 6.93 (s, 1H), 6.85 (d, J=8.3 Hz, 1H), 5.57 (m, 1H), 4.40 (d, J=17 Hz, 1H), 3.93 (d, J=17 Hz, 1H), 3.88 (s, 3H), 3.86 (s, 3H), 3.7-2.7

(m, 9H), 2.64 (s, 3H), 2.5-1.8 (m, 8H), 1.41 (t, J=7.3 Hz, 3H); LC/MS (ES+) m/z 612.3 (M+1).

EXAMPLE 8

4-{2-[(1R)-4-dibenzylamino-1-(3,4-dimethoxy-phenyl)-butyl]-1-oxo-2,3-dihydro-1H-isoindol-4-yl}-1-ethyl-1-methyl-piperazin-1-ium trifluoroacetate Cpd 38

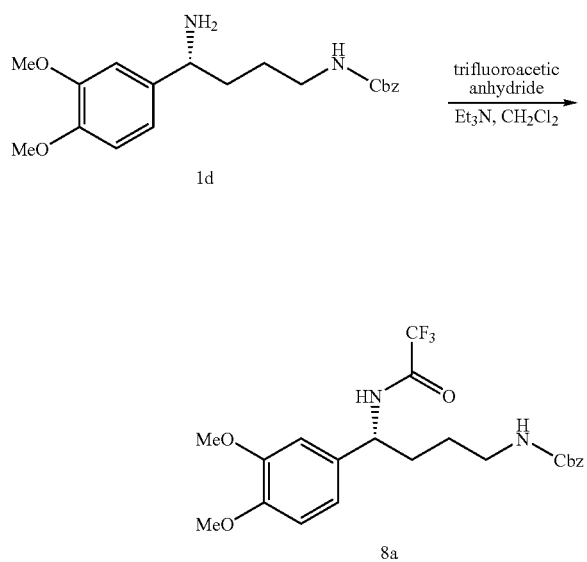

A 500-mL round bottom flask was charged with Compound 1d (15.66 g, 0.044 mol) and DCM (220 mL) in an ice/water bath. TEA (7.4 mL, 0.053 mol) was added followed by the dropwise addition of trifluoroacetic anhydride (6.8 mL, 0.049 mol). After 3 hours the mixture was extracted with DCM (200 mL) and washed with 1N HCl (1×100 mL), 1N NaOH (1×100 mL), and water (1×100 mL). The organic layer was dried with MgSO$_4$, filtered through Celite®, concentrated in vacuo to give 19.49 g (98%) of Compound 8a as a white solid. $^1$H NMR (300 MHz, CDCl$_3$) δ7.31-7.35 (m, 5H), 6.80-6.89 (m, 3H), 5.10 (s, 2H), 4.81-4.93 (m, 1H), 3.87 (ovs, 6H), 3.13-3.28 (m, 2H), 1.80-2.00 (m, 2H), and 1.42-1.59 (m, 2H); MS (ES$^+$) 455 (M+1).

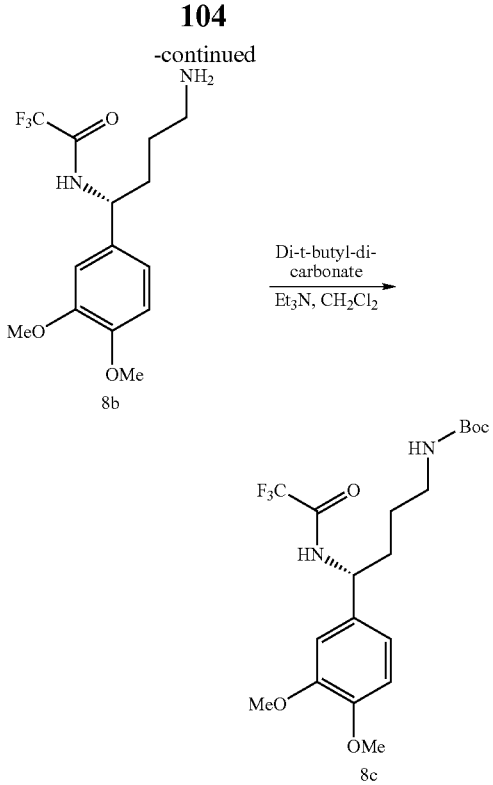

A 500-mL hydrogenation vessel was charged with Compound 8a (19.49 g, 0.043 mol), EtOAc (80 mL), ethanol (70 mL), 1N HCl (20 mL), and 10% palladium on carbon (2.0 g). The mixture was hydrogenated at 50 psig hydrogen for 24 hours. The mixture was filtered through Celite® and concentrated in vacuo to give 13.77 g (90%) of Compound 8b HCl as a white solid. $^1$H NMR (300 MHz, CDCl$_3$) δ 7.29-7.33 (m, 5H), 6.81-6.86 (m, 3H), 5.07 (s, 2H), 4.80-4.89 (m, 1H), 3.86 (ovs, 6H), 3.15-3.25 (m, 2H), and 1.35-1.64 (m, 6H); MS (ES$^+$) 321 (M+1).

A 500-mL round bottom flash was charged with Compound 8b HCl (16.85 g, 0.047 mol), DCM (220 mL), and TEA (14.0 mL, 0.10 mol). The mixture was cooled in an ice/water bath and treated with di-tert-butyl dicarbonate (9.77 g, 0.045 mol) in one portion. The mixture was stirred at room temperature for 18 hours. The mixture was diluted with DCM (300 mL) and washed with 1N HCl (1×100 mL), 1N NaOH (1×100 mL), and water (1×100 mL). The organic layer was dried with MgSO$_4$, filtered through Celite®, and concentrated in vacuo to give 12.78 g (64%) of Compound 8c as a white solid. $^1$H NMR (300 MHz, CDCl$_3$) δ 6.81-6.85 (m, 2H), 6.78 (s, 1H), 4.86-4.94 (m, 1H), 3.89 (s, 3H), 3.87 (s, 1H), 3.09-3.24 (m, 2H), 1.82-2.00 (m, 2H), 1.47-1.57 (m, 2H), and 1.44 (s, 9H).

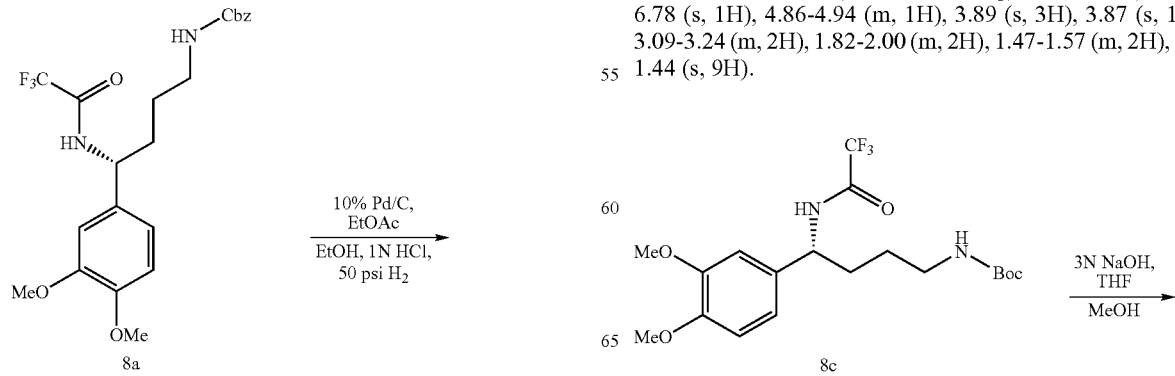

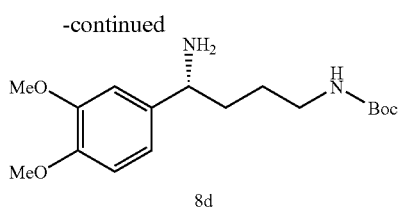

A 500-mL round bottom flask was charged with Compound 8c (12.78 g, 0.030 mol), THF (150 mL), methanol (40 mL), and 3N sodium hydroxide (30 mL). After 3 hours the mixture was diluted with DCM (500 mL) and washed with water (1×100 mL). The organic layer was dried with MgSO$_4$, filtered through Celite®, and concentrated in vacuo. The crude material was purified via flash chromatography (230-400 mesh silica gel 60, gradient 90:10-40:60 hexanes:EtOAc) to give 9.73 g (99%) of Compound 8d as a white solid. $^1$H NMR (300 MHz, CDCl$_3$) δ 6.87 (s, 1H), 6.82-6.84 (m, 2H), 3.84-3.90 (m, 7H), 3.08-3.14 (m, 2H), 1.62-1.71 (m, 4H), and 1.43 (s, 9H); MS (ES$^+$) 325 (M+1).

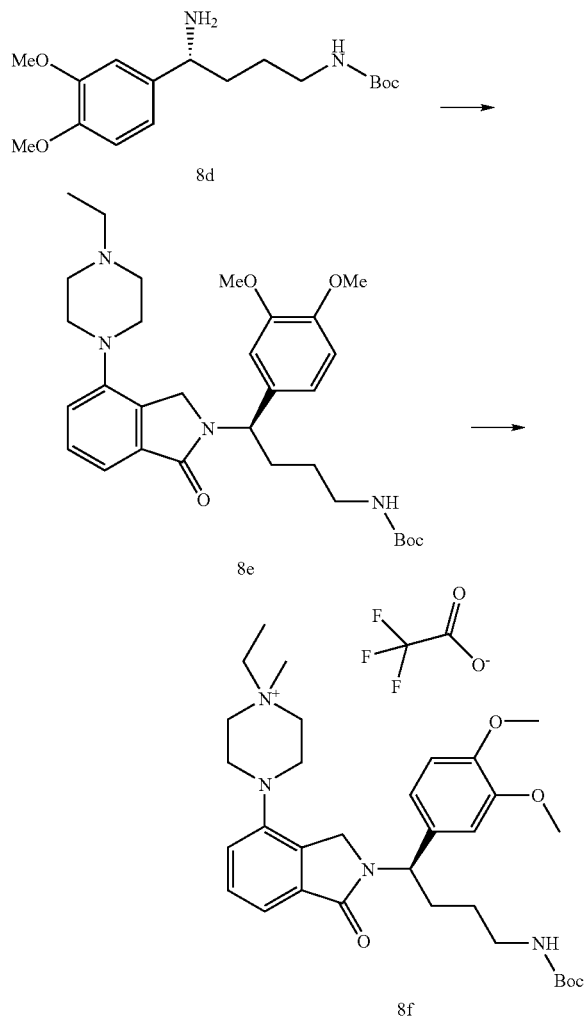

Compound 8d was converted to Compound 8e by the same methods of Example 1 in which Compound 1d was converted to Compound 1i. Compound 8e (70 mg, 0.13 mmol) was dissolved in dry THF (1 mL) in a pressure tube and treated with 60% sodium hydride (7 mg, 0.2 mmol) and iodomethane (13 µL, 0.2 mmol). The reaction mixture was sealed and heated at 50° C. overnight, cooled to rt, quenched with water (2 mL), extracted with EtOAc (2×30 mL), dried (Na$_2$SO$_4$), and concentrated to afford a brown solid. This material was combined with another 0.18 mmol batch and purified by reversed phase HPLC [Phenomenex, Kromasil C18, 10µ, 110 Å, 250×50 mm, gradient elution with 10-90% acetonitrile (0.16% TFA) in water (0.2% TFA)] to yield Compound 8f (58 mg, 27%) as a white solid. $^1$H NMR (300 MHz, CDCl$_3$) δ 7.64 (d, J=7.5 Hz, 1H), 7.45 (t, J=7.8 Hz, 1H), 7.15 (br d, J=7.6 Hz, 1H), 6.98 (d, J=8.2 Hz, 1H), 6.92 (s, 1H), 6.85 (d, J=8.3 Hz, 1H), 5.51 (t, J=8 Hz, 1H), 4.74 (br m, NH), 4.33 (d, J=17 Hz, 1H), 3.94 (d, J=17 Hz, 1H), 3.86 (s, 3H), 3.84 (s, 3H), 3.7-2.7 (m, 12H), 3.23 (s, 3H), 2.11 (m, 2H), 1.55 (m, 2H), 1.47 (t, J=7.1 Hz, 3H), 1.39 (s, 9H); LC/MS (ES+) m/z 567.5 (M$^+$).

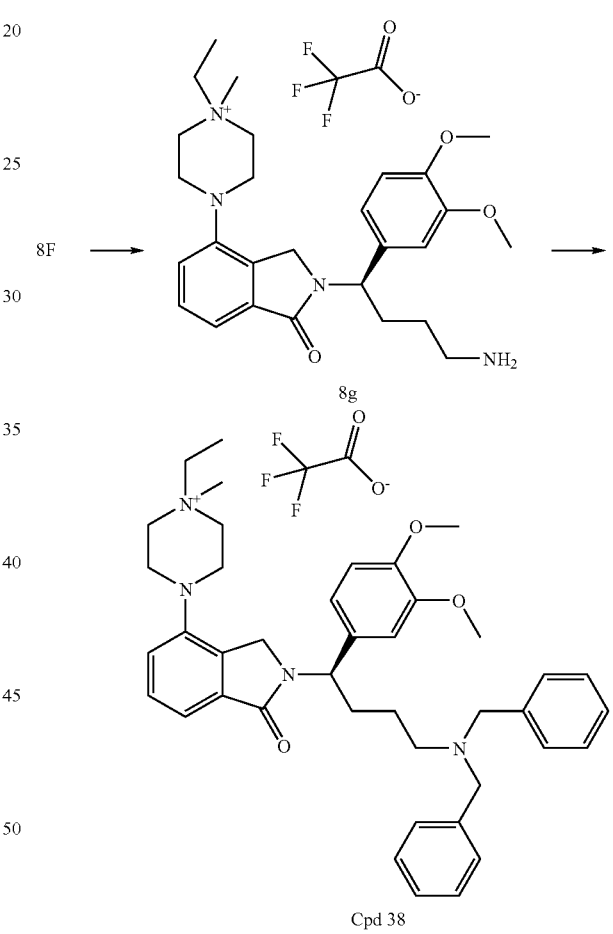

Compound 8f (55 mg, 0.08 mmol) was dissolved in dioxane (2.5 mL) and treated with 4N hydrogen chloride in dioxane and a drop of anisole. After 3 h the reaction was concentrated, evaporated from acetonitrile, triturated from diethyl ether, and concentrated to afford Compound 8g (57 mg, quantitative) as a light yellow glassy solid. LC/MS (ES+) m/z 467.4 (M$^+$). Compound 8g was converted to Cpd 38 by the same method used to convert Compound 3c to Cpd 3 in Example 3. Cpd 38-diTFA: $^1$H NMR (300 MHz, CDCl$_3$) δ 7.57 (d, J=7.5 Hz, 1H), 7.44-7.36 (m, 11H), 7.14 (d, J=7.8 Hz, 1H), 6.95 (d, J=8.2 Hz, 1H), 6.88 (s, 1H), 6.86 (d, J=8.3 Hz, 1H), 5.42 (m, 1H), 4.47 (d, J=18 Hz, 1H), 4.3-4.0 (m, 4H), 3.91 (d, J=18 Hz, 1H), 3.83 (s, 3H), 3.82 (s, 3H), 3.7-2.7 (m, 12H), 3.22 (s, 3H), 2.4-1.7 (m, 4H), 1.40 (t, J=6.8 Hz, 3H); LC/MS (ES+) m/z 647.4 (M+).

EXAMPLE 9

2-[(1R)-1-(3,4-dimethoxy-phenyl)-4-phenylamino-butyl]-4-(4-ethyl-piperazin-1-yl)-2,3-dihydro-isoindol-1-one Cpd 40

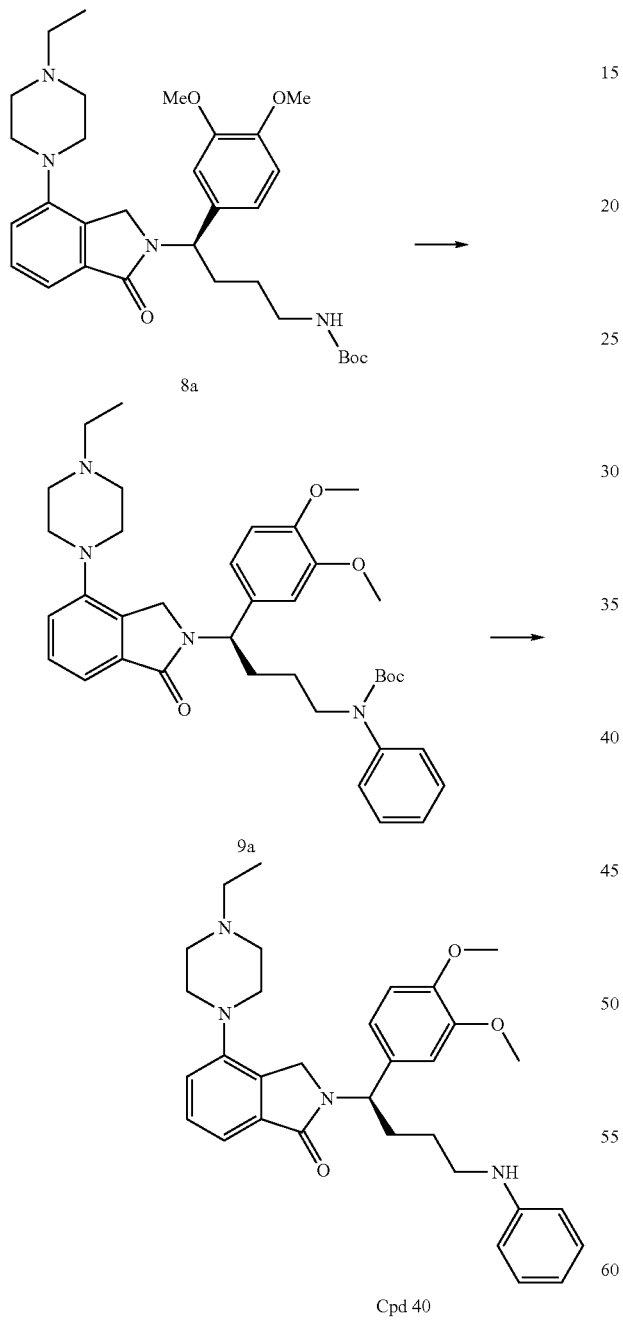

with argon, sealed, and heated at 100° C. overnight. Additional reagents (same amount as above) were added and the reaction continued another 24 h. The reaction mixture was filtered, concentrated in vacuo, and purified by reversed phase HPLC [Phenomenex, Kromasil C18, 10μ, 110 Å, 250×50 mm, gradient elution with 30-90% acetonitrile (0.16% TFA) in water (0.2% TFA)] to afford pure Compound 9a (11 mg, 11%) as a TFA salt. $^1$H NMR (300 MHz, CDCl$_3$) δ 7.62 (d, J=7.5 Hz, 1H), 7.46 (t, J=7.7 Hz, 1H), 7.33-7.11 (m, 6H), 6.92-6.81 (m, 3H), 5.50 (m, 1H), 4.20 (d, J=17 Hz, 1H), 3.87 (buried d, J=17 Hz, 1H), 3.87 (s, 3H), 3.83 (s, 3H), 3.8-3.2 (m, 10H), 2.95 (m, 2H), 2.10 (m, 2H), 1.79 (s, 9H), 1.62 (m, 2H), 1.42 (t, J=7.3 Hz, 3H); LC/MS (ES+) m/z 629.4 (M+1).

Compound 9a-TFA salt (10 mg, 0.013 mmol) was dissolved in dioxane (1.5 mL) and treated with 4 N hydrogen chloride in dioxane (1.5 mL) and a drop of anisole for 4 h. The reaction mixture was concentrated in vacuo, triturated with diethyl ether, and dried in vacuo to afford Cpd 40 (8 mg, quantitative) as the HCl salt. LC/MS (ES+) m/z 529.3 (M+1).

EXAMPLE 10

2-[(1R)-1-(3,4-dimethoxy-phenyl)-4-phenoxy-butyl]-4-(4-ethyl-piperazin-1-yl)-2,3-dihydro-isoindol-1-one Cpd 50

2-[(1R)-4-(1,3-dihydro-isoindol-2-yl)-1-(3,4-dimethoxy-phenyl)-butyl]-4-(4-ethyl-piperazin-1-yl)-2,3-dihydro-isoindol-1-one Cpd 100

2-[(1R)-1-(3,4-dimethoxy-phenyl)-4-imidazol-1-yl-butyl]-4-(4-ethyl-piperazin-1-yl)-2,3-dihydro-isoindol-1-one Cpd 32

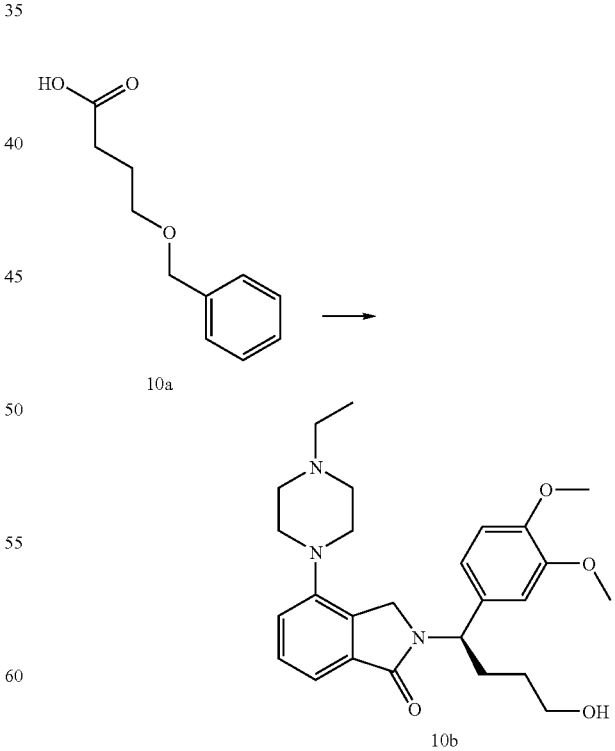

Compound 8a (84 mg, 0.15 mmol), bromobenzene (13 μL, 0.13 mmol), Pd$_2$(dba)$_3$ (2.5 mg, 0.0027 mmol), Xantphos® (5 mg, 0.009 mmol), and cesium carbonate (58 mg, 0.18 mmol) were combined in dioxane (1 mL) in a pressure tube, flushed Compound 10b was prepared from Compound 10a by the same methods of Example 1 by which Compound 1j was prepared from Compound 1a.

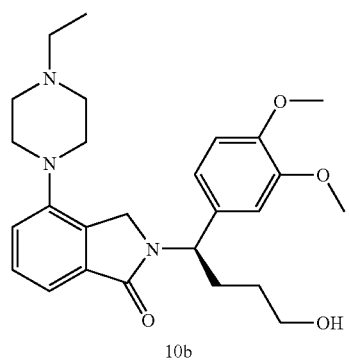

10b

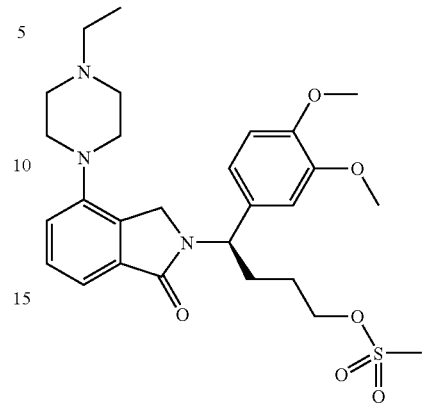

10c

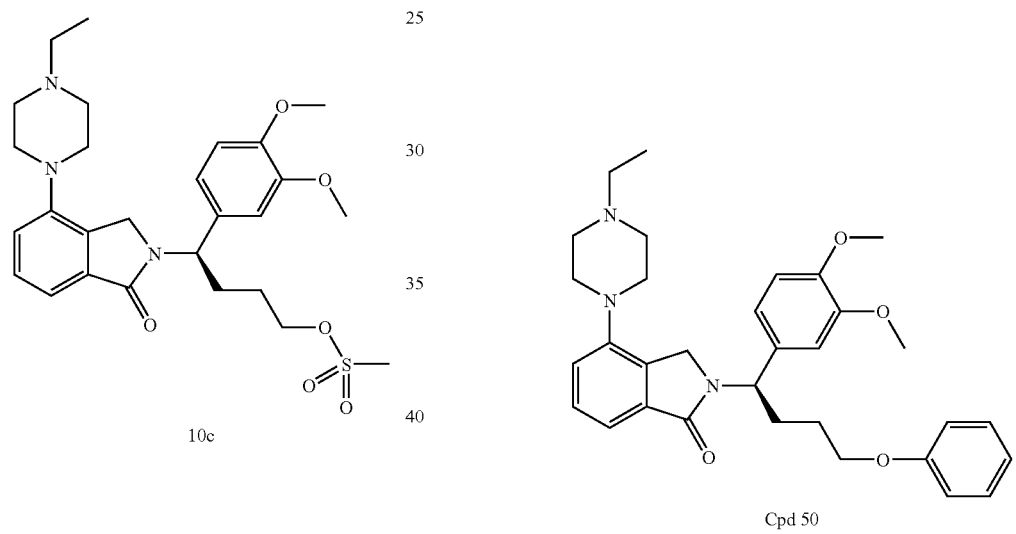

10c

Cpd 50

Compound 10b (1.85 g, 4.08 mmol) and TEA (2.83 mL, 20.4 mmol) were dissolved in DCM (45 mL) under nitrogen, cooled in an ice bath, and treated with methanesulfonyl chloride (350 μL, 4.50 mmol) in DCM (5 mL). After 45 min, the reaction mixture was quenched with saturated ammonium chloride solution (50 mL) and layers separated. The organic layer was washed with saturated sodium carbonate solution (50 mL) and brine (50 mL), then dried over sodium sulfate, filtered, and concentrated to afford Compound 10c as a yellow oil. Purification by reversed phase HPLC [Phenomenex, Kromasil C18, 10μ, 110 Å, 250×50 mm, gradient elution with 15-90% acetonitrile (0.16% TFA) in water (0.2% TFA)] afforded pure Compound 10c as the TFA salt (1.42 g, 54%; 40% yield, excluding a close running impurity). $^1$H NMR (300 MHz, CDCl$_3$) δ 7.51 (d, J=7.4 Hz, 1H), 7.41 (t, J=7.6 Hz, 1H), 7.10 (d, J=7.8 Hz, 1H), 6.97-6.84 (m, 3H), 5.58 (t, J=7.7 Hz, 1H), 4.33 (m, 2H), 4.23 (d, J=17.0 Hz, 1H), 3.92 (buried d, J=17.0 Hz, 1H), 3.88 (s, 3H), 3.85 (s, 3H), 3.07 (m, 4H), 2.61 (m, 4H), 2.50 (q, J=7.2 Hz, 2H), 2.26 (m, 2H), 2.04 (s, 3H), 1.80 (m, 2H), 1.13 (t, J=7.2 Hz, 3H); LC/MS (ES+) m/z 532.2 (M+1).

Compound 10c was prepared in situ from Compound 10b (90 mg, 0.18 mmol), TEA (77 μL, 0.55 mmol), DCM (5 mL), and methanesulfonyl chloride (21 μL, 0.27 mmol) at 0° C. for 15 min. After warming to rt the reaction mixture was evaporated. Crude Compound 10c was dissolved in dry DMF (2 mL) and treated sodium phenoxide (104 mg, 0.90 mmol) at 50° C. for 4 h. The reaction mixture was diluted with DCM (30 mL), washed with 1N sodium hydroxide solution (4×20 mL) and water (20 mL), dried (Na$_2$SO$_4$), concentrated and purified on a flash column (1 cm diameter, elution with 5% methanol in DCM) to yield Cpd 50 (23 mg, 22% for two steps). $^1$H NMR (300 MHz, CDCl$_3$) δ 7.53 (d, J=7.1 Hz, 1H), 7.41 (t, J=7.7 Hz, 1H), 7.26 (t, J=8.0 Hz, 2H), 7.08 (d, J=7.4 Hz, 1H), 7.00-6.83 (m, 6H), 5.62 (m, 1H), 4.28 (d, J=17.0 Hz, 1H), 4.0 (m, 2H), 3.90 (d, J=17.0 Hz, 1H), 3.87 (s, 3H), 3.85 (s, 3H), 3.06 (m, 4H), 2.60 (m, 4H), 2.50 (q, J=7.2 Hz, 2H), 2.30 (m, 2H), 1.87 (m, 2H), 1.13 (t, J=7.2 Hz, 3H); LC/MS (ES+) m/z 530.4 (M+1).

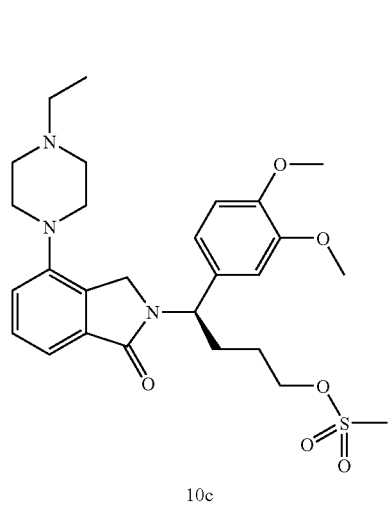

10c

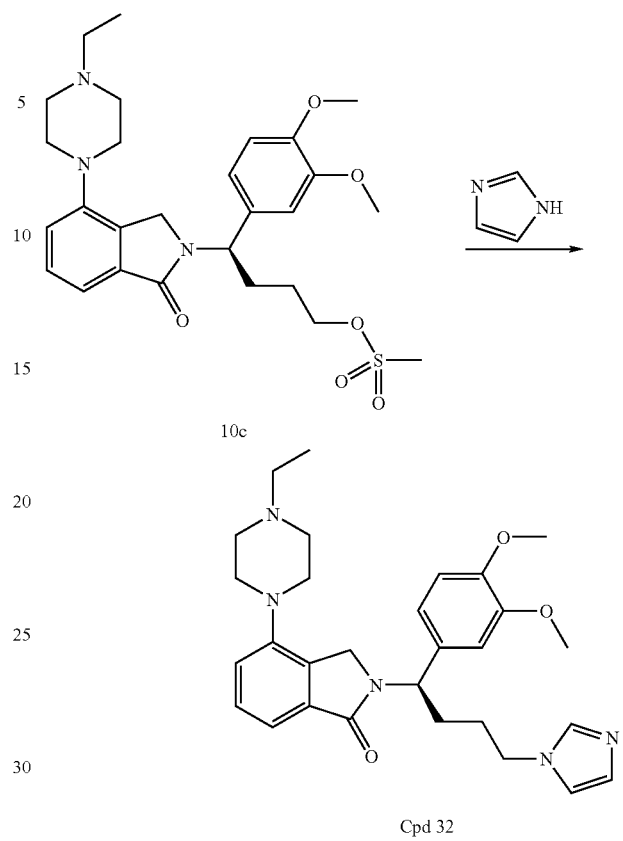

10c

Cpd 32

Imidazole (612 mg, 9.0 mmol) was dissolved in dry THF (15 mL), chilled in an ice bath, and treated with 95% sodium hydride (196 mg, 7.8 mmol) for 15 min. The reaction mixture was stirred for 1 h at rt and added to a solution of Compound 10c (500 mg, 0.94 mmol) in DMF (6 mL) and THF (3 mL) in a tube (100 mL), which was sealed and heated at 55° C. for 3 h. The reaction mixture was concentrated and purified by reversed phase HPLC [Phenomenex, Kromasil C18, 10μ, 110 Å, 250×50 mm, gradient elution with 0-90% acetonitrile (0.16% TFA) in water (0.2% TFA)] to yield Cpd 32 as the di-TFA salt. Cpd 32 di-TFA was converted to the Cpd 32 di-HCl salt (178 mg, 33%), as described for Cpd 100 above. Cpd 32 di-HCl salt: $^1$H NMR (300 MHz, CD$_3$OD) δ 8.88 (m, 1H), 7.56 (m, 1H), 7.47-7.34 (m, 3H), 7.15 (dd, J=7.4 and 1.3 Hz, 1H), 6.91-6.81 (m, 3H), 5.37 (m, 1H), 4.46 (d, J=17.8 Hz, 1H), 4.28 (m, 2H), 3.93 (d, J=17.8 Hz, 1H), 3.68 (s, 3H), 3.67 (s, 3H), 3.56-3.03 (m, 10H), 2.23-2.04 (m, 2H), 1.84 (m, 2H), 1.27 (t, J=7.3 Hz, 3H); LC/MS (ES+) m/z 504.3 (M+1).

Other compounds of the present invention may be prepared by those skilled in the art by varying the starting materials, reagent(s) and conditions used. Using the procedure of Example 10, the following compounds were prepared:

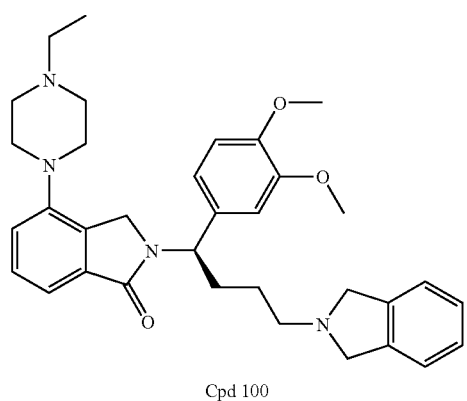

Cpd 100

Compound 10c (77 mg, 0.12 mmol) was dissolved in THF under nitrogen and treated with isoindoline (49 mL, 0.44 mmol) at 55° C. for 3 h. The reaction mixture was concentrated and purified by reversed phase HPLC [Phenomenex, Kromasil C18, 5μ, 100 Å, 100×21 mm, gradient elution with 10-90% acetonitrile (0.16% TFA) in water (0.2% TFA)] to yield Cpd 100 as the di-TFA salt. This material was converted to the di-HCl salt by dissolving in methanol, treating with 1 N HCl in diethyl ether (2 mL), and evaporating to yield Cpd 100 as the di-HCl salt (42 mg, 56%). $^1$H NMR of TFA salt (300 MHz, CDCl$_3$) δ 7.61 (d, J=7.4 Hz, 1H), 7.47 (t, J=7.7 Hz, 1H), 7.38 (dd, J=5.6 and 3.1 Hz, 2H), 7.28 (m, 2H), 7.18 (d, J=7.5 Hz, 1H), 6.96 (dd, J=8.2 and 1.9 Hz, 1H), 6.87 (m, 2H), 5.56 (m, 1H), 4.99 (d, J=14 Hz, 1H), 4.92 (d, J=14 Hz, 1H), 4.41 (d, J=17.6 Hz, 1H), 4.23 (br d, J=14 Hz, 2H), 3.87 (buried d, J=17 Hz, 1H), 3.88 (s, 3H), 3.84 (s, 3H), 3.68 (m, 2H), 3.44-3.09 (m, 10H), 2.99 (m, 2H), 2.43 (m, 1H), 2.25 (m, 1H), 1.91 (p, J=7 Hz, 2H), 1.39 (t, J=7.3 Hz, 3H); LC/MS (ES+) m/z 555.3 (M+1).

| Cpd | Name |
|---|---|
| 14 | 2-[(1R)-1-(3,4-dimethoxy-phenyl)-4-tetrazol-1-yl-butyl]-4-(4-ethyl-piperazin-1-yl)-2,3-dihydro-isoindol-1-one<br>Observed Parent Peak 506.4; MS M + 1 calc'd: 506.3. |
| 15 | 2-[(1R)-1-(3,4-dimethoxy-phenyl)-4-tetrazol-2-yl-butyl]-4-(4-ethyl-piperazin-1-yl)-2,3-dihydro-isoindol-1-one<br>Observed Parent Peak 506.4; MS M + 1 calc'd: 506.3. |

-continued

| Cpd | Name |
|---|---|
| 25 | 2-[(1R)-1-(3,4-dimethoxy-phenyl)-4-[1,2,4]triazol-1-yl-butyl]-4-(4-ethyl-piperazin-1-yl)-2,3-dihydro-isoindol-1-one<br>Observed Parent Peak 505.4; MS M + 1 calc'd: 505.3. |
| 27 | 2-[(1R)-1-(3,4-dimethoxy-phenyl)-4-(4,6-dimethyl-pyrimidin-2-ylsulfanyl)-butyl]-4-(4-ethyl-piperazin-1-yl)-2,3-dihydro-isoindol-1-one<br>Observed Parent Peak 576.3; MS M + 1 calc'd: 576.3. |
| 29 | 2-[(1R)-4-benzoimidazol-1-yl-1-(3,4-dimethoxy-phenyl)-butyl]-4-(4-ethyl-piperazin-1-yl)-2,3-dihydro-isoindol-1-one<br>Observed Parent Peak 554.4; MS M + 1 calc'd: 554.3. |
| 31 | {(4R)-4-(3,4-dimethoxy-phenyl)-4-[4-(4-ethyl-piperazin-1-yl)-1-oxo-1,3-dihydro-isoindol-2-yl]-butylsulfanyl}-pyridine 1-oxide<br>Observed Parent Peak 563.4; MS M + 1 calc'd: 563.3. |
| 74 | 2-[(1R)-4-benzyloxy-1-(3,4-dimethoxy-phenyl)-butyl]-4-(4-ethyl-piperazin-1-yl)-2,3-dihydro-isoindol-1-one<br>Observed Parent Peak 544.4; MS M + 1 calc'd: 544.3. |
| 90 | 2-[(1R)-4-[cyclopropyl-(4-fluoro-benzyl)-amino]-1-(3,4-dimethoxy-phenyl)-butyl]-4-(4-ethyl-piperazin-1-yl)-2,3-dihydro-isoindol-1-one<br>Observed Parent Peak 601.3; MS M + 1 calc'd: 601.4. |
| 91 | 2-[(1R)-1-(3,4-dimethoxy-phenyl)-4-(4-fluoro-benzylamino)-butyl]-4-(4-ethyl-piperazin-1-yl)-2,3-dihydro-isoindol-1-one<br>Observed Parent Peak 561.3; MS M + 1 calc'd: 561.3. |
| 96 | 2-[(1R)-4-(benzyl-isopropyl-amino)-1-(3,4-dimethoxy-phenyl)-butyl]-4-(4-ethyl-piperazin-1-yl)-2,3-dihydro-isoindol-1-one<br>Observed Parent Peak 585.4; MS M + 1 calc'd: 585.4. |
| 97 | 2-{(1R)-1-(3,4-dimethoxy-phenyl)-4-[(2-fluoro-benzyl)-methyl-amino]-butyl}-4-(4-ethyl-piperazin-1-yl)-2,3-dihydro-isoindol-1-one<br>Observed Parent Peak 575.3; MS M + 1 calc'd: 575.3 |
| 98 | 2-{(1R)-1-(3,4-dimethoxy-phenyl)-4-[(3-fluoro-benzyl)-methyl-amino]-butyl}-4-(4-ethyl-piperazin-1-yl)-2,3-dihydro-isoindol-1-one<br>Observed Parent Peak 575.3; MS M + 1 calc'd: 575.3 |
| 99 | 2-{(1R)-1-(3,4-dimethoxy-phenyl)-4-[(4-fluoro-benzyl)-methyl-amino]-butyl}-4-(4-ethyl-piperazin-1-yl)-2,3-dihydro-isoindol-1-one<br>Observed Parent Peak 575.3; MS M + 1 calc'd: 575.3 |
| 101 | 2-[(1R)-4-(3,4-dihydro-1H-isoquinolin-2-yl)-1-(3,4-dimethoxy-phenyl)-butyl]-4-(4-ethyl-piperazin-1-yl)-2,3-dihydro-isoindol-1-one<br>Observed Parent Peak 569.4; MS M + 1 calc'd: 569.4 |
| 102 | 2-[(1R)-1-(3,4-dimethoxy-phenyl)-4-(2,4-dimethyl-imidazol-1-yl)-butyl]-4-(4-ethyl-piperazin-1-yl)-2,3-dihydro-isoindol-1-one<br>Observed Parent Peak 532.3; MS M + 1 calc'd: 532.3 |
| 103 | 2-[(1R)-1-(3,4-dimethoxy-phenyl)-4-(2-methyl-imidazol-1-yl)-butyl]-4-(4-ethyl-piperazin-1-yl)-2,3-dihydro-isoindol-1-one<br>Observed Parent Peak 518.4; MS M + 1 calc'd: 518.3 |
| 104 | 2-[(1R)-1-(3,4-dimethoxy-phenyl)-4-(2-isopropyl-imidazol-1-yl)-butyl]-4-(4-ethyl-piperazin-1-yl)-2,3-dihydro-isoindol-1-one<br>Observed Parent Peak 546.5; MS M + 1 calc'd: 546.3 |

EXAMPLE 11

2-[(1R)-4-(2,6-difluoro-benzyloxy)-1-(3,4-dimethoxy-phenyl)-butyl]-4-(4-ethyl-piperazin-1-yl)-2,3-dihydro-isoindol-1-one Cpd 46

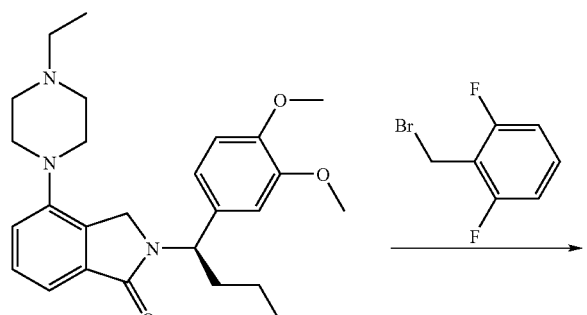

-continued

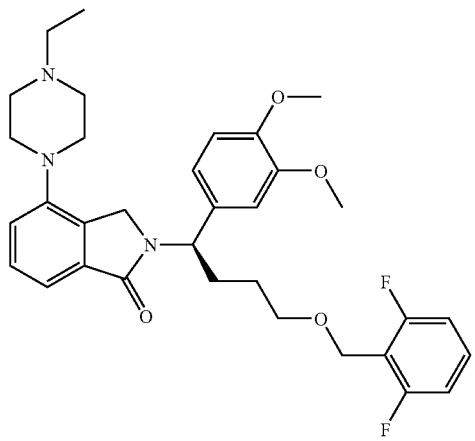

Cpd 46

Compound 10b-HCl (62 mg, 0.13 mmol) was dissolved in dry DMF (2 mL), chilled to 0° C., and treated with 95% sodium hydride (7 mg, 0.27 mmol). The reaction mixture was stirred for 10 min and then brought to rt over 30 min. In a second flask, a solution of 2,6-difluorobenzyl bromide (28 mg, 0.14 mmol) in DMF was treated with 4 Å molecular sieves over 30 min. The benzyl bromide was added to the sodium salt by syringe, the reaction mixture was stirred at rt for 20 h and 40° C. for 4 h. The reaction mixture was poured into water (5 mL) and extracted with EtOAc. The organic layer was washed with water (3×5 mL), dried ($Na_2SO_4$), concentrated, and purified by reversed phase HPLC [Phenomenex, Kromasil C18, 10μ, 110 Å, 100×21 mm, gradient elution with 15-90% acetonitrile (0.16% TFA) in water (0.2% TFA)] to yield Cpd 46 (16 mg, 15%) as the di-TFA salt. $^1$H NMR (300 MHz, $CD_3OD$) δ 7.67-7.57 (m, 2H), 7.43 (m, 2H), 7.26 (m, 1H), 7.16 (t, J=8.5 Hz, 2H), 6.91-6.82 (m, 2H), 5.37 (t, J=8 Hz, 1H), 4.76 (s, 2H), 4.46 (d, J=17.9 Hz, 1H), 3.97 (d, J=17.9 Hz, 1H), 3.71 (s, 3H), 3.70 (s, 3H), 3.59-3.20 (m, 12H), 2.13 (m, 2H), 1.42 (m, 5H); LC/MS (ES+) m/z 580.3 (M+1).

Other compounds of the present invention may be prepared by those skilled in the art by varying the starting materials, reagent(s) and conditions used. Using the procedure of Example 11, the following compounds were prepared:

| Cpd | Name |
|---|---|
| 47 | 2-[(1R)-4-(2-chloro-benzyloxy)-1-(3,4-dimethoxy-phenyl)-butyl]-4-(4-ethyl-piperazin-1-yl)-2,3-dihydro-isoindol-1-one<br>Observed Parent Peak 578.4; MS M + 1 calc'd: 578.3. |
| 51 | 2-[(1R)-1-(3,4-dimethoxy-phenyl)-4-(2-fluoro-benzyloxy)-butyl]-4-(4-ethyl-piperazin-1-yl)-2,3-dihydro-isoindol-1-one<br>Observed Parent Peak 562.3; MS M + 1 calc'd: 562.3. |
| 52 | 2-[(1R)-1-(3,4-dimethoxy-phenyl)-4-(3-fluoro-benzyloxy)-butyl]-4-(4-ethyl-piperazin-1-yl)-2,3-dihydro-isoindol-1-one<br>Observed Parent Peak 562.3; MS M + 1 calc'd: 562.3. |
| 55 | 2-[(1R)-1-(3,4-dimethoxy-phenyl)-4-(3-methyl-benzyloxy)-butyl]-4-(4-ethyl-piperazin-1-yl)-2,3-dihydro-isoindol-1-one<br>Observed Parent Peak 558.5; MS M + 1 calc'd: 558.3. |

EXAMPLE 12

4-(4-cyclopropyl-piperazin-1-yl)-2-[(1R)-1-(3,4-dimethoxy-phenyl)-4-phenoxy-butyl]-2,3-dihydro-isoindol-1-one Cpd 28

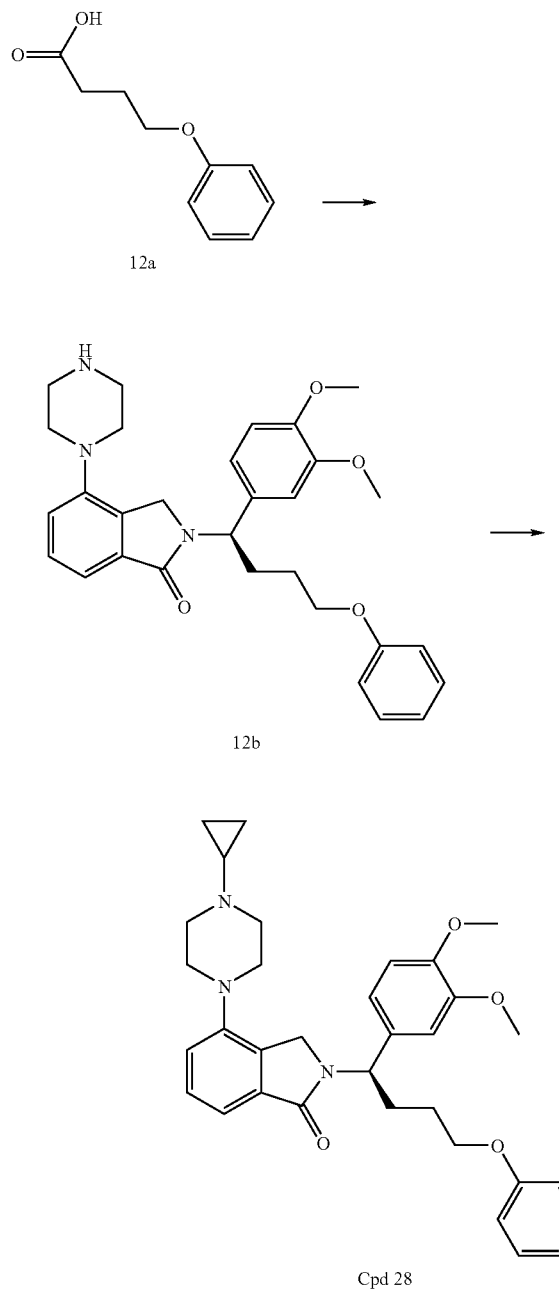

Compound 12b was prepared from Compound 12a by combining the methods from Examples 1 and 5, in which Compound 1a was converted to Compound 1h (Example 1) and Compound 1h to 5a and Compound 5c were converted to Cpd 30 (Example 5). Compound 12b was converted to Cpd 28 by the method of Example 5, in which Cpd 30 was converted to Cpd 7. Cpd 28-diTFA: $^1$H NMR (300 MHz, D$_6$-DMSO) δ 7.47 (t, J=7.7 Hz, 1H), 7.39 (d, J=7.3 Hz, 1H), 7.27 (m, 2H), 7.20 (d, J=7.7 Hz, 1H), 6.99-6.89 (m, 6H), 5.39 (m, 1H), 4.57 (d, J=17.8 Hz, 1H), 4.04 (m, 3H), 3.74 (s, 3H), 3.73 (s, 3H), 3.5-2.8 (m, 11H), 2.27 (m, 2H), 1.70 (m, 2H), 0.99 (m, 1H), 0.84 (m, 1H); LC/MS (ES+) m/z 542.4 (M+1).

Other compounds of the present invention may be prepared by those skilled in the art by varying the starting materials, reagent(s) and conditions used. Using the procedure of Example 12 and preceding examples (e.g., Example 10), the following compounds were prepared:

| Cpd | Name |
|---|---|
| 24 | 2-[(1R)-1-(3,4-dimethoxy-phenyl)-4-(1-methyl-1H-tetrazol-5-ylsulfanyl)-butyl]-4-piperazin-1-yl-2,3-dihydro-isoindol-1-one<br>Observed Parent Peak 524.3; MS M + 1 calc'd: 524.2. |
| 33 | 2-[(1R)-1-(3,4-dimethoxy-phenyl)-4-(methyl-phenyl-amino)-butyl]-4-piperazin-1-yl-2,3-dihydro-isoindol-1-one<br>Observed Parent Peak 515.4; MS M + 1 calc'd: 515.3. |
| 34 | 4-(4-benzyl-piperazin-1-yl)-2-[(1R)-1-(3,4-dimethoxy-phenyl)-4-phenoxy-butyl]-2,3-dihydro-isoindol-1-one<br>Observed Parent Peak 592.3; MS M + 1 calc'd: 592.3. |
| 35 | 2-[(1R)-1-(3,4-dimethoxy-phenyl)-4-imidazol-1-yl-butyl]-4-piperazin-1-yl-2,3-dihydro-isoindol-1-one<br>Observed Parent Peak 476.2; MS M + 1 calc'd: Exact Mass: 476.3. |
| 36 | 2-[(1R)-1-(3,4-dimethoxy-phenyl)-4-phenylsulfanyl-butyl]-4-piperazin-1-yl-2,3-dihydro-isoindol-1-one<br>Observed Parent Peak 518.2; MS M + 1 calc'd: 518.2. |
| 37 | 2-[(1R)-1-(3,4-dimethoxy-phenyl)-4-phenoxy-butyl]-4-piperazin-1-yl-2,3-dihydro-isoindol-1-one<br>Observed Parent Peak 502.4; MS M + 1 calc'd: 502.3. |
| 41 | 2-[(1R)-4-benzyloxy-1-(3,4-dimethoxy-phenyl)-butyl]-4-piperazin-1-yl-2,3-dihydro-isoindol-1-one<br>Observed Parent Peak 516.3; MS M + 1 calc'd: 516.3. |

EXAMPLE 13

N-{(4R)-4-(3,4-dimethoxy-phenyl)-4-[4-(4-ethyl-piperazin-1-yl)-1-oxo-1,3-dihydro-isoindol-2-yl]-butyl}-N-(4-fluoro-benzyl)-acetamide Cpd 88

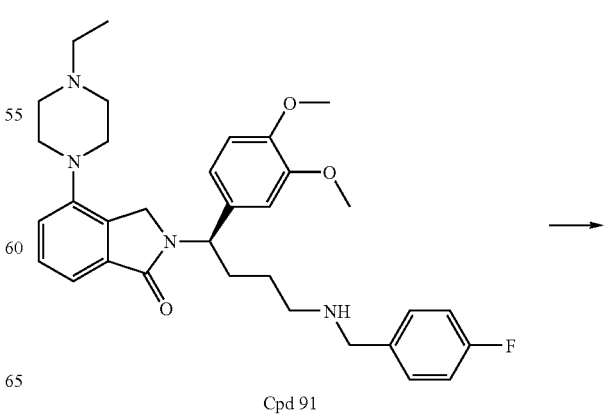

Cpd 91

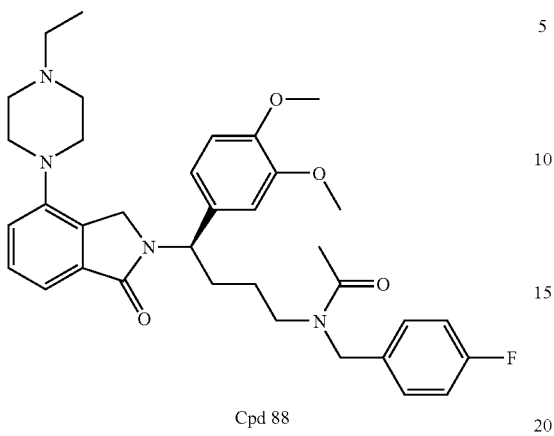

Cpd 88

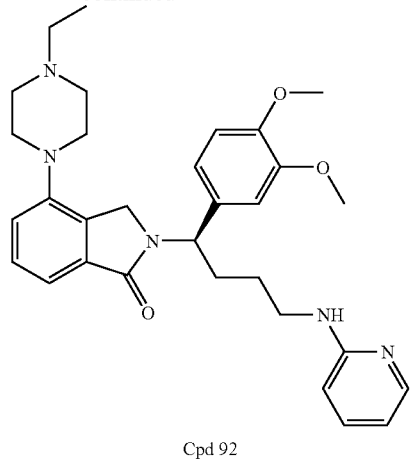

Cpd 92

Cpd 91, which was prepared by the methods described in Example 10, was converted to Cpd 88 by the same method of Example 1 in which Compound 1j was converted to Cpd 56. Cpd 88-TFA: $^1$H NMR (400 MHz, CDCl$_3$) δ 7.64 (dd, J=11 and 7.5 Hz, 1H), 7.48 (dd, J=15 and 7.3 Hz, 1H), 7.18 (m, 2H), 7.11 (m, 1H), 7.01 (t, J=8.5 Hz, 1H), 6.92-6.82 (m, 4H), 5.50 (m, 1H), 4.58, 4.45 (d, J=17 Hz, 1H), 4.47 (m, 2H), 4.22, 4.12 (d, J=17 Hz, 1H), 3.89, 3.87 (s, 3H), 3.84, 3.83 (s, 3H), 3.7-3.2 (m, 10H), 2.96 (m, 2H), 2.17, 2.12 (s, 3H), 2.05 (m, 2H), 1.59 (m, 2H), 1.42 (t, J=7.3 Hz, 3H); LC/MS (ES+) m/z 603.3 (M+1).

EXAMPLE 14

2-[(1R)-1-(3,4-dimethoxy-phenyl)-4-(pyridin-2-ylamino)-butyl]-4-(4-ethyl-piperazin-1-yl)-2,3-dihydro-isoindol-1-one Cpd 92

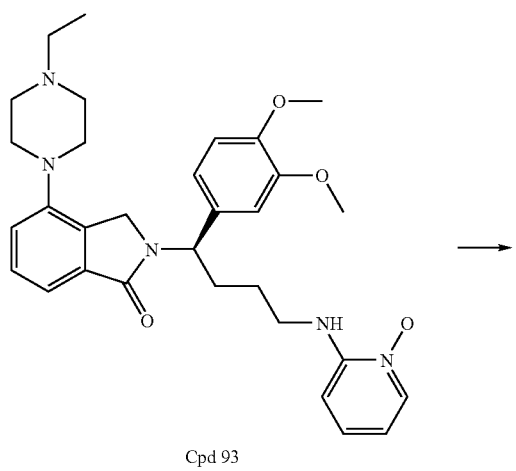

Cpd 93

Cpd 93-TFA (150 mg, 0.23 mmol), which was prepared by the methods described in Example 4, was dissolved in ethanol (8 mL) and treated with 10% palladium on carbon (40 mg) and ammonium formate (185 mg, 2.9 mmol) at 80° C. for 6 h and left at rt overnight. The reaction mixture was filtered, evaporated, purified by reversed phase HPLC [Phenomenex, Kromasil C18, 10μ, 110 Å, 250×50 mm, gradient elution with 0-80% acetonitrile (0.16% TFA) in water (0.2% TFA)], and converted to the HCl salt as described in Example 10 (Cpd 100) to afford Cpd 92-diHCl (20 mg, 14%). $^1$H NMR (400 MHz, CDCl$_3$) δ 7.99 (m, 1H), 7.51 (d, J=7.4 Hz, 1H), 7.40 (m, 2H), 7.08 (d, J=7.3 Hz, 1H), 6.96-6.82 (m, 3H), 6.54 (m, 1H), 6.39 (d, J=8.5 Hz, 1H), 5.60 (m, 1H), 4.22 (d, J=17 Hz, 1H), 3.91 (d, J=17 Hz, 1H), 3.87 (s, 3H), 3.83 (s, 3H), 3.7-2.6 (m, 12H), 2.2 (m, 2H), 1.7 (m, 2H), 1.42 (t, J=7.2 Hz, 3H); LC/MS (ES+) m/z 530.2 (M+1).

BIOLOGICAL EXAMPLES

Example 1

Rat UII Calcium Mobilization FLIPR Assay

A calcium mobilization assay based on a Fluorescence Imaging Plate Reader (FLIPR, Molecular Devices, Sunnyvale, Calif.) was used to determine antagonist activity, after a 5 min incubation, in response to the agonist cyclic peptide (Ac)-CFWK(2-Nal)C—NH$_2$ (FLIPR EC$_{50}$=0.54±0.2 nM, rU-II Ki=0.12±0.05 nM) at 1 nM (W. A. Kinney, H. R. Almond, Jr., J. Qi, C. E. Smith, R. J. Santulli, L. de Garavilla, P. Andrade-Gordon, D. S. Cho, A. M. Everson, M. A. Feinstein, P. A. Leung, B. E. Maryanoff, *Angew. Chem., Int. Ed.* 2002, 41, 2940-2944), in CHO cells transfected with rat GPR14 (U-II receptor) (M. Tal, D. A. Ammar, M. Karpuj, V. Krizhanovsky, M. Naim, D. A. Thompson, *Biochem. Biophys. Res. Commun.* 1995, 209, 752-759. A. Marchese, M. Heiber, T. Nguyen, H. H. Heng, V. R. Saldivia, R. Cheng, P. M. Murphy, L. C. Tsui, X. Shi, P. Gregor, *Genomics* 1995, 29, 335-344).

To derive these cells, the complete coding sequence of rat U-II (Genbank Accession No. U32673) was amplified by nested PCR from rat heart marathon-Ready cDNA. PCR was carried out by using the DNA polymerase PFU (Stratagene) following conditions suggested by the manufacturer. The PCR products were cloned into pcDNA3 (Invitrogen) digested with EcoR I and Xba I. Clones containing rat U-II receptor were verified by complete sequencing of the U-II receptor insert to ensure a lack of PCR-introduced errors. The constructed vector was transfected into CHO cells by using lipofectamine (GIBCO BRL). CHO cells with high expression of rat U-II receptor were selected and established as stable cell lines by using G418. CHO cells were seeded at 25,000 cells per well into 96-well, black-wall, clear-bottom microtiter plates 24 h before assay. Cells in culture media (DMEM/F12 containing 15 mM HEPES, L-glutamine, pyridoxine hydrochloride; 10% fetal bovine serum; 1 mg/mL G418 sulfate; antibiotic-antimycotic; pH 7.4) were loaded with proprietary dye, from the FLIPR Calcium Assay Kit (Molecular Devices), prepared in assay buffer (Hanks Balanced Salts Solution, 20 mM HEPES, 0.1% BSA, 2.5 mM probenecid, pH 7.4), and incubated for 1 h at 37° C. Calcium mobilization determinations were performed at room temperature (23° C.). The use of rat GPR14 was considered acceptable, because human U-II has similar affinity for human or rat GPR14 in the transfected cells (S. A. Douglas, E. H. Ohlstein, *Trends Cardiovasc. Med.* 2000, 10, 229-237).

Results for Calcium Mobilization using the Rat U11 FLIPR Assay are shown in Table 1 and Table 2. Table 2 contains $IC_{50}$ values which represent an average value for the compound tested.

TABLE 1

Rat UII FLIPR Average $IC_{50}$ (μM)

| Cpd | $IC_{50}$ |
|---|---|
| 1 | 0.007 |
| 2 | 0.032 |
| 3 | 0.004 |
| 4 | 1.70 |
| 5 | 0.016 |
| 6 | 0.008 |
| 7 | 0.013 |
| 8 | 0.002 |
| 9 | 0.004 |
| 10 | 0.004 |
| 11 | 0.001 |
| 12 | 0.012 |
| 13 | 0.167 |
| 14 | 0.031 |
| 15 | 0.057 |
| 16 | 0.031 |
| 17 | 0.337 |
| 18 | 0.009 |
| 19 | 0.138 |
| 20 | 0.034 |
| 21 | 0.004 |
| 22 | 0.003 |
| 23 | 0.019 |
| 24 | 0.165 |
| 25 | 0.145 |
| 26 | 0.016 |
| 27 | 0.003 |
| 28 | 0.025 |
| 29 | 0.014 |
| 30 | 0.039 |
| 31 | 0.011 |
| 32 | 0.045 |
| 33 | 0.307 |
| 34 | 0.105 |
| 35 | 1.90 |
| 36 | 0.019 |
| 37 | 0.014 |
| 38 | 0.185 |
| 39 | 0.138 |
| 40 | 0.010 |
| 41 | 0.022 |
| 42 | 3.60 |
| 43 | 0.173 |
| 44 | 7.33 |
| 45 | 0.465 |
| 46 | 7.73 |

TABLE 1-continued

Rat UII FLIPR Average $IC_{50}$ (μM)

| Cpd | $IC_{50}$ |
|---|---|
| 47 | 1.30 |
| 48 | 0.061 |
| 49 | 0.002 |
| 50 | 0.007 |
| 51 | 2.55 |
| 52 | 3.13 |
| 53 | 0.053 |
| 54 | 0.081 |
| 55 | 2.15 |
| 56 | 0.079 |
| 57 | 0.245 |
| 58 | 0.081 |
| 59 | 0.082 |
| 60 | 0.016 |
| 61 | 0.069 |
| 62 | 0.007 |
| 63 | 0.007 |
| 64 | 0.143 |
| 65 | 0.003 |
| 66 | 0.023 |
| 67 | 0.050 |
| 68 | 0.178 |
| 69 | 0.820 |
| 70 | 0.008 |
| 71 | 0.457 |
| 72 | 0.006 |
| 73 | 0.026 |
| 74 | 0.005 |
| 75 | 0.037 |
| 76 | 0.046 |
| 77 | 0.005 |
| 78 | 0.015 |
| 79 | 0.006 |
| 80 | 0.021 |
| 81 | 0.007 |
| 82 | 0.023 |
| 83 | 0.045 |
| 84 | 0.001 |
| 85 | 0.006 |
| 86 | <1 |
| 87 | 0.006 |
| 88 | 0.006 |
| 89 | 0.260 |
| 90 | 0.006 |
| 91 | 0.003 |
| 92 | 0.074 |
| 93 | 0.082 |
| 94 | 0.004 |
| 95 | 0.005 |
| 96 | 0.015 |
| 97 | 0.004 |
| 98 | 0.004 |
| 99 | 0.004 |
| 100 | 0.008 |
| 101 | 0.005 |
| 102 | 0.093 |
| 103 | 0.141 |
| 104 | 0.016 |

\* Referenced in: "Structure-Function Analysis of Urotensin II and Its Use in the Construction of a Ligand-Receptor Working Model" W. A. Kinney, H. R. Almond, Jr., J. Qi, C. E. Smith, R. J. Santulli, L. de Garavilla, P. Andrade-Gordon, D. S. Cho, A. M. Everson, M. A. Feinstein, P. A. Leung, B. E. Maryanoff, Angewandte Chemie, Int. Ed. 2002, 41, 2940-2944.

Example 2

Human Radioligand Binding Assay

Human Skeletal Muscle Myoblasts (HSMM) were obtained from Cambrex, and were cultured according to manufacturer's instruction. Cell viability was examined by trypan blue exclusion. Cells at less than 4 passages were used in all studies. For the ($^{125}$I)-U-II binding experiments (Described in: "Characterization of Functional Urotensin II Receptors in Human Skeletal Muscle Myoblasts: Comparison with Angiotensin II Receptors" J. Qi, L. K. Minor, C. Smith, B, Hu, J. Yang, P. Andrade-Gordon, B. Damiano, *Peptides* 2005, 26, 683-690), HSMM were plated in 12-well Costar plates in complete medium for 48 h to reach 70% confluence. The binding medium used was Dulbecco's modified Eagle's medium (DMEM) containing 2 mg/ml BSA and 25 mM HEPES (pH 7.4). The cells were washed at room temperature 2× with the binding medium, and were incubated with 0.2 ml per well of prepared binding medium containing 0.150 nM ($^{125}$I)-U-II and compounds for 3 h. The cells were washed 4× with the binding medium and solubilized in 1% SDS and 0.5 N NaOH. Radioactivity was quantified by gamma counting.

Radiolabeled ($^{125}$I)-U-II bound specifically and saturably to intact adherent HSMM (FIG. 1A). The binding assays were performed at 25° C. to lower nonspecific uptake of ($^{125}$I)-U-II by the cells that was seen at 37° C. Using this method, the nonspecific binding was below 10% of total binding. Analysis of the saturation data using the non-linear curve-fitting technique of GraphPad Prism Version 3.0 revealed that the best fit observed was for a one-site model. The derived Kd value was 0.309±0.022 nM (N=3 experiments) with the Hill slope close to unity. Based on the number of cells in a well and Bmax value, the number of UT receptors in HSMM was 2311±236 per cell (N=3 experiments). A time course experiment demonstrated that ($^{125}$I)-U-II binding to HSMM reached steady state at 3 h, and remained constant up to 5 hr, the longest time point measured. Human U-II, when add at time 0, efficiently displaced specific binding of ($^{125}$I)-U-II with a Ki of 0.425±0.096 nM (N=3 experiments). The resulting data is shown in Table 3 and Table 4. Table 4 contains IC$_{50}$ values which represent an average value for the compound tested.

TABLE 2

Human UII Average Binding Ki (µM)

| Cpd | Binding Ki |
| --- | --- |
| 1 | 0.055 |
| 2 | 0.050 |
| 3 | 0.034 |
| 4 | >0.3 |
| 5 | 0.045 |
| 6 | 0.120 |
| 7 | 0.059 |
| 8 | 0.011 |
| 9 | 0.044 |
| 10 | 0.081 |
| 11 | 0.062 |
| 12 | 0.054 |
| 13 | >0.3 |
| 14 | 0.129 |
| 15 | 0.172 |
| 16 | 0.066 |
| 17 | 0.074 |
| 18 | 0.019 |
| 19 | >0.3 |
| 20 | 0.048 |
| 21 | 0.008 |
| 22 | 0.013 |
| 23 | 0.013 |
| 24 | 0.300 |
| 25 | 0.301 |
| 26 | <0.006 |
| 27 | 0.019 |
| 28 | 0.154 |
| 29 | 0.056 |
| 30 | 0.049 |
| 31 | 0.135 |
| 32 | 0.157 |
| 33 | 0.520 |
| 34 | 0.032 |
| 35 | 1.100 |
| 36 | 0.122 |
| 37 | 0.050 |
| 38 | >0.3 |
| 39 | 0.162 |
| 40 | 0.075 |
| 41 | 0.165 |
| 42 | >0.3 |
| 43 | >0.3 |
| 44 | >0.3 |
| 45 | >0.3 |
| 46 | >0.3 |
| 47 | >0.3 |
| 48 | 0.048 |
| 49 | 0.013 |
| 50 | 0.023 |
| 51 | >0.3 |
| 53 | 0.056 |
| 54 | 0.077 |
| 56 | 0.125 |
| 57 | 0.049 |
| 58 | 0.109 |
| 59 | >0.3 |
| 60 | 0.011 |
| 61 | 0.029 |
| 62 | <0.005 |
| 63 | 0.008 |
| 64 | >0.3 |
| 65 | 0.004 |
| 66 | 0.084 |
| 67 | 0.043 |
| 68 | >0.3 |
| 69 | 0.199 |
| 70 | 0.054 |
| 71 | >0.3 |
| 72 | 0.018 |
| 73 | 0.053 |
| 74 | 0.019 |
| 75 | 0.242 |
| 76 | 0.033 |
| 77 | 0.026 |
| 78 | 0.02 |
| 79 | 0.039 |
| 80 | 0.018 |
| 81 | 0.018 |
| 82 | 0.025 |
| 83 | 0.017 |
| 84 | 0.004 |
| 85 | 0.015 |
| 86 | 0.386 |
| 87 | 0.037 |
| 88 | 0.010 |
| 89 | >0.3 |
| 90 | 0.034 |
| 91 | 0.062 |
| 92 | 0.060 |
| 93 | 0.125 |
| 94 | 0.043 |
| 95 | 0.023 |
| 96 | 0.069 |
| 97 | 0.026 |
| 98 | 0.059 |
| 99 | 0.047 |
| 100 | 0.024 |
| 101 | 0.021 |
| 102 | >0.3 |
| 103 | 0.158 |
| 104 | 0.046 |

Example 3

Human UII Calcium Mobilization Assay

6D9 human rhabdomyosarcoma cells were seeded into tissue culture treated 384-well black-walled clear bottom plates (3712, Corning Incorporated, Corning, N.Y.) at 8,000 cells/well in 25 µL of culture medium, and maintained in an incubator (5% $CO_2$ at 37° C.) for 22 hrs prior to the calcium mobilization assay. 25 µL of dye solution was added to the wells such that the final liquid volume before agonist/antagonist treatment was 50 µL for all assays. The cell plates were incubated at 37° C. for 45 minutes and the fluorescence intensity was measured on a Fluorometric Imaging Plate Reader (FLIPR$^{TETRA}$, Molecular Devices, Sunnyvale, Calif.).

Antagonist and agonist U-II were added at room temperature on the FLIPR$^{TETRA}$, and the fluorescence intensity before and after addition was measured over a period of 4 minutes. The dye incubation time and temperature as well as instrument setting was adjusted so the fluorescence intensity could be compared between plates on the same day. $EC_{50}$ and $IC_{50}$ were analyzed using GraphPad Prism 4 software (GraphPad Software Inc., San Diego, Calif.).

Materials and reagent Preparation: Human Rhabdomyosarcoma cells (6D9: isolated by dilution subcloning of RMS13 cells, ATCC® Number: CRL-2061, American Type Culture Collection ATCC, Manassas, Va.) was maintained in RPMI-1640 medium (30-2001, ATCC, Manassas, Va.) supplemented with 10% (v/v) Fetal Bovine Serum (SH30071.03, Hyclone, Logan, Utah).

Dye preparation: BD™ Calcium Assay Kit (80500-301, BD Biosciences, Rockville, Md.) was prepared according to the manufacture's instruction in 1× Hanks' balanced salt solution (HBSS, 21-023-CV, Mediatech, Inc. Herndon, Va.) containing 20 mM HEPES buffer (25-060-CI, Mediatech, Inc. Herndon, Va.). Final dye loading conditions included 1.25 mM probenecid (P36400, Invitrogen, Carlsbad, Calif.) and 0.01% FBS.

Agonist and antagonist preparation: Human U-II stock (U-7257, Sigma, St. Louis, Mo.) was prepared in acidified water (pH 4.95) at 5 mM. Urantide (PUT-3639-PI, Peptide International, Louisville, Ky.) was prepared in water at 5 mM. For assays, U-II agonist, U-II antagonist and urantide were diluted with HBSS/HEPES containing 0.01% FBS.

Test compounds were dissolved in DMSO at 10 mM concentration. The serial dilutions were carried out in HBSS/HEPES. The highest final DMSO concentration was at 0.1%.

TABLE 3

Human UII Ca$^+$ Mobilization Average $IC_{50}$ (µM)

| Cpd | $IC_{50}$ |
|---|---|
| 1 | 0.204 |
| 2 | 0.695 |
| 3 | 0.071 |
| 4 | 7.01 |
| 5 | 0.857 |
| 6 | 0.536 |
| 7 | 1.17 |
| 8 | 0.177 |
| 9 | 0.511 |
| 10 | 0.617 |
| 11 | 0.496 |
| 12 | 0.844 |
| 13 | 1.98 |
| 14 | 1.39 |
| 15 | 1.59 |
| 16 | 1.27 |
| 17 | 0.662 |
| 18 | 0.659 |
| 19 | 2.38 |
| 20 | 0.491 |
| 21 | 0.620 |
| 22 | 0.187 |
| 23 | 0.316 |
| 24 | 1.55 |
| 25 | 2.11 |
| 26 | 0.337 |
| 27 | 0.106 |
| 28 | 1.21 |
| 29 | 0.380 |
| 30 | 0.409 |
| 31 | 0.602 |
| 32 | 2.04 |
| 33 | 4.68 |
| 34 | 0.310 |
| 35 | >10 |
| 36 | 1.15 |
| 37 | 0.448 |
| 38 | 2.85 |
| 39 | 0.988 |
| 40 | 0.370 |
| 41 | 0.450 |
| 42 | >10 |
| 43 | 2.68 |
| 44 | 3.06 |
| 45 | 3.32 |
| 46 | >10 |
| 47 | 6.14 |
| 48 | 0.496 |
| 49 | 0.064 |
| 50 | 0.482 |
| 51 | >10 |
| 52 | >10 |
| 53 | 0.278 |
| 54 | 0.628 |
| 55 | >10 |
| 56 | 0.699 |
| 57 | 0.913 |
| 58 | 0.449 |
| 59 | 1.26 |
| 60 | 0.130 |
| 61 | 0.858 |
| 62 | 0.088 |
| 63 | 0.020 |
| 64 | 3.66 |
| 65 | 0.053 |
| 66 | 0.842 |
| 67 | 0.865 |
| 68 | 2.04 |
| 69 | >10 |
| 70 | 0.097 |
| 71 | 1.79 |
| 72 | 0.059 |
| 73 | 0.178 |
| 74 | 0.145 |
| 75 | 2.59 |
| 76 | 0.674 |
| 77 | 0.047 |
| 78 | 0.394 |
| 79 | 0.133 |
| 80 | 0.311 |
| 81 | 0.137 |
| 82 | 0.051 |
| 83 | 0.2 |
| 84 | 0.008 |
| 85 | 0.325 |
| 90 | 0.168 |
| 91 | 0.106 |
| 92 | 0.911 |
| 93 | 0.555 |
| 94 | 0.074 |
| 95 | 0.092 |
| 96 | 0.152 |

TABLE 3-continued

Human UII Ca⁺ Mobilization Average IC$_{50}$ (μM)

| Cpd | IC$_{50}$ |
|---|---|
| 97 | 0.056 |
| 98 | 0.105 |
| 99 | 0.238 |
| 100 | 0.319 |
| 101 | 0.069 |
| 102 | 1.281 |
| 103 | 1.40 |
| 104 | 0.206 |

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

All publications disclosed in the above specification are hereby incorporated by reference in full.

What is claimed is:

1. A compound of Formula (I):

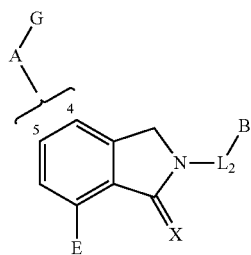

Formula (I)

wherein:

A is a-1, wherein, the lower portion of A is attached, relative to the nitrogen atom of Formula (I), to the 3 or 4 position on the benzene ring portion of Formula (I);

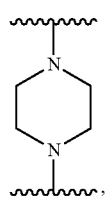

a-1 wherein, when A is present, then G is hydrogen, or one substituent selected from $C_{1-8}$alkyl, $C_{2-8}$alkenyl, $C_{3-14}$cycloalkyl or a —C[(R$_1$)(R$_{11}$)]-L-D moiety:

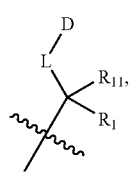

or two $C_{1-4}$alkyl substituents both attached to the common ring nitrogen atom of Formula (I), thus forming a quaternary ammonium salt;

R$_1$ is selected from the group consisting of hydrogen, $C_{1-8}$alkyl, $C_{2-8}$alkenyl, and $C_{2-8}$alkynyl;

R$_{11}$ is selected from the group consisting of hydrogen, $C_{1-8}$alkyl and cyclopropyl;

L is absent or $C_{1-4}$alkyl;

D is aryl, $C_{3-14}$cycloalkyl, $C_{5-14}$cycloalkenyl, heterocyclyl, or heteroaryl, wherein aryl and heteroaryl are optionally substituted with one, two, three or four substitutents independently selected from the group consisting of $C_{1-3}$alkyl, $C_{1-3}$alkoxy, $C_{2-8}$alkenyl, $C_{2-3}$alkenyloxy, hydroxy, $C_{1-3}$alkylthio, fluoro, chloro, cyano, $C_{1-3}$alkylcarbonyl, ($C_{1-3}$alkylcarbonyl)amino, ($C_{1-3}$alkyl)amino, di($C_{1-3}$alkyl)amino and $C_{3-14}$cycloalkyl, wherein $C_{3-14}$cycloalkyl is optionally substituted with one, two, three or four $C_{1-3}$alkyl substituents;

L$_2$ is —C(R$_2$)(R$_5$)—(CR$_6$R$_7$)$_r$—, wherein r is 0, 1 or 2; and wherein R$_5$, R$_6$, and R$_7$ are independently hydrogen or $C_{1-3}$alkyl;

R$_2$ is selected from the group consisting of heteroaryl, phenyl, heterocyclyl and $C_{1-6}$alkyl, wherein phenyl is optionally substituted with [(R$_{200}$—C$_{1-6}$alkyl)(R$_1$)]amino, [(R$_{200}$-sulfonyl)(R$_a$)]amino or [(hydroxysulfonyl)(R$_a$)]amino, wherein heterocyclyl is optionally substituted with $C_{1-4}$alkyl, aryl, heteroaryl, R$_{200}$—C$_{1-6}$alkyl or R$_{200}$-sulfonyl, and wherein $C_{1-6}$alkyl is optionally substituted with carboxy, hydroxy, R$_{200}$, NR$_a$R$_b$, $C_{1-6}$alkoxy, R$_{200}$—C$_{1-6}$alkoxy, R$_{200}$-oxy, R$_{200}$-thio, aminocarbonyl, carboxy-$C_{1-6}$alkoxy, aminocarbonyl-$C_{1-6}$alkoxy, ($C_{1-6}$alkyl)aminocarbonyl, di($C_{1-6}$alkyl)aminocarbonyl, [(R$_{200}$—C$_{1-6}$alkyl)(R$_a$)]amino, (R$_{200}$—C$_{1-6}$alkyl)-$_2$-amino, ($C_{1-6}$alkylcarbonyl)amino, (trihalo-$C_{1-4}$alkylcarbonyl)amino, (R$_{200}$—C$_{1-6}$alkylcarbonyl)amino, ($C_{1-6}$alkoxycarbonyl)amino, (R$_{200}$—C$_{1-6}$alkoxycarbonyl)amino, ($C_{1-6}$alkoxy-$C_{1-6}$alkylcarbonyl)amino, (R$_{200}$-carbonyl)amino, (amino-$C_{1-6}$alkylcarbonyl)amino, [($C_{1-6}$alkyl)amino-$C_{1-6}$alkylcarbonyl]amino, [di($C_{1-6}$alkyl)amino-$C_{1-6}$alkylcarbonyl]amino, ($C_{1-6}$alkylcarbonyl-acetonitrile-carbonyl)amino, ureido, thioureido, acetamidino, guanidino, ({[(R$_{200}$)(R$_a$)]aminocarbonyl}(R$_a$))amino, [(R$_{200}$-oxycarbonyl)(R$_a$)]amino, [(R$_{200}$)(R$_a$)]aminocarbonyloxy, aminosulfonyl, $C_{1-6}$alkylsulfonyl, hydroxysulfonyl, ($C_{1-6}$alkylsulfonyl)amino, (R$_{200}$—C$_{1-6}$alkylsulfonyl)amino, (R$_{200}$—C$_{2-6}$alkenylsulfonyl)amino, ($C_{1-6}$alkylsulfonyl-$C_{1-6}$alkylsulfonyl)amino, R$_{200}$-sulfonyloxy, aminosulfonyloxy, ($C_{1-6}$alkyl)aminosulfonyloxy, di($C_{1-6}$alkyl)aminosulfonyloxy, [(aminosulfonyl)(R$_a$)]amino, {[($C_{1-6}$alkyl)aminosulfonyl](R$_a$)}amino, {[di($C_{1-6}$alkyl)aminosulfonyl](R$_a$)}amino, [(hydroxysulfonyl)(R$_a$)]amino, [(R$_{200}$-oxysulfonyl)(R$_a$)]amino, [(R$_{200}$-sulfonyl)(R$_a$)]amino, [(R$_{200}$)(R$_a$)]aminosulfonyloxy, or ({[(R$_{200}$)(R$_a$)]aminosulfonyl}(R$_c$))amino;

R$_a$ is selected from the group consisting of hydrogen, $C_{1-6}$alkyl, $C_{1-6}$alkylcarbonyl and $C_{3-8}$cycloalkyl;

R$_b$ is selected from the group consisting of hydrogen, $C_{1-6}$alkyl or R$_{201}$, R$_{200}$ is $C_{6-10}$aryl, heteroaryl, $C_{3-8}$cycloalkyl or heterocyclyl each optionally substituted with one, two or three substituents independently selected from the group consisting of $C_{1-4}$alkyl, trihalo-$C_{1-4}$alkyl, $C_{1-4}$alkoxy, trihalo-$C_{1-4}$alkoxy, $C_{1-6}$alkylcarbonyl, $C_{1-6}$alkoxycarbonyl, amino, $C_{1-6}$alkyl-amino, di$C_{1-6}$alkyl-amino, ($C_{1-6}$alkylcarbonyl)amino, $C_{1-6}$alkylsulfonyl, hydroxysulfonyl, aminosulfonyl, chloro, fluoro, bromo and R$_{202}$, wherein $C_{3-8}$cycloalkyl or heterocyclyl is optionally substituted with one, two or three oxo substituents on available carbon atom ring members, and wherein heteroaryl having a nitrogen atom ring member is optionally substituted on the ring nitrogen atom with an oxy substituent and thus forms an oxide;

$R_{201}$ is $C_{6-10}$aryl, heteroaryl, $C_{3-8}$cycloalkyl or heterocyclyl, wherein aryl, heteroaryl, $C_{3-8}$cycloalkyl or heterocyclyl are each optionally substituted with one, two or three substituents independently selected from the group consisting of $C_{1-4}$alkyl, trihalo-$C_{1-4}$alkyl, $C_{1-4}$alkoxy, trihalo-$C_{1-4}$alkoxy, amino, $C_{1-6}$alkyl-amino, di$C_{1-6}$alkylamino, $C_{1-6}$alkylcarbonyl, $C_{1-6}$alkoxycarbonyl, ($C_{1-6}$alkylcarbonyl)amino, $C_{1-6}$alkylsulfonyl, hydroxysulfonyl, aminosulfonyl, chloro, fluoro, bromo, aryl, heteroaryl, aryl-$C_{1-6}$alkyl, aryl-sulfonyl and heteroaryl-sulfonyl, wherein $C_{3-8}$cycloalkyl or heterocyclyl is optionally substituted with one, two or three oxo substituents on available carbon atom ring members, and wherein heteroaryl having a nitrogen atom ring member is optionally substituted on the ring nitrogen atom with an oxy substituent and thus forms an oxide;

$R_{202}$ is aryl, heteroaryl, aryl-$C_{1-6}$alkyl, [(aryl-$C_{1-6}$alkyl)($R_a$)]amino, hydroxysulfonyl, aryl-sulfonyl, heteroaryl-sulfonyl or [(heteroaryl-sulfonyl)($R_a$)]amino, wherein each aryl and heteroaryl are optionally substituted with one, two or three $C_{1-4}$alkyl substituents;

B is $C_{6-10}$aryl, tetralinyl, indanyl, or a heteroaryl selected from the group consisting of pyridin-2-yl, pyridin-4-yl, pyrazol-4-yl, pyrimidin-4-yl, pyrimidin-5-yl, pyrazin-2-yl, imidazol-1-yl, thien-2-yl, isoquinolinyl, indolyl, quinolinyl, and thiazol-5-yl, wherein B is optionally substituted with one, two or three substituents independently selected from the group consisting of $C_{1-4}$alkyl, $C_{1-4}$alkoxy, fluorinated ($C_{1-4}$) alkoxy, halogen, cyano, hydroxy, aminocarbonyl, ($C_{1-4}$)alkylaminocarbonyl, di($C_{1-4}$)alkylaminocarbonyl, aminosulfonyl, ($C_{1-4}$)alkylaminosulfonyl, di($C_{1-4}$)alkylaminosulfonyl, hydroxysulfonyl, aminosulfonylamino, ($C_{1-4}$)alkylaminosulfonylamino, di($C_{1-4}$)alkylaminosulfonylamino, aminosulfonyloxy, ($C_{1-4}$)alkylaminosulfonyloxy, and di($C_{1-4}$)alkylaminosulfonyloxy, provided that when B is selected from the group consisting of $C_{6-10}$aryl, tetralinyl, indanyl, thien-2-yl, and indolyl, then B is independently substituted with two to three substitutents selected from the group consisting of $C_{1-3}$alkoxy and hydroxy, provided that, when B is phenyl substituted at the 3,4-, 3,5- or 4,5-positions with an unbranched $C_{1-3}$alkoxy substituent at each position, then phenyl may be further optionally substituted at a remaining open 3-, 4-, or 5-position with an additional $C_{1-3}$alkoxy or hydroxy substituent;

E is hydrogen, halogen, cyano, $C_{1-3}$alkyl, $C_{1-3}$alkoxy, $C_{2-5}$alkenyl, amino, ($C_{1-3}$alkyl)amino or di($C_{1-3}$alkyl) amino;

X is O or S;

and enantiomers, diastereomers, tautomers, and pharmaceutically acceptable salts thereof.

2. A compound of Formula (Ia):

Formula (Ia)

wherein:

Z is N;

G is hydrogen, or one substituent selected from $C_{1-8}$alkyl, $C_{2-8}$alkenyl, $C_{3-14}$cycloalkyl or a $-C[(R_1)(R_{11})]$-L-D moiety:

or two $C_{1-4}$alkyl substituents both attached to the common ring nitrogen atom of Formula (Ia), thus forming a quaternary ammonium salt;

$R_1$ is selected from the group consisting of hydrogen, $C_{1-8}$alkyl, $C_{2-8}$alkenyl, and $C_{2-8}$alkynyl;

$R_{11}$ is selected from the group consisting of hydrogen, $C_{1-8}$alkyl and cyclopropyl;

L is absent or $C_{1-4}$alkyl;

D is aryl, $C_{3-14}$cycloalkyl, $C_{5-14}$cycloalkenyl, heterocyclyl, or heteroaryl, wherein aryl and heteroaryl are optionally substituted with one, two, three or four substitutents independently selected from the group consisting of $C_{1-3}$alkyl, $C_{1-3}$alkoxy, $C_{2-8}$alkenyl, $C_{2-3}$alkenyloxy, hydroxy, $C_{1-3}$alkylthio, fluoro, chloro, cyano, $C_{1-3}$alkylcarbonyl, ($C_{1-3}$alkylcarbonyl)amino, ($C_{1-3}$alkyl)amino, di($C_{1-3}$alkyl)amino and $C_{3-14}$cycloalkyl, wherein $C_{3-14}$cycloalkyl is optionally substituted with one, two, three or four $C_{1-3}$alkyl substituents;

$R_2$ is selected from the group consisting of heteroaryl, phenyl, heterocyclyl and $C_{1-6}$alkyl, wherein phenyl is optionally substituted with [($R_{200}$—$C_{1-6}$alkyl)($R_a$)]amino, [($R_{200}$-sulfonyl)($R_a$)]amino or [(hydroxysulfonyl)($R_a$)]amino, wherein heterocyclyl is optionally substituted with $C_{1-4}$alkyl, aryl, heteroaryl, $R_{200}$—$C_{1-6}$alkyl or $R_{200}$-sulfonyl, and wherein $C_{1-6}$alkyl is optionally substituted with carboxy, hydroxy, $R_{200}$, $NR_aR_b$, $C_{1-6}$alkoxy, $R_{200}$—$C_{1-6}$alkoxy, $R_{200}$-oxy, $R_{200}$-thio, aminocarbonyl, carboxy-$C_{1-6}$alkoxy, aminocarbonyl-$C_{1-6}$alkoxy, ($C_{1-6}$alkyl)aminocarbonyl, di($C_{1-6}$alkyl)aminocarbonyl, [($R_{200}$—$C_{1-6}$alkyl)($R_a$)]amino, ($R_{200}$—$C_{1-6}$alkyl)-2-amino, ($C_{1-6}$alkylcarbonyl)amino, (trihalo-$C_{1-4}$alkylcarbonyl)amino, ($R_{200}$—$C_{1-6}$alkylcarbonyl)amino, ($C_{1-6}$alkoxycarbonyl)amino, ($R_{200}$—$C_{1-6}$alkoxycarbonyl)amino, ($C_{1-6}$alkoxy-$C_{1-6}$alkylcarbonyl)amino, ($R_{200}$- carbonyl)amino, (amino-$C_{1-6}$alkylcarbonyl)amino, [($C_{1-6}$alkyl)amino-$C_{1-6}$alkylcarbonyl]amino, [di($C_{1-6}$alkyl)amino-$C_{1-6}$alkylcarbonyl]amino, ($C_{1-6}$alkylcarbonyl-acetonitrile-carbonyl)amino, ureido, thioureido, acetamidino, guanidino, ({[($R_{200}$)($R_a$)]aminocarbonyl}($R_a$))amino, [($R_{200}$-oxycarbonyl)($R_a$)]amino, [($R_{200}$)($R_a$)]aminocarbonyloxy, aminosulfonyl, $C_{1-6}$alkylsulfonyl, hydroxysulfonyl, ($C_{1-6}$alkylsulfonyl)amino, ($R_{200}$—$C_{1-6}$alkylsulfonyl)amino, ($R_{200}$—$C_{2-6}$alkenylsulfonyl)amino, ($C_{1-6}$alkylsulfonyl-$C_{1-6}$alkylsulfonyl)amino, $R_{200}$-sulfonyloxy, aminosulfonyloxy, ($C_{1-6}$alkyl)aminosulfonyloxy, di($C_{1-6}$alkyl)aminosulfonyloxy, [(aminosulfonyl)($R_a$)]amino, {[($C_{1-6}$alkyl)aminosulfonyl]($R_a$)}amino, {[di($C_{1-6}$alkyl)aminosulfonyl]($R_a$)}amino, [(hydroxysulfonyl)($R_a$)]amino, [($R_{200}$-oxysulfonyl)($R_a$)]amino, [($R_{200}$-sulfonyl)($R_a$)]amino, [($R_{200}$)($R_a$)]aminosulfonyloxy, or ({[($R_{200}$)($R_a$)]aminosulfonyl}($R_a$)amino;

$R_a$ is selected from the group consisting of hydrogen, $C_{1-6}$alkyl, $C_{1-6}$alkylcarbonyl and $C_{3-8}$cycloalkyl;

$R_b$ is selected from the group consisting of hydrogen, $C_{1-6}$alkyl or $R_{201}$, $R_{200}$ is $C_{6-10}$aryl, heteroaryl, $C_{3-8}$cycloalkyl or heterocyclyl each optionally substituted with one, two or three substituents independently selected from the group consisting of $C_{1-4}$alkyl, trihalo-$C_{1-4}$alkyl, $C_{1-4}$alkoxy, trihalo-$C_{1-4}$alkoxy, $C_{1-6}$alkylcarbonyl, $C_{1-6}$alkoxycarbonyl, amino, $C_{1-6}$alkyl-amino, di$C_{1-6}$alkyl-amino, ($C_{1-6}$alkylcarbonyl)amino, $C_{1-6}$alkylsulfonyl, hydroxysulfonyl, aminosulfonyl, chloro, fluoro, bromo and $R_{202}$, wherein $C_{3-8}$cycloalkyl or heterocyclyl is optionally substituted with one, two or three oxo substituents on available carbon atom ring members, and wherein heteroaryl having a nitrogen atom ring member is optionally substituted on the ring nitrogen atom with an oxy substituent and thus forms an oxide;

$R_{201}$ is $C_{6-10}$aryl, heteroaryl, $C_{3-8}$cycloalkyl or heterocyclyl, wherein aryl, heteroaryl, $C_{3-8}$cycloalkyl or heterocyclyl are each optionally substituted with one, two or three substituents independently selected from the group consisting of $C_{1-4}$alkyl, trihalo-$C_{1-4}$alkyl, $C_{1-4}$alkoxy, trihalo-$C_{1-4}$alkoxy, amino, $C_{1-6}$alkyl-amino, di$C_{1-6}$alkyl-amino, $C_{1-6}$alkylcarbonyl, $C_{1-6}$alkoxycarbonyl, ($C_{1-6}$alkylcarbonyl)amino, $C_{1-6}$alkylsulfonyl, hydroxysulfonyl, aminosulfonyl, chloro, fluoro, bromo, aryl, heteroaryl, aryl-$C_{1-6}$alkyl, aryl-sulfonyl and heteroaryl-sulfonyl, wherein $C_{3-8}$cycloalkyl or heterocyclyl is optionally substituted with one, two or three oxo substituents on available carbon atom ring members, and wherein heteroaryl having a nitrogen atom ring member is optionally substituted on the ring nitrogen atom with an oxy substituent and thus forms an oxide; and, $R_{202}$ is aryl, heteroaryl, aryl-$C_{1-6}$alkyl, [(aryl-$C_{1-6}$alkyl)($R_a$)amino, hydroxysulfonyl, aryl-sulfonyl, heteroaryl-sulfonyl or [(heteroaryl-sulfonyl)($R_a$)]amino, wherein each aryl and heteroaryl are optionally substituted with one, two or three $C_{1-4}$alkyl substituents;

and enantiomers, diastereomers, tautomers, and pharmaceutically acceptable salts thereof.

3. The compound of claim 1, wherein G is hydrogen, or one substituent selected from $C_{1-8}$alkyl, $C_{3-14}$cycloalkyl, —$CH_2$-aryl or —$CH(C_{1-8}$alkyl)-aryl.

4. The compound of claim 1, wherein G is hydrogen, or one substituent selected from $C_{1-6}$alkyl, $C_{3-8}$cycloalkyl, —$CH_2$-aryl or —$CH(C_{1-4}$alkyl)-aryl.

5. The compound of claim 1, wherein G is hydrogen, or one substituent selected from methyl, ethyl, isopropyl, cyclopropyl, cyclobutyl, —$CH_2$-phenyl or —CH(methyl)-phenyl.

6. The compound of claim 1, wherein G is $C_{1-6}$alkyl, wherein $C_{1-6}$alkyl is selected from methyl, ethyl or isopropyl.

7. The compound of claim 1, wherein G is ethyl.

8. The compound of claim 1, wherein $R_2$ is selected from the group consisting of heteroaryl, phenyl, heterocyclyl and $C_{1-6}$alkyl, wherein phenyl is optionally substituted with [($R_{200}$—$C_{1-6}$alkyl)($R_a$)]amino or [($R_{200}$-sulfonyl)($R_a$)]amino, wherein heterocyclyl is optionally substituted with $C_{1-4}$alkyl, $R_{200}$—$C_{1-6}$alkyl or $R_{200}$-sulfonyl, and wherein $C_{1-6}$alkyl is substituted with $R_{200}$, $NR_aR_b$, $R_{200}$—$C_{1-6}$alkoxy, $R_{200}$-oxy, $R_{200}$-thio, [($R_{200}$-$C_{1-6}$alkyl)($R_a$)]amino, ($R_{200}$—$C_{1-6}$alkyl)-2-amino, ($C_{1-6}$alkylcarbonyl)amino, (trihalo-$C_{1-4}$alkylcarbonyl)amino, ($R_{200}$-carbonyl)amino, ureido, ({[($R_{200}$)($R_a$)]aminocarbonyl}($R_a$))amino, hydroxysulfonyl, [(aminosulfonyl)($R_a$)]amino, {[di($C_{1-6}$alkyl)aminosulfonyl]($R_a$)}amino, [(hydroxysulfonyl)($R_a$)]amino or [($R_{200}$-sulfonyl)($R_a$)]amino;

$R_a$ is selected from the group consisting of hydrogen, $C_{1-6}$alkyl, $C_{1-6}$alkylcarbonyl and $C_{3-8}$cycloalkyl;

$R_b$ is selected from the group consisting of hydrogen, $C_{1-6}$alkyl or $R_{201}$, $R_{200}$ is $C_{6-10}$aryl, heteroaryl, $C_{3-8}$cycloalkyl or heterocyclyl each optionally substituted with one or two substituents independently selected from the group consisting of $C_{1-4}$alkyl, hydroxysulfonyl, chloro, fluoro or $R_{202}$, wherein heteroaryl, having a nitrogen atom, is optionally substituted on the nitrogen atom with an oxy substituent and thus forms an oxide;

$R_{201}$ is $C_{6-10}$-aryl, heteroaryl or $C_{3-8}$cycloalkyl, wherein heteroaryl and $C_{3-8}$cycloalkyl are each optionally substituted with one or two substituents independently selected from the group consisting of $C_{1-4}$alkyl, trihalo-$C_{1-4}$alkyl, $C_{1-4}$alkoxy, amino and chloro, wherein $C_{3-8}$cycloalkyl is optionally substituted with two oxo substituents on available carbon atom ring members, and wherein heteroaryl having a nitrogen atom ring member is optionally substituted on the ring nitrogen atom with an oxy substituent and thus forms an oxide; and, $R_{202}$ is aryl-$C_{1-6}$alkyl, [(aryl-$C_{1-6}$alkyl)($R_a$)]amino, hydroxysulfonyl, heteroaryl-sulfonyl or [(heteroaryl-sulfonyl)($R_a$)]amino, wherein each heteroaryl is optionally substituted with two $C_{1-4}$alkyl substituents.

9. The compound of claim 2, wherein $R_2$ is selected from the group consisting of heteroaryl, phenyl, piperidinyl and $C_{1-6}$alkyl, wherein phenyl is optionally substituted with [($R_{200}$—$C_{1-6}$alkyl)($R_a$)]amino or [($R_{200}$-sulfonyl)($R_a$)]amino, wherein piperidinyl is optionally substituted with $C_{1-4}$alkyl, $R_{200}$—$C_{1-6}$alkyl or $R_{200}$-sulfonyl, and wherein $C_{1-6}$alkyl is substituted with $R_{200}$, $NR_aR_b$, $R_{200}$—$C_{1-6}$alkoxy, $R_{200}$-oxy, $R_{200}$-thio, [($R_{200}$—$C_{1-6}$alkyl)($R_a$)]amino, ($R_{200}$—$C_{1-6}$alkyl)-2-amino, ($C_{1-6}$alkylcarbonyl)amino, (trihalo-$C_{1-4}$alkylcarbonyl)amino, ($R_{200}$-carbonyl)amino, ureido, ({[($R_{200}$)($R_a$)]aminocarbonyl}($R_a$))amino, hydroxysulfonyl, [(aminosulfonyl)($R_a$)]

amino, {[di($C_{1-6}$alkyl)aminosulfonyl]($R_a$)}amino, [(hydroxysulfonyl)($R_a$)]amino or [($R_{200}$-sulfonyl)($R_a$)]amino;

$R_a$ is selected from the group consisting of hydrogen, $C_{1-6}$alkyl, $C_{1-6}$alkylcarbonyl and cyclopropyl;

$R_b$ is selected from the group consisting of hydrogen, $C_{1-6}$alkyl or $R_{201}$, $R_{200}$ is phenyl, thienyl, furanyl, isoxazolyl, pyrazolyl, pyridinyl, pyrimidinyl, pyridazinyl, benzoimidazolyl, [1,2,4]triazolyl, cyclobutyl, piperidinyl, 1H-imidazolyl, 1H-tetrazolyl, 2H-tetrazolyl, 1,3-dihydro-isoindolyl, 3,4-dihydro-1H-isoquinolinlyl or 5,6,7,8-tetrahydro-[1,8]naphthyridinyl, each optionally substituted with one or two substituents independently selected from the group consisting of $C_{1-4}$alkyl, hydroxysulfonyl, chloro, fluoro or $R_{202}$, wherein pyridinyl, having a nitrogen atom, is optionally substituted on the nitrogen atom with an oxy substituent and thus forms an oxide;

$R_{201}$ is phenyl, pyrimidinyl, pyridinyl, quinolinyl or cyclobut-3-enyl, wherein pyrimidinyl and cyclobut-3-enyl are each optionally substituted with one or two substituents independently selected from the group consisting of $C_{1-4}$alkyl, trihalo-$C_{1-4}$alkyl, $C_{1-4}$alkoxy, amino and chloro, wherein cyclobut-3-enyl is optionally substituted with two oxo substituents on available carbon atom ring members, and wherein pyridinyl having a nitrogen atom ring member is optionally substituted on the ring nitrogen atom with an oxy substituent and thus forms an oxide; and, $R_{202}$ is phenyl-$C_{1-6}$alkyl, hydroxysulfonyl or thienyl-sulfonyl.

10. The compound of claim 2, wherein $R_2$ is $C_{1-6}$alkyl substituted with $R_{200}$, $R_{200}$—$C_{1-6}$alkoxy or ($R_{200}$-sulfonyl)amino; and, $R_{200}$ is phenyl or thienyl.

11. The compound of claim 2, wherein $R_2$ is n-propyl substituted with phenyl, benzyloxy or (thienyl-sulfonyl)amino.

12. The compound of claim 2, wherein

Z or N;

G is hydrogen, or one substituent selected from methyl, ethyl, isopropyl, cyclopropyl, cyclobutyl, —CH$_2$-phenyl or —CH(methyl)-phenyl, or two methyl or ethyl substituents both attached to the common ring nitrogen atom of Formula (Ia), thus forming a quaternary ammonium salt;

$R_2$ is selected from the group consisting of heteroaryl, phenyl, piperidinyl and $C_{1-6}$alkyl, wherein phenyl is optionally substituted with [($R_{200}$—$C_{1-6}$alkyl)($R_a$)]amino or [($R_{200}$-sulfonyl)($R_a$)]amino, wherein piperidinyl is optionally substituted with $C_{1-4}$alkyl, $R_{200}$—$C_{1-6}$alkyl or $R_{200}$-sulfonyl, and wherein $C_{1-6}$alkyl is substituted with $R_{200}$, $NR_aR_b$, $R_{200}$—$C_{1-6}$alkoxy, $R_{200}$-oxy, $R_{200}$-thio, [($R_{200}$—$C_{1-6}$alkyl)($R_a$)]amino, ($R_{200}$—$C_{1-6}$alkyl)-2-amino, ($C_{1-6}$alkylcarbonyl)amino, (trihalo-$C_{1-4}$alkylcarbonyl)amino, ($R_{200}$-carbonyl)amino, ureido, ({[($R_{200}$)($R_a$)]aminocarbonyl}($R_a$))amino, hydroxysulfonyl, [(aminosulfonyl)($R_a$)]amino, {[di($C_{1-6}$alkyl)aminosulfonyl]($R_a$)}amino, [(hydroxysulfonyl)($R_a$)]amino or [($R_{200}$-sulfonyl)($R_a$)]amino;

$R_a$ is selected from the group consisting of hydrogen, $C_{1-6}$alkyl, $C_{1-6}$alkylcarbonyl and cyclopropyl;

$R_b$ is selected from the group consisting of hydrogen, $C_{1-6}$alkyl or $R_{201}$, $R_{200}$ is phenyl, thienyl, furanyl, isoxazolyl, pyrazolyl, pyridinyl, pyrimidinyl, pyridazinyl, benzoimidazolyl, [1,2,4]triazolyl, cyclobutyl, piperidinyl, 1H-imidazolyl, 1H-tetrazolyl, 2H-tetrazolyl, 1,3-dihydro-isoindolyl, 3,4-dihydro-1H-isoquinolinlyl or 5,6,7,8-tetrahydro-[1,8]naphthyridinyl, each optionally substituted with one or two substituents independently selected from the group consisting of $C_{1-4}$alkyl, hydroxysulfonyl, chloro, fluoro or $R_{202}$, wherein pyridinyl, having a nitrogen atom, is optionally substituted on the nitrogen atom with an oxy substituent and thus forms an oxide;

$R_{201}$ is phenyl, pyrimidinyl, pyridinyl, quinolinyl or cyclobut-3-enyl, wherein pyrimidinyl and cyclobut-3-enyl are each optionally substituted with one or two substituents independently selected from the group consisting of $C_{1-4}$alkyl, trihalo-$C_{1-4}$alkyl, $C_{1-4}$alkoxy, amino and chloro, wherein cyclobut-3-enyl is optionally substituted with two oxo substituents on available carbon atom ring members, and wherein pyridinyl having a nitrogen atom ring member is optionally substituted on the ring nitrogen atom with an oxy substituent and thus forms an oxide; and, $R_{202}$ is phenyl-$C_{1-6}$alkyl, hydroxysulfonyl or thienyl-sulfonyl.

13. The compound of claim 2, wherein the compound is selected from the group consisting of:

dimethylaminosulfonic acid {(4R)-4-(3,4-dimethoxy-phenyl)-4-[4-(4-ethyl-piperazin-1-yl)-1-oxo-1,3-dihydro-isoindol-2-yl]-butyl}-methyl-amide, 2-[(1R)-4-(benzyl-methyl-amino)-1-(3,4-dimethoxy-phenyl)-butyl]-4-(4-ethyl-piperazin-1-yl)-2,3-dihydro-isoindol-1-one, 4-(4-cyclopropyl-piperazin-1-yl)-2-[(1R)-1-(3,4-dimethoxy-phenyl)-4-(4-trifluoromethyl-pyrimidin-2-ylamino)-butyl]-2,3-dihydro-isoindol-1-one, 4-(4-benzyl-piperazin-1-yl)-2-[(1R)-1-(3,4-dimethoxy-phenyl)-4-(4-trifluoromethyl-pyrimidin-2-ylamino)-butyl]-2,3-dihydro-isoindol-1-one, 2-[(1R)-1-(3,4-dimethoxy-phenyl)-4-(4-trifluoromethyl-pyrimidin-2-ylamino)-butyl]-4-piperazin-1-yl-2,3-dihydro-isoindol-1-one, thiophene-2-sulfonic acid [(4R)-4-[4-(4-cyclopropyl-piperazin-1-yl)-1-oxo-1,3-dihydro-isoindol-2-yl]-4-(3,4-dimethoxy-phenyl)-butyl]-methyl-amide, thiophene-2-sulfonic acid {(4R)-4-(3,4-dimethoxy-phenyl)-4-[4-(4-isopropyl-piperazin-1-yl)-1-oxo-1,3-dihydro-isoindol-2-yl]-butyl}-methyl-amide, thiophene-2-sulfonic acid [(4R)-4-[4-(4-cyclobutyl-piperazin-1-yl)-1-oxo-1,3-dihydro-isoindol-2-yl]-4-(3,4-dimethoxy-phenyl)-butyl]-methyl-amide, 2-[(1R)-1-(3,4-dimethoxy-phenyl)-4-(4,6-dimethoxy-pyrimidin-2-ylamino)-butyl]-4-(4-ethyl-piperazin-1-yl)-2,3-dihydro-isoindol-1-one, 2-[(1R)-4-(4-chloro-pyrimidin-2-ylamino)-1-(3,4-dimethoxy-phenyl)-butyl]-4-(4-ethyl-piperazin-1-yl)-2,3-dihydro-isoindol-1-one, 2-[(1R)-1-(3,4-dimethoxy-phenyl)-4-(4,6-dimethyl-pyrimidin-2-ylamino)-butyl]-4-(4-ethyl-piperazin-1-yl)-2,3-dihydro-isoindol-1-one, 2-[2-(1-benzyl-piperidin-4-yl)-1-(3,4-dimethoxy-phenyl)-ethyl]-4-(4-ethyl-piperazin-1-yl)-2,3-dihydro-isoindol-1-one, 2-[(1R)-1-(3,4-dimethoxy-phenyl)-4-tetrazol-1-yl-butyl]-4-(4-ethyl-piperazin-1-yl)-2,3-dihydro-isoindol-1-one, 2-[(1R)-1-(3,4-dimethoxy-phenyl)-4-tetrazol-2-yl-butyl]-4-(4-ethyl-piperazin-1-yl)-2,3-dihydro-isoindol-1-one,
thiophene-2-sulfonic acid (3-{(3,4-dimethoxy-phenyl)-[4-(4-ethyl-piperazin-1-yl)-1-oxo-1,3-dihydro-isoindol-2-yl]-methyl}-phenyl)-amide,
4-{2-(3,4-dimethoxy-phenyl)-2-[4-(4-ethyl-piperazin-1-yl)-1-oxo-1,3-dihydro-isoindol-2-yl]-ethyl}-piperidine-1-sulfonic acid,
2-{1-(3,4-dimethoxy-phenyl)-2-[1-(thiophene-2-sulfonyl)-piperidin-4-yl]-ethyl}-4-(4-ethyl-piperazin-1-yl)-2,3-dihydro-isoindol-1-one,
2-[(3-benzylamino-phenyl)-(3,4-dimethoxy-phenyl)-methyl]-4-(4-ethyl-piperazin-1-yl)-2,3-dihydro-isoindol-1-one,
2-[(1R)-1-(3,4-dimethoxy-phenyl)-4-(4-ethyl-pyrimidin-2-ylamino)-butyl]-4-(4-ethyl-piperazin-1-yl)-2,3-dihydro-isoindol-1-one,
2-[(1R)-1-(3,4-dimethoxy-phenyl)-4-(4-methoxy-pyrimidin-2-ylamino)-butyl]-4-(4-ethyl-piperazin-1-yl)-2,3-dihydro-isoindol-1-one,
2-[(1R)-1-(3,4-dimethoxy-phenyl)-4-(4-trifluoromethyl-pyrimidin-2-ylamino)-butyl]-4-(4-ethyl-piperazin-1-yl)-2,3-dihydro-isoindol-1-one,
2-[(1R)-1-(3,4-dimethoxy-phenyl)-4-(4-methyl-pyrimidin-2-ylamino)-butyl]-4-(4-ethyl-piperazin-1-yl)-2,3-dihydro-isoindol-1-one,
2-[(1R)-1-(3,4-dimethoxy-phenyl)-4-(1-methyl-1H-tetrazol-5-ylsulfanyl)-butyl]-4-piperazin-1-yl-2,3-dihydro-isoindol-1-one,
2-[(1R)-1-(3,4-dimethoxy-phenyl)-4-[1,2,4]triazol-1-yl-butyl]-4-(4-ethyl-piperazin-1-yl)-2,3-dihydro-isoindol-1-one,
thiophene-2-sulfonic acid {(4R)-4-(3,4-dimethoxy-phenyl)-4-[4-(4-methyl-piperazin-1-yl)-1-oxo-1,3-dihydro-isoindol-2-yl]-butyl}-methyl-amide,
2-[(1R)-1-(3,4-dimethoxy-phenyl)-4-(4,6-dimethyl-pyrimidin-2-ylsulfanyl)-butyl]-4-(4-ethyl-piperazin-1-yl)-2,3-dihydro-isoindol-1-one,
4-(4-cyclopropyl-piperazin-1-yl)-2-[(1R)-1-(3,4-dimethoxy-phenyl)-4-phenoxy-butyl]-2,3-dihydro-isoindol-1-one,
2-[(1R)-4-benzoimidazol-1-yl-1-(3,4-dimethoxy-phenyl)-butyl]-4-(4-ethyl-piperazin-1-yl)-2,3-dihydro-isoindol-1-one,
thiophene-2-sulfonic acid [(4R)-4-(3,4-dimethoxy-phenyl)-4-(1-oxo-4-piperazin-1-yl-1,3-dihydro-isoindol-2-yl)-butyl]-methyl-amide,
{(4R)-4-(3,4-dimethoxy-phenyl)-4-[4-(4-ethyl-piperazin-1-yl)-1-oxo-1,3-dihydro-isoindol-2-yl]-butylsulfanyl}-pyridine 1-oxide,
2-[(1R)-1-(3,4-dimethoxy-phenyl)-4-imidazol-1-yl-butyl]-4-(4-ethyl-piperazin-1-yl)-2,3-dihydro-isoindol-1-one,
2-[(1R)-1-(3,4-dimethoxy-phenyl)-4-(methyl-phenyl-amino)-butyl]-4-piperazin-1-yl-2,3-dihydro-isoindol-1-one,
4-(4-benzyl-piperazin-1-yl)-2-[(1R)-1-(3,4-dimethoxy-phenyl)-4-phenoxy-butyl]-2,3-dihydro-isoindol-1-one,
2-[(1R)-1-(3,4-dimethoxy-phenyl)-4-imidazol-1-yl-butyl]-4-piperazin-1-yl-2,3-dihydro-isoindol-1-one,
2-[(1R)-1-(3,4-dimethoxy-phenyl)-4-phenylsulfanyl-butyl]-4-piperazin-1-yl-2,3-dihydro-isoindol-1-one,
2-[(1R)-1-(3,4-dimethoxy-phenyl)-4-phenoxy-butyl]-4-piperazin-1-yl-2,3-dihydro-isoindol-1-one,
4-{2-[(1R)-4-dibenzylamino-1-(3,4-dimethoxy-phenyl)-butyl]-1-oxo-2,3-dihydro-1H-isoindol-4-yl}-1-ethyl-1-methyl-piperazin-1-ium trifluoroacetate,
1,2-dimethyl-1H-imidazole-4-sulfonic acid {(4R)-4-(3,4-dimethoxy-phenyl)-4-[4-(4-ethyl-piperazin-1-yl)-1-oxo-1,3-dihydro-isoindol-2-yl]-butyl}-methyl-amide,
2-[(1R)-1-(3,4-dimethoxy-phenyl)-4-phenylamino-butyl]-4-(4-ethyl-piperazin-1-yl)-2,3-dihydro-isoindol-1-one,
2-[(1R)-4-benzyloxy-1-(3,4-dimethoxy-phenyl)-butyl]-4-piperazin-1-yl-2,3-dihydro-isoindol-1-one,
2-[(3,4-dimethoxy-phenyl)-(1-ethyl-piperidin-4-yl)-methyl]-4-(4-ethyl-piperazin-1-yl)-2,3-dihydro-isoindol-1-one,
2-[(1-benzyl-piperidin-4-yl)-(3,4-dimethoxy-phenyl)-methyl]-4-(4-ethyl-piperazin-1-yl)-2,3-dihydro-isoindol-1-one,
2-{(3,4-dimethoxy-phenyl)-[1-(1,2-dimethyl-1H-imidazole-4-sulfonyl)-piperidin-4-yl]-methyl}-4-(4-ethyl-piperazin-1-yl)-2,3-dihydro-isoindol-1-one,
2-{(3,4-dimethoxy-phenyl)-[1-(thiophene-2-sulfonyl)-piperidin-4-yl]-methyl}-4-(4-ethyl-piperazin-1-yl)-2,3-dihydro-isoindol-1-one,
2-[(1R)-4-(2,6-difluoro-benzyloxy)-1-(3,4-dimethoxy-phenyl)-butyl]-4-(4-ethyl-piperazin-1-yl)-2,3-dihydro-isoindol-1-one,
2-[(1R)-4-(2-chloro-benzyloxy)-1-(3,4-dimethoxy-phenyl)-butyl]-4-(4-ethyl-piperazin-1-yl)-2,3-dihydro-isoindol-1-one,
2-[(1R)-1-(3,4-dimethoxy-phenyl)-4-(pyrimidin-2-ylamino)-butyl]-4-(4-ethyl-piperazin-1-yl)-2,3-dihydro-isoindol-1-one,
2,3-dimethyl-3H-imidazole-4-sulfonic acid {(4R)-4-(3,4-dimethoxy-phenyl)-4-[4-(4-ethyl-piperazin-1-yl)-1-oxo-1,3-dihydro-isoindol-2-yl]-butyl}-amide,
2-[(1R)-1-(3,4-dimethoxy-phenyl)-4-phenoxy-butyl]-4-(4-ethyl-piperazin-1-yl)-2,3-dihydro-isoindol-1-one,
2-[(1R)-1-(3,4-dimethoxy-phenyl)-4-(2-fluoro-benzyloxy)-butyl]-4-(4-ethyl-piperazin-1-yl)-2,3-dihydro-isoindol-1-one,
2-[(1R)-1-(3,4-dimethoxy-phenyl)-4-(3-fluoro-benzyloxy)-butyl]-4-(4-ethyl-piperazin-1-yl)-2,3-dihydro-isoindol-1-one,
1-methyl-1H-imidazole-4-sulfonic acid {(4R)-4-(3,4-dimethoxy-phenyl)-4-[4-(4-ethyl-piperazin-1-yl)-1-oxo-1,3-dihydro-isoindol-2-yl]-butyl}-amide,
N-{(4R)-4-(3,4-dimethoxy-phenyl)-4-[4-(4-ethyl-piperazin-1-yl)-1-oxo-1,3-dihydro-isoindol-2-yl]-butyl}-isonicotinamide,
2-[(1R)-1-(3,4-dimethoxy-phenyl)-4-(3-methyl-benzyloxy)-butyl]-4-(4-ethyl-piperazin-1-yl)-2,3-dihydro-isoindol-1-one,
1-methyl-1H-imidazole-2-carboxylic acid {(4R)-4-(3,4-dimethoxy-phenyl)-4-[4-(4-ethyl-piperazin-1-yl)-1-oxo-1,3-dihydro-isoindol-2-yl]-butyl}-amide,
1-methyl-1H-imidazole-4-carboxylic acid {(4R)-4-(3,4-dimethoxy-phenyl)-4-[4-(4-ethyl-piperazin-1-yl)-1-oxo-1,3-dihydro-isoindol-2-yl]-butyl}-amide, aminosulfonic acid {(4R)-4-(3,4-dimethoxy-phenyl)-4-[4-(4-ethyl-piperazin-1-yl)-1-oxo-1,3-dihydro-isoindol-2-yl]-butyl}-amide,
3-methyl-3H-imidazole-4-carboxylic acid {(4R)-4-(3,4-dimethoxy-phenyl)-4-[4-(4-ethyl-piperazin-1-yl)-1-oxo-1,3-dihydro-isoindol-2-yl]-butyl}-amide,
3,5-dimethyl-1H-pyrazole-4-carboxylic acid {(4R)-4-(3,4-dimethoxy-phenyl)-4-[4-(4-ethyl-piperazin-1-yl)-1-oxo-1,3-dihydro-isoindol-2-yl]-butyl}-amide,
pyridazine-4-carboxylic acid {(4R)-4-(3,4-dimethoxy-phenyl)-4-[4-(4-ethyl-piperazin-1-yl)-1-oxo-1,3-dihydro-isoindol-2-yl]-butyl}-amide, thiophene-2-sulfonic acid {(4R)-4-(3,4-dimethoxy-phenyl)-4-[4-(4-ethyl-piperazin-1-yl)-1-oxo-1,3-dihydro-isoindol-2-yl]-butyl}-methyl-amide, 2-[(1R)-4-(bis-pyridin-4-ylmethyl-amino)-1-(3,4-dimethoxy-phenyl)-butyl]-4-(4-ethyl-piperazin-1-yl)-2,3-dihydro-isoindol-1-one, {(4R)-4-(3,4-dimethoxy-phenyl)-4-[4-(4-ethyl-piperazin-1-yl)-1-oxo-1,3-dihydro-isoindol-2-yl]-butyl}-urea, thiophene-2-sulfonic acid {(4R)-4-(3,4-dimethoxy-phenyl)-4-[4-(4-isopropyl-piperazin-1-yl)-1-oxo-1,3-dihydro-isoindol-2-yl]-butyl}-amide, 1-{(4R)-4-(3,4-dimethoxy-phenyl)-4-[4-(4-ethyl-piperazin-1-yl)-1-oxo-1,3-dihydro-isoindol-2-yl]-butyl}-3-phenyl-urea, N-{(4R)-4-(3,4-dimethoxy-phenyl)-4-[4-(4-ethyl-piperazin-1-yl)-1-oxo-1,3-dihydro-isoindol-2-yl]-butyl}-2,2,2-trifluoro-acetamide, 2-[(1R)-4-diethylamino-1-(3,4-dimethoxy-phenyl)-butyl]-4-(4-ethyl-piperazin-1-yl)-2,3-dihydro-isoindol-1-one, 2-[(1R)-1-(3,4-dimethoxy-phenyl)-4-ethylamino-butyl]-4-(4-ethyl-piperazin-1-yl)-2,3-dihydro-isoindol-1-one, dimethylaminosulfonic acid {(4R)-4-(3,4-dimethoxy-phenyl)-4-[4-(4-ethyl-piperazin-1-yl)-1-oxo-1,3-dihydro-isoindol-2-yl]-butyl}-amide, {(4R)-4-(3,4-dimethoxy-phenyl)-4-[4-(4-ethyl-piperazin-1-yl)-1-oxo-1,3-dihydro-isoindol-2-yl]-butyl}-sulfamic acid, 2-{(1R)-1-(3,4-dimethoxy-phenyl)-4-[(thiophen-2-ylmethyl)-amino]-butyl}-4-(4-ethyl-piperazin-1-yl)-2,3-dihydro-isoindol-1-one, 2-[(1R)-4-dibenzylamino-1-(3,4-dimethoxy-phenyl)-butyl]-4-(4-ethyl-piperazin-1-yl)-2,3-dihydro-isoindol-1-one, 2-[(1R)-4-benzyloxy-1-(3,4-dimethoxy-phenyl)-butyl]-4-(4-ethyl-piperazin-1-yl)-2,3-dihydro-isoindol-1-one, 2-[(1R)-1-(3,4-dimethoxy-phenyl)-4-(2,2-dimethyl-propylamino)-butyl]-4-(4-ethyl-piperazin-1-yl)-2,3-dihydro-isoindol-1-one, 3-amino-4-{(4R)-4-(3,4-dimethoxy-phenyl)-4-[4-(4-ethyl-piperazin-1-yl)-1-oxo-1,3-dihydro-isoindol-2-yl]-butylamino}-cyclobut-3-ene-1,2-dione, 2-[(1R)-4-benzylamino-1-(3,4-dimethoxy-phenyl)-butyl]-4-(4-ethyl-piperazin-1-yl)-2,3-dihydro-isoindol-1-one, furan-2-carboxylic acid {(4R)-4-(3,4-dimethoxy-phenyl)-4-[4-(4-ethyl-piperazin-1-yl)-1-oxo-1,3-dihydro-isoindol-2-yl]-butyl}-amide, 1H-pyrazole-4-carboxylic acid {(4R)-4-(3,4-dimethoxy-phenyl)-4-[4-(4-ethyl-piperazin-1-yl)-1-oxo-1,3-dihydro-isoindol-2-yl]-butyl}-amide, cyclobutanecarboxylic acid {(4R)-4-(3,4-dimethoxy-phenyl)-4-[4-(4-ethyl-piperazin-1-yl)-1-oxo-1,3-dihydro-isoindol-2-yl]-butyl}-amide, thiophene-2-carboxylic acid {(4R)-4-(3,4-dimethoxy-phenyl)-4-[4-(4-ethyl-piperazin-1-yl)-1-oxo-1,3-dihydro-isoindol-2-yl]-butyl}-amide, 1,2-dimethyl-1H-imidazole-4-sulfonic acid {(4R)-4-(3,4-dimethoxy-phenyl)-4-[4-(4-ethyl-piperazin-1-yl)-1-oxo-1,3-dihydro-isoindol-2-yl]-butyl}-amide, N-{(4R)-4-(3,4-dimethoxy-phenyl)-4-[4-(4-ethyl-piperazin-1-yl)-1-oxo-1,3-dihydro-isoindol-2-yl]-butyl}-2,2-dimethyl-propionamide, thiophene-2-sulfonic acid {(4R)-4-(3,4-dimethoxy-phenyl)-4-[4-(4-ethyl-piperazin-1-yl)-1-oxo-1,3-dihydro-isoindol-2-yl]-butyl}-amide, 5-methyl-isoxazole-4-carboxylic acid ((4R)-4-(3,4-dimethoxy-phenyl)-4-{1-oxo-4-[4-(1-phenyl-ethyl)-piperazin-1-yl]-1,3-dihydro-isoindol-2-yl}-butyl)-amide, 2-[(1R)-1-(3,4-dimethoxy-phenyl)-3-(5,6,7,8-tetrahydro-[1,8]naphthyridin-2-yl)-propyl]-4-(4-ethyl-piperazin-1-yl)-2,3-dihydro-isoindol-1-one, 2-[(1R)-1-(3,4-dimethoxy-phenyl)-4-phenyl-butyl]-4-(4-ethyl-piperazin-1-yl)-2,3-dihydro-isoindol-1-one, N-{(4R)-4-(3,4-dimethoxy-phenyl)-4-[4-(4-ethyl-piperazin-1-yl)-1-oxo-1,3-dihydro-isoindol-2-yl]-butyl}-N-(4-fluoro-benzyl)-acetamide, 2-[(1R)-1-(3,4-dimethoxy-phenyl)-4-(quinolin-2-ylamino)-butyl]-4-(4-ethyl-piperazin-1-yl)-2,3-dihydro-isoindol-1-one, 2-[(1R)-4-[cyclopropyl-(4-fluoro-benzyl)-amino]-1-(3,4-dimethoxy-phenyl)-butyl]-4-(4-ethyl-piperazin-1-yl)-2,3-dihydro-isoindol-1-one, 2-[(1R)-1-(3,4-dimethoxy-phenyl)-4-(4-fluoro-benzylamino)-butyl]-4-(4-ethyl-piperazin-1-yl)-2,3-dihydro-isoindol-1-one, 2-[(1R)-1-(3,4-dimethoxy-phenyl)-4-(pyridin-2-ylamino)-butyl]-4-(4-ethyl-piperazin-1-yl)-2,3-dihydro-isoindol-1-one, 2-[(1R)-1-(3,4-dimethoxy-phenyl)-4-(1-oxy-pyridin-2-ylamino)-butyl]-4-(4-ethyl-piperazin-1-yl)-2,3-dihydro-isoindol-1-one, 2-[(1R)-1-(3,4-dimethoxy-phenyl)-4-(furan-2-ylmethyl-methyl-amino)-butyl]-4-(4-ethyl-piperazin-1-yl)-2,3-dihydro-isoindol-1-one, 2-[(1R)-1-(3,4-dimethoxy-phenyl)-4-(methyl-thiophen-2-ylmethyl-amino)-butyl]-4-(4-ethyl-piperazin-1-yl)-2,3-dihydro-isoindol-1-one, 2-[(1R)-4-(benzyl-isopropyl-amino)-1-(3,4-dimethoxy-phenyl)-butyl]-4-(4-ethyl-piperazin-1-yl)-2,3-dihydro-isoindol-1-one, 2-{(1R)-1-(3,4-dimethoxy-phenyl)-4-[(2-fluoro-benzyl)-methyl-amino]-butyl}-4-(4-ethyl-piperazin-1-yl)-2,3-dihydro-isoindol-1-one, 2-{(1R)-1-(3,4-dimethoxy-phenyl)-4-[(3-fluoro-benzyl)-methyl-amino]-butyl}-4-(4-ethyl-piperazin-1-yl)-2,3-dihydro-isoindol-1-one, 2-{(1R)-1-(3,4-dimethoxy-phenyl)-4-[(4-fluoro-benzyl)-methyl-amino]-butyl}-4-(4-ethyl-piperazin-1-yl)-2,3-dihydro-isoindol-1-one, 2-[(1R)-4-(1,3-dihydro-isoindol-2-yl)-1-(3,4-dimethoxy-phenyl)-butyl]-4-(4-ethyl-piperazin-1-yl)-2,3-dihydro-isoindol-1-one, 2-[(1R)-4-(3,4-dihydro-1H-isoquinolin-2-yl)-1-(3,4-dimethoxy-phenyl)-butyl]-4-(4-ethyl-piperazin-1-yl)-2,3-dihydro-isoindol-1-one, 2-[(1R)-1-(3,4-dimethoxy-phenyl)-4-(2,4-dimethyl-imidazol-1-yl)-butyl]-4-(4-ethyl-piperazin-1-yl)-2,3-dihydro-isoindol-1-one, 2-[(1R)-1-(3,4-dimethoxy-phenyl)-4-(2-methyl-imidazol-1-yl)-butyl]-4-(4-ethyl-piperazin-1-yl)-2,3-dihydro-isoindol-1-one, and 2-[(1R)-1-(3,4-dimethoxy-phenyl)-4-(2-isopropyl-imidazol-1-yl)-butyl]-4-(4-ethyl-piperazin-1-yl)-2,3-dihydro-isoindol-1-one.

14. The compound of claim 13, wherein the compound is selected from the group consisting of:

dimethylaminosulfonic acid {(4R)-4-(3,4-dimethoxy-phenyl)-4-[4-(4-ethyl-piperazin-1-yl)-1-oxo-1,3-dihydro-isoindol-2-yl]-butyl}-methyl-amide, 2-[(1R)-4-(benzyl-methyl-amino)-1-(3,4-dimethoxy-phenyl)-butyl]-4-(4-ethyl-piperazin-1-yl)-2,3-dihydro-isoindol-1-one,
4-(4-benzyl-piperazin-1-yl)-2-[(1R)-1-(3,4-dimethoxy-phenyl)-4-(4-trifluoromethyl-pyrimidin-2-ylamino)-butyl]-2,3-dihydro-isoindol-1-one,
2-[(1R)-1-(3,4-dimethoxy-phenyl)-4-(4-trifluoromethyl-pyrimidin-2-ylamino)-butyl]-4-piperazin-1-yl-2,3-dihydro-isoindol-1-one,
thiophene-2-sulfonic acid [(4R)-4-[4-(4-cyclopropyl-piperazin-1-yl)-1-oxo-1,3-dihydro-isoindol-2-yl]-4-(3,4-dimethoxy-phenyl)-butyl]-methyl-amide,
thiophene-2-sulfonic acid {(4R)-4-(3,4-dimethoxy-phenyl)-4-[4-(4-isopropyl-piperazin-1-yl)-1-oxo-1,3-dihydro-isoindol-2-yl]-butyl}-methyl-amide,
thiophene-2-sulfonic acid [(4R)-4-[4-(4-cyclobutyl-piperazin-1-yl)-1-oxo-1,3-dihydro-isoindol-2-yl]-4-(3,4-dimethoxy-phenyl)-butyl]-methyl-amide,
2-[(1R)-1-(3,4-dimethoxy-phenyl)-4-(4,6-dimethoxy-pyrimidin-2-ylamino)-butyl]-4-(4-ethyl-piperazin-1-yl)-2,3-dihydro-isoindol-1-one,
2-[(1R)-4-(4-chloro-pyrimidin-2-ylamino)-1-(3,4-dimethoxy-phenyl)-butyl]-4-(4-ethyl-piperazin-1-yl)-2,3-dihydro-isoindol-1-one,
2-[(1R)-1-(3,4-dimethoxy-phenyl)-4-(4,6-dimethyl-pyrimidin-2-ylamino)-butyl]-4-(4-ethyl-piperazin-1-yl)-2,3-dihydro-isoindol-1-one,
2-[2-(1-benzyl-piperidin-4-yl)-1-(3,4-dimethoxy-phenyl)-ethyl]-4-(4-ethyl-piperazin-1-yl)-2,3-dihydro-isoindol-1-one,
2-[(1R)-1-(3,4-dimethoxy-phenyl)-4-tetrazol-1-yl-butyl]-4-(4-ethyl-piperazin-1-yl)-2,3-dihydro-isoindol-1-one,
2-[(1R)-1-(3,4-dimethoxy-phenyl)-4-tetrazol-2-yl-butyl]-4-(4-ethyl-piperazin-1-yl)-2,3-dihydro-isoindol-1-one,
thiophene-2-sulfonic acid (3-{(3,4-dimethoxy-phenyl)-[4-(4-ethyl-piperazin-1-yl)-1-oxo-1,3-dihydro-isoindol-2-yl]-methyl}-phenyl)-amide,
4-{2-(3,4-dimethoxy-phenyl)-2-[4-(4-ethyl-piperazin-1-yl)-1-oxo-1,3-dihydro-isoindol-2-yl]-ethyl}-piperidine-1-sulfonic acid,
2-{1-(3,4-dimethoxy-phenyl)-2-[1-(thiophene-2-sulfonyl)-piperidin-4-yl]-ethyl}-4-(4-ethyl-piperazin-1-yl)-2,3-dihydro-isoindol-1-one,
2-[(3-benzylamino-phenyl)-(3,4-dimethoxy-phenyl)-methyl]-4-(4-ethyl-piperazin-1-yl)-2,3-dihydro-isoindol-1-one,
2-[(1R)-1-(3,4-dimethoxy-phenyl)-4-(4-ethyl-pyrimidin-2-ylamino)-butyl]-4-(4-ethyl-piperazin-1-yl)-2,3-dihydro-isoindol-1-one,
2-[(1R)-1-(3,4-dimethoxy-phenyl)-4-(4-methoxy-pyrimidin-2-ylamino)-butyl]-4-(4-ethyl-piperazin-1-yl)-2,3-dihydro-isoindol-1-one,
2-[(1R)-1-(3,4-dimethoxy-phenyl)-4-(4-trifluoromethyl-pyrimidin-2-ylamino)-butyl]-4-(4-ethyl-piperazin-1-yl)-2,3-dihydro-isoindol-1-one,
2-[(1R)-1-(3,4-dimethoxy-phenyl)-4-(4-methyl-pyrimidin-2-ylamino)-butyl]-4-(4-ethyl-piperazin-1-yl)-2,3-dihydro-isoindol-1-one,
2-[(1R)-1-(3,4-dimethoxy-phenyl)-4-(1-methyl-1H-tetrazol-5-ylsulfanyl)-butyl]-4-piperazin-1-yl-2,3-dihydro-isoindol-1-one,
2-[(1R)-1-(3,4-dimethoxy-phenyl)-4-[1,2,4]triazol-1-yl-butyl]-4-(4-ethyl-piperazin-1-yl)-2,3-dihydro-isoindol-1-one,
thiophene-2-sulfonic acid {(4R)-4-(3,4-dimethoxy-phenyl)-4-[4-(4-methyl-piperazin-1-yl)-1-oxo-1,3-dihydro-isoindol-2-yl]-butyl}-methyl-amide,
2-[(1R)-1-(3,4-dimethoxy-phenyl)-4-(4,6-dimethyl-pyrimidin-2-ylsulfanyl)-butyl]-4-(4-ethyl-piperazin-1-yl)-2,3-dihydro-isoindol-1-one,
4-(4-cyclopropyl-piperazin-1-yl)-2-[(1R)-1-(3,4-dimethoxy-phenyl)-4-phenoxy-butyl]-2,3-dihydro-isoindol-1-one,
2-[(1R)-4-benzoimidazol-1-yl-1-(3,4-dimethoxy-phenyl)-butyl]-4-(4-ethyl-piperazin-1-yl)-2,3-dihydro-isoindol-1-one,
thiophene-2-sulfonic acid [(4R)-4-(3,4-dimethoxy-phenyl)-4-[1-oxo-4-piperazin-1-yl-1,3-dihydro-isoindol-2-yl]-butyl]-methyl-amide,
{(4R)-4-(3,4-dimethoxy-phenyl)-4-[4-(4-ethyl-piperazin-1-yl)-1-oxo-1,3-dihydro-isoindol-2-yl]-butylsulfanyl}-pyridine 1-oxide,
2-[(1R)-1-(3,4-dimethoxy-phenyl)-4-imidazol-1-yl-butyl]-4-(4-ethyl-piperazin-1-yl)-2,3-dihydro-isoindol-1-one,
4-(4-benzyl-piperazin-1-yl)-2-[(1R)-1-(3,4-dimethoxy-phenyl)-4-phenoxy-butyl]-2,3-dihydro-isoindol-1-one,
2-[(1R)-1-(3,4-dimethoxy-phenyl)-4-phenylsulfanyl-butyl]-4-piperazin-1-yl-2,3-dihydro-isoindol-1-one,
2-[(1R)-1-(3,4-dimethoxy-phenyl)-4-phenoxy-butyl]-4-piperazin-1-yl-2,3-dihydro-isoindol-1-one,
4-{2-[(1R)-4-dibenzylamino-1-(3,4-dimethoxy-phenyl)-butyl]-1-oxo-2,3-dihydro-1H-isoindol-4-yl}-1-ethyl-1-methyl-piperazin-1-ium trifluoroacetate,
1,2-dimethyl-1H-imidazole-4-sulfonic acid {(4R)-4-(3,4-dimethoxy-phenyl)-4-[4-(4-ethyl-piperazin-1-yl)-1-oxo-1,3-dihydro-isoindol-2-yl]-butyl}-methyl-amide,
2-[(1R)-1-(3,4-dimethoxy-phenyl)-4-phenylamino-butyl]-4-(4-ethyl-piperazin-1-yl)-2,3-dihydro-isoindol-1-one,
2-[(1R)-4-benzyloxy-1-(3,4-dimethoxy-phenyl)-butyl]-4-piperazin-1-yl-2,3-dihydro-isoindol-1-one,
2-[(1-benzyl-piperidin-4-yl)-(3,4-dimethoxy-phenyl)-methyl]-4-(4-ethyl-piperazin-1-yl)-2,3-dihydro-isoindol-1-one,
2-[(1R)-1-(3,4-dimethoxy-phenyl)-4-(pyrimidin-2-ylamino)-butyl]-4-(4-ethyl-piperazin-1-yl)-2,3-dihydro-isoindol-1-one,
2,3-dimethyl-3H-imidazole-4-sulfonic acid {(4R)-4-(3,4-dimethoxy-phenyl)-4-[4-(4-ethyl-piperazin-1-yl)-1-oxo-1,3-dihydro-isoindol-2-yl]-butyl}-amide,
2-[(1R)-1-(3,4-dimethoxy-phenyl)-4-phenoxy-butyl]-4-(4-ethyl-piperazin-1-yl)-2,3-dihydro-isoindol-1-one,
1-methyl-1H-imidazole-4-sulfonic acid {(4R)-4-(3,4-dimethoxy-phenyl)-4-[4-(4-ethyl-piperazin-1-yl)-1-oxo-1,3-dihydro-isoindol-2-yl]-butyl}-amide,
N-{(4R)-4-(3,4-dimethoxy-phenyl)-4-[4-(4-ethyl-piperazin-1-yl)-1-oxo-1,3-dihydro-isoindol-2-yl]-butyl}-isonicotinamide,
1-methyl-1H-imidazole-2-carboxylic acid {(4R)-4-(3,4-dimethoxy-phenyl)-4-[4-(4-ethyl-piperazin-1-yl)-1-oxo-1,3-dihydro-isoindol-2-yl]-butyl}-amide,
1-methyl-1H-imidazole-4-carboxylic acid {(4R)-4-(3,4-dimethoxy-phenyl)-4-[4-(4-ethyl-piperazin-1-yl)-1-oxo-1,3-dihydro-isoindol-2-yl]-butyl}-amide, aminosulfonic acid {(4R)-4-(3,4-dimethoxy-phenyl)-4-[4-(4-ethyl-piperazin-1-yl)-1-oxo-1,3-dihydro-isoindol-2-yl]-butyl}-amide,
3-methyl-3H-imidazole-4-carboxylic acid {(4R)-4-(3,4-dimethoxy-phenyl)-4-[4-(4-ethyl-piperazin-1-yl)-1-oxo-1,3-dihydro-isoindol-2-yl]-butyl}-amide,
3,5-dimethyl-1H-pyrazole-4-carboxylic acid {(4R)-4-(3,4-dimethoxy-phenyl)-4-[4-(4-ethyl-piperazin-1-yl)-1-oxo-1,3-dihydro-isoindol-2-yl]-butyl}-amide, pyridazine-4-carboxylic acid {(4R)-4-(3,4-dimethoxy-phenyl)-4-[4-(4-ethyl-piperazin-1-yl)-1-oxo-1,3-dihydro-isoindol-2-yl]-butyl}-amide,
thiophene-2-sulfonic acid {(4R)-4-(3,4-dimethoxy-phenyl)-4-[4-(4-ethyl-piperazin-1-yl)-1-oxo-1,3-dihydro-isoindol-2-yl]-butyl}-methyl-amide,
2-[(1R)-4-(bis-pyridin-4-ylmethyl-amino)-1-(3,4-dimethoxy-phenyl)-butyl]-4-(4-ethyl-piperazin-1-yl)-2,3-dihydro-isoindol-1-one,
{(4R)-4-(3,4-dimethoxy-phenyl)-4-[4-(4-ethyl-piperazin-1-yl)-1-oxo-1,3-dihydro-isoindol-2-yl]-butyl}-urea,
thiophene-2-sulfonic acid {(4R)-4-(3,4-dimethoxy-phenyl)-4-[4-(4-isopropyl-piperazin-1-yl)-1-oxo-1,3-dihydro-isoindol-2-yl]-butyl}-amide,
1-{(4R)-4-(3,4-dimethoxy-phenyl)-4-[4-(4-ethyl-piperazin-1-yl)-1-oxo-1,3-dihydro-isoindol-2-yl]-butyl}-3-phenyl-urea,
N-{(4R)-4-(3,4-dimethoxy-phenyl)-4-[4-(4-ethyl-piperazin-1-yl)-1-oxo-1,3-dihydro-isoindol-2-yl]-butyl}-2,2,2-trifluoro-acetamide,
2-[(1R)-4-diethylamino-1-(3,4-dimethoxy-phenyl)-butyl]-4-(4-ethyl-piperazin-1-yl)-2,3-dihydro-isoindol-1-one,
2-[(1R)-1-(3,4-dimethoxy-phenyl)-4-ethylamino-butyl]-4-(4-ethyl-piperazin-1-yl)-2,3-dihydro-isoindol-1-one,
dimethylaminosulfonic acid {(4R)-4-(3,4-dimethoxy-phenyl)-4-[4-(4-ethyl-piperazin-1-yl)-1-oxo-1,3-dihydro-isoindol-2-yl]-butyl}-amide,
2-{(1R)-1-(3,4-dimethoxy-phenyl)-4-[(thiophen-2-ylmethyl)-amino]-butyl}-4-(4-ethyl-piperazin-1-yl)-2,3-dihydro-isoindol-1-one,
2-[(1R)-4-dibenzylamino-1-(3,4-dimethoxy-phenyl)-butyl]-4-(4-ethyl-piperazin-1-yl)-2,3-dihydro-isoindol-1-one,
2-[(1R)-4-benzyloxy-1-(3,4-dimethoxy-phenyl)-butyl]-4-(4-ethyl-piperazin-1-yl)-2,3-dihydro-isoindol-1-one,
2-[(1R)-1-(3,4-dimethoxy-phenyl)-4-(2,2-dimethyl-propylamino)-butyl]-4-(4-ethyl-piperazin-1-yl)-2,3-dihydro-isoindol-1-one,
3-amino-4-{(4R)-4-(3,4-dimethoxy-phenyl)-4-[4-(4-ethyl-piperazin-1-yl)-1-oxo-1,3-dihydro-isoindol-2-yl]-butylamino}-cyclobut-3-ene-1,2-dione,
2-[(1R)-4-benzylamino-1-(3,4-dimethoxy-phenyl)-butyl]-4-(4-ethyl-piperazin-1-yl)-2,3-dihydro-isoindol-1-one, furan-2-carboxylic acid {(4R)-4-(3,4-dimethoxy-phenyl)-4-[4-(4-ethyl-piperazin-1-yl)-1-oxo-1,3-dihydro-isoindol-2-yl]-butyl}-amide,
1H-pyrazole-4-carboxylic acid {(4R)-4-(3,4-dimethoxy-phenyl)-4-[4-(4-ethyl-piperazin-1-yl)-1-oxo-1,3-dihydro-isoindol-2-yl]-butyl}-amide, cyclobutanecarboxylic acid {(4R)-4-(3,4-dimethoxy-phenyl)-4-[4-(4-ethyl-piperazin-1-yl)-1-oxo-1,3-dihydro-isoindol-2-yl]-butyl}-amide,
thiophene-2-carboxylic acid {(4R)-4-(3,4-dimethoxy-phenyl)-4-[4-(4-ethyl-piperazin-1-yl)-1-oxo-1,3-dihydro-isoindol-2-yl]-butyl}-amide,
1,2-dimethyl-1H-imidazole-4-sulfonic acid {(4R)-4-(3,4-dimethoxy-phenyl)-4-[4-(4-ethyl-piperazin-1-yl)-1-oxo-1,3-dihydro-isoindol-2-yl]-butyl}-amide,
N-{(4R)-4-(3,4-dimethoxy-phenyl)-4-[4-(4-ethyl-piperazin-1-yl)-1-oxo-1,3-dihydro-isoindol-2-yl]-butyl}-2,2-dimethyl-propionamide,
thiophene-2-sulfonic acid {(4R)-4-(3,4-dimethoxy-phenyl)-4-[4-(4-ethyl-piperazin-1-yl)-1-oxo-1,3-dihydro-isoindol-2-yl]-butyl}-amide,
5-methyl-isoxazole-4-carboxylic acid ((4R)-4-(3,4-dimethoxy-phenyl)-4-{1-oxo-4-[4-(1-phenyl-ethyl)-piperazin-1-yl]-1,3-dihydro-isoindol-2-yl}-butyl)-amide,
2-[(1R)-1-(3,4-dimethoxy-phenyl)-4-phenyl-butyl]-4-(4-ethyl-piperazin-1-yl)-2,3-dihydro-isoindol-1-one,
N-{(4R)-4-(3,4-dimethoxy-phenyl)-4-[4-(4-ethyl-piperazin-1-yl)-1-oxo-1,3-dihydro-isoindol-2-yl]-butyl}-N-(4-fluoro-benzyl)-acetamide,
2-[(1R)-1-(3,4-dimethoxy-phenyl)-4-(quinolin-2-ylamino)-butyl]-4-(4-ethyl-piperazin-1-yl)-2,3-dihydro-isoindol-1-one,
2-[(1R)-4-[cyclopropyl-(4-fluoro-benzyl)-amino]-1-(3,4-dimethoxy-phenyl)-butyl]-4-(4-ethyl-piperazin-1-yl)-2,3-dihydro-isoindol-1-one,
2-[(1R)-1-(3,4-dimethoxy-phenyl)-4-(4-fluoro-benzylamino)-butyl]-4-(4-ethyl-piperazin-1-yl)-2,3-dihydro-isoindol-1-one,
2-[(1R)-1-(3,4-dimethoxy-phenyl)-4-(pyridin-2-ylamino)-butyl]-4-(4-ethyl-piperazin-1-yl)-2,3-dihydro-isoindol-1-one,
2-[(1R)-1-(3,4-dimethoxy-phenyl)-4-(1-oxy-pyridin-2-ylamino)-butyl]-4-(4-ethyl-piperazin-1-yl)-2,3-dihydro-isoindol-1-one,
2-[(1R)-1-(3,4-dimethoxy-phenyl)-4-(furan-2-ylmethyl-methyl-amino)-butyl]-4-(4-ethyl-piperazin-1-yl)-2,3-dihydro-isoindol-1-one,
2-[(1R)-1-(3,4-dimethoxy-phenyl)-4-(methyl-thiophen-2-ylmethyl-amino)-butyl]-4-(4-ethyl-piperazin-1-yl)-2,3-dihydro-isoindol-1-one,
2-[(1R)-4-(benzyl-isopropyl-amino)-1-(3,4-dimethoxy-phenyl)-butyl]-4-(4-ethyl-piperazin-1-yl)-2,3-dihydro-isoindol-1-one,
2-{(1R)-1-(3,4-dimethoxy-phenyl)-4-[(2-fluoro-benzyl)-methyl-amino]-butyl}-4-(4-ethyl-piperazin-1-yl)-2,3-dihydro-isoindol-1-one,
2-{(1R)-1-(3,4-dimethoxy-phenyl)-4-[(3-fluoro-benzyl)-methyl-amino]-butyl}-4-(4-ethyl-piperazin-1-yl)-2,3-dihydro-isoindol-1-one,
2-{(1R)-1-(3,4-dimethoxy-phenyl)-4-[(4-fluoro-benzyl)-methyl-amino]-butyl}-4-(4-ethyl-piperazin-1-yl)-2,3-dihydro-isoindol-1-one,
2-[(1R)-4-(1,3-dihydro-isoindol-2-yl)-1-(3,4-dimethoxy-phenyl)-butyl]-4-(4-ethyl-piperazin-1-yl)-2,3-dihydro-isoindol-1-one,
2-[(1R)-4-(3,4-dihydro-1H-isoquinolin-2-yl)-1-(3,4-dimethoxy-phenyl)-butyl]-4-(4-ethyl-piperazin-1-yl)-2,3-dihydro-isoindol-1-one,
2-[(1R)-1-(3,4-dimethoxy-phenyl)-4-(2,4-dimethyl-imidazol-1-yl)-butyl]-4-(4-ethyl-piperazin-1-yl)-2,3-dihydro-isoindol-1-one,
2-[(1R)-1-(3,4-dimethoxy-phenyl)-4-(2-methyl-imidazol-1-yl)-butyl]-4-(4-ethyl-piperazin-1-yl)-2,3-dihydro-isoindol-1-one, and
2-[(1R)-1-(3,4-dimethoxy-phenyl)-4-(2-isopropyl-imidazol-1-yl)-butyl]-4-(4-ethyl-piperazin-1-yl)-2,3-dihydro-isoindol-1-one.

15. The compound of claim 13, wherein the compound is selected from the group consisting of:
dimethylaminosulfonic acid {(4R)-4-(3,4-dimethoxy-phenyl)-4-[4-(4-ethyl-piperazin-1-yl)-1-oxo-1,3-dihydro-isoindol-2-yl]-butyl}-methyl-amide,
2-[(1R)-4-(benzyl-methyl-amino)-1-(3,4-dimethoxy-phenyl)-butyl]-4-(4-ethyl-piperazin-1-yl)-2,3-dihydro-isoindol-1-one, 4-(4-benzyl-piperazin-1-yl)-2-[(1R)-1-(3,4-dimethoxy-phenyl)-4-(4-trifluoromethyl-pyrimidin-2-ylamino)-butyl]-2,3-dihydro-isoindol-1-one, 2-[(1R)-1-(3,4-dimethoxy-phenyl)-4-(4-trifluoromethyl-pyrimidin-2-ylamino)-butyl]-4-piperazin-1-yl-2,3-dihydro-isoindol-1-one, thiophene-2-sulfonic acid [(4R)-4-[4-(4-cyclopropyl-piperazin-1-yl)-1-oxo-1,3-dihydro-isoindol-2-yl]-4-(3,4-dimethoxy-phenyl)-butyl]-methyl-amide, thiophene-2-sulfonic acid {(4R)-4-(3,4-dimethoxy-phenyl)-4-[4-(4-isopropyl-piperazin-1-yl)-1-oxo-1,3-dihydro-isoindol-2-yl]-butyl}-methyl-amide, thiophene-2-sulfonic acid [(4R)-4-[4-(4-cyclobutyl-piperazin-1-yl)-1-oxo-1,3-dihydro-isoindol-2-yl]-4-(3,4-dimethoxy-phenyl)-butyl]-methyl-amide, 2-[(1R)-1-(3,4-dimethoxy-phenyl)-4-(4,6-dimethoxy-pyrimidin-2-ylamino)-butyl]-4-(4-ethyl-piperazin-1-yl)-2,3-dihydro-isoindol-1-one, 2-[(1R)-4-(4-chloro-pyrimidin-2-ylamino)-1-(3,4-dimethoxy-phenyl)-butyl]-4-(4-ethyl-piperazin-1-yl)-2,3-dihydro-isoindol-1-one, 2-[(1R)-1-(3,4-dimethoxy-phenyl)-4-(4,6-dimethyl-pyrimidin-2-ylamino)-butyl]-4-(4-ethyl-piperazin-1-yl)-2,3-dihydro-isoindol-1-one, 2-[(1R)-1-(3,4-dimethoxy-phenyl)-4-tetrazol-1-yl-butyl]-4-(4-ethyl-piperazin-1-yl)-2,3-dihydro-isoindol-1-one, 2-[(1R)-1-(3,4-dimethoxy-phenyl)-4-tetrazol-2-yl-butyl]-4-(4-ethyl-piperazin-1-yl)-2,3-dihydro-isoindol-1-one, thiophene-2-sulfonic acid (3-{(3,4-dimethoxy-phenyl)-4-[4-(4-ethyl-piperazin-1-yl)-1-oxo-1,3-dihydro-isoindol-2-yl]-methyl}-phenyl)-amide, 4-{2-(3,4-dimethoxy-phenyl)-2-[4-(4-ethyl-piperazin-1-yl)-1-oxo-1,3-dihydro-isoindol-2-yl]-ethyl}-piperidine-1-sulfonic acid, 2-{1-(3,4-dimethoxy-phenyl)-2-[1-(thiophene-2-sulfonyl)-piperidin-4-yl]-ethyl}-4-(4-ethyl-piperazin-1-yl)-2,3-dihydro-isoindol-1-one, 2-[(1R)-1-(3,4-dimethoxy-phenyl)-4-(4-ethyl-pyrimidin-2-ylamino)-butyl]-4-(4-ethyl-piperazin-1-yl)-2,3-dihydro-isoindol-1-one, 2-[(1R)-1-(3,4-dimethoxy-phenyl)-4-(4-methoxy-pyrimidin-2-ylamino)-butyl]-4-(4-ethyl-piperazin-1-yl)-2,3-dihydro-isoindol-1-one, 2-[(1R)-1-(3,4-dimethoxy-phenyl)-4-(4-trifluoromethyl-pyrimidin-2-ylamino)-butyl]-4-(4-ethyl-piperazin-1-yl)-2,3-dihydro-isoindol-1-one, 2-[(1R)-1-(3,4-dimethoxy-phenyl)-4-(4-methyl-pyrimidin-2-ylamino)-butyl]-4-(4-ethyl-piperazin-1-yl)-2,3-dihydro-isoindol-1-one, thiophene-2-sulfonic acid {(4R)-4-(3,4-dimethoxy-phenyl)-4-[4-(4-methyl-piperazin-1-yl)-1-oxo-1,3-dihydro-isoindol-2-yl]-butyl}-methyl-amide, 2-[(1R)-1-(3,4-dimethoxy-phenyl)-4-(4,6-dimethyl-pyrimidin-2-ylsulfanyl)-butyl]-4-(4-ethyl-piperazin-1-yl)-2,3-dihydro-isoindol-1-one, 4-(4-cyclopropyl-piperazin-1-yl)-2-[(1R)-1-(3,4-dimethoxy-phenyl)-4-phenoxy-butyl]-2,3-dihydro-isoindol-1-one, 2-[(1R)-4-benzoimidazol-1-yl-1-(3,4-dimethoxy-phenyl)-butyl]-4-(4-ethyl-piperazin-1-yl)-2,3-dihydro-isoindol-1-one, thiophene-2-sulfonic acid [(4R)-4-(3,4-dimethoxy-phenyl)-4-[1-oxo-4-piperazin-1-yl-1,3-dihydro-isoindol-2-yl]-butyl]-methyl-amide, {(4R)-4-(3,4-dimethoxy-phenyl)-4-[4-(4-ethyl-piperazin-1-yl)-1-oxo-1,3-dihydro-isoindol-2-yl]-butylsulfanyl}-pyridine 1-oxide, 2-[(1R)-1-(3,4-dimethoxy-phenyl)-4-imidazol-1-yl-butyl]-4-(4-ethyl-piperazin-1-yl)-2,3-dihydro-isoindol-1-one, 2-[(1R)-1-(3,4-dimethoxy-phenyl)-4-phenylsulfanyl-butyl]-4-piperazin-1-yl-2,3-dihydro-isoindol-1-one, 2-[(1R)-1-(3,4-dimethoxy-phenyl)-4-phenoxy-butyl]-4-piperazin-1-yl-2,3-dihydro-isoindol-1-one, 2-[(1R)-1-(3,4-dimethoxy-phenyl)-4-phenylamino-butyl]-4-(4-ethyl-piperazin-1-yl)-2,3-dihydro-isoindol-1-one, 2-[(1R)-4-benzyloxy-1-(3,4-dimethoxy-phenyl)-butyl]-4-piperazin-1-yl-2,3-dihydro-isoindol-1-one, 2-[(1R)-1-(3,4-dimethoxy-phenyl)-4-(pyrimidin-2-ylamino)-butyl]-4-(4-ethyl-piperazin-1-yl)-2,3-dihydro-isoindol-1-one, 2,3-dimethyl-3H-imidazole-4-sulfonic acid {(4R)-4-(3,4-dimethoxy-phenyl)-4-[4-(4-ethyl-piperazin-1-yl)-1-oxo-1,3-dihydro-isoindol-2-yl]-butyl}-amide, 2-[(1R)-1-(3,4-dimethoxy-phenyl)-4-phenoxy-butyl]-4-(4-ethyl-piperazin-1-yl)-2,3-dihydro-isoindol-1-one, 1-methyl-1H-imidazole-4-sulfonic acid {(4R)-4-(3,4-dimethoxy-phenyl)-4-[4-(4-ethyl-piperazin-1-yl)-1-oxo-1,3-dihydro-isoindol-2-yl]-butyl}-amide, N-{(4R)-4-(3,4-dimethoxy-phenyl)-4-[4-(4-ethyl-piperazin-1-yl)-1-oxo-1,3-dihydro-isoindol-2-yl]-butyl}-isonicotinamide, 1-methyl-1H-imidazole-2-carboxylic acid {(4R)-4-(3,4-dimethoxy-phenyl)-4-[4-(4-ethyl-piperazin-1-yl)-1-oxo-1,3-dihydro-isoindol-2-yl]-butyl}-amide, 1-methyl-1H-imidazole-4-carboxylic acid {(4R)-4-(3,4-dimethoxy-phenyl)-4-[4-(4-ethyl-piperazin-1-yl)-1-oxo-1,3-dihydro-isoindol-2-yl]-butyl}-amide, aminosulfonic acid {(4R)-4-(3,4-dimethoxy-phenyl)-4-[4-(4-ethyl-piperazin-1-yl)-1-oxo-1,3-dihydro-isoindol-2-yl]-butyl}-amide, 3-methyl-3H-imidazole-4-carboxylic acid {(4R)-4-(3,4-dimethoxy-phenyl)-4-[4-(4-ethyl-piperazin-1-yl)-1-oxo-1,3-dihydro-isoindol-2-yl]-butyl}-amide, 3,5-dimethyl-1H-pyrazole-4-carboxylic acid {(4R)-4-(3,4-dimethoxy-phenyl)-4-[4-(4-ethyl-piperazin-1-yl)-1-oxo-1,3-dihydro-isoindol-2-yl]-butyl}-amide, pyridazine-4-carboxylic acid {(4R)-4-(3,4-dimethoxy-phenyl)-4-[4-(4-ethyl-piperazin-1-yl)-1-oxo-1,3-dihydro-isoindol-2-yl]-butyl}-amide, thiophene-2-sulfonic acid {(4R)-4-(3,4-dimethoxy-phenyl)-4-[4-(4-ethyl-piperazin-1-yl)-1-oxo-1,3-dihydro-isoindol-2-yl]-butyl}-methyl-amide, 2-[(1R)-4-(bis-pyridin-4-ylmethyl-amino)-1-(3,4-dimethoxy-phenyl)-butyl]-4-(4-ethyl-piperazin-1-yl)-2,3-dihydro-isoindol-1-one, thiophene-2-sulfonic acid {(4R)-4-(3,4-dimethoxy-phenyl)-4-[4-(4-isopropyl-piperazin-1-yl)-1-oxo-1,3-dihydro-isoindol-2-yl]-butyl}-amide, 1-{(4R)-4-(3,4-dimethoxy-phenyl)-4-[4-(4-ethyl-piperazin-1-yl)-1-oxo-1,3-dihydro-isoindol-2-yl]-butyl}-3-phenyl-urea, N-{(4R)-4-(3,4-dimethoxy-phenyl)-4-[4-(4-ethyl-piperazin-1-yl)-1-oxo-1,3-dihydro-isoindol-2-yl]-butyl}-2,2,2-trifluoro-acetamide, dimethylaminosulfonic acid {(4R)-4-(3,4-dimethoxy-phenyl)-4-[4-(4-ethyl-piperazin-1-yl)-1-oxo-1,3-dihydro-isoindol-2-yl]-butyl}-amide, 2-{(1R)-1-(3,4-dimethoxy-phenyl)-4-[(thiophen-2-ylmethyl)-amino]-butyl}-4-(4-ethyl-piperazin-1-yl)-2,3-dihydro-isoindol-1-one, 2-[(1R)-4-dibenzylamino-1-(3,4-dimethoxy-phenyl)-butyl]-4-(4-ethyl-piperazin-1-yl)-2,3-dihydro-isoindol-1-one,
2-[(1R)-4-benzyloxy-1-(3,4-dimethoxy-phenyl)-butyl]-4-(4-ethyl-piperazin-1-yl)-2,3-dihydro-isoindol-1-one,
2-[(1R)-1-(3,4-dimethoxy-phenyl)-4-(2,2-dimethyl-propylamino)-butyl]-4-(4-ethyl-piperazin-1-yl)-2,3-dihydro-isoindol-1-one,
3-amino-4-{(4R)-4-(3,4-dimethoxy-phenyl)-4-[4-(4-ethyl-piperazin-1-yl)-1-oxo-1,3-dihydro-isoindol-2-yl]-butylamino}-cyclobut-3-ene-1,2-dione,
2-[(1R)-4-benzylamino-1-(3,4-dimethoxy-phenyl)-butyl]-4-(4-ethyl-piperazin-1-yl)-2,3-dihydro-isoindol-1-one,
furan-2-carboxylic acid {(4R)-4-(3,4-dimethoxy-phenyl)-4-[4-(4-ethyl-piperazin-1-yl)-1-oxo-1,3-dihydro-isoindol-2-yl]-butyl}-amide,
1H-pyrazole-4-carboxylic acid {(4R)-4-(3,4-dimethoxy-phenyl)-4-[4-(4-ethyl-piperazin-1-yl)-1-oxo-1,3-dihydro-isoindol-2-yl]-butyl}-amide,
cyclobutanecarboxylic acid {(4R)-4-(3,4-dimethoxy-phenyl)-4-[4-(4-ethyl-piperazin-1-yl)-1-oxo-1,3-dihydro-isoindol-2-yl]-butyl}-amide,
thiophene-2-carboxylic acid {(4R)-4-(3,4-dimethoxy-phenyl)-4-[4-(4-ethyl-piperazin-1-yl)-1-oxo-1,3-dihydro-isoindol-2-yl]-butyl}-amide,
1,2-dimethyl-1H-imidazole-4-sulfonic acid {(4R)-4-(3,4-dimethoxy-phenyl)-4-[4-(4-ethyl-piperazin-1-yl)-1-oxo-1,3-dihydro-isoindol-2-yl]-butyl}-amide,
N-{(4R)-4-(3,4-dimethoxy-phenyl)-4-[4-(4-ethyl-piperazin-1-yl)-1-oxo-1,3-dihydro-isoindol-2-yl]-butyl}-2,2-dimethyl-propionamide,
thiophene-2-sulfonic acid {(4R)-4-(3,4-dimethoxy-phenyl)-4-[4-(4-ethyl-piperazin-1-yl)-1-oxo-1,3-dihydro-isoindol-2-yl]-butyl}-amide,
5-methyl-isoxazole-4-carboxylic acid ((4R)-4-(3,4-dimethoxy-phenyl)-4-{1-oxo-4-[4-(1-phenyl-ethyl)-piperazin-1-yl]-1,3-dihydro-isoindol-2-yl}-butyl)-amide,
2-[(1R)-1-(3,4-dimethoxy-phenyl)-4-phenyl-butyl]-4-(4-ethyl-piperazin-1-yl)-2,3-dihydro-isoindol-1-one,
N-{(4R)-4-(3,4-dimethoxy-phenyl)-4-[4-(4-ethyl-piperazin-1-yl)-1-oxo-1,3-dihydro-isoindol-2-yl]-butyl}-N-(4-fluoro-benzyl)-acetamide,
2-[(1R)-4-[cyclopropyl-(4-fluoro-benzyl)-amino]-1-(3,4-dimethoxy-phenyl)-butyl]-4-(4-ethyl-piperazin-1-yl)-2,3-dihydro-isoindol-1-one,
2-[(1R)-1-(3,4-dimethoxy-phenyl)-4-(4-fluoro-benzylamino)-butyl]-4-(4-ethyl-piperazin-1-yl)-2,3-dihydro-isoindol-1-one,
2-[(1R)-1-(3,4-dimethoxy-phenyl)-4-(pyridin-2-ylamino)-butyl]-4-(4-ethyl-piperazin-1-yl)-2,3-dihydro-isoindol-1-one,
2-[(1R)-1-(3,4-dimethoxy-phenyl)-4-(1-oxy-pyridin-2-ylamino)-butyl]-4-(4-ethyl-piperazin-1-yl)-2,3-dihydro-isoindol-1-one,
2-[(1R)-1-(3,4-dimethoxy-phenyl)-4-(furan-2-ylmethyl-methyl-amino)-butyl]-4-(4-ethyl-piperazin-1-yl)-2,3-dihydro-isoindol-1-one,
2-[(1R)-1-(3,4-dimethoxy-phenyl)-4-(methyl-thiophen-2-ylmethyl-amino)-butyl]-4-(4-ethyl-piperazin-1-yl)-2,3-dihydro-isoindol-1-one,
2-[(1R)-4-(benzyl-isopropyl-amino)-1-(3,4-dimethoxy-phenyl)-butyl]-4-(4-ethyl-piperazin-1-yl)-2,3-dihydro-isoindol-1-one,
2-{(1R)-1-(3,4-dimethoxy-phenyl)-4-[(2-fluoro-benzyl)-methyl-amino]-butyl}-4-(4-ethyl-piperazin-1-yl)-2,3-dihydro-isoindol-1-one,
2-{(1R)-1-(3,4-dimethoxy-phenyl)-4-[(3-fluoro-benzyl)-methyl-amino]-butyl}-4-(4-ethyl-piperazin-1-yl)-2,3-dihydro-isoindol-1-one,
2-{(1R)-1-(3,4-dimethoxy-phenyl)-4-[(4-fluoro-benzyl)-methyl-amino]-butyl}-4-(4-ethyl-piperazin-1-yl)-2,3-dihydro-isoindol-1-one,
2-[(1R)-4-(1,3-dihydro-isoindol-2-yl)-1-(3,4-dimethoxy-phenyl)-butyl]-4-(4-ethyl-piperazin-1-yl)-2,3-dihydro-isoindol-1-one,
2-[(1R)-4-(3,4-dihydro-1H-isoquinolin-2-yl)-1-(3,4-dimethoxy-phenyl)-butyl]-4-(4-ethyl-piperazin-1-yl)-2,3-dihydro-isoindol-1-one,
2-[(1R)-1-(3,4-dimethoxy-phenyl)-4-(2,4-dimethyl-imidazol-1-yl)-butyl]-4-(4-ethyl-piperazin-1-yl)-2,3-dihydro-isoindol-1-one, and
2-[(1R)-1-(3,4-dimethoxy-phenyl)-4-(2-isopropyl-imidazol-1-yl)-butyl]-4-(4-ethyl-piperazin-1-yl)-2,3-dihydro-isoindol-1-one.

16. The compound of claim 13, wherein the compound is selected from the group consisting of:
dimethylaminosulfonic acid {(4R)-4-(3,4-dimethoxy-phenyl)-4-[4-(4-ethyl-piperazin-1-yl)-1-oxo-1,3-dihydro-isoindol-2-yl]-butyl}-methyl-amide,
2-[(1R)-4-(benzyl-methyl-amino)-1-(3,4-dimethoxy-phenyl)-butyl]-4-(4-ethyl-piperazin-1-yl)-2,3-dihydro-isoindol-1-one,
4-(4-benzyl-piperazin-1-yl)-2-[(1R)-1-(3,4-dimethoxy-phenyl)-4-(4-trifluoromethyl-pyrimidin-2-ylamino)-butyl]-2,3-dihydro-isoindol-1-one,
2-[(1R)-1-(3,4-dimethoxy-phenyl)-4-(4-trifluoromethyl-pyrimidin-2-ylamino)-butyl]-4-piperazin-1-yl-2,3-dihydro-isoindol-1-one,
thiophene-2-sulfonic acid [(4R)-4-[4-(4-cyclopropyl-piperazin-1-yl)-1-oxo-1,3-dihydro-isoindol-2-yl]-4-(3,4-dimethoxy-phenyl)-butyl]-methyl-amide,
thiophene-2-sulfonic acid {(4R)-4-(3,4-dimethoxy-phenyl)-4-[4-(4-isopropyl-piperazin-1-yl)-1-oxo-1,3-dihydro-isoindol-2-yl]-butyl}-methyl-amide,
thiophene-2-sulfonic acid [(4R)-4-[4-(4-cyclobutyl-piperazin-1-yl)-1-oxo-1,3-dihydro-isoindol-2-yl]-4-(3,4-dimethoxy-phenyl)-butyl]-methyl-amide,
2-[(1R)-1-(3,4-dimethoxy-phenyl)-4-(4,6-dimethoxy-pyrimidin-2-ylamino)-butyl]-4-(4-ethyl-piperazin-1-yl)-2,3-dihydro-isoindol-1-one,
2-[(1R)-4-(4-chloro-pyrimidin-2-ylamino)-1-(3,4-dimethoxy-phenyl)-butyl]-4-(4-ethyl-piperazin-1-yl)-2,3-dihydro-isoindol-1-one,
2-[(1R)-1-(3,4-dimethoxy-phenyl)-4-(4,6-dimethyl-pyrimidin-2-ylamino)-butyl]-4-(4-ethyl-piperazin-1-yl)-2,3-dihydro-isoindol-1-one,
2-[(1R)-1-(3,4-dimethoxy-phenyl)-4-tetrazol-1-yl-butyl]-4-(4-ethyl-piperazin-1-yl)-2,3-dihydro-isoindol-1-one,
thiophene-2-sulfonic acid (3-{(3,4-dimethoxy-phenyl)-[4-(4-ethyl-piperazin-1-yl)-1-oxo-1,3-dihydro-isoindol-2-yl]-methyl}-phenyl)-amide,
2-{1-(3,4-dimethoxy-phenyl)-2-[1-(thiophene-2-sulfonyl)-piperidin-4-yl]-ethyl}-4-(4-ethyl-piperazin-1-yl)-2,3-dihydro-isoindol-1-one,
2-[(1R)-1-(3,4-dimethoxy-phenyl)-4-(4-ethyl-pyrimidin-2-ylamino)-butyl]-4-(4-ethyl-piperazin-1-yl)-2,3-dihydro-isoindol-1-one,
2-[(1R)-1-(3,4-dimethoxy-phenyl)-4-(4-methoxy-pyrimidin-2-ylamino)-butyl]-4-(4-ethyl-piperazin-1-yl)-2,3-dihydro-isoindol-1-one, 2-[(1R)-1-(3,4-dimethoxy-phenyl)-4-(4-trifluoromethyl-pyrimidin-2-ylamino)-butyl]-4-(4-ethyl-piperazin-1-yl)-2,3-dihydro-isoindol-1-one,
2-[(1R)-1-(3,4-dimethoxy-phenyl)-4-(4-methyl-pyrimidin-2-ylamino)-butyl]-4-(4-ethyl-piperazin-1-yl)-2,3-dihydro-isoindol-1-one,
thiophene-2-sulfonic acid {(4R)-4-(3,4-dimethoxy-phenyl)-4-[4-(4-methyl-piperazin-1-yl)-1-oxo-1,3-dihydro-isoindol-2-yl]-butyl}-methyl-amide,
2-[(1R)-1-(3,4-dimethoxy-phenyl)-4-(4,6-dimethyl-pyrimidin-2-ylsulfanyl)-butyl]-4-(4-ethyl-piperazin-1-yl)-2,3-dihydro-isoindol-1-one,
2-[(1R)-4-benzoimidazol-1-yl-1-(3,4-dimethoxy-phenyl)-butyl]-4-(4-ethyl-piperazin-1-yl)-2,3-dihydro-isoindol-1-one,
thiophene-2-sulfonic acid [(4R)-4-(3,4-dimethoxy-phenyl)-4-(1-oxo-4-piperazin-1-yl-1,3-dihydro-isoindol-2-yl)-butyl]-methyl-amide,
{(4R)-4-(3,4-dimethoxy-phenyl)-4-[4-(4-ethyl-piperazin-1-yl)-1-oxo-1,3-dihydro-isoindol-2-yl]-butylsulfanyl}-pyridine 1-oxide,
2-[(1R)-1-(3,4-dimethoxy-phenyl)-4-imidazol-1-yl-butyl]-4-(4-ethyl-piperazin-1-yl)-2,3-dihydro-isoindol-1-one,
2-[(1R)-1-(3,4-dimethoxy-phenyl)-4-phenylsulfanyl-butyl]-4-piperazin-1-yl-2,3-dihydro-isoindol-1-one,
2-[(1R)-1-(3,4-dimethoxy-phenyl)-4-phenoxy-butyl]-4-piperazin-1-yl-2,3-dihydro-isoindol-1-one,
2-[(1R)-4-benzyloxy-1-(3,4-dimethoxy-phenyl)-butyl]-4-piperazin-1-yl-2,3-dihydro-isoindol-1-one,
2-[(1R)-1-(3,4-dimethoxy-phenyl)-4-(pyrimidin-2-ylamino)-butyl]-4-(4-ethyl-piperazin-1-yl)-2,3-dihydro-isoindol-1-one,
2,3-dimethyl-3H-imidazole-4-sulfonic acid {(4R)-4-(3,4-dimethoxy-phenyl)-4-[4-(4-ethyl-piperazin-1-yl)-1-oxo-1,3-dihydro-isoindol-2-yl]-butyl}-amide,
2-[(1R)-1-(3,4-dimethoxy-phenyl)-4-phenoxy-butyl]-4-(4-ethyl-piperazin-1-yl)-2,3-dihydro-isoindol-1-one,
1-methyl-1H-imidazole-4-carboxylic acid {(4R)-4-(3,4-dimethoxy-phenyl)-4-[4-(4-ethyl-piperazin-1-yl)-1-oxo-1,3-dihydro-isoindol-2-yl]-butyl}-amide,
3,5-dimethyl-1H-pyrazole-4-carboxylic acid {(4R)-4-(3,4-dimethoxy-phenyl)-4-[4-(4-ethyl-piperazin-1-yl)-1-oxo-1,3-dihydro-isoindol-2-yl]-butyl}-amide,
pyridazine-4-carboxylic acid {(4R)-4-(3,4-dimethoxy-phenyl)-4-[4-(4-ethyl-piperazin-1-yl)-1-oxo-1,3-dihydro-isoindol-2-yl]-butyl}-amide,
thiophene-2-sulfonic acid {(4R)-4-(3,4-dimethoxy-phenyl)-4-[4-(4-ethyl-piperazin-1-yl)-1-oxo-1,3-dihydro-isoindol-2-yl]-butyl}-methyl-amide,
2-[(1R)-4-(bis-pyridin-4-ylmethyl-amino)-1-(3,4-dimethoxy-phenyl)-butyl]-4-(4-ethyl-piperazin-1-yl)-2,3-dihydro-isoindol-1-one,
thiophene-2-sulfonic acid {(4R)-4-(3,4-dimethoxy-phenyl)-4-[4-(4-isopropyl-piperazin-1-yl)-1-oxo-1,3-dihydro-isoindol-2-yl]-butyl}-amide,
1-{(4R)-4-(3,4-dimethoxy-phenyl)-4-[4-(4-ethyl-piperazin-1-yl)-1-oxo-1,3-dihydro-isoindol-2-yl]-butyl}-3-phenyl-urea,
N-{(4R)-4-(3,4-dimethoxy-phenyl)-4-[4-(4-ethyl-piperazin-1-yl)-1-oxo-1,3-dihydro-isoindol-2-yl]-butyl}-2,2,2-trifluoro-acetamide,
dimethylaminosulfonic acid {(4R)-4-(3,4-dimethoxy-phenyl)-4-[4-(4-ethyl-piperazin-1-yl)-1-oxo-1,3-dihydro-isoindol-2-yl]-butyl}-amide,
2-{(1R)-1-(3,4-dimethoxy-phenyl)-4-[(thiophen-2-ylmethyl)-amino]-butyl}-4-(4-ethyl-piperazin-1-yl)-2,3-dihydro-isoindol-1-one,
2-[(1R)-4-dibenzylamino-1-(3,4-dimethoxy-phenyl)-butyl]-4-(4-ethyl-piperazin-1-yl)-2,3-dihydro-isoindol-1-one,
2-[(1R)-4-benzyloxy-1-(3,4-dimethoxy-phenyl)-butyl]-4-(4-ethyl-piperazin-1-yl)-2,3-dihydro-isoindol-1-one,
2-[(1R)-1-(3,4-dimethoxy-phenyl)-4-(2,2-dimethyl-propylamino)-butyl]-4-(4-ethyl-piperazin-1-yl)-2,3-dihydro-isoindol-1-one,
3-amino-4-{(4R)-4-(3,4-dimethoxy-phenyl)-4-[4-(4-ethyl-piperazin-1-yl)-1-oxo-1,3-dihydro-isoindol-2-yl]-butylamino}-cyclobut-3-ene-1,2-dione,
2-[(1R)-4-benzylamino-1-(3,4-dimethoxy-phenyl)-butyl]-4-(4-ethyl-piperazin-1-yl)-2,3-dihydro-isoindol-1-one,
furan-2-carboxylic acid {(4R)-4-(3,4-dimethoxy-phenyl)-4-[4-(4-ethyl-piperazin-1-yl)-1-oxo-1,3-dihydro-isoindol-2-yl]-butyl}-amide,
1H-pyrazole-4-carboxylic acid {(4R)-4-(3,4-dimethoxy-phenyl)-4-[4-(4-ethyl-piperazin-1-yl)-1-oxo-1,3-dihydro-isoindol-2-yl]-butyl}-amide,
cyclobutanecarboxylic acid {(4R)-4-(3,4-dimethoxy-phenyl)-4-[4-(4-ethyl-piperazin-1-yl)-1-oxo-1,3-dihydro-isoindol-2-yl]-butyl}-amide,
thiophene-2-carboxylic acid {(4R)-4-(3,4-dimethoxy-phenyl)-4-[4-(4-ethyl-piperazin-1-yl)-1-oxo-1,3-dihydro-isoindol-2-yl]-butyl}-amide,
1,2-dimethyl-1H-imidazole-4-sulfonic acid {(4R)-4-(3,4-dimethoxy-phenyl)-4-[4-(4-ethyl-piperazin-1-yl)-1-oxo-1,3-dihydro-isoindol-2-yl]-butyl}-amide,
N-{(4R)-4-(3,4-dimethoxy-phenyl)-4-[4-(4-ethyl-piperazin-1-yl)-1-oxo-1,3-dihydro-isoindol-2-yl]-butyl}-2,2-dimethyl-propionamide,
thiophene-2-sulfonic acid {(4R)-4-(3,4-dimethoxy-phenyl)-4-[4-(4-ethyl-piperazin-1-yl)-1-oxo-1,3-dihydro-isoindol-2-yl]-butyl}-amide,
5-methyl-isoxazole-4-carboxylic acid ((4R)-4-(3,4-dimethoxy-phenyl)-4-{1-oxo-4-[4-(1-phenyl-ethyl)-piperazin-1-yl]-1,3-dihydro-isoindol-2-yl}-butyl)-amide,
2-[(1R)-1-(3,4-dimethoxy-phenyl)-4-phenyl-butyl]-4-(4-ethyl-piperazin-1-yl)-2,3-dihydro-isoindol-1-one,
N-{(4R)-4-(3,4-dimethoxy-phenyl)-4-[4-(4-ethyl-piperazin-1-yl)-1-oxo-1,3-dihydro-isoindol-2-yl]-butyl}-N-(4-fluoro-benzyl)-acetamide,
2-[(1R)-4-[cyclopropyl-(4-fluoro-benzyl)-amino]-1-(3,4-dimethoxy-phenyl)-butyl]-4-(4-ethyl-piperazin-1-yl)-2,3-dihydro-isoindol-1-one,
2-[(1R)-1-(3,4-dimethoxy-phenyl)-4-(4-fluoro-benzylamino)-butyl]-4-(4-ethyl-piperazin-1-yl)-2,3-dihydro-isoindol-1-one, 2-[(1R)-1-(3,4-dimethoxy-phenyl)-4-(furan-2-ylmethyl-methyl-amino)-butyl]-4-(4-ethyl-piperazin-1-yl)-2,3-dihydro-isoindol-1-one, 2-[(1R)-1-(3,4-dimethoxy-phenyl)-4-(methyl-thiophen-2-ylmethyl-amino)-butyl]-4-(4-ethyl-piperazin-1-yl)-2,3-dihydro-isoindol-1-one, 2-[(1R)-4-(benzyl-isopropyl-amino)-1-(3,4-dimethoxy-phenyl)-butyl]-4-(4-ethyl-piperazin-1-yl)-2,3-dihydro-isoindol-1-one, 2-{(1R)-1-(3,4-dimethoxy-phenyl)-4-[(2-fluoro-benzyl)-methyl-amino]-butyl}-4-(4-ethyl-piperazin-1-yl)-2,3-dihydro-isoindol-1-one, 2-{(1R)-1-(3,4-dimethoxy-phenyl)-4-[(3-fluoro-benzyl)-methyl-amino]-butyl}-4-(4-ethyl-piperazin-1-yl)-2,3-dihydro-isoindol-1-one, 2-{(1R)-1-(3,4-dimethoxy-phenyl)-4-[(4-fluoro-benzyl)-methyl-amino]-butyl}-4-(4-ethyl-piperazin-1-yl)-2,3-dihydro-isoindol-1-one, 2-[(1R)-4-(1,3-dihydro-isoindol-2-yl)-1-(3,4-dimethoxy-phenyl)-butyl]-4-(4-ethyl-piperazin-1-yl)-2,3-dihydro-isoindol-1-one, 2-[(1R)-4-(3,4-dihydro-1H-isoquinolin-2-yl)-1-(3,4-dimethoxy-phenyl)-butyl]-4-(4-ethyl-piperazin-1-yl)-2,3-dihydro-isoindol-1-one, and 2-[(1R)-1-(3,4-dimethoxy-phenyl)-4-(2-isopropyl-imidazol-1-yl)-butyl]-4-(4-ethyl-piperazin-1-yl)-2,3-dihydro-isoindol-1-one.

17. The compound of claim 13, wherein the compound is selected from the group consisting of:

dimethylaminosulfonic acid {(4R)-4-(3,4-dimethoxy-phenyl)-4-[4-(4-ethyl-piperazin-1-yl)-1-oxo-1,3-dihydro-isoindol-2-yl]-butyl}-methyl-amide, 2-[(1R)-4-(benzyl-methyl-amino)-1-(3,4-dimethoxy-phenyl)-butyl]-4-(4-ethyl-piperazin-1-yl)-2,3-dihydro-isoindol-1-one, 2-[(1R)-1-(3,4-dimethoxy-phenyl)-4-(4-trifluoromethyl-pyrimidin-2-ylamino)-butyl]-4-piperazin-1-yl-2,3-dihydro-isoindol-1-one, thiophene-2-sulfonic acid {(4R)-4-(3,4-dimethoxy-phenyl)-4-[4-(4-isopropyl-piperazin-1-yl)-1-oxo-1,3-dihydro-isoindol-2-yl]-butyl}-methyl-amide, thiophene-2-sulfonic acid [(4R)-4-[4-(4-cyclobutyl-piperazin-1-yl)-1-oxo-1,3-dihydro-isoindol-2-yl]-4-(3,4-dimethoxy-phenyl)-butyl]-methyl-amide, 2-[(1R)-1-(3,4-dimethoxy-phenyl)-4-(4,6-dimethoxy-pyrimidin-2-ylamino)-butyl]-4-(4-ethyl-piperazin-1-yl)-2,3-dihydro-isoindol-1-one, 2-[(1R)-4-(4-chloro-pyrimidin-2-ylamino)-1-(3,4-dimethoxy-phenyl)-butyl]-4-(4-ethyl-piperazin-1-yl)-2,3-dihydro-isoindol-1-one, 2-{1-(3,4-dimethoxy-phenyl)-2-[1-(thiophene-2-sulfonyl)-piperidin-4-yl]-ethyl}-4-(4-ethyl-piperazin-1-yl)-2,3-dihydro-isoindol-1-one, 2-[(1R)-1-(3,4-dimethoxy-phenyl)-4-(4-methoxy-pyrimidin-2-ylamino)-butyl]-4-(4-ethyl-piperazin-1-yl)-2,3-dihydro-isoindol-1-one, 2-[(1R)-1-(3,4-dimethoxy-phenyl)-4-(4-trifluoromethyl-pyrimidin-2-ylamino)-butyl]-4-(4-ethyl-piperazin-1-yl)-2,3-dihydro-isoindol-1-one, thiophene-2-sulfonic acid {(4R)-4-(3,4-dimethoxy-phenyl)-4-[4-(4-methyl-piperazin-1-yl)-1-oxo-1,3-dihydro-isoindol-2-yl]-butyl}-methyl-amide, 2-[(1R)-1-(3,4-dimethoxy-phenyl)-4-(4,6-dimethyl-pyrimidin-2-ylsulfanyl)-butyl]-4-(4-ethyl-piperazin-1-yl)-2,3-dihydro-isoindol-1-one, 2,3-dimethyl-3H-imidazole-4-sulfonic acid {(4R)-4-(3,4-dimethoxy-phenyl)-4-[4-(4-ethyl-piperazin-1-yl)-1-oxo-1,3-dihydro-isoindol-2-yl]-butyl}-amide, 2-[(1R)-1-(3,4-dimethoxy-phenyl)-4-phenoxy-butyl]-4-(4-ethyl-piperazin-1-yl)-2,3-dihydro-isoindol-1-one, thiophene-2-sulfonic acid {(4R)-4-(3,4-dimethoxy-phenyl)-4-[4-(4-ethyl-piperazin-1-yl)-1-oxo-1,3-dihydro-isoindol-2-yl]-butyl}-methyl-amide, 2-[(1R)-4-(bis-pyridin-4-ylmethyl-amino)-1-(3,4-dimethoxy-phenyl)-butyl]-4-(4-ethyl-piperazin-1-yl)-2,3-dihydro-isoindol-1-one, thiophene-2-sulfonic acid {(4R)-4-(3,4-dimethoxy-phenyl)-4-[4-(4-isopropyl-piperazin-1-yl)-1-oxo-1,3-dihydro-isoindol-2-yl]-butyl}-amide, dimethylaminosulfonic acid {(4R)-4-(3,4-dimethoxy-phenyl)-4-[4-(4-ethyl-piperazin-1-yl)-1-oxo-1,3-dihydro-isoindol-2-yl]-butyl}-amide, 2-{(1R)-1-(3,4-dimethoxy-phenyl)-4-[(thiophen-2-ylmethyl)-amino]-butyl}-4-(4-ethyl-piperazin-1-yl)-2,3-dihydro-isoindol-1-one, 2-[(1R)-4-benzyloxy-1-(3,4-dimethoxy-phenyl)-butyl]-4-(4-ethyl-piperazin-1-yl)-2,3-dihydro-isoindol-1-one, 2-[(1R)-4-benzylamino-1-(3,4-dimethoxy-phenyl)-butyl]-4-(4-ethyl-piperazin-1-yl)-2,3-dihydro-isoindol-1-one, 1H-pyrazole-4-carboxylic acid {(4R)-4-(3,4-dimethoxy-phenyl)-4-[4-(4-ethyl-piperazin-1-yl)-1-oxo-1,3-dihydro-isoindol-2-yl]-butyl}-amide, thiophene-2-carboxylic acid {(4R)-4-(3,4-dimethoxy-phenyl)-4-[4-(4-ethyl-piperazin-1-yl)-1-oxo-1,3-dihydro-isoindol-2-yl]-butyl}-amide, thiophene-2-sulfonic acid {(4R)-4-(3,4-dimethoxy-phenyl)-4-[4-(4-ethyl-piperazin-1-yl)-1-oxo-1,3-dihydro-isoindol-2-yl]-butyl}-amide, 5-methyl-isoxazole-4-carboxylic acid ((4R)-4-(3,4-dimethoxy-phenyl)-4-{1-oxo-4-[4-(1-phenyl-ethyl)-piperazin-1-yl]-1,3-dihydro-isoindol-2-yl}-butyl)-amide, 2-[(1R)-1-(3,4-dimethoxy-phenyl)-4-phenyl-butyl]-4-(4-ethyl-piperazin-1-yl)-2,3-dihydro-isoindol-1-one, N-{(4R)-4-(3,4-dimethoxy-phenyl)-4-[4-(4-ethyl-piperazin-1-yl)-1-oxo-1,3-dihydro-isoindol-2-yl]-butyl}-N-(4-fluoro-benzyl)-acetamide, 2-[(1R)-4-[cyclopropyl-(4-fluoro-benzyl)-amino]-1-(3,4-dimethoxy-phenyl)-butyl]-4-(4-ethyl-piperazin-1-yl)-2,3-dihydro-isoindol-1-one, 2-[(1R)-1-(3,4-dimethoxy-phenyl)-4-(4-fluoro-benzylamino)-butyl]-4-(4-ethyl-piperazin-1-yl)-2,3-dihydro-isoindol-1-one, 2-[(1R)-1-(3,4-dimethoxy-phenyl)-4-(furan-2-ylmethyl-methyl-amino)-butyl]-4-(4-ethyl-piperazin-1-yl)-2,3-dihydro-isoindol-1-one, 2-[(1R)-1-(3,4-dimethoxy-phenyl)-4-(methyl-thiophen-2-ylmethyl-amino)-butyl]-4-(4-ethyl-piperazin-1-yl)-2,3-dihydro-isoindol-1-one, 2-{(1R)-1-(3,4-dimethoxy-phenyl)-4-[(2-fluoro-benzyl)-methyl-amino]-butyl}-4-(4-ethyl-piperazin-1-yl)-2,3-dihydro-isoindol-1-one, 2-{(1R)-1-(3,4-dimethoxy-phenyl)-4-[(3-fluoro-benzyl)-methyl-amino]-butyl}-4-(4-ethyl-piperazin-1-yl)-2,3-dihydro-isoindol-1-one, 2-{(1R)-1-(3,4-dimethoxy-phenyl)-4-[(4-fluoro-benzyl)-methyl-amino]-butyl}-4-(4-ethyl-piperazin-1-yl)-2,3-dihydro-isoindol-1-one, 2-[(1R)-4-(1,3-dihydro-isoindol-2-yl)-1-(3,4-dimethoxy-phenyl)-butyl]-4-(4-ethyl-piperazin-1-yl)-2,3-dihydro-isoindol-1-one, and 2-[(1R)-4-(3,4-dihydro-1H-isoquinolin-2-yl)-1-(3,4-dimethoxy-phenyl)-butyl]-4-(4-ethyl-piperazin-1-yl)-2,3-dihydro-isoindol-1-one.

18. The compound of claim 13, wherein the compound is selected from the group consisting of:

2-[(1R)-4-benzyloxy-1-(3,4-dimethoxy-phenyl)-butyl]-4-(4-ethyl-piperazin-1-yl)-2,3-dihydro-isoindol-1-one, thiophene-2-sulfonic acid {(4R)-4-(3,4-dimethoxy-phenyl)-4-[4-(4-ethyl-piperazin-1-yl)-1-oxo-1,3-dihydro-isoindol-2-yl]-butyl}-amide, and 2-[(1R)-1-(3,4-dimethoxy-phenyl)-4-phenyl-butyl]-4-(4-ethyl-piperazin-1-yl)-2,3-dihydro-isoindol-1-one.

19. A pharmaceutical composition comprising a compound according to claim 1 and a pharmaceutically acceptable carrier.

* * * * *